US008911983B2

(12) United States Patent
Caimi et al.

(10) Patent No.: US 8,911,983 B2
(45) Date of Patent: Dec. 16, 2014

(54) **PNP GENE MODIFICATION FOR IMPROVED XYLOSE UTILIZATION IN *ZYMOMONAS***

(71) Applicant: E I Du Pont De Nemours and Company, Wilmington, DE (US)

(72) Inventors: Perry G G Caimi, Kennett Square, PA (US); Min Qi, Hockessin, DE (US); Luan Tao, Wallingford, PA (US); Paul V Viitanen, West Chester, PA (US); Jianjun Yang, Hockessin, DE (US)

(73) Assignee: E I Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/711,646

(22) Filed: Dec. 12, 2012

(65) Prior Publication Data
US 2013/0157331 A1 Jun. 20, 2013

Related U.S. Application Data

(60) Provisional application No. 61/577,871, filed on Dec. 20, 2011.

(51) Int. Cl.
| C12N 1/20 | (2006.01) |
| C12N 15/74 | (2006.01) |
| C12P 7/06 | (2006.01) |
| C07H 21/04 | (2006.01) |

(52) U.S. Cl.
CPC ..................................... *C12N 15/74* (2013.01)
USPC ........ 435/252.3; 435/161; 435/471; 536/23.2

(58) Field of Classification Search
None
See application file for complete search history.

(56) References Cited

U.S. PATENT DOCUMENTS

| 5,514,583 | A | 5/1996 | Picataggio et al. |
| 5,712,133 | A | 1/1998 | Picataggio et al. |
| 5,843,760 | A | 12/1998 | Zhang et al. |
| 6,566,107 | B1 | 5/2003 | Zhang |
| 7,223,575 | B2 | 5/2007 | Zhang et al. |
| 7,629,156 | B2 | 12/2009 | Viitanen et al. |
| 7,741,119 | B2 | 6/2010 | Viitanen et al. |
| 7,998,722 | B2 | 8/2011 | Viitanen et al. |
| 2009/0246876 | A1 | 10/2009 | Viitanen et al. |
| 2011/0318801 | A1 | 12/2011 | Kahsay et al. |
| 2012/0156746 | A1 | 6/2012 | Caimi et al. |

FOREIGN PATENT DOCUMENTS

| WO | 9528476 A1 | 10/1995 |
| WO | 2009120730 A2 | 10/2009 |
| WO | 2012006061 A1 | 1/2012 |

OTHER PUBLICATIONS

Jana et al. Appl Microbiol Biotechnol (2005), 67: 289-298.*
Shi et al. RNA, 14: 2361-2371, 2007.*
Kuyper et al. FEMS Yeast Research (2005), 5: 399-409.*
Stickney, Leigh M. et al., Function of the Conserved S1 and KH Domains in Polynucleotide Phosphorylase, Journal of Bacteriology, Nov. 2005, pp. 7214-7221, vol. 187, No. 1.
Nurmohamed, Salima et al., Polynucleotide Phosphorylase Activity May Be Modulated by Metabolites in *Escherichia coli*, Journal of Biological Chemistry, Apr. 22, 2011, pp. 14315-14323, vol. 286, No. 16.
International Search Report dated Apr. 8, 2013, International Application No. PCT/US/2012/070456.
Feldmann, Sigrun D. et al., Pentose metabolism in *Zymomonas mobilis* wild-type and recombinant strains, Applied Microbiology and Biotechnology, 1992, pp. 354-361, vol. 38.
Yanese, Hideshi et al., Genetic Engineering of *Zymobacter palmae* for Production of Ethanol from Xylose, Applied and Environmental Microbiology, Feb. 16, 2007, pp. 2592-2599, vol. 73, No. 8.
Zhang, Min et al., Metabolic Engineering of a Pentose Metabolism Pathway in Ethanologenic *Zymomonas mobilis*, Science, Jan. 13, 1995, pp. 240-243, vol. 267.
Agrawal, Manoj et al., Engineering efficient xylose metabolism into an acetic acid-tolerant *Zymomonas mobilis* strain by introducing adaption-induced mutations, Biotechnology Letters, Original Research Paper, May 16, 2012.
Makrides, Savvas C., Strategies for Achieving High-Level Expression of Genes in *Escherichia coli*, Microbiolological Reviews, Sep. 1996, pp. 512-538, vol. 60, No. 3.
Donovan, William P. et al., Polynucleotide phosphorylase and ribonuclease II are required for cell viability and mRNA turnover in *Escherichia coli* K-12, Proc. Natl. Acad. Sci., USA, Jan. 1986, pp. 120-124, vol. 83.
Donovan, William P. et al., Amplification of ribonuclease II (rnb) activity in *Escherichia coli* K-12, Nucleic Acids Research, 1983, pp. 265-275, vol. 11, No. 2.
Mohanty, Bijoy K. et al., Genomic analysis in *Escherichia coli* demonstrates differential roles for polynucleotide phosphorylase and RNase II in mRNA abundance and decay, Molecular Microbiology, 2003, pp. 645-658, vol. 50, No. 2.
Bernstein, Jonathan A., et al., Global analysis of *Escherichia coli* RNA degradosome function using DNA microarrays, PNAS, Mar. 2, 2004, pp. 2758-2763, vol. 101, No. 9.

* cited by examiner

*Primary Examiner* — Iqbal H Chowdhury

(57) ABSTRACT

The endogenous pnp gene encoding polynucleotide phosphorylase in the *Zymomonas* genome was identified as a target for modification to provide improved xylose utilizing cells for ethanol production. The cells are in addition genetically modified to have increased expression of ribose-5-phosphate isomerase (RPI) activity, as compared to cells without this genetic modification, and are not limited in xylose isomerase activity in the absence of the pnp modification.

16 Claims, 27 Drawing Sheets

| I Strain | (1) | MFDIKRQEIDWGGKKLTLETGQVARQADGAVIATLGETVVLCAVTAAKTVKEGQDFFPLTVHYQEKYSAA |
| Wild Type | (1) | MFDIKRQEIDWGGKKLTLETGQVARQADGAVIATLGETVVLCAVTAAKTVKEGQDFFPLTVHYQEKYSAA 140 |
| I Strain | (71) | GRIPGGFFKRERGATERETLISRLIDRPIRPLFPEGFYNETLVIAQVMSYDGENEPDILAMIAASAALAL |
| Wild Type | (71) | GRIPGGFFKRERGATERETLISRLIDRPIRPLFPEGFYNETLVIAQVMSYDGENEPDILAMIAASAALAL 210 |
| I Strain | (141) | SGVPFLGPIGAARVGYQDGEFIILNPTLEQLEKSDLDLVVGATRDAVMVESEANELPEEVMLNAVSFAHE |
| Wild Type | (141) | SGVPFLGPIGAARVGYQDGEFIILNPTLEQLEKSDLDLVVGATRDAVMVESEANELPEEVMLNAVSFAHE 280 |
| I Strain | (211) | SLQPVIKAIINLAEQAAKEPWELVSVYDDSALAAKVEELCYDNFDKAYRLTRKAERVDALSKAKAVLDEAP |
| Wild Type | (211) | SLQPVIKAIINLAEQAAKEPWELVSVYDDSALAAKVEELCYDNFDKAYRLFRKAERVDALSKAKAVLDEAP 350 |
| I Strain | (281) | PEADPTEKLRIQKLAKKLEAKTVRTAILKEGRRIDGRDLKTVRPIRSQVGFLPRTHGSALFTRGETQALV |
| Wild Type | (281) | PEADPTEKLRIQKLAKKLEAKTVRTAILKEGRRIDGRDLKTVRPIRSQVGFLPRTHGSALFTRGETQALV 420 |
| I Strain | (351) | STTLGTADAEQMIDGLTGLHYERFMLHYNFPPYSVGEVGRFCAPGRREIGHGKLAWRALHPVLPSKADFP |
| Wild Type | (351) | STTLGTADAEQMIDGLTGLHYERFMLHYNFPPYSVGEVGRFGAPGRREIGHGKLAWRALHPVLPSKADFP 490 |
| I Strain | (421) | YTIRVLSDITESNGSSSMATVCGGCLAIMDAGVPLITRPVSGIAMGLILEKDGFAILSDIMGDEDHLGMD |
| Wild Type | (421) | YTIRVLSDITESNGSSSMATVCGGCLAIMDAGVPLITRPVSGIAMGLILEKDGFAILSDIMGDEDHLGMD 560 |
| I Strain | (491) | FKVAGTEKGIITSLQMDIKVAGITEEIMQKALEQAKGGPRAHILGEMSKALGEVRSEISNLAPRIETMSVPK |
| Wild Type | (491) | FKVAGTEKGIITSLQMDEKVAGITEEIMQKALEQAKGGRAHILGEMSKALGEVRSEISNLAPRIETMSVPK 630 |
| I Strain | (561) | DKIRDVGTGGKVIREIVATTGAKVDIEDDGTVRLSSSDPANIEAAREWINGIVEEPEVGKIYNGKVVNI |
| Wild Type | (561) | DKIRDVGTGGKVIREIVATTGAKVDIEDDGTVRLSSSDPANIEAAREWINGIVEEPEVGKIYNGKVVNI 700 |
| I Strain | (631) | VDFGAFVNFMGGRDGLIVHVSEIKNERVNKVSDVLSEGQEVKVKVLEIDNRGKVRLSMRVVDQETGAELDD |
| Wild Type | (631) | VDFGAFVNFMGGRDGLIVHVSEIKNERVNKVSDVLSEGQEVKVKVLEIDNRGKVRLSMRVVDQETGAELDD 748 |
| I Strain | (701) | NRPPRENAEPVSYTHLNPEALVG--------------------- SEQ ID NO:9 |
| Wild Type | (701) | NRPPRENAERRGGERPRRDRGPRRESGDRPARRDMEPEFAPAFLRKDS SEQ ID NO:2 |

PNP GENE MODIFICATION FOR IMPROVED XYLOSE UTILIZATION IN ZYMOMONAS

This application claims the benefit of U.S. Provisional Application 61/577,871, filed Dec. 20, 2011, and is incorporated by reference in its entirety.

STATEMENT OF GOVERNMENT RIGHTS

This invention was made with United States government support under Contract No. DE-FC36-07GO17056 awarded by the Department of Energy. The government has certain rights in this invention.

FIELD OF THE INVENTION

The invention relates to the fields of microbiology and genetic engineering. More specifically, the pnp gene in the Zymomonas genome was identified as a target for modification to provide improved xylose utilization and ethanol production.

BACKGROUND OF THE INVENTION

Production of ethanol by microorganisms provides an alternative energy source to fossil fuels and is therefore an important area of current research. It is desirable that microorganisms producing ethanol, as well as other useful products, be capable of using xylose as a carbon source since xylose is the major pentose in hydrolyzed lignocellulosic biomass. Biomass can provide an abundantly available, low cost carbon substrate. Zymomonas mobilis and other bacterial ethanologens which do not naturally utilize xylose have been genetically engineered for xylose utilization by introduction of genes encoding 1) xylose isomerase, which catalyses the conversion of xylose to xylulose; 2) xylulokinase, which phosphorylates xylulose to form xylulose 5-phosphate; 3) transketolase; and 4) transaldolase (U.S. Pat. Nos. 5,514,583, 5,712,133, 6,566,107, WO 95/28476, Feldmann et al. (1992) Appl. Microbiol. Biotechnol. 38: 354-361, Zhang et al. (1995) Science 267:240-243; Yanase et al. (2007) Appl. Environ. Mirobiol. 73:2592-2599). Typically the coding regions used were from E. coli genes.

Even with expression of this xylose utilization pathway, typically the engineered strains do not grow and produce ethanol as well on xylose as on glucose. Strains engineered for xylose utilization have been adapted by serial passage on xylose medium, resulting in strains with improved xylose utilization as described in U.S. Pat. No. 7,223,575 and U.S. Pat. No. 7,741,119. The latter also discloses inactivation of the GFOR locus encoding glucose-fructose oxidoreductase to improve xylose utilization. Disclosed in U.S. Pat. No. 7,998,722 is engineering for improved xylose utilization by expression of E. coli xylose isomerase from a mutated, highly active Zymomonas mobilis. glyceraldehyde-3-phosphate dehydrogenase gene promoter (Pgap).

There remains a need for engineered strains of Zymomonas and other bacterial ethanolagens with improved xylose utilization and ethanol production in xylose-containing medium, and processes for using these strains to produce ethanol.

SUMMARY OF THE INVENTION

The invention provides recombinant xylose-utilizing Zymomonas or Zymobacter cells in which an endogenous pnp gene encoding polynucleotide phosphorylase is modified. In addition the cells have increased ribose-5-phosphate isomerase (RPI) activity and non-limiting xylose isomerase activity. Xylose utilization and ethanol production in xylose-containing media are improved in these cells.

Accordingly, the invention provides a recombinant bacterial host cell comprising:
  a) a xylose metabolic pathway comprising at least one polypeptide having xylose isomerase activity;
  b) at least one genetic modification which increases ribose-5-phosphate isomerase activity in the host cell as compared with ribose-5-phosphate isomerase activity in the host cell lacking said genetic modification; and
  c) at least one genetic modification in the sequence of an endogenous gene encoding polynucleotide phosphorylase that shortens the coding region resulting in expression of a C-terminal truncated protein;
  wherein the bacterial host cell utilizes xylose to produce ethanol, xylose isomerase activity is not limiting in the bacterial host cell.

In another embodiment the invention provides a process for producing ethanol comprising:
  a) providing the recombinant host cell described above; and
  b) culturing the host cell of (a) in a medium comprising xylose whereby xylose is converted to ethanol.

BRIEF DESCRIPTION OF THE DRAWINGS AND SEQUENCE DESCRIPTIONS

Applicants have made the following biological deposits under the terms of the Budapest Treaty on the International Recognition of the Deposit of Microorganisms for the Purposes of Patent Procedure:

Information on Deposited Strains

| Depositor Identification Reference | International Depository Designation | Date of Deposit |
|---|---|---|
| Zymomonas ZW658 | ATCC No PTA-7858 | Sep. 12, 2006 |

FIG. 7 shows an alignment of amino acid sequences of the wild type Z. mobilis strain ZM4 pnp encoded polynucleotide phosphorylase (SEQ ID NO:2) and the fusion protein encoded by the modified pnp gene of the I strain (SEQ ID NO:9).

Figure 1:
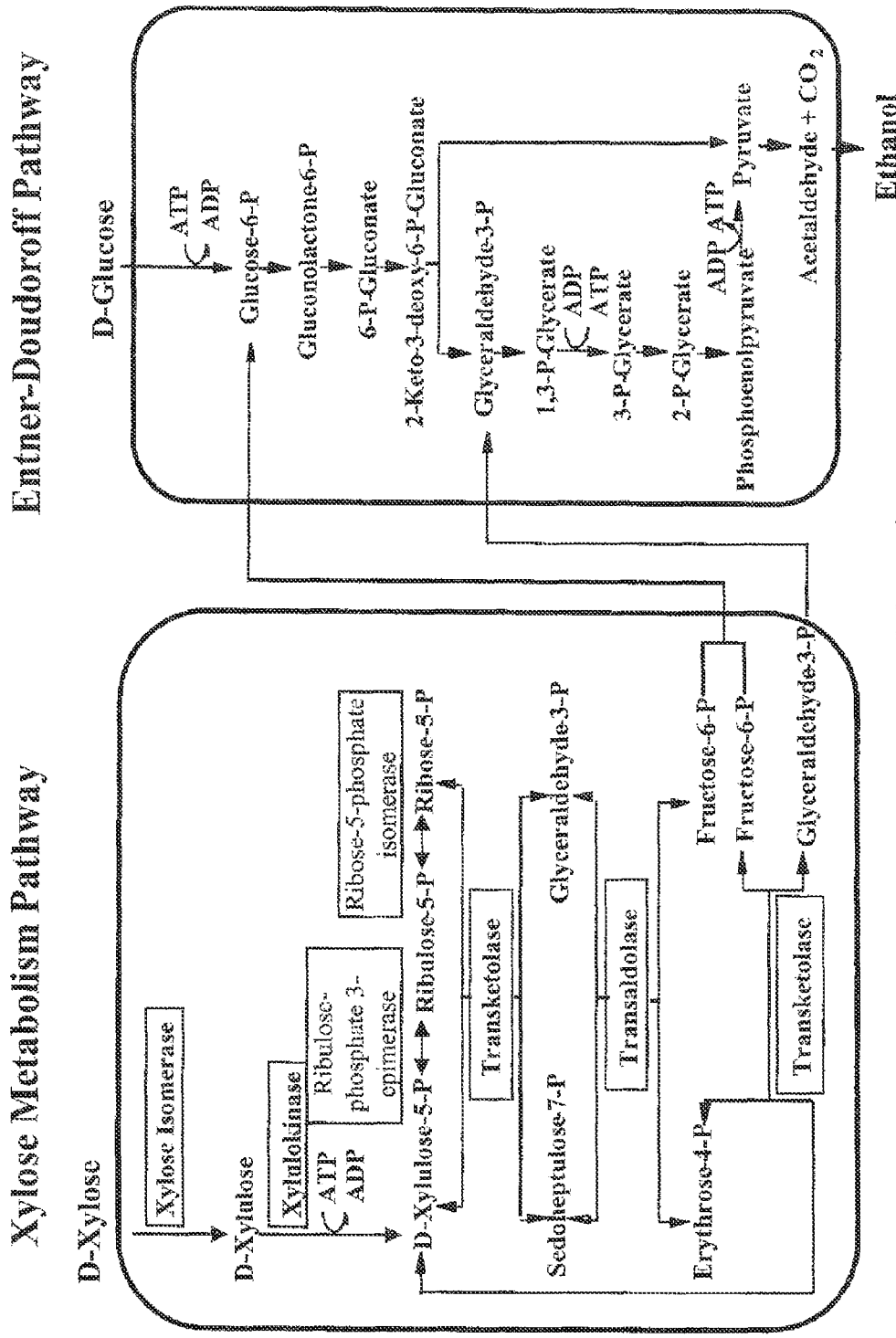
FIG. 1 shows a diagram of pathways for xylose metabolism and ethanol production.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the pnp coding region from *Zymomonas mobilis* strain ZM4.

SEQ ID NO:2 is the amino acid sequence of the pnp encoded polynucleotide phosphorylase from *Zymomonas mobilis* strain ZM4.

SEQ ID NO:3 is the nucleotide sequence of the pnp coding region from *Zymomonas mobilis* strain NCIMB 11163.

SEQ ID NO:4 is the amino acid sequence of the pnp encoded polynucleotide phosphorylase from *Zymomonas mobilis* strain NCIMB 11163.

SEQ ID NO:5 is the nucleotide sequence of the pnp coding region from *Zymomonas mobilis* strain ATCC 10988.

SEQ ID NO:6 is the amino acid sequence of the pnp encoded polynucleotide phosphorylase from *Zymomonas mobilis* strain ATCC 10988.

SEQ ID NO:7 is the nucleotide sequence of the pnp coding region from *Zymomonas mobilis* pomaceae ATCC 29192.

SEQ ID NO:8 is the amino acid sequence of the pnp encoded polynucleotide phosphorylase from *Zymomonas mobilis* strain ATCC 29192.

SEQ ID NO:9 is the amino acid sequence of the modified pnp encoded fusion protein of the I strain, having 709 native N-terminal amino acids and 14 additional C-terminal amino acids.

SEQ ID NO:10 is the amino acid sequence of a modified pnp encoded fusion protein having 695 native N-terminal amino acids and 2 additional C-terminal amino acids.

SEQ ID NO:11 is the amino acid sequence of a modified pnp encoded fusion protein having 368 native N-terminal amino acids and 10 additional C-terminal amino acids.

SEQ ID NO:12 is the amino acid sequence of a modified pnp encoded fusion protein having 32 native N-terminal amino acids and 17 additional C-terminal amino acids.

SEQ ID NO:13 is the nucleotide sequence of the coding region for the *Z. mobilis* RPI protein.

SEQ ID NO:14 is the amino acid sequence of the *Z. mobilis* RPI protein.

SEQ ID NO:15 is the nucleotide sequence of the coding region for the *E. coli* RPI protein SEQ ID NO:16 is the amino acid sequence of the *E. coli* RPI protein.

SEQ ID NO:17 is nucleotide sequence of the coding region for *Actinoplanes missouriensis* xylose isomerase that is codon-optimized for expression in *Zymomonas mobilis*.

SEQ ID NO:18 is the amino acid sequence of the *Actinoplanes missouriensis* xylose isomerase.

SEQ ID NO:19 is nucleotide sequence of the coding region for *Zymomonas mobilis* ribulose-phosphate 3-epimerase.

SEQ ID NO:20 is the amino acid sequence of the *Zymomonas mobilis* ribulose-phosphate 3-epimerase.

SEQ ID NO:21 is the nucleotide sequence of the $P_{gapS}$ (also called 801gap) mutant promoter.

SEQ ID NO:22 is the nucleotide sequence of the RPI expression cassette that is in plasmid pZB188aadA/Gap/Zymo RPI/EcoliSL, that is located between the unique NcoI and NotI sites.

SEQ ID NOs:23 and 24 are primers PPI-F and PPI-R-SbfI.

SEQ ID NO:25 is the nucleotide sequence of plasmid pZX21.

SEQ ID NO:26 is the nucleotide sequence of the GFO-L fragment.

SEQ ID NO:27 is the nucleotide sequence of the gfor coding sequence.

SEQ ID NO:28 is the nucleotide sequence of the GFO-R fragment.

SEQ ID NO:29 is the nucleotide sequence of a 1,661-bp chimeric xylA gene containing the 304-bp *Z. mobilis* Super GAP promoter, a 1,185-bp *A. missouriensis* xylA coding sequence, and a 166-bp *E. coli* araD 3'UTR with a 5' XbaI site.

SEQ ID NO:30 is the nucleotide sequence of a 1,960-bp chimeric xylB gene containing a 191 bp $P_{eno}$, a 1,455-bp *E. coli* xylB coding sequence and a 314-bp *E. coli* xylB 3'UTR.

SEQ ID NO:31 is the nucleotide sequence of a 1,014 bp aadA marker (for spectinomycin resistance; Spec-R) bounded by lox sites.

SEQ ID NO:32 is the nucleotide sequence of shuttle vector pZX52.

SEQ ID NO:33 is the nucleotide sequence of the LDH-L fragment.

SEQ ID NO:34 is the nucleotide sequence of the LDH-R fragment.

SEQ ID NO:35 is the nucleotide sequence of the ldhA coding sequence.

SEQ ID NO:36 is the nucleotide sequence of a 3,339 bp $P_{gapT}$-Tal-Tkt operon containing a 304-bp T-mutant of the *Z. mobilis* GAP promoter ($P_{gapT}$), a 954-bp *E. coli* Tal coding region, a 1,992-bp *E. coli* Tkt coding region, and a 68-bp *E. coli* Tkt 3'UTR.

SEQ ID NO:37 is the nucleotide sequence of the $P_{gapT}$ promoter.

SEQ ID NO:38 is the nucleotide sequence of a 1,443 bp $P_{eno}$-Rpi-Rpe operon containing a 191 bp $P_{eno}$, a 471 bp *Z. mobilis* Rpi coding sequence, a 663 bp *Z. mobilis* Rpe coding sequence, and a 35 bp *E. coli* xylA 3'UTR.

SEQ ID NO:39 is the nucleotide sequence of the DCO shuttle vector pZX6.

SEQ ID NO:40 is the nucleotide sequence of the PNP-L fragment.

SEQ ID NO:41 is the nucleotide sequence of the PNP-R fragment.

SEQ ID NOs:42 to 54 are PCR primers.

SEQ ID NO:55 is the nucleotide sequence of the DCO suicide vector pPNP-I.

SEQ ID NO:56 is the nucleotide sequence of the upstream flanking sequence for integration into the pnp gene.

SEQ ID NO:57 is the nucleotide sequence of the downstream flanking sequence for integration into the pnp gene.

SEQ ID NO:58 is the nucleotide sequence of the DCO suicide vector pPNP-IN.

SEQ ID NO:59 is the nucleotide sequence of the PNP-U fragment.

SEQ ID NO:60 is the nucleotide sequence of the PNP-D fragment.

SEQ ID NO:61 is the nucleotide sequence of the DCO suicide vector pPNP-C.

SEQ ID NO:62 is the nucleotide sequence of the DCO suicide vector pPNP-M.

SEQ ID NO:63 is the nucleotide sequence of the PNPm-L fragment.

SEQ ID NO:64 is the nucleotide sequence of the PNPm-R fragment.

SEQ ID NO:65 is the nucleotide sequence of the coding region for the *Z. mobilis* RPI protein with the start codon mutated to ATG.

DETAILED DESCRIPTION

Disclosed herein are xylose-utilizing bacterial cells, and particularly, *Zymomonas* or *Zymobacter* cells, that have genetic modifications of an endogenous pnp gene (pnp modification). The cells are in addition genetically modified to have increased expression of ribose-5-phosphate isomerase (RPI) activity, as compared to cells without this genetic modification. In addition the cells are not limited in xylose isomerase activity in the absence of the pnp modification. Cells with these properties have improved xylose utilization, which is desired for growth in media containing xylose including saccharified biomass, leading to increased ethanol production. Ethanol is an important compound for use in replacing fossil fuels, and saccharified biomass provides an abundantly available renewable carbon source for ethanol production by fermentation.

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "carbon substrate" or "fermentable carbon substrate" refers to a carbon source capable of being metabolized by host organisms of the present invention and particularly carbon sources selected from the group consisting of monosaccharides, oligosaccharides, and polysaccharides.

"Gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "locus" is a region of a genome that contains a gene.

The term "genetic construct" refers to a nucleic acid fragment that encodes for expression of one or more specific proteins or functional RNA molecules. In a gene construct the gene may be native, chimeric, or foreign in nature. Typically a genetic construct will comprise a "coding sequence". A "coding sequence" refers to a DNA sequence that encodes a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "genetic modification" refers, non-inclusively, to any modification, mutation, base deletion, base addition, codon modification, gene over-expression, gene suppression, promoter modification or substitution, gene addition (either single or multicopy), antisense expression or suppression, or any other change to the genetic elements of a host cell or bacterial strain, whether they produce a change in phenotype or not.

The term "recombinant bacterial host cell" refers to a bacterial cell that comprises at least one heterologus gene or genetic construct or nucleic acid fragment.

The term "expression", as used herein, refers to the transcription and stable accumulation of coding (mRNA) or functional RNA derived from a gene. Expression may also refer to translation of mRNA into a protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts or fragments capable of suppressing the expression of identical or substantially similar foreign or endogenous genes (U.S. Pat. No. 5,231,020). The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded protein. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the protein encoded by the DNA.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to physical, chemical and/or thermal pretreatment to increase accessibility of polysaccharides in the biomass prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat straw, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated or pre-processed prior to saccharification.

The term "xylose metabolic pathway" or "xylose utilization pathway" refers to a series of enzymes (encoded by genes) that metabolize xylose through to fructose-6-phosphate and/or glyceraldehyde-6-phosphate and include 1) xylose isomerase, which catalyses the conversion of xylose to xylulose; 2) xylulokinase, which phosphorylates xylulose to form xylulose 5-phosphate; 3) transketolase; and 4) transaldolase.

The term "xylose isomerase" refers to an enzyme that catalyzes the interconversion of D-xylose and D-xylulose. Xylose isomerases (XI) belong to the group of enzymes classified as EC 5.3.1.5.

The term "E-value", as known in the art of bioinformatics, is "Expect-value" which provides the probability that a match will occur by chance. It provides the statistical significance of the match to a sequence. The lower the E-value, the more significant the hit.

The term "ribose-5-phosphate isomerase" or "RPI" refers to an enzyme that catalyzes the interconversion of ribulose-5-phosphate and ribose-5-phosphate. Ribose-5-phosphate isomerases belong to the group of enzymes classified as EC 5.3.1.6.

The term "ribulose-phosphate 3-epimerase" or "RPE" refers to an enzyme catalyzes the interconversion of D-ribulose 5-phosphate and D-xylulose 5-phosphate and is classified as EC 5.1.3.1.

The term "Z. mobilis RPI-A" refers to the Z. mobilis RPI which has been labeled in the art as RPI-A. However, the Z. mobilis RPI protein has closer sequence identity to the E. coli RPI-B protein (36%) than to the E. coli RPI-A protein (20%) and further analysis of RP's described in commonly owned and co-pending U.S. patent application Ser. No. 13/161,734, published as WO2012/006061, which is incorporated herein by reference, places the Z mobilis RPI in the RPI-B group. However, herein the Z. mobilis RPI is called RPI-A to be consistent with its publicly known name.

The term "pnp gene" refers to a gene encoding polynucleotide phosphorylase, also called polyribonucleotide nucleotidyltransferase. This enzyme is bifunctional with a phosphorylitic 3' to 5' exoribonuclease activity and a 3' terminal oligonucleotide polymerase activity. It is involved with mRNA processing and degradation and is classified as EC 2.7.7.8.

The term "native amino acids" refers to amino acids as they occur in positions of the peptide sequence that is encoded by an endogenous gene.

The term "non-native amino acids" refers to amino acids in positions that are not encoded by an endogenous gene.

The term "N-terminal amino acid sequence" refers to amino acid sequence starting at the N-terminus of a polypeptide. The first N-terminal amino acid is counted as "1".

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual, 2nd* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment"

corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities may include, but are not limited to: 25%, 30%, 35%, 40%, 45%, 50%, 55%, 60%, 65%, 70%, 75%, 80%, 85%, 90%, or 95%, or any integer percentage from 25% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, and more preferably at least 150 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, $5^{th}$ Ed. Current Protocols. John Wiley and Sons, Inc., N.Y., 2002.

The present invention relates to engineered cells of xylose-utilizing bacteria, and particularly *Zymomonas* or *Zymobacter* that have improved xylose utilization when fermented in xylose containing media. A challenge for improving ethanol production by fermentation of a biocatalyst in media that includes biomass hydrolysate, produced typically by pretreatment and saccharification of biomass, is obtaining optimal utilization of xylose. Xylose is one of the predominant pentose sugars in hydrolyzed lignocellulosic biomass, the other being arabinose. Applicants have discovered that modification of the endogenous pnp gene, in combination with increased expression of ribose-5-phosphate isomerase and in the presence of non-limiting xylose isomerase activity, in xylose-utilizing cells leads to increased efficiency in xylose utilization, and thus to higher ethanol yields when fermentation is in xylose containing media.

Endogenous pnp Gene Modification

The present invention is directed to cells of engineered xylose utilizing *Zymomonas* or *Zymobacter* that have a modified endogenous pnp gene. The coding region of the endogenous pnp gene encodes a protein with polynucleotide phosphorylase activity. The encoded protein is also called polyribonucleotide nucleotidyltransferase. Modifications in the coding region of the endogenous pnp gene were found herein to improve xylose utilization in cells of engineered *Zymomonas* that are additionally engineered as described below.

Any gene of *Zymomonas* or *Zymobacter* that is identified as encoding a protein with polynucleotide phosphorylase or polyribonucleotide nucleotidyltransferase activity may provide the target endogenous pnp gene for modification as described herein. The pnp coding region of *Zymomonas mobilis* strain ZM4 has the sequence of SEQ ID NO:1. Known endogenous pnp coding regions from other strains of *Zymomonas* have sequences with identities to SEQ ID NO:1 of 99% (*Z. mobilis* NCIMB 11163; SEQ ID NO:3), 98% (*Z. mobilis* ATCC 10988; SEQ ID NO:5), and 83% (*Z. mobilis pomaceae* ATCC 29192; SEQ ID NO:7). Any of these sequences, or any sequence with at least about 95%, 96%, 97%, 98%, or 99% identity to any one of these sequences and identified as encoding a polynucleotide phosphorylase or polyribonucleotide nucleotidyltransferase may be used as the target for modification as described below. Additional target endogenous pnp gene sequences may be identified using BLAST analysis or other sequence comparison analyses that are well known to one skilled in the art.

In the present cells the pnp coding region is modified to shorten the coding region at the 3' end resulting in expression of a C-terminal truncated protein, as compared to the naturally encoded protein. The native encoded polynucleotide phosphorylase of *Zymomonas mobilis* is a protein of about 748 amino acids, which is any of SEQ ID NOs:2, 4, 6, 8 or any sequence with at least about 95%, 96%, 97%, 98%, or 99% identity to any one of these sequences and identified as a polynucleotide phosphorylase or polyribonucleotide nucleotidyltransferase. In one embodiment the truncated protein expressed from the modified pnp coding region retains at least about 350 amino acids of the N-terminal amino acid sequence encoded by the endogenous gene encoding polynucleotide phosphorylase, which are native N-terminal amino acids. The truncated protein retains at least about 350, 360, 370, 380, 390, 400, 410, 420, 430, 440, 450, 460, 470, 480, 490, 500, 510, 520, 530, 540, 550. 560, 570, 580, 590, 600, 610, 620, 630, 640, 650, 660, 670, 680, 690, 700, or 710 of the native N-terminal amino acids.

In one embodiment, the genetic modification to the endogenous pnp coding region adds coding sequence for non-native amino acids adjacent to and in frame with the truncated native coding region so that a fusion protein is produced. For example, coding region for additionally between about 1 and about 20 amino acids, which are not encoded by the endogenous gene, may be added adjacent to and in frame with the truncated native coding region producing a fusion protein having up to about 20 non-native amino acids at the C-terminus. The C-terminal truncated protein is then part of the fusion protein. In various embodiments there may be 1, 2, 3, 4, 5, 6, 7, 8, 9, 10, 11, 12, 13, 14, 15, 16, 17, 18, 19, 20, or more non-native amino acids at the C-terminus. Some non-limiting examples of fusion proteins that may result from genetic modification of an endogenous gene encoding polynucleotide phosphorylase include proteins that: 1) retain 709 native N-terminal amino acids and include 14 additional C-terminal amino acids (SEQ ID NO:9); 2) retain 695 native N-terminal amino acids and include 2 additional C-terminal amino acids (SEQ ID NO:10); 3) retain 368 native N-terminal amino acids and include 10 additional C-terminal amino acids (SEQ ID NO:11); and 4) retain 32 native N-terminal amino acids and include 17 additional C-terminal amino acids (SEQ ID NO:12).

The endogenous pnp coding region may be modified as described above by any method known to one skilled in the art. Typically the coding region is targeted by recombination targeting DNA sequences that are portions of the pnp coding region and may include surrounding adjacent genomic DNA. The recombination targeting DNA sequences direct insertion of DNA sequences bounded by them into the endogenous pnp gene by homologous recombination. In one embodiment the bounded DNA sequence includes a coding sequence for up to about 20 amino acids that is designed to be in reading frame with a position in the native pnp coding region, as described above, following integration by homologous recombination. Alternatively, the entire native pnp coding region may be replaced, using homologous recombination, with a coding region designed to produce a protein with a C-terminal truncation as described above. In addition, the replacement coding region may encode additional non-native amino acids at the C-terminus of the protein as described above, resulting in production of a fusion protein.

Engineered Xylose Utilizing *Zymomonas* or *Zymobacter*

The endogenous pnp gene is modified in a *Zymomonas* or *Zymobacter* cell that contains a xylose metabolic pathway conferring the ability to utilize xylose for production of ethanol. *Zymobacter palmae* is an ethanol-producing bacterium that has been engineered for xylose utilization by expressing genes for xylose utilization as described below for *Zymomonas*, using *Z. mobilis* glyceraldehyde-3-phosphate dehydrogenase and enolase promoters (Yanase et al. *Applied and Environmental Microbiology* (2007) 73:2592-2599).

Strains of *Zymomonas*, such as *Z. mobilis* have been engineered for xylose fermentation to ethanol. Typically four genes have been introduced into *Z. mobilis* for expression of four enzymes involved in xylose metabolism forming a xylose metabolic pathway in the cell (FIG. 1 in bold) as described in U.S. Pat. Nos. 5,514,583, 5,712,133, 6,566,107, WO 95/28476, Feldmann et al. ((1992) Appl Microbiol Biotechnol 38: 354-361), and Zhang et al. ((1995) Science 267: 240-243). These include genes encoding xylose isomerase which catalyzes the conversion of xylose to xylulose, and xylulokinase which phosphorylates xylulose to form xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of xylose to ethanol (see FIG. 1). DNA sequences encoding these enzymes may be obtained from any of numerous microorganisms that are able to metabolize xylose, such as enteric bacteria, and some yeasts and fungi. Sources for the coding regions may include *Xanthomonas, Klebsiella, Escherichia, Rhodobacter, Flavobacterium, Acetobacter, Gluconobacter, Rhizobium, Agrobacterium, Salmonella, Pseudomonads*, and *Zymomonas*. The coding regions of *E. coli* are typically used.

Endogenous genes may provide part of a xylose fermentation pathway, or may be altered by any known genetic manipulation technique to provide a protein with enzyme activity useful for xylose metabolism. For example, the endogenous transketolase may complement other introduced enzyme activities in creating a xylose utilization pathway.

*Zymomonas* or *Zymobacter* strains that are additionally engineered to utilize other sugars that, like xylose, are not natural substrates, may also be used in the present process. An example is a strain of *Z. mobilis* engineered for arabinose utilization is described in U.S. Pat. No. 5,843,760, which is incorporated herein by reference. Strains may be modified in other additional ways to improve xylose utilization and ethanol production.

Increased Expression of RPI

The present cells are additionally engineered for increased expression of ribose-5-phosphate isomerase (RPI) activity. RPI catalyzes the interconversion of ribulose-5-phosphate and ribose-5-phosphate (see FIG. 1). Increased expression of RPI is disclosed in commonly owned and co-pending U.S. patent application Ser. No. 13/161,734, published as WO2012/006061, which is incorporated herein by reference, which discloses increased RPI expression conferring increased efficiency of xylose utilization associated with reduced production of ribulose.

Increased RPI expression may be accomplished using any protein or polypeptide with ribose-5-phosphate isomerase activity in *Zymomonas* as disclosed in U.S. patent application Ser. No. 13/161,734, published as WO2012006061. Polypeptides having ribose-5-phosphate isomerase activity have the EC classification EC 5.3.1.6. There are two groups of ribose-5-phosphate isomerase enzymes that are called RPI-A and RPI-B. The RPI-B enzymes belong to the RpiB/LacA/LacB family of sugar-phosphate isomerases. *E. coli* has both types of RPI proteins. *Z. mobilis* has a single RPI protein that is annotated as RPI-A. However, the *Z. mobilis* RPI protein has closer sequence identity to the *E. coli* RPI-B protein (36%) than to the *E. coli* RPI-A protein (20%). Further analysis of RP's disclosed in U.S. patent application Ser. No. 13/161, 734, published as WO2012/006061, placed the *Z. mobilis* RPI in the RPI-B group.

The sequences of RPI proteins that may be used in the present cells are very diverse as exemplified by the *Z. mobilis* and *E. coli* RPI proteins (SEQ ID NOs:14 and 16, respectively; coding regions SEQ ID NOs:13 and 15, respectively).

RPI proteins that may be used in the present microorganisms may be identified using bioinformatics analysis. Identification using a structure/function bioinformatics analysis based on Profile Hidden Markov Modeling (using the hmmsearch algorithm of the HMMER software package; Janelia Farm Research Campus, Ashburn, Va.), active site residue identification, and additional identifying amino acid screening is described in Example 8 of U.S. patent application Ser. No. 13/161,734, published as WO2012/006061.

Examples of RPI-A and RPI-B proteins that fit these criteria and that may be used in the present microorganisms are described in U.S. patent application Ser. No. 13/161,734, published as US20120156746A1, which is incorporated herein by reference. Additional RP's may be readily identified in the literature and in bioinformatics databases as is well known to the skilled person and as described above. Identification of protein and/or coding sequences using bioinformatics is typically through BLAST (described above) searching of publicly available databases with RPI amino acid sequences or encoding sequences, such as those provided herein. Identities are based on the Clustal W method of alignment using the default parameters of GAP PENALTY=10, GAP LENGTH PENALTY=0.1, and Gonnet 250 series of protein weight matrix.

In the present cell, a genetic modification is made which increases ribose-5-phosphate isomerase activity as compared to ribose-5-phosphate isomerase activity in the cell lacking the genetic modification. Increased expression of RPI activity may be obtained by expressing an isolated DNA molecule encoding a protein having ribose-5-phosphate isomerase activity that is active in the host cell. Useful proteins with ribose-5-phosphate isomerase activity belong to the EC classification EC 5.3.1.6 and include ribose-5-phosphate isomerase A and ribose-5-phosphate isomerase B proteins that are described above.

Any method for increasing activity of an enzyme in a cell may be used to increase RPI activity. Such methods are well known to one skilled in the art and include increasing the encoding gene copy number and/or expression by a gene containing a high expression promoter. The present strains may be engineered for increased expression of an endogenous RPI coding region, and/or expression of an introduced heterologous RPI coding region to give increased enzyme activity. In addition, RPI activity may be increased by mutation and screening of expressed mutated genes to identify cells having increased activity.

Typically, increased expression of RPI is achieved by transforming with a DNA molecule encoding RPI that is operably linked to a promoter in a chimeric gene or operon. Coding sequences for RP's that may be used include any sequences encoding the RPI-A and RPI-B proteins described above.

When using a heterologous coding region, the sequence may be codon-optimized for maximal expression in the target host cell, as well known to one skilled in the art. If the native start codon is GTG, it may be changed to ATG for increased protein expression. Methods for gene expression in bacteria are well known in the art. Expression of genes in bacteria typically requires a promoter, operably linked to a coding region of interest, and a transcriptional terminator. Promoters that may be used are promoters that are expressed in *Zymomonas* or *Zymobacter* cells such as the promoters of *Z. mobilis* glyceraldehyde-3-phosphate dehydrogenase (GAP promoter; $P_{gap}$) gene, of *Z. mobilis* enolase (ENO promoter; Peno) gene, and of the *Actinoplanes missouriensis* xylose isomerase encoding gene (GI promoter, Pgi). Particularly high expression promoters that may be used are the $P_{gap}$ promoters with mutations causing high expression as disclosed in U.S. Pat. No. 7,998,722, which is incorporated herein by reference.

A chimeric gene or operon for RPI expression is typically constructed in or transferred to a vector for further manipulations. Vectors are well known in the art. Certain vectors are capable of replicating in a broad range of host bacteria and can be transferred by conjugation. The complete and annotated sequence of pRK404 and three related vectors: pRK437, pRK442, and pRK442(H) are available. These derivatives have proven to be valuable tools for genetic manipulation in gram-negative bacteria (Scott et al., *Plasmid* 50(1):74-79 (2003)).

Particularly useful for expression in *Zymomonas* are vectors that can replicate in both *E. coli* and *Zymomonas*, such as pZB188 which is described in U.S. Pat. No. 5,514,583, which is incorporated herein by reference. Vectors may include plasmids for autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

Bacterial cells may be engineered by introducing a vector having a chimeric gene comprising an RPI coding region by well known methods, such as using freeze-thaw transformation, calcium-mediated transformation, electroporation, or conjugation. Any bacterial cell to be engineered for improved xylose utilization by increasing expression of an RPI enzyme is a target host cell for transformation to engineer a strain as described herein. Particularly suitable host cells are *Zymomonas* and *Zymobacter*. The introduced chimeric gene may be maintained in the cell on a stably replicating plasmid, or integrated into the genome following introduction.

For engineering a strain with an integrated RPI chimeric gene or operon in the bacterial cell genome, methods may be used that are well known in the art such as homologous recombination, transposon insertion, or transposome insertion. In homologous recombination, DNA sequences flanking a target integration site are placed bounding a spectinomycin-resistance gene, or other selectable marker, and RPI chimeric gene leading to insertion of the selectable marker and the RPI chimeric gene into the target genomic site. In addition, the selectable marker may be bounded by site-specific recombination sites, so that after expression of the corresponding site-specific recombinase, the resistance gene is excised from the genome.

In addition, the promoter of the endogenous RPI expressing gene may be replaced with a more highly expressed promoter to increase RPI activity in the cell. This may be accomplished by homologous recombination using vectors and methods as described above.

Xylose Isomerase Activity

The present cells have a level of xylose isomerase activity that is not limiting. Xylose isomerase (XI) activity is not limiting when it is not the rate-limiting step for function of the xylose utilization and ethanol production pathways as shown in FIG. 1. Xylose isomerase activity is not limiting when an increase in xylose isomerase activity does not improve xylose utilization and ethanol production. This situation indicates that one or more other pathway steps are limiting. As found herein the xylose isomerase activity in ZW658 cells, measured using an assay including xylose, NADH, $MgSO_4$, triethanolamine, and sorbitol dehydrogenase that is described in Example 11 herein, is about 0.25 µmoles product/mg protein/minute. This level of xylose isomerase activity is not limiting in the ZW658 strain as described in example 3 herein. The ZW658 strain is a precursor to the ZW801-4 strain used herein as described in the Zymomonas mobilis strain construction section, herein. In one embodiment, non-limiting XI activity is greater than about 0.25 µmoles product/mg protein/minute as measured in a cell free extract using the assay described in Example 11 herein. Non-limiting XI activity may be greater than about 0.25, 0.3, 0.35, 0.4, 0.45, or 0.5 µmoles product/mg protein/minute.

When XI activity is limiting in a cell, the cell may be engineered to have non-limiting XI activity by increasing expression level of an XI enzyme or introducing expression of a more highly active XI enzyme. Increasing expression level may be by any method known to one skilled in the art such as increasing copy number of a gene encoding XI or using a more highly active promoter to express an XI enzyme.

For example, an XI coding region may be expressed using a mutated promoter that has increased expression level as compared to the non-mutated promoter. An example of a mutated high expression promoter is the mutated promoter of the Z. mobilis glyceraldehyde-3-phosphate dehydrogenase gene that is disclosed in U.S. Pat. No. 7,989,206 called herein the Super GAP promoter ($P_{gapS}$).

Xylose isomerase enzymes that may provide high activity by expression in multiple copy or from a mutated high expression promoter are any of those described in U.S. Pat. No. 7,998,722, which is incorporated herein by reference. As disclosed therein, xylose isomerases enzymes belong to EC 5.3.1.5 and may be identified using a Profile HMM (described above for RPI) and in addition four catalytic site amino acids found to be characteristic of xylose isomerases.

Alternatively or in addition, high XI activity may be obtained by expressing an XI enzyme having higher activity in Zymomonas cells than the commonly used E. coli XI. Commonly owned and co-pending US Patent Application Publication US20110318801, which is incorporated herein by reference, discloses that xylose isomerase enzymes identified by EC 5.3.1.5 and belonging to Group I have higher activity than the E. coli XI, which belongs to Group II. In addition, a Group I XI may be expressed from a mutated high expression promoter, as described above, to obtain high XI activity in a host cell.

Group I xylose isomerases as disclosed in US Patent Application Publication US20110318801 refers to a xylose isomerase protein that belongs to Group I as defined by at least one of the following criteria: a) it falls within a 50% threshold sequence identity grouping that includes the A. missouriensis XI that is prepared using molecular phylogenetic bioinformatics analysis as in Example 4 of US Patent Application Publication US20110318801; b) it substantially fits the amino acids for Group I in the specificity determining positions (SDP) identified using GroupSim analysis of the Group I and Group II XI sets determined from molecular phylogenetic analysis in Example 4 of US Patent Application Publication US20110318801; and/or c) it has an E-value of 1E-15 or less when queried using a Profile Hidden Markov Model prepared as described in Example 4 of US Patent Application Publication US20110318801. For example XI from Actinoplanes missouriensis (for example, SEQ ID NO:18) was identified as belonging to Group I and when expressed in Zymomonas mobilis cells it provides higher activity than similarly expressed E. coli XI.

Chimeric genes, vectors, transformation, integration, codon-optimization, and expression of XI is as described for RPI above and is well-known to one skilled in the art.

Increased Expression of RPE

In one embodiment the present cells are additionally engineered for increased expression of ribulose-phosphate 3-epimerase (RPE) activity. RPE catalyzes the interconversion of D-ribulose 5-phosphate and D-xylulose 5-phosphate (see FIG. 1) and is classified as EC 5.1.3.1. At least one genetic modification is made that increases RPE activity in the cell as compared to RPE activity in the cell lacking the genetic modification. Modifications for increased expression are as described above for RPI, and may use any enzyme belonging to EC 5.1.3.1 with RPE activity. For example, additional copies of the Z. mobilis RPE (SEQ ID NO:20; coding sequence SEQ ID NO:19) may be expressed in the cell, or an RPE coding region may be expressed from a high expression promoter.

Fermentation of Improved Xylose-Utilizing Strain

The present engineered xylose-utilizing Zymomonas or Zymobacter cells may be used in fermentation to produce ethanol. As an example, production of ethanol by a Z. mobilis strain of the invention is described.

For production of ethanol, recombinant xylose-utilizing Z. mobilis having increased RPI activity, non-limiting XI activity, and endogenous pnp gene modification is brought in contact with medium that contains xylose. Xylose may be the sole sugar, but typically the medium contains a mixture of sugars including xylose and glucose. The medium may contain biomass hydrolysate that includes these sugars that are derived from treated cellulosic or lignocellulosic biomass.

When the mixed sugars concentration is high such that growth is inhibited, the medium includes sorbitol, mannitol, or a mixture thereof as disclosed in commonly owned U.S. Pat. No. 7,629,156. Galactitol or ribitol may replace or be combined with sorbitol or mannitol. The Z. mobilis cells grow in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The fermentations may be run at temperatures that are between about 30° C. and about 37° C., at a pH of about 4.5 to about 7.5.

The present Z. mobilis cells may be grown in medium containing mixed sugars including xylose in laboratory scale fermenters, and in scaled up fermentation where commercial quantities of ethanol are produced. Where commercial production of ethanol is desired, a variety of culture methodologies may be applied. For example, large-scale production from the present Z. mobilis cells may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for growth of the present Z. mobilis cells and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired Z. mobilis cells of the present invention are grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/L), ammonium sulfate (0-2.0 g/L), magnesium sulfate (0-5.0 g/L), a complex nitrogen source such as yeast extract or soy based products (0-10 g/L). A final concentration of about 5 mM sorbitol or mannitol is present in the medium. Mixed sugars including xylose and at least one additional sugar such as glucose (or sucrose), providing a carbon source, are continually added to the fermentation vessel on depletion of the initial batched carbon source (50-200 g/L) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class-silicone based, organic based etc) are added to the vessel as needed. An antibiotic, for which there is an antibiotic resistant marker in the strain, such as kanamycin, may be used optionally to minimize contamination.

Any set of conditions described above, and additionally variations in these conditions that are well known in the art, are suitable conditions for production of ethanol by xylose-utilizing recombinant *Zymomonas* cells.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used here are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "µL" means microliter(s), "µg" means microgram(s), "ng" means nanogram(s), "mM" means millimolar, "µM" means micromolar, "nm" means nanometer(s), "µmol" means micromole(s), "pmol" means picomole(s), "Cm" means chloramphenicol, "$Cm^r$" or "Cm-R" means chloramphenicol resistant, "$Cm^s$" means chloramphenicol sensitive, "$Spec^r$" or "Spec-R" means spectinomycin resistance, "$Sp^s$" means spectinomycin sensitive, "XI" is xylose isomerase, "XK" is xylulokinase, "TAL" is transaldolase, "TKT" is transketolase, "OD600" means optical density measured at a wavelength of 600 nm, "PCR" means polymerase chain reaction, "kDa" means kilodaltons, "g" means the gravitation constant, "bp" means base pair(s), "kbp" means kilobase pair(s), "HPLC" means high performance liquid chromatography, and "GC" means gas chromatography, "RM" means rich medium containing 10 g/L yeast extract plus 2 g/L $KH_2PO_4$, "MM" means mating medium containing 10 g/L yeast extract, 5 g/L tryptone, 2.5 g/L $(NH_4)_2SO_4$ and 0.2 g/L $KH_2PO_4$.

Transformation of Z. mobilis

Replicating and non-replicating plasmid DNA was introduced into Z. mobilis using electroporation, essentially as described in U.S. Pat. No. 5,514,583, which is incorporated herein by reference. Briefly, the 50-µl transformation reactions contained ~$10^{10}$ cells/ml in 10% (v/v) glycerol and ~0.5-2.0 µg of non-methylated plasmid DNA that was isolated from E. coli SCS110. Control reactions were treated identically, but did not receive any plasmid DNA. The settings for the electroporator were 16 kv/cm, 200 Ω, and 25 µF, and the gap width of the cuvette was 0.1 cm. Following electroporation, the transformation reactions were diluted with MMG medium (50 g/L glucose, 10 g/L yeast extract, 5 g/L of tryptone, 2.5 g/L of $(NH_4)_2SO_4$, 0.2 g/L $K_2HPO_4$, and 1 mM $MgSO_4$) and the cells were allowed to recover at 30° C. before they were plated on MMG medium that contained 1.5% agar (MMG agar plate) with or without antibiotics as indicated. Plates were incubated in an anaerobic chamber at 30° C., until colonies appeared. Additional details are described in the Examples below.

Shake Flask Experiments

Unless otherwise noted, all experiments described below were conducted at 30° C. in shake flasks (15-ml loosely-capped, conical shaped test tubes) using synthetic media that contained glucose or xylose as the sole carbon source. mRM3-G10 medium contains 10 g/L yeast extract, 2 g/L $KH_2PO_4$, 1 g/L $MgSO_4$ ($7H_2O$) and 100 g/L glucose. mRM3-X10 medium is identical but it contains 100 g/L xylose instead of glucose. Cell growth was monitored spectrophotometrically by following changes in optical density at 600 nm as a function of time. In the text and figure legends "OD" or "OD600" means optical density at 600 nm. At indicated times during the shake flask growth studies, 1.0-ml aliquots of the cultures were removed for HPLC analysis using an Agilent 1100 equipped with a refractive index detector (Hewlett-Packard, Palo Alto, Calif.) to determine the concentrations of glucose, xylose, ribulose, and ethanol that were present in the fermentation broth. Prior to HPLC analysis, cells were removed by centrifugation and the supernatant was filtered through a 0.22 µm cellulose acetate Spin-X centrifuge tube filter (Costar, catalog number 8160) to remove small particles. Compounds were separated on an Aminex HPX-87H column (Bio-Rad) that was run at 55° C. under isocratic conditions using a flow rate of 0.6 ml/min and 0.01 $NH_2SO_4$ as the mobile phase. Authentic standards of known concentration were used to quantify the peaks of interest and all results are expressed in g/L.

Zymomonas mobilis Strain Construction

A detailed description of the construction of the xylose-utilizing recombinant strain, ZW801-4, starting from the wild type parent strain, ZW1, is provided in U.S. Pat. No. 7,741, 119, which is herein incorporated by reference. Strain ZW801-4 was derived from strain ZW800, which was derived from strain ZW658, all as described in U.S. Pat. No. 7,741,084, which is herein incorporated by reference. ZW658 was constructed by integrating two operons, $P_{gap}$xylAB and $P_{gap}$taltkt, containing four xylose-utilizing genes encoding xylose isomerase (xylA), xylulokinase (xylB), transaldose (tal), and transketolase (tkt), with coding regions from E. coli genes, into the genome of ZW1 (rename of strain ZM4; ATCC 31821) via sequential transposition events followed by adaptation on selective medium containing xylose to produce strain X13L3, which was renamed ZW641. Further adaptation of ZW641 on xylose-containing growth media gave rise to ZW658, which grows much better in xylose and was deposited under the Budapest Treaty as ATCC PTA-7858. As disclosed in commonly owned U.S. Pat. No. 7,989,206, which is herein incorporated by reference, ZW658 has much more xylose isomerase activity due to a point mutation in the promoter ($P_{gap}$) expressing the xylA coding region. This promoter (SEQ ID NO:21), herein called either the 801GAP promoter or the Super GAP promoter or $P_{gapS}$, has a "T" instead of "G" in position 116 in SEQ ID NO:21, when compared to the native $P_{gap}$ in ZW641 (the 641GAP promoter). The $P_{gapS}$ has expression strength 3 to 4 times higher than the $P_{gap}$ in Z. mobilis.

In ZW658, the gene encoding glucose-fructose oxidoreductase was insertionally-inactivated using host-mediated, double-crossover, homologous recombination and spectinomycin resistance as a selectable marker to create strain ZW800. The spectinomycin resistance marker, which was bounded by loxP sites, was removed by site specific recombination using Cre recombinase to create strain ZW801-4.

Preparation of Cell-Free Extracts of Zymomonas for Enzymatic Assay

Cells were grown in 50 ml of RM+2% glucose at 30° C. overnight to an $OD_{600}$ of 1.0-1.2. Cells were harvested by centrifugation at 4500 rpm for 10 min at 4° C. The supernatant was discarded and the cell pellet washed with 25 ml ice-cold sonication buffer (10 mM Tris, pH 7.6, 10 mM $MgCl_2$), followed by centrifugation at 4500 rpm for 10 min. The pellet was resuspended in 2.0-2.5 ml sonication buffer plus 1 mM dithiothreitol. A 500 µL aliquot was centrifuged for 1 min in an eppendorf centrifuge at 4° C. Most of supernatant was discarded, leaving about 10-20 µL behind to keep the pellet from drying out. The cells were frozen and stored at about 80° C. until assayed. Prior to assay, the cells were thawed and resuspended with 500 µL of sonication buffer plus 1 mM dithiothreitol. The mix was sonicated 2× for 45 seconds at 62% duty cycle and an output control of 2 using a Branson sonifier 450, letting samples cool about 3-5 min between sonications. Samples were centrifuged at 14,000 rpm for 60 min in a Beckman microfuge at 4° C. The supernatant was transferred to a new tube and kept at 4° C. The Pierce BCA assay was used for determining protein concentrations.

Example 1

Figure 2:
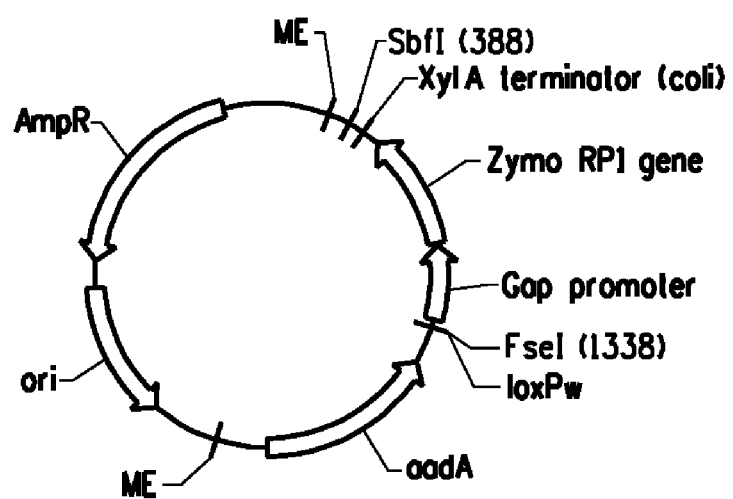
FIG. 2 shows a plasmid map of pMODlinker-Spec-GapRpi.

Construction of pMODlinker-Spec-GapRPi pMODLinker-Spec-GapRpi (FIG. 2) is a plasmid that can be used to generate a transposon that contains a Z. mobilis RPI expression cassette and a lox-flanked Spec-resistance cassette. The Z. mobilis RPI expression cassette was generated by PCR using plasmid pZB188aadA/Gap/Zymo RPI/EcoliSL as a template. The latter plasmid is described in U.S. Pat. No. 7,989,206, which is incorporated herein by reference. It contains an expression cassette for the Z. mobilis ribose 5-phosphate isomerase (RPI), that consists of (from 5' to 3') a full-length 641 GAP promoter sequence, the entire open reading frame of the Z. mobilis RPI gene (SEQ ID NO:13), and the XylA stem-loop region that is present in the intergenic region of the E. coli XylA/B operon. The entire RPI expression construct described above (SEQ ID NO:22) is located between the unique NcoI and NotI sites of plasmid pZB188aadA/Gap/Zymo RPI/EcoliSL.

A PCR-generated DNA fragment containing this expression cassette was inserted into pMOD-Linker-Spec, which is also described in U.S. Pat. No. 7,989,206. pMOD-Linker-Spec was derived from the commercially available vector pMOD™-2<MCS> Transposon Construction Vector (Cat. No. MOD0602; EPICENTRE® Biotechnologies, Madison, Wis.). The original multi-cloning site was replaced with unique restriction sites for AsiSi, FseI and SbfI. A DNA fragment that confers resistance to spectinomycin (Spec$^r$) and has a wild type loxP site at both ends was inserted between the AsiSI and FseI sites creating pMOD-Linker-Spec.

pMOD-Linker-Spec was sequentially digested with SbfI and FseI, and the 3.6 kb large vector fragment was purified from a 1% agarose gel. Next, the Z. molilis RPI chimeric gene with its associated 641 GAP promoter and E. coli Xyl A terminator was PCR amplified from plasmid pZB188aadA/Gap/Zymo RPI/EcoliSL using primer PPI-F (SEQ ID NO:23) and primer PPI-R-SbfI (SEQ ID NO:24). The resulting 0.96 kbp PCR product was also cut with FseI and SbfI, and the purified DNA fragment was then ligated to the FseI/SbfI-digested, pMOD-Linker-Spec vector fragment to yield pMODlinker-Spec-GapRpi, shown in FIG. 2.

Example 2

Overexpression of RPI in ZW801-4: Generation and Characterization of the I Strain A transposon generated from pMODlinker-Spec-GapRpi (Example 1) was introduced into strain ZW801-4 (see General Methods) to increase RPI expression. The transposable element in this plasmid that randomly integrates into DNA after conversion to a transposome is the entire DNA fragment that is situated between two mosaic ends (ME) in the vector, which includes both the Z. mobilis RPI expression cassette and the Spec$^r$-cassette. The transposome was generated in vitro essentially as described in U.S. Pat. No. 7,989,206 using the general protocol that is outlined in the EPICENTRE® instruction manual for the EZ::TN™pMOD™-2<MCS> Transposon Construction Vector (Cat. No. MOD0602). The resulting transposome was electroporated into ZW801-4 cells and transformants were recovered on MMG and MMX (same medium with 50 g/L xylose instead of 50 g/L glucose) agar plates that contained spectinomycin (200 µg/ml). Since the transposable element randomly inserts into DNA, which can result in detrimental gene disruption events and/or position effects that alter the expression level of the integrated RPI gene, a preliminary experiment was conducted to determine which transformants were best to pursue. Thus, 30 colonies from the mRM3-G10/Spec plates and 6 from the mRM3-X10/Spec plates were screened for growth in shake flask experiments (see General Methods) using mRM3-X10 as the test medium, and the three strains that grew to the highest final OD values (strains B9, B11 and I) were selected for further characterization. Strains B9 and B11 were recovered from the MMG/Spec plates and the I strain was recovered from a MMX/Spec plate.

In commonly owned and co-pending U.S. patent application Ser. No. 13/161,734, published as US20120156746A1, which is incorporated herein by reference, RPI was disclosed as being the rate-limiting enzyme for xylose metabolism in ZW801-4, and expressing RPI from a multicopy plasmid in this strain resulted in better growth and faster xylose utilization in shake flask experiments with mRM3-X10. Although cells grew to a higher final OD value with additional RPI there was little or no change in the exponential growth rate. Plasmid overexpression of RPI in ZW801-4 also reduced the amount of ribulose that was produced, and this resulted in a higher metabolic yield for ethanol production from xylose.

Figure 3A:
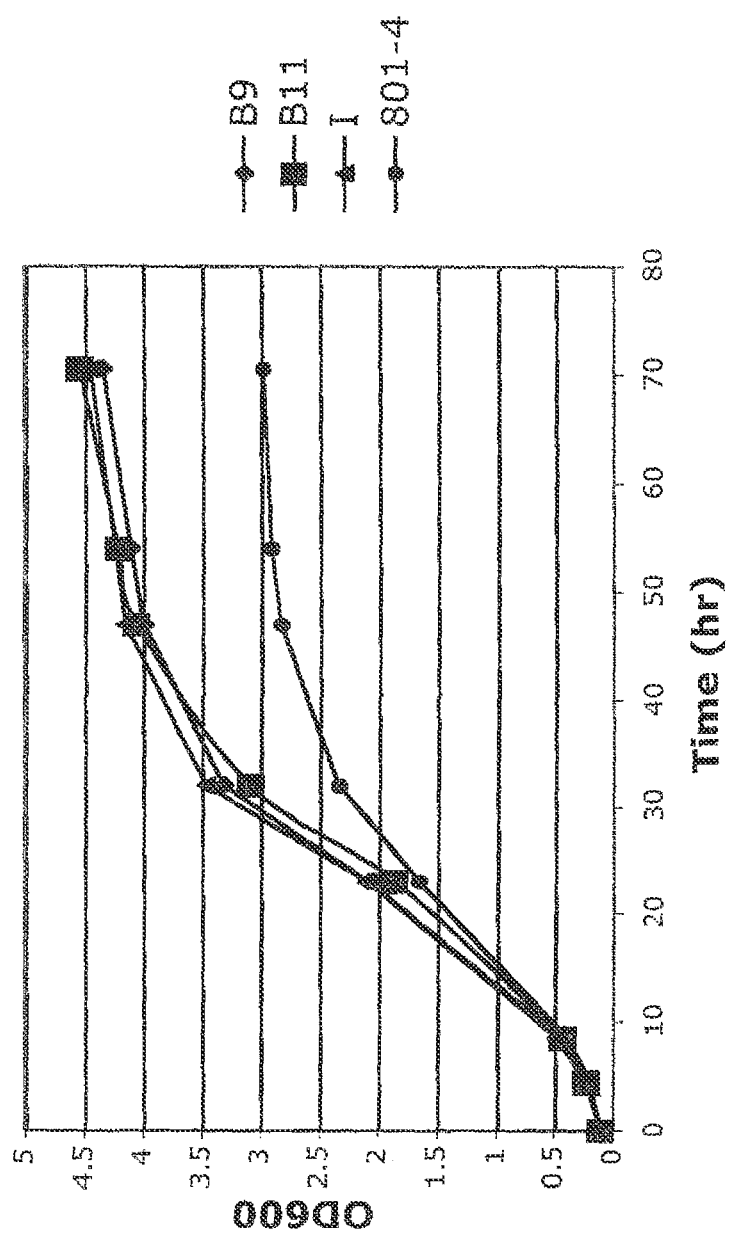
FIG. 3 shows for strains B9, B11, I, each with RPI overexpression, and parent strain ZW801-4: growth in mRM3-X10 (A); xylose consumption and ribulose production at 54 hours (B), and growth in mRM3-G10 (C).
Figure 3B:
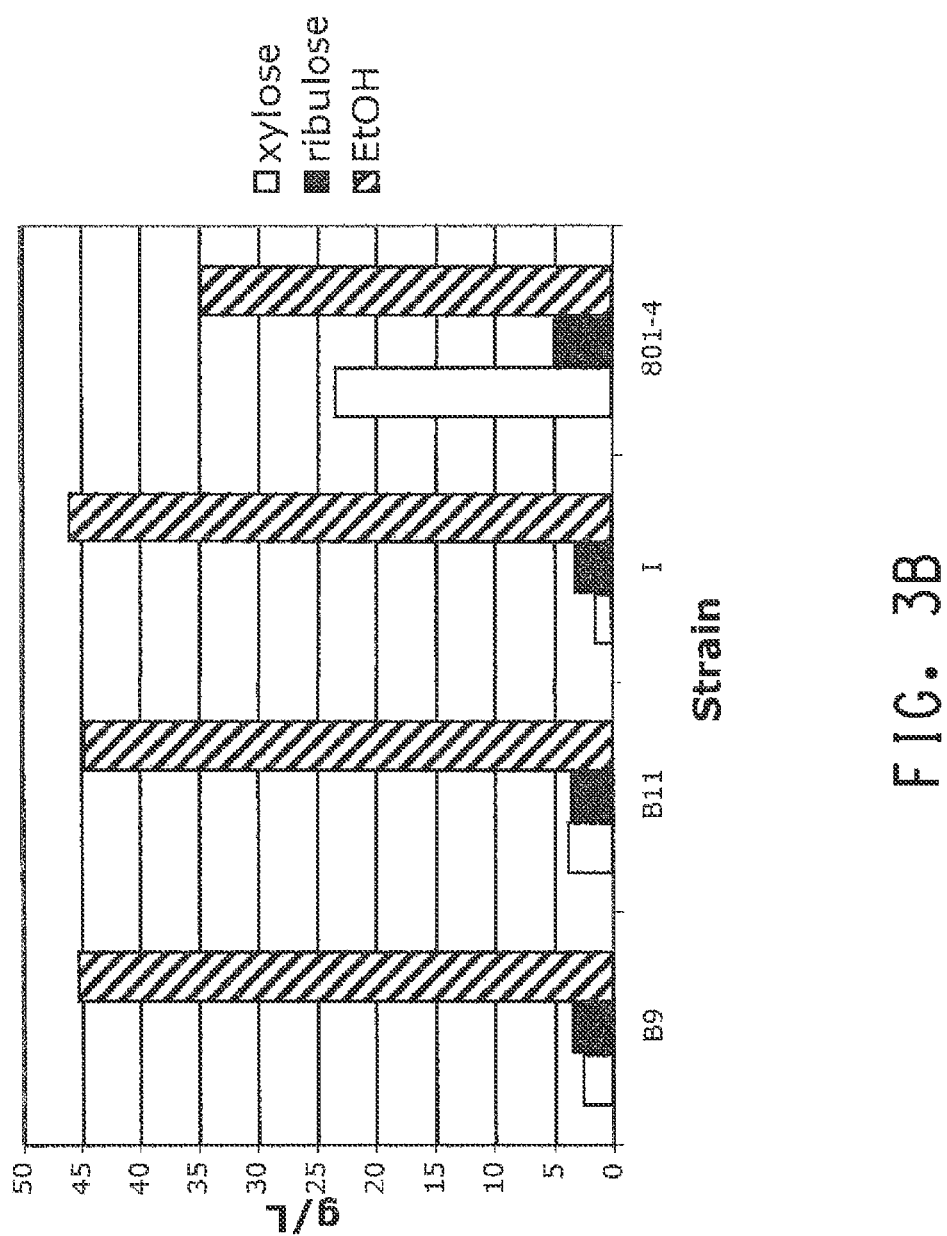

As shown in FIG. 3, similar results were obtained for the tested strains having a single copy of the RPI expression transposon randomly integrated into the ZW801-4 genome. Seed cultures of the B9, B11, and I strains, along with the ZW801-4 control, were grown in mRM3-X10 and used to inoculate mRM3-X10 in shake flasks to an initial OD600 value of ~0.1 for each culture. The cultures were grown at 30° C. and assayed over time for growth by OD600, and for xylose, ribulose, and ethanol as described in General Methods. As shown in FIG. 3A, the three strains that contain the RPI expression transposon grew to a nearly 50% higher OD than the parent strain, ZW801-4. As shown in FIG. 3B, they also consumed xylose at a much faster rate and produced less ribulose than the control strain: at the 54-hr time point, nearly all of the xylose was gone for B9, B11 and the I strain, while the parent strain ZW801-4 had only used ~75% of the xylose. At a 71-hr time point there was still ~8 g/L residual xylose for ZW801-4. The three strains with the RPI expression transposon also produced less ribulose than ZW801-4 despite the fact that they consumed more xylose; the final concentration of ribulose in the growth media at the 72-hr time point for ZW801-4 was 5.3 g/L versus 3.2-3.6 g/L for the other three strains.

Figure 3C:
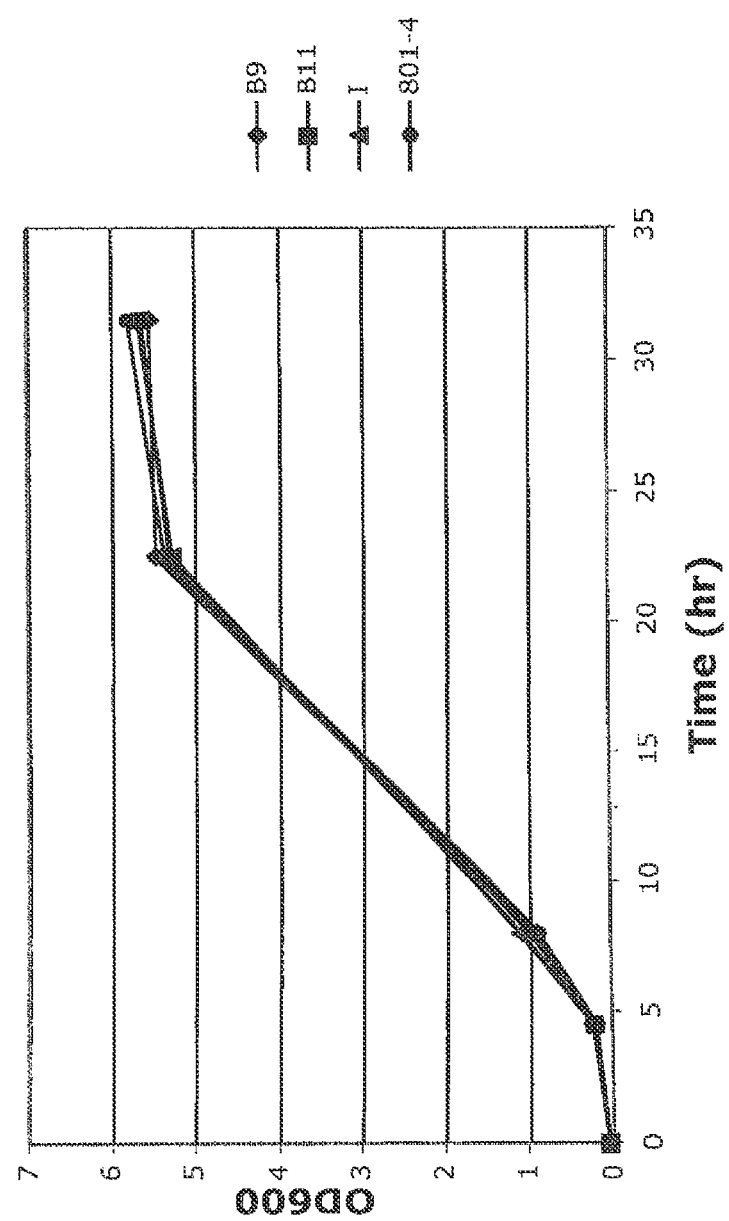

The same 4 strains were grown in mRM3-G10 medium at 30° C. and assayed over time for growth by OD600 (FIG. 3C). In contrast to the results obtained with xylose, all four strains showed similar growth rates when grown on glucose, reaching an OD600 of about 1 at 8 hr and 5.2-5.5 at 20 hr. This result suggests that the stimulatory effect of RP1 overexpression on growth in the xylose shake flask experiments with B9, B11 and the I strain is carbon source dependent.

Example 3

Overexpression of E. coli Xylose Isomerase in B9, B11 and I Strains

Although B9, B11 and I strains performed very similarly in the shake flask experiments with glucose and xylose as described above, subsequent experiments revealed an important difference between the I strain and the other two strains that also have an integrated copy of the RPI expression transposon. This difference was found by assessing whether higher expression of xylose isomerase in the 3 strains would result in a further increase in the rate of carbon flux through the engineered xylose pathway.

Xylose isomerase was the rate-limiting enzyme for xylose metabolism in strain ZW641, which was overcome in strain ZW658 by a point mutation in the $P_{gap}$ promoter that drives the E. coli XylA/B operon, which resulted in increased expression of xylose isomerase (see strain construction in General Methods). As disclosed in commonly owned and co-pending U.S. patent application Ser. No. 13/161,734, published US20120156746A1 subsequent experiments established that the new rate-limiting step for xylose metabolism in both ZW658 and ZW801-4 (a ZW658 derivative having glucose-fructose oxidoreductase gene inactivation) was RPI.

Based on these observations it was of interest to determine whether elimination of the RPI bottleneck, as provided by increased RPI expression in the B9, B11 and I strains, would allow a higher level of expression of xylose isomerase to result in a further increase in the rate of carbon flux through the xylose pathway. To test this hypothesis we used a transposon that was generated from the plasmid pMODlinker-Cm-801GapXylA. This plasmid is identical to pMOD-Linker-Spec-801GapXylA that is described in U.S. Pat. No. 7,989,206 except that it has a Cm-resistance cassette between the two lox sites instead of a Spec-resistance cassette. pMOD-Linker-Spec-801GapXylA is pMOD-Linker-Spec with an added DNA fragment that was obtained from ZW801-4 that contains the Pgap, the XylA coding region, and the stem-loop region that is between the XylA and XylB open reading frames. Thus the promoter that drives XylA is the 801gap promoter (SEQ ID NO:21), which has the G to T point mutation at position 116 that makes it more active, and is the same mutant promoter that drives the *E. coli* XylA/B operon in ZW658.

In addition to the Cm-resistance cassette, the transposon that was generated from pMODlinker-Cm-801GapXylA (referred to below as the "801GapXylA-Cm transposon") contains the above xylose isomerase expression cassette that consists of the 801GAP promoter, the *E. coli* XylA open reading frame and the stabilizing XylA stem-loop region that immediately follows the stop codon as described in detail in U.S. Pat. No. 7,989,206. The 801GapXylA-Cm transposon was converted to a transposome as described in Example 2 and the latter was electroporated into the I strain. Transformants were selected on MMG agar plates that contained chloramphenicol (120 µg/ml).

In a preliminary study, ten randomly selected $Cm^r$ colonies that were recovered from the transformation reaction with the 801GapXylA-Cm transposon were tested for growth in mRM3-X10 at 30° C. in a shake flask experiment where OD600 was measured periodically. Although all ten strains grew better in xylose than the parent strain (based on initial rates of growth and final OD values), only seven of them were selected for further characterization: I(cm1), I(cm2), I(cm$^3$), I(cm4), I(cm5), I(cm8) and I(cm9). To examine these strains in greater detail, the shake flask experiment was repeated using seed cultures that were grown in mRM3-X10, and ZW801-4 and the I strain were included as controls. The initial OD was 0.075 in all cases and the two control strains were run in duplicate.

Figure 4A:
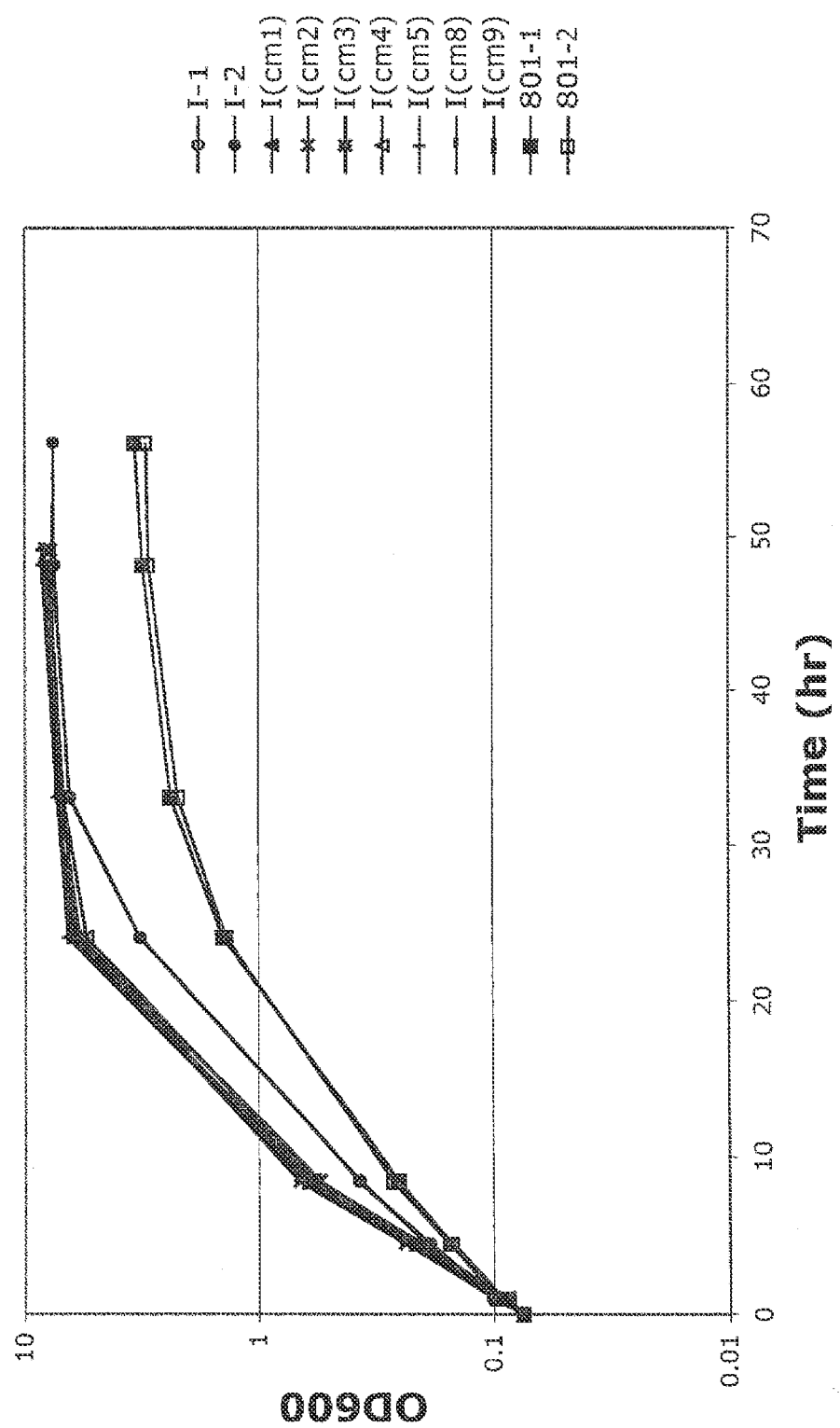
FIG. 4 shows for seven I strain transformants with additional xylose isomerase (I(cm1-5,8,9)) as well as I strain (I-1,2) and ZW801 (801-1,2) controls: growth in mRM3-X10 (A), and growth in mRM3-G10 (B).

Consistent with previous experiments the I strain, which has a higher expression level of RPI, grew much better in xylose than ZW801-4, as shown in FIG. 4A. Note that growth curves for the I strain duplicates were superimposable and cannot be distinguished. The final concentration of ribulose in the growth medium, at the 56-hr time point, was lower for the I strain than for ZW801-4: 1.8 and 1.9 g/L versus 3.4 and 4.2 g/L. Over-expression of xylose isomerase in the I strain greatly improved growth on xylose. All seven strains that contained the 801GapXylA-Cm transposon grew much faster than ZW801-4 and the I strain, and their growth curves were virtually identical despite the fact that they have different transposon insertion sites. This was actually confirmed by DNA sequencing of the insertion sites for I(cm1)-I(cm6). Although the transposon insert sites were not determined for the other four strains they are probably also in different genomic locations due to the extremely low transformation frequency of *Z. mobilis* and the EPICENTRE® procedure that was used.

Increased expression of xylose isomerase enzyme activity in the I strain also increased the exponential growth rate, and this resulted in a more rapid build up of biomass and faster xylose utilization. End point values for ribulose for the seven strains that contained the 801GapXylA-Cm transposon ranged from 2.9-3.7 g/L. Although these values are similar to the amount of ribulose that ZW801-4 produced, they are actually smaller on a per sugar used basis since at the 56-hr time point the strains that over-expressed xylose isomerase had consumed all of the xylose in the medium while ZW801-4 had used less than 80%.

Figure 4B:
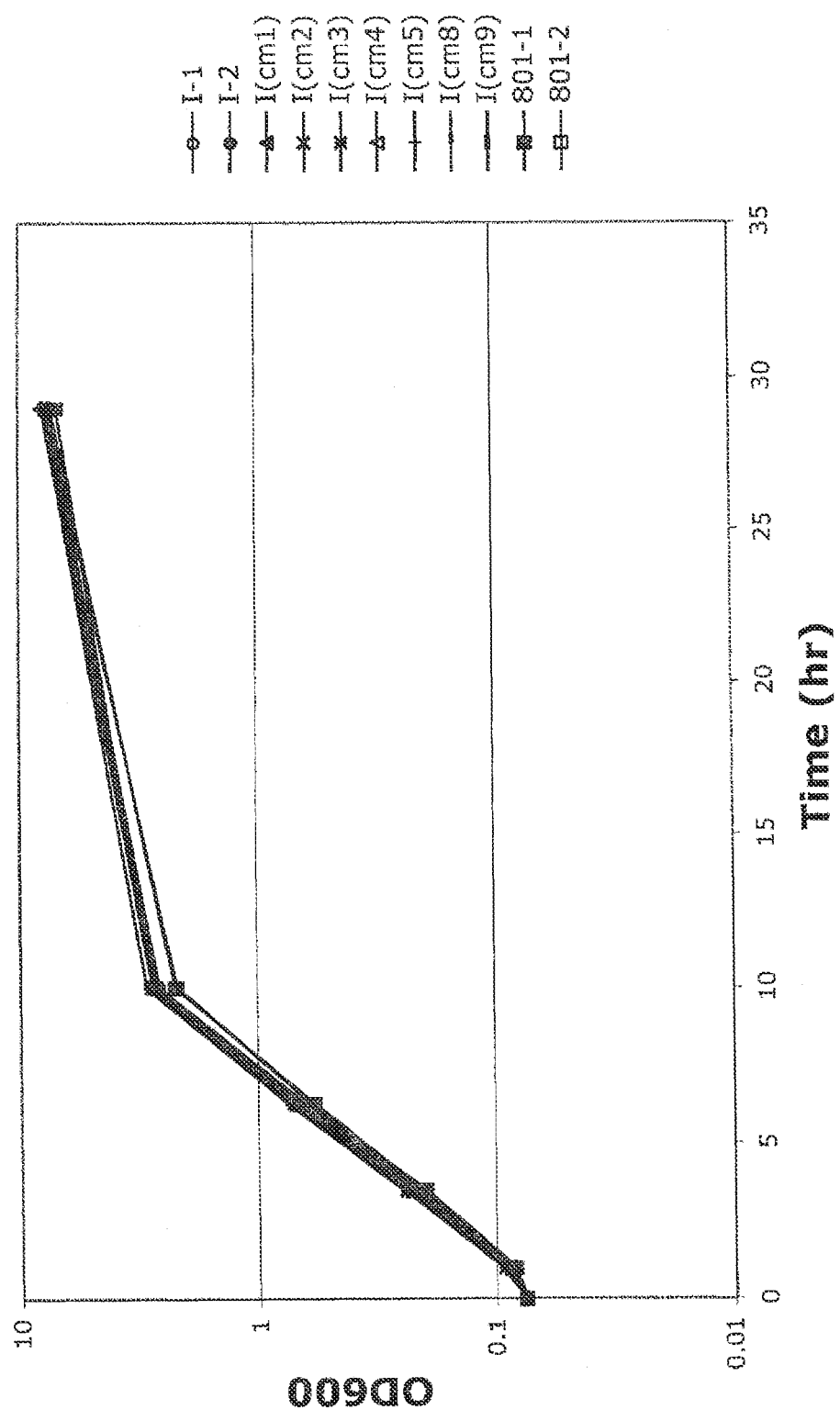

These results clearly demonstrate that xylose isomerase is the rate-limiting enzyme for xylose metabolism in the I strain. They also reveal that the I strain has sufficient RPI enzyme activity to support a much higher expression level of xylose isomerase. The fact that all seven I strain derivatives that contained the 801GapXylA-Cm transposon in different locations in the chromosome grew with the same kinetics in xylose containing medium strongly suggests that gene disruption events and/or position effects caused by the transposon did not significantly contribute to the observed phenotype (i.e. better growth in xylose). This conclusion is also supported by the experiment that is shown FIG. 4B where the seven strains that contained the transposon all grew just as well as ZW801-4 and the I strain in shake flask experiments with mRM3-G10 at 30° C.

Figure 5:
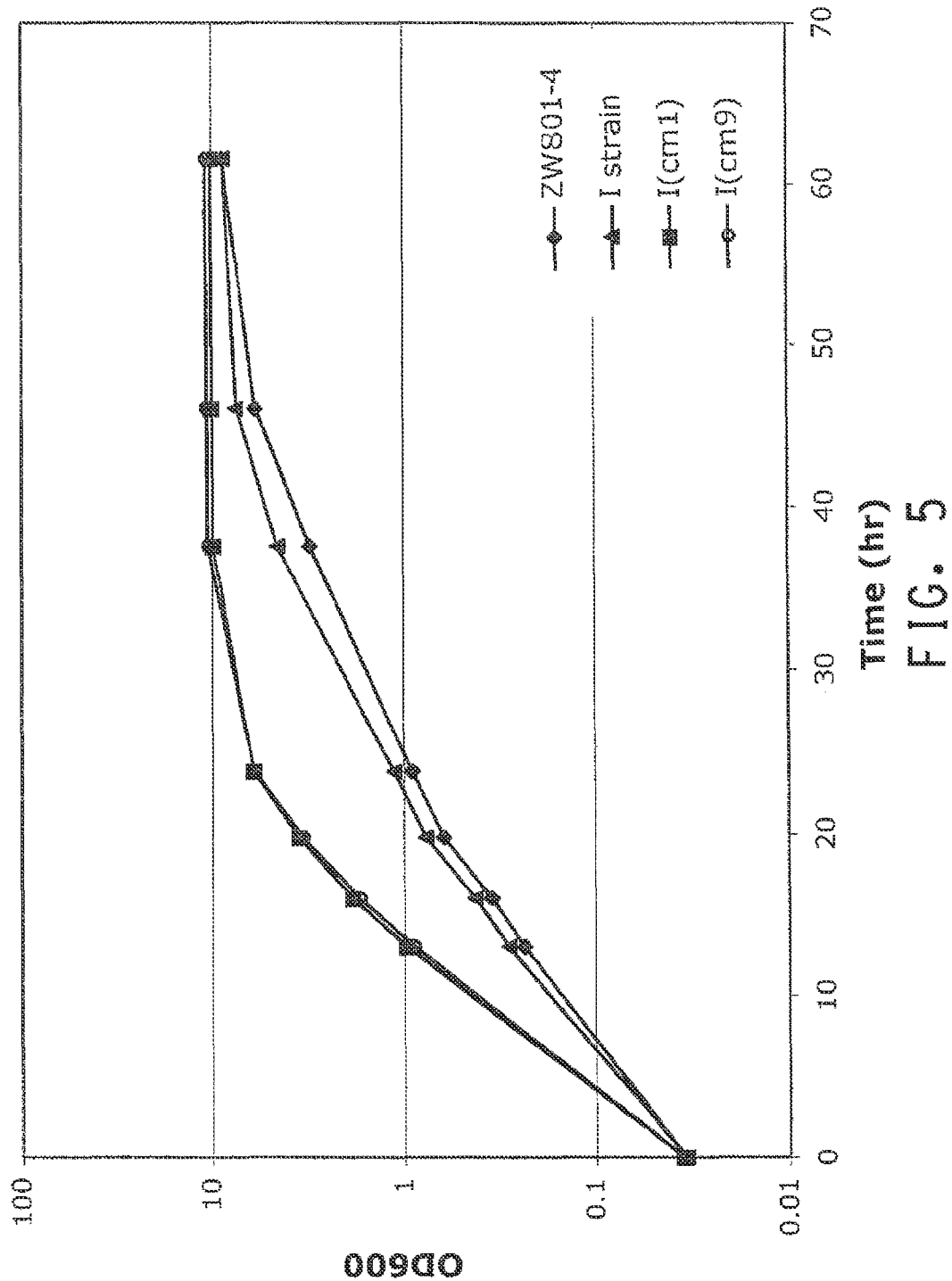
FIG. 5 shows growth in mRM3-X10 under pH-controlled conditions of two I strain transformants with additional xylose isomerase (I(cm1,9)), as well as I strain and ZW801-4 controls.

The above observations were confirmed using pH-controlled conditions as follows. During shake flask experiments the pH of the growth medium can drop by greater than 1 pH unit, and this has an inhibitory effect on *Z. mobilis* growth especially when xylose is the sole carbon source. To circumvent this problem the pH-controlled bioreactor experiment that is shown in FIG. 5 was performed. Since all of the I strain derivatives that over-express xylose isomerase behaved the same in shake flasks, only two of them were used for this experiment, I(cm1) and I(Cm9). Seed cultures were grown in mRM3-X10 at 30° C. in shake flasks to an OD of ~0.5, and the starting OD in the bioreactors was 0.035. The bioreactors also contained mRM3-X10, and temperature and pH were held constant at 30° C. and 5.8, respectively, using 2N KOH for pH control.

The growth curves for the I strain and ZW801-4 were very similar under pH-controlled conditions (FIG. 5), although it was clear that the I strain did grow slightly better toward the end of the experiment. Interestingly, however, neither strain produced much ribulose under these conditions; endpoint values for ZW801-4 and the I strain were 1.92 and 1.16 g/L, respectively. These observations suggest that RPI is not as big a bottleneck for xylose metabolism in ZW801-4 when the pH of the growth is maintained at 5.8. They also indicate that the native RPI gene in ZW801-4 is almost able to keep pace with the existing level of xylose isomerase activity under such conditions. Nevertheless, it was clear from the growth curves that are shown in FIG. 5 that over-expressing xylose isomerase in the I strain greatly improved xylose metabolism even when the pH of the growth medium was held constant at pH 5.8.

Figure 6A:
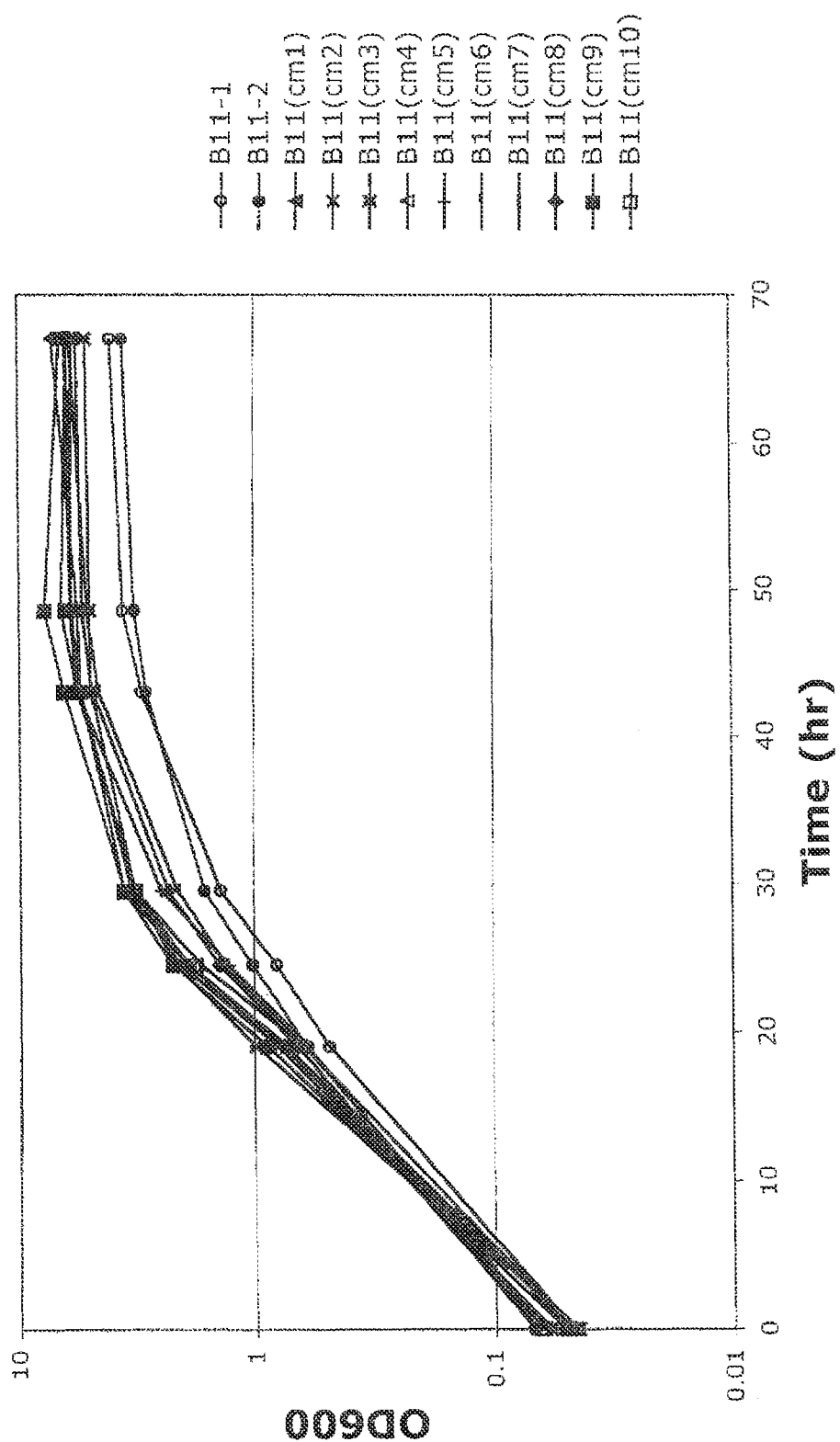
FIG. 6 shows growth in mRM3-X10 for ten B11 strain transformants with additional xylose isomerase (B11(cm1-10)), along with B11 controls (B11-1,2) (A); or ten B9 strain transformants with additional xylose isomerase (B9(cm1-10)), as along with B9 controls (B9-1,2) (B).
Figure 6B:
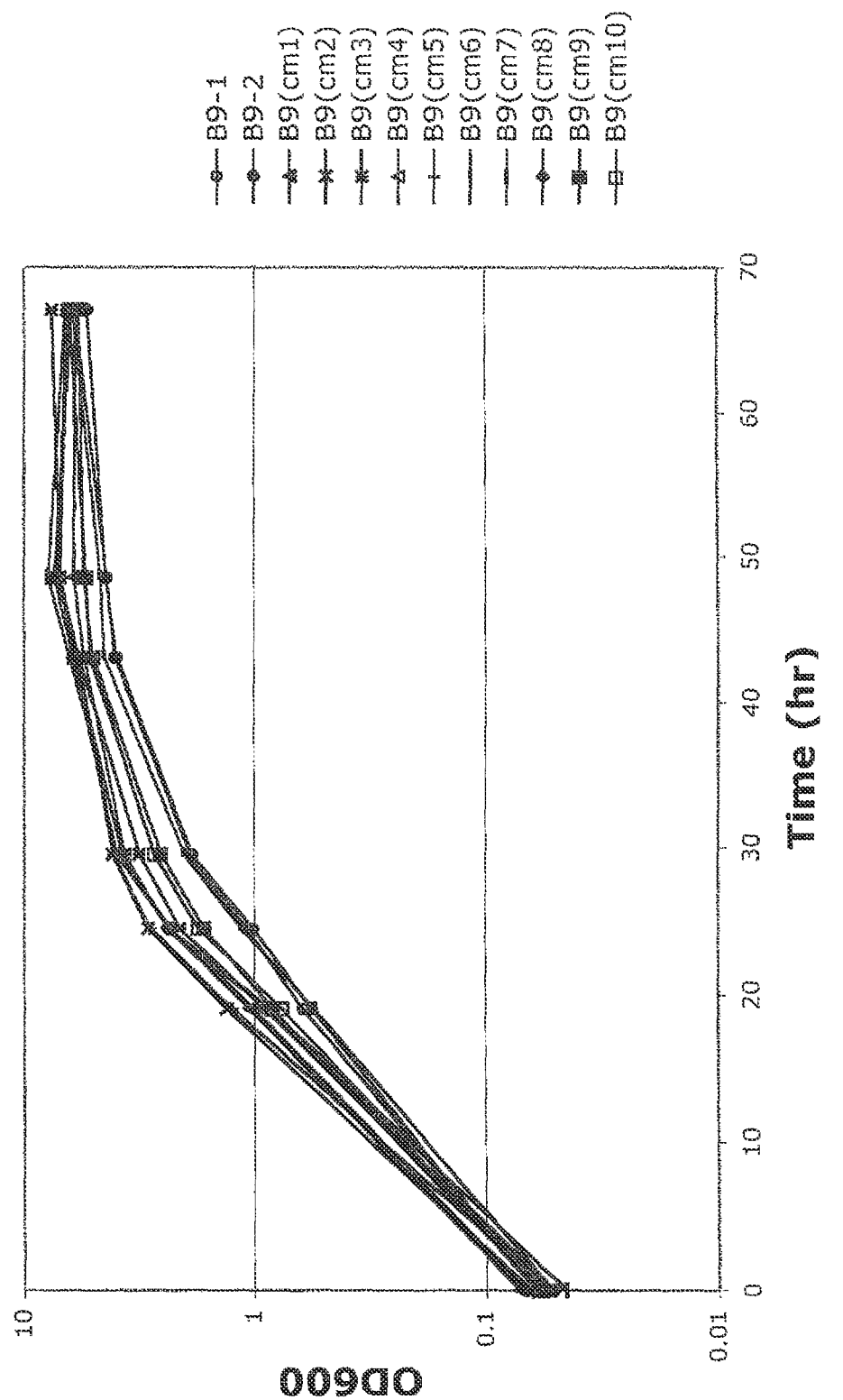

The 801GapXylA-Cm transposon was also electroporated into the B9 and B11 strains using the same procedure as used for the I strain, and ten primary transformants for each of these strains were tested for growth in xylose in shake flask experiments with mRM3-X10 at 30° C. (FIG. 6). Although some of the transformants did grow better in xylose than the parent strain, in both cases the results were not nearly as dramatic as those that were obtained with the I strain. There was also a high degree of variation between the different transformants, suggesting that gene disruption events and/or insertional position effects were contributing to the observed phenotypes. These observations suggested that there might be something significant about the chromosomal location of the RPI expression transposon in the I strain that is beneficial to xylose growth and metabolism in addition to an elevated expression level of RPI.

The site of insertion for the RPI expression transposon in the I strain was determined by DNA sequencing to be between nts 543506 and 543507 of the Z. mobilis genome (GenBank accession number AE008692). Sequencing of the insertion region showed that integration of the transposon caused a frame shift at the 3' end of the open reading frame of the pnp gene that codes for polyribonucleotide nucleotidyl transferase. An alignment of the wild type pnp gene product and the predicted pnp gene product for the I stain is shown in FIG. 7. Note that the mutant protein is missing the last 39 amino acid residues of the native protein (retains 709 amino acids starting from the N-terminus) and has 14 new amino acids at its C-terminus (SEQ ID NO:9). It is not known if this hypothetical protein is functional, and if it is, to what extent it might contribute to the I strain phenotype in addition to RPI overexpression. Regardless of the answer, the above results indicate that overexpressing RPI at the same location as in the I strain, in the pnp coding region, resulted in better growth in xylose and allowed a higher expression level of xylose isomerase to be effective.

Example 4

Vector Constructs for Building Xylose Utilizing Z. mobilis Strains Using Targeted Integration A new xylose utilizing Z. mobilis strain was constructed by introducing chimeric xylA, xylB, tal, and tkt genes into the ZW1 strain. The xylB, tal, and tkt coding regions were from E. coli genes as in the ZW658 strain described in General Methods. The xylA coding region was from Actinoplanes missouriensis (AMxylA) which is disclosed in commonly owned and co-pending US Patent Application Publication US20110318801, which is incorporated herein by reference, as encoding an enzyme having higher activity than the E. coli xylose isomerase in Z. mobilis. The coding region for the AMxylA was codon optimized for expression in Z. mobilis (SEQ ID NO:17). Additional copies of Z. mobilis rpi and rpe genes were also introduced in order to increase ribose-5-phosphate-isomerase (RPI) and ribulose-phosphate 3-epimerase (RPE) activities. Double crossover (DCO) transformation vectors were designed to specifically integrate the chimeric genes into target regions in Z. mobilis genome.

Figure 8A:
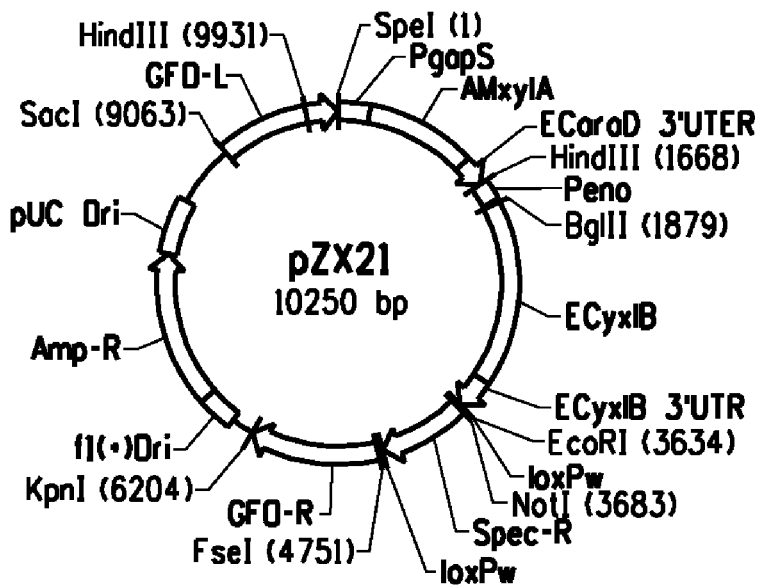
FIG. 8 shows plasmid maps of pZX21 (A), pZX52 (B), and pZX6 (C).

Standard molecular recombination methods were used to construct DCO (double cross over) suicide integration vectors. To express xylose isomerase and xylulose kinase in Z. mobilis, a 10,250-bp DCO suicide vector pZX21 (SEQ ID NO:25; FIG. 8A) was constructed. This vector has a pBluescript backbone which contains a replication origin for E. coli but no Z. mobilis replication origin, thus it cannot be propagated in Z. mobilis making it a suicide vector. It contains DNA sequences from the Z. mobilis gene encoding glucose-fructose oxidoreductase, GFO-L and GFO-R, flanking the sequences to be integrated. Both fragments were synthesized by PCR, using Z. mobilis genomic DNA as template. The 1,186-bp GFO-L fragment (SEQ ID NO:26) includes the first 654 bp (from nt-1 to nt-653) of the gfor coding sequence (SEQ ID NO:27) and 533 bp of upstream genomic sequence. The 1,446-bp GFO-R fragment (SEQ ID NO:28) includes the last 480 bp (from nt-823 to nt-1302) of the GFOR coding sequence and 966 bp of downstream genomic sequence. The GFO-L and GFO-R sequences direct integration into the gfor locus, replacing a segment of the gfor coding sequence (from nt-655 to nt-822) in the Z. mobilis genome. This disrupts expression of glucose-fructose oxidoreductase, which reduces xylitol production and increases ethanol production as disclosed in U.S. Pat. No. 7,741,119, which is incorporated herein by reference.

The region in pZX21 between GFO-L and GFO-R includes three chimeric genes. One is a 1,661-bp chimeric xylA gene (SEQ ID NO:29) containing the 304-bp Z. mobilis Super GAP promoter ($P_{gapS}$; described in U.S. Pat. No. 7,989,206), a 1,185-bp A. missouriensis xylA coding sequence (AMxylA) and a 166-bp E. coli araD 3'UTR with a 5' XbaI site (ECaraD 3'UTR). The AMxylA coding region was optimized for expression in Z. mobilis according to codon bias of Z. mobilis ZM4 (SEQ ID NO:17). The ECaraD 3'UTR was from the E. coli araBAD operon. The second gene is a 1,960-bp chimeric xylB gene (SEQ ID NO:30) containing a 191 bp $P_{eno}$, a 1,455-bp E. coli xylB coding sequence (ECxylB) and a 314-bp E. coli xylB 3'UTR (ECxylB 3'UTR). $P_{eno}$ is a strong constitutive promoter from the Z. mobilis genomic DNA having approximately 28% activity of $P_{gap}$. The third gene is a 1,014 bp aadA marker (for spectinomycin resistance; Spec-R) bounded by lox sites (SEQ ID NO:31). The marker can be removed after integration by expressing Cre recombinase.

Figure 8B:
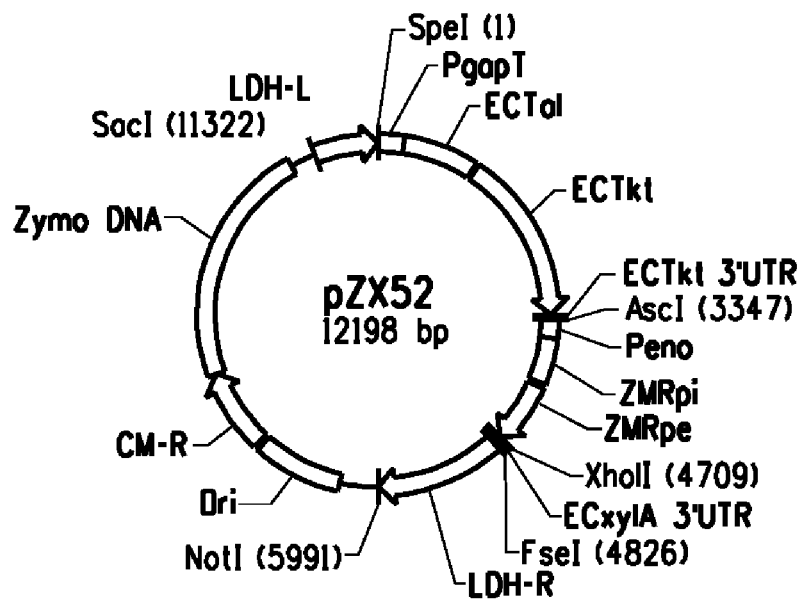

To express transaldolase, transketolase, ribose-5-P-isomerase, and D-ribulose-P-3-epimerase in Z. mobilis, a 12,198-bp DCO shuttle vector pZX52 (SEQ ID NO:32; FIG. 8B) was constructed. This vector is a Zymomonas-E. coli shuttle vector which is based on the vector pZB188 (Zhang et al. (1995) Science 267:240-243; U.S. Pat. No. 5,514,583), which includes a 2,582 bp Z. mobilis genomic DNA fragment containing a replication origin allowing the vector to replicate in Zymomonas cells, and a 909-bp E. coli replication origin (Ori). It has a 911 bp chloramphenicol resistance marker (Cm-R) for selection of either E. coli or Z. mobilis transformants. pZX52 contains DNA sequences from the Z. mobilis ldhA gene encoding lactate dehydrogenase, LDH-L (875 bp; SEQ ID NO:33) and LDH-R (1,149 bp; SEQ ID NO:34), flanking the sequences to be integrated. These sequences direct integration into the ldhA coding sequence (SEQ ID NO:35) in the Z. mobilis genome between nucleotides 493 and 494, thereby disrupting expression of lactate dehydrogenase.

The region in pZX52 between LDH-L and LDH-R includes two chimeric operons. The first one is a 3,339 bp $P_{gapT}$-Tal-Tkt operon (SEQ ID NO:36) containing a 304-bp T-mutant of the Z. mobilis GAP promoter ($P_{gapT}$), a 954-bp E. coli Tal coding region (ECTal), a 1,992-bp E. coli Tkt coding region, and a 68-bp E. coli Tkt 3'UTR (ECTkt 3'UTR). This operon is identical to the naturally existing E. coli Tal-Tkt operon except for the $P_{gapT}$ promoter (SEQ ID NO:37), which is a $P_{gap}$ with a "G" to an "A" change at position 83 in SEQ ID NO:21 and a "T" missing at position 285. The other chimeric operon is a 1,443 bp $P_{eno}$-Rpi-Rpe operon (SEQ ID NO:38), containing a 191 bp $P_{eno}$, a 471 bp Z. mobilis Rpi coding sequence with first codon changed to ATG (SEQ ID NO:65) (ZMRpi), a 663 bp Z. mobilis Rpe coding sequence (ZMRpe), and a 35 bp E. coli xylA 3'UTR (ECxylA 3'UTR).

Figure 8C:
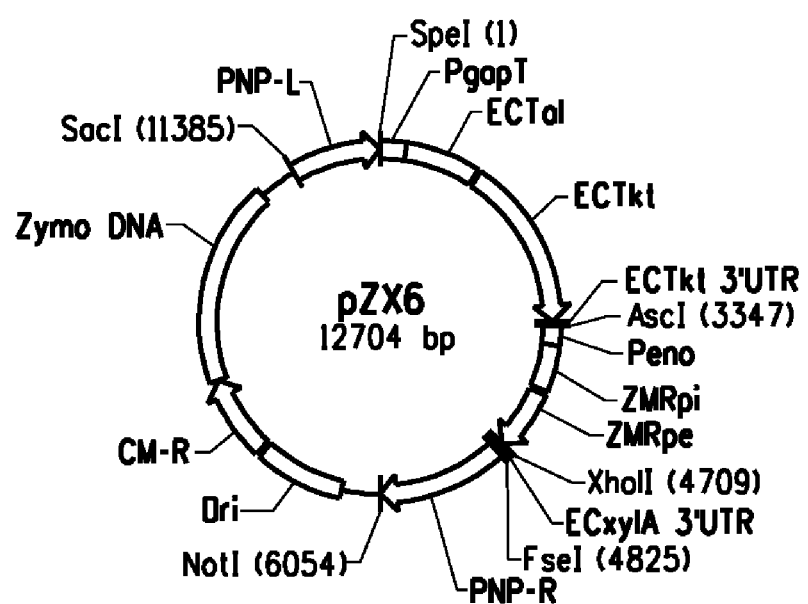

Another DCO shuttle vector named pZX6 (SEQ ID NO:39; FIG. 8C) was constructed. This 12,704 bp vector is a modification of pZX52 having LDH-L and LDH-R sequences replaced with sequences from the Z. mobilis pnp gene encoding polynucleotide phosphorylase. The 1,318 bp PNP-L fragment (SEQ ID NO:40) is a segment of the pnp coding sequence (SEQ ID NO:1) from nt-767 to nt-2,084, while the 1,225 bp PNP-R fragment (SEQ ID NO:41) includes the last 59 bp (from nt-2189 to nt-2247) of the pnp coding sequence and 1,166 bp of downstream genomic sequence. Therefore, pZX6 is able to direct integration of the $P_{gapT}$-Tal-Tkt operon and the $P_{eno}$-Rpi-Rpe operon into the endogenous pnp gene near the end of the pnp coding sequence and replace a segment of the pnp coding sequence (from nt-2,084 to nt-2,188) in the Z. mobilis genome.

Example 5

Development of Xylose Utilizing Z. mobilis Strains

The ZW1 strain was transformed with two plasmids in two steps. Competent cells of ZW1 were prepared by growing seed cells overnight in mRM3-G5 (1% yeast extract, 15 mM $KH_2PO_4$, 4 mM $MgSO_4$, and 50 g/L glucose) at 30° C. with 150 rpm shaking, to an $OD_{600}$ value near 5. Cells were harvested and resuspended in fresh medium to an $OD_{600}$ value of 0.05. The cells were grown under the same conditions to early to middle log phase ($OD_{600}$ near 0.5). Cells were harvested and washed twice with ice-cold water and then once with ice-cold 10% glycerol. The resulting competent cells were collected and resuspended in ice-cold 10% glycerol to an $OD_{600}$ value near 100. Since transformation of Z. mobilis requires non-methylated DNA, DCO plasmids pZX21, pZX52, and pZX6 were each transformed into E. coli SCS110 competent cells (Stratagene, La Jolla, Calif.). For each transformation, one colony of transformed cells was grown in 10 mL LB-Amp100 (LB broth containing 100 mg/L ampicillin) overnight at 37° C. DNA was prepared from the 10 mL culture, using QIAprep Spin DNA Miniprep Kit (Qiagen).

Approximately 1 µg non-methylated pZX21 DNA was mixed with 50 µL ZW1 competent cells in a 1 mM Electroporation Cuvette (VWR, West Chester, Pa.). The plasmid DNA was electroporated into the cells at 2.0 KV using a BT720 Transporter Plus (BTX-Genetronics, San Diego, Calif.). Transformed cells were recovered in 1 mL MMG5 medium (10 g/L glucose, 10 g/L yeast extract, 5 g/L tryptone, 2.5 g/L $(NH_4)_2SO_4$, 2 g/L $K_2HPO_4$, and 1 mM $MgSO_4$) for 4 hours at 30° C. and grown on MMG5-Spec250 plates (MMG5 with 250 mg/L spectinomycin and 15 g/L agar) for 3 days at 30° C., inside an anaerobic jar with an AnaeroPack (Mitsubishi Gas Chemical, New York, N.Y.).

Since pZX21 is a DCO suicide vector, surviving $Spec^R$ colonies had the $P_{gapS}$-AMxylA::$P_{eno}$-ECxylB::Spec-R segment integrated into the gfor locus. The colonies were streaked and grown on a fresh MMG5-Spec250 plate, and then subjected to PCR to inspect chimeric gene integration. The first PCR used forward primer ara285 (SEQ ID NO:42) and reverse primer ara120 (SEQ ID NO:43) to inspect double crossover recombination mediated by the GFO-L fragment in pZX21. The ara285 primer matches a segment of Z. mobilis genomic sequence that is 494 bp upstream of the GFO-L fragment in the genome, while ara120 complements the last 18 bp of $P_{gapS}$ and the first 17 bp of AMxylA in pZX21. If integration had occurred as designed, PCR would amplify a 1,903 bp fragment from the transformants. The 2nd PCR used forward primer ara46 (SEQ ID NO:44) and reverse primer ara274 (SEQ ID NO:45) to inspect double crossover recombination mediated by the GFO-R fragment in pZX21. The ara46 primer is a sequence near the end of the $Spec^R$ gene in pZX21, while ara274 complements a segment of Z. mobilis genomic DNA that is 83 bp downstream of the GFO-R fragment. This PCR would amplify a 1,864-bp fragment from the colonies having successful integration. Both inspections produced the expected PCR products and thus confirmed accurate transgene integration. The resulting strain was named ZW1-pZX21.

In the second step, ZW1-pZX21 was transformed with pZX52 and selected on a MMG5-Spec250-CM120 (MMG5-Spec250 with 120 mg/L of chloramphenicol) plate. Because pZX52 is a DCO shuttle vector having the $Cm^R$ marker for plasmid selection and a markerless integration segment ($P_{gapT}$-ECTal-ECTkt::$P_{eno}$-ZMRpi-ZMRpe), the recovered colonies should contain not only the previously integrated construct $P_{gapS}$-AMxylA::$P_{eno}$-ECxylB::Spec-R in the Z. mobilis genome, but also the non-integrated construct $P_{gapT}$-ECTal-ECTkt::$P_{eno}$-ZMRpi-ZMRpe in the propagated pZX52 plasmid. These transformants should have all required genes for the xylose utilization pathway. To demonstrate that all transgenes were functional in Z. mobilis, ten selected colonies were subjected to a 48-hour growth assay in xylose. In the assay, 2 mL of mRM3-G5-Spec200-CM120 (mRM3-G5 with 200 mg/L spectinomycin and 120 mg/L chloramphenicol) in a 14 mL Falcon polypropylene round-bottom tube was inoculated with a selected colony and cultured overnight at 30° C. with 150 rpm shaking. Tubes were tightly capped, but a hole was punched in the top of the cap using a 23G1 needle for pressure release during cell growth and fermentation. Cells were harvested, washed with MRM3X10 (MRM3 with 100 g/L xylose), and resuspended in mRM3-X10-Spec200-CM120 (mRM3-X10 containing 200 mg/L spectinomycin and 120 mg/L chloramphenicol) to have a starting $OD_{600}$ of 0.1. Five mL of the suspension was placed in a new 14 mL Falcon polypropylene round-bottom tube. Tubes were capped with a hole on the top. Cells were grown for 48 hrs at 30° C. with 150 rpm shaking and $OD_{600}$ was measured on a Shimadzu UV-1201 Spectrophotometer. Then, 1 mL of culture was centrifuged at 10,000×g to remove cells. The supernatant was filtered through a 0.22 µm Costar Spin-X Centrifuge Tube Filter (Corning Inc, Corning, N.Y.) and analyzed for xylose and ethanol by running through a BioRad Aminex HPX-A7H ion exclusion column (BioRad, Hercules, Calif.) with 0.01 $NH_2SO_4$ at a speed of 0.6 mL/min at 55° C. on an Agilent 1100 HPLC system (Agilent Technologies, Santa Clara, Calif.). Results indicated that all 10 of the transformants had acquired the xylose utilization pathway for ethanol production. The new strain was named ZW1-pZX21-pZX52 and one of the cultures was used in further experiments.

ZW1-pZX21-pZX52 then went through three post-transformation procedures sequentially for integration of the $P_{gapT}$-ECTal-ECTkt::$P_{eno}$-ZMRpi-ZMRpe construct.
(1) The strain was adapted on xylose. In this procedure, ZW1-pZX21-pZX52 was suspended in a 5-mL mRM3-G1X9-Spec200-CM120 medium (MRM3 with 10 g/L glucose, 90 g/L xylose, 200 mg/L spectinomycin and 120 mg/L chloramphenicol) with a starting $OD_{600}$ value of 0.2 and grown for 3 to 4 doublings at 30° C. ($OD_{600}$ value from 0.2 to 2; one passage). The culture was then diluted to the starting $OD_{600}$ value and grown for another passage. Totally, 4 passages (approximately 15 doublings) were completed.
(2) Plasmid curing and integration of the $P_{gapT}$-ECTal-ECTkt::$P_{eno}$-ZMRpi-ZMRpe construct were carried out by growing 10 µL of the adaptation cell pool in 2 mL mRM3-G5-Spec200 medium at higher temperature (37° C.) for overnight. The 10 µL culture was then diluted in 2 mL mRM3-G5-Spec200 medium and grown for another passage. Totally, 5 passages were performed at 37° C. in glucose medium. As a result of the high temperature growth, the majority of the population should not host the pZP52 plasmid any more, but the $P_{gapT}$-ECTal-ECTkt::$P_{eno}$-ZMRpi-ZMRpe construct (lacking a selective marker) should have been integrated into the IdhA gene of the Z. mobilis genome. A minority of the population may maintain pZX52, without integration.

(3) The population was enriched by growing 50 µL of the cell pool in 2 mL mRM3-X10-Spec200 at 30° C. for overnight. The enriched population was grown on a MMG5-Spec250 plate at 30° C. for overnight. Individual colonies were selected and streaked on MMG5 plates and MMG5-CM120 plates in replica. After incubating at 30° C. for overnight, those colonies that grew on MMG5 but not on MMG5-CM120 were selected for further PCR inspection. The first PCR used forward primer ara45 (SEQ ID NO:46) and reverse primer ara356 (SEQ ID NO:47) to inspect double crossover recombination mediated by the LDH-L fragment in pZX52. The ara45 primer matches a segment of Z. mobilis genomic DNA that is 86 bp upstream of the LDH-L fragment in the genome, and ara356 complements a fragment (from nt-91 to nt-112) of the ECTaI coding region in pZX52. The PCR would amplify a 1,383-bp fragment from the colonies if integration had occurred as designed. The 2nd PCR used forward primer ara354 (SEQ ID NO:48) and reverse primer ara43 (SEQ ID NO:49) to inspect double crossover recombination mediated by the LDH-R fragment in pZX52. The ara354 primer is a sequence near the 3' end of ZMRpe in pZX52. The ara43 primer complements a segment of Z. mobilis genomic DNA that is 122 bp downstream of the LDH-R fragment. This PCR would amplify a 1,468 bp fragment from the colonies when recombination was as expected. Both PCRs produced DNA fragments with the expected sizes, which confirmed that the $P_{gapT}$-ECTaI-ECTkt::$P_{eno}$-ZMRpi-ZMRpe construct had been accurately integrated as designed in all inspected colonies. The resulting colonies were named ZW1-X109.

In a second approach, the ZW1-pZX21 strain was transformed with the pZX6 DCO shuttle vector and the three post-transformation procedures were performed as described above for ZW1-X109, except that adaptation was for 10 passages rather than 4 passages. Therefore, the $P_{gapT}$-ECTaI-ECTkt::$P_{eno}$-ZMRpi-ZMRpe construct was targeted to the endogenous pnp gene. As described for construction of ZW1-X109, the 48-hour growth assay was preformed prior to the three post-transformation procedures to make sure that all transgenes were functioning as expected. After the three post-transformation procedures, the integration was also inspected by PCR. The first PCR used forward primer ara340 (SEQ ID NO:50) and reverse primer ara356 (SEQ ID NO:47) to inspect double crossover recombination mediated by the PNP-L fragment in pZX6. The ara340 primer matches Z. mobilis genomic DNA that is 75 bp upstream of the PNP-L fragment. The ara356 primer used here complements a fragment (from nt-91 to nt-112) of ECTaI in pZX6. The PCR produced a 1,815-bp fragment from the transformants, as expected for an accurate integration event. The 2nd PCR used forward primer ara354 (SEQ ID NO:48) and reverse primer ara339 (SEQ ID NO:51) to inspect double crossover recombination mediated by PNP-R fragment in pZX6. In this case, the ara354 primer matches a sequence near the 3' end of ZMRpe in pZX6, and the ara339 primer complements a segment of Z. mobilis genomic DNA that is 59 bp downstream of the PNP-R fragment sequence. This PCR amplified a 1,549 bp fragment from the transformants, a size that was expected for successful integration.

Therefore, PCR inspection confirmed that the $P_{gapT}$-ECTaI-ECTkt::$P_{eno}$-ZMRpi-ZMRpe construct had been accurately integrated in all inspected colonies. This new strain was named ZW1-X210.

In summary, two xylose utilizing Z. mobilis strains were rebuilt de novo from wild type ZW1. They both had a $P_{gapS}$-AMxylA::$P_{eno}$-ECxylB::Spec-R construct integrated into the gfor locus. The ZW1-X109 strain had a $P_{gapT}$-ECTaI-ECTkt::$P_{eno}$-ZMRpi-ZMRpe construct integrated into the IdhA locus, while the ZW1-X210 strain had the same construct integrated in the endogenous pnp gene. Both strains had one marker gene in the integrated $P_{gapS}$-AMxylA::$P_{eno}$-ECxylB::Spec-R construct, which could be removed by introduction of Cre recombinase.

Example 6

Characterization of New Xylose Utilizing Z. mobilis Strains

Figure 9A:
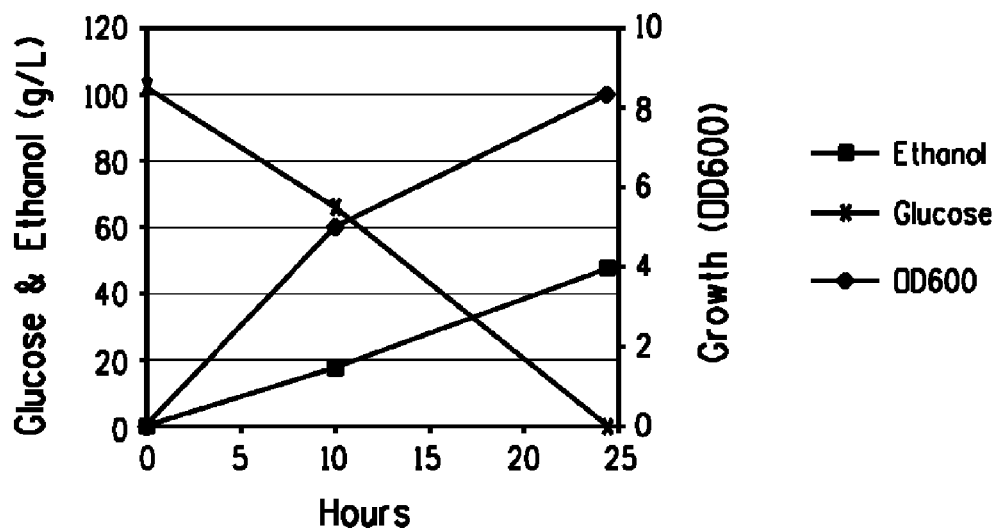
FIG. 9 shows graphs of growth, glucose used, and ethanol produced for cultures grown in mRM3-G10 of ZW1-X109 (A), ZW1-X210 (B), and control ZW1 (C).
Figure 9B:
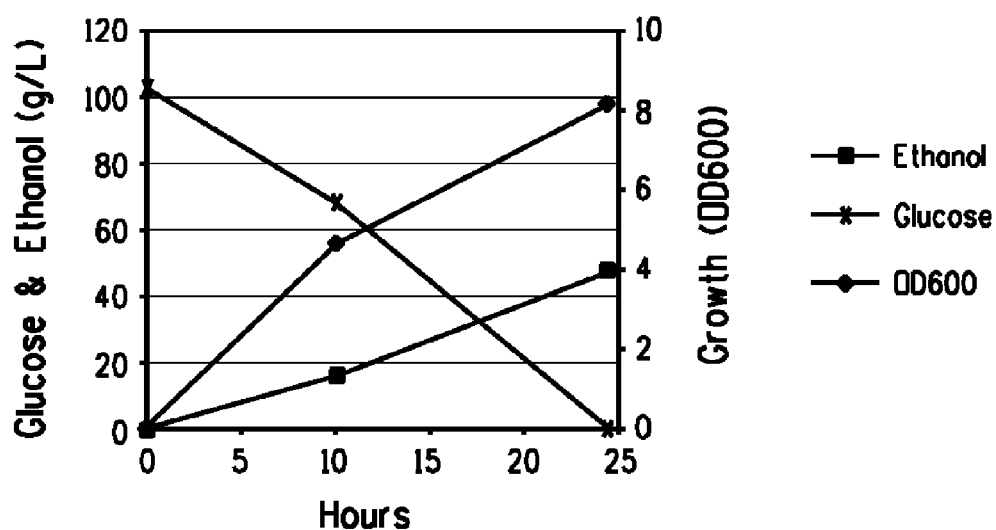
Figure 9C:
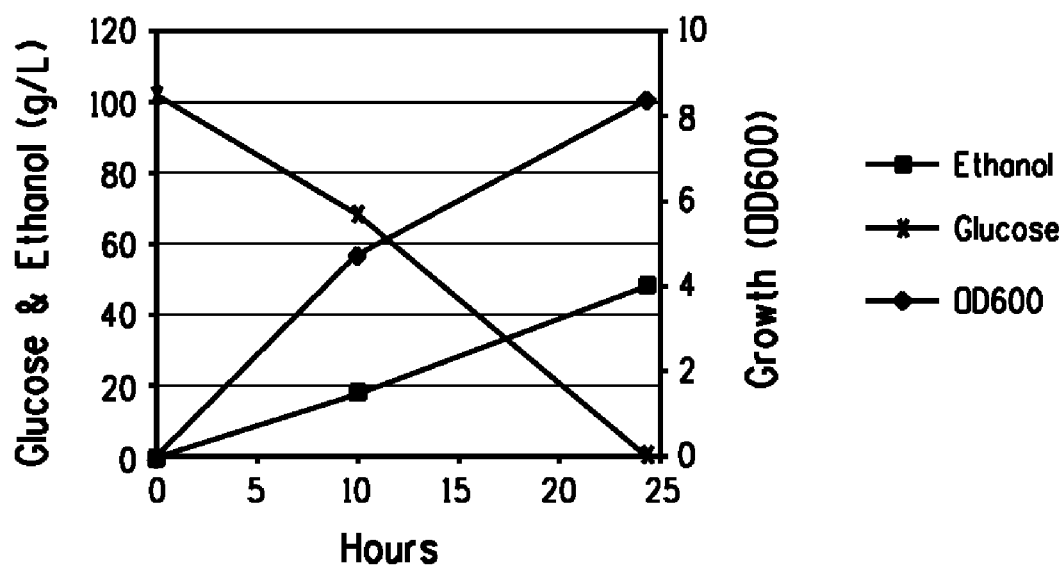

The ability of the ZW1-X109 and ZW1-X210 strains to ferment xylose was demonstrated by a standard growth assay as described in Example 5. To quantitatively determine the growth and metabolic profiles of these new strains and compare them to ZW1, these strains were characterized in shake flask fermentation assays. First they were subjected to the shake flask fermentation using MRM3G10 in order to determine their basal glucose metabolism. The strains were grown overnight in 2 mL mRM3-G5-Spec250 at 30° C., with 150 rpm shaking. Cells were harvested, washed with mRM3-G10, and resuspended in mRM3G10 to have a starting $OD_{600}$ of 0.1. Twenty mL of the suspension were placed in a 45 mL screw capped VWR centrifuge tube and grown at 30° C. with 150 rpm shaking. To prevent pressure buildup due to ethanol evaporation during fermentation, the caps were closed tightly and then loosened for one turn. During the time course, $OD_{600}$ was measured on a Shimadzu UV-1201 Spectrophotometer at 0, 10, and 24 hour time points. At each time point, 1 mL of culture was centrifuged at 10,000×g to remove cells. The supernatant was filtered through a 0.22 µm Costar Spin-X Centrifuge Tube Filter and analyzed by running through a BioRad Aminex HPX-A7H ion exclusion column with 0.01 $NH_2SO_4$ in a speed of 0.6 mL/min at 55° C. on an Agilent 1100 HPLC system. Wild type ZW1 was grown without antibiotics and analyzed as a control. Results given in FIG. 9 show that each strain quickly exhausted available glucose in 24 hours; both ZW1-X109 and ZW1-X210 strains (FIG. 8A, 8B, respectively) utilized glucose similarly to ZW1 (FIG. 8C). For example, after 10 hours of fermentation, ZW1-X109 had utilized approximately 34.8% of glucose (a reduction from 102.7 g/L to 66.9 g/L) to support an ethanol titer of 16.4 g/L and a biomass growth to $OD_{600}$ value of 4.88; ZW1-X210 had utilized approximately 32.1% of glucose (a reduction from 102.7 g/L to 69.7 g/L) to support an ethanol titer of 15.2 g/L and a biomass growth to $OD_{600}$ value of 4.68; ZW1 had utilized approximately 33.9% glucose (a reduction from 103.1 g/L to 68.2 g/L) to support an ethanol titer of 16.4 g/L and a biomass growth to $OD_{600}$ value of 4.6. Therefore, both new strains have robust basal glucose metabolism.

Figure 10A:
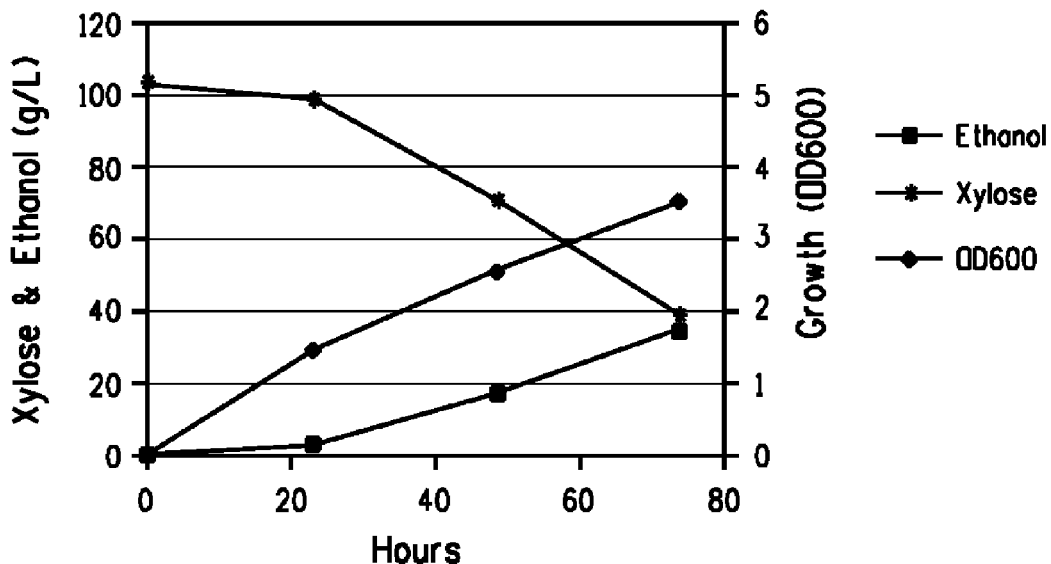
FIG. 10 shows graphs of growth, glucose used, and ethanol produced for cultures grown in mRM3-X10 of ZW1-109 (A), ZW1-210 (B), and control ZW1 (C).
Figure 10B:
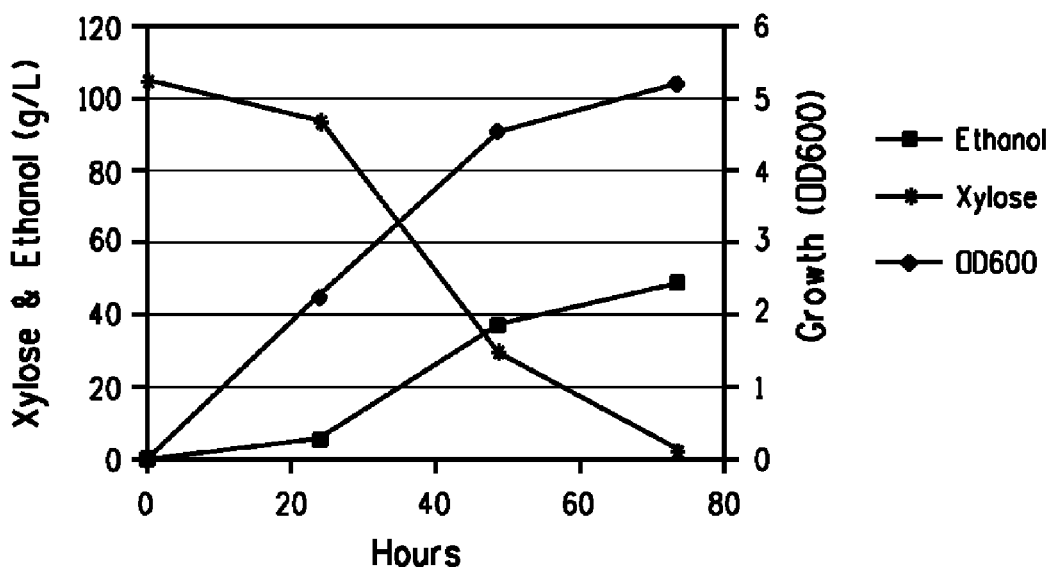
Figure 10C:
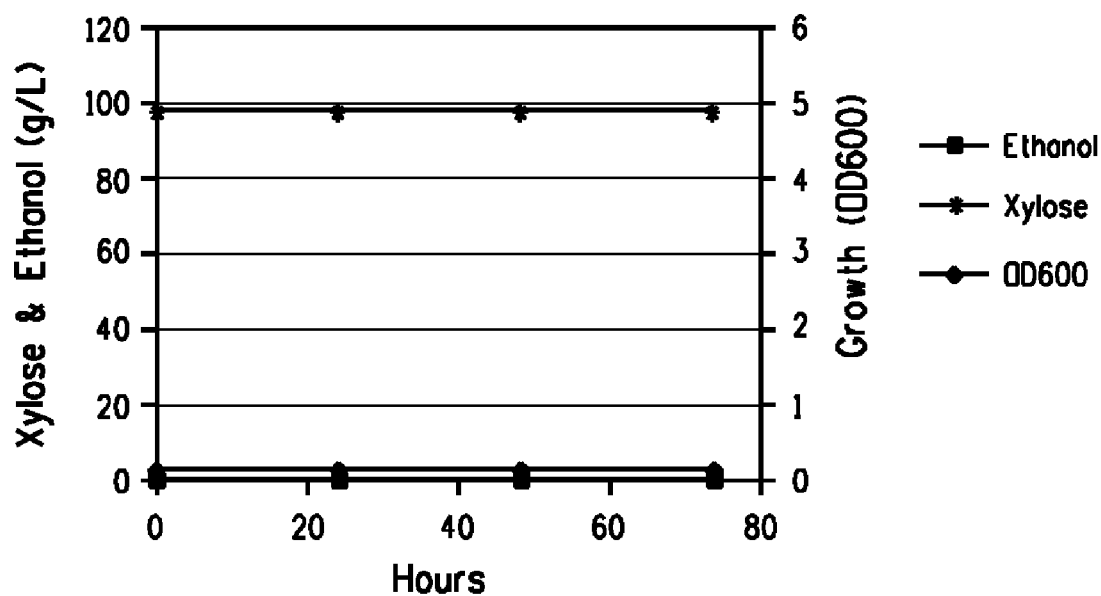

Shake flask fermentation was carried out in 20 mL mRM3-X10 in order to determine each strain's ability to use xylose. $OD_{600}$ value and both xylose and ethanol concentrations were measured at 0, 24, 48, and 72 hours. FIG. 10 is a summary of the results for ZW1-X109 (A), ZW1-210 (B) and ZW1 (C). The results also confirm that both new strains were able to ferment xylose. After 72 hours of fermentation, ZW1-X109 had utilized approximately 64.2% of xylose (a reduction from 105.6 g/L to 37.8 g/L) to support an ethanol titer of 31.5 g/L and biomass growth to $OD_{600}$ value of 3.51; ZW1-X210 had utilized almost all available xylose (a reduction from 105.6 g/L to 1.6 g/L) to support an ethanol titer of 48.5 g/L and a biomass growth to $OD_{600}$ value of 5.22. However, ZW1 could not grow in mRM3-X10 due to lacking the xylose metabolic pathway. Therefore, among new strains, ZW1-X210 could ferment xylose faster than ZW1-X109, in the xylose-containing single sugar medium. The major difference between ZW1-X109 and ZW1-X210 is that the $P_{gapT}$-ECTal-ECTkt::$P_{eno}$-ZMRpi-ZMRpe construct was inserted into the ldhA locus in ZW1-X109, and into the endogenous pnp gene in ZW1-X210. This result indicates that interruption of the pnp gene may benefit xylose metabolism in Z. mobilis.

Example 7

Figure 11A:
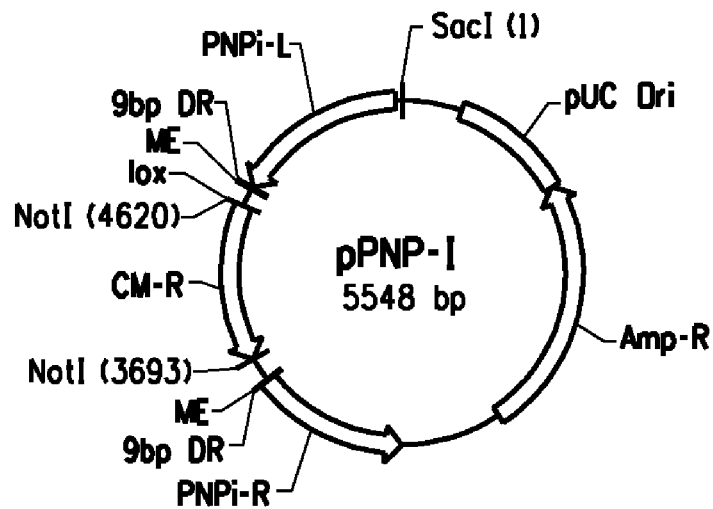
FIG. 11 shows plasmid maps of pPNP-I (A), pPNP-IN (B), pPNP-C (C), and pPNP-M (D).
Figure 11B:
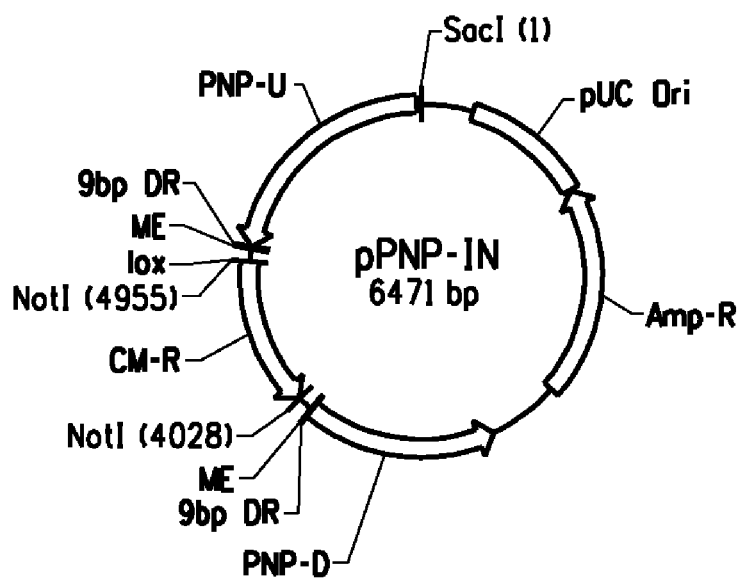
Figure 11C:
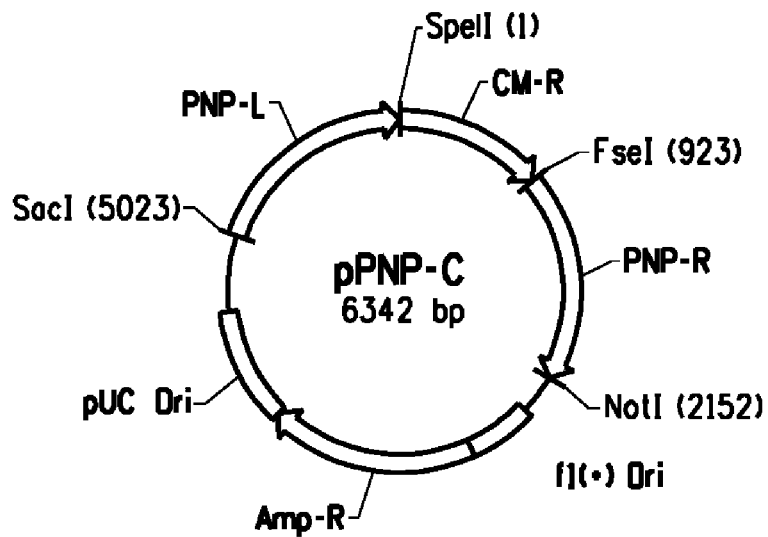

Vector Constructs for Interruption of the Endogenous pnp Gene in Z. mobilis Strains To directly test whether interruption of the endogenous pnp gene benefits xylose metabolism, four DCO suicide vectors shown in FIG. 4 were constructed by standard molecular recombination methods.

pPNP-I (SEQ ID NO:55; FIG. 11A) is a 5,548-bp pUC18 based DCO vector. Its backbone contains a 653 bp replication origin (pUC Ori) and a 1,144 bp ampicillin resistance marker (Amp-R) which allow the vector to propagate and be selected for in E. coli. pPNP-I contains a 911 bp chloramphenicol-resistance gene (Cm-R) and flanking sequences that target integration of this gene into the endogenous pnp gene. The 891 bp upstream flanking sequence (SEQ ID NO:56) consists of a 775 bp PNPi-L sequence (pnp coding region (SEQ ID NO:1) from nt-1,345 to nt-2,119), a 9 bp directly reversed segment (DR), a 19-bp ME (mosaic end) element, and a 34 bp Lox element. The 1,030 bp downstream flanking sequence (SEQ ID NO:57) consists of a 19 bp ME element, a 9 bp directly reversed segment (DR), and a 916 bp PNPi-R sequence. The PNPi-R sequence includes the last 116 bp of the pnp coding region (from nt-2,129 to nt-2,244) and an 800 bp DNA sequence downstream of the pnp coding sequence. Both PNPi-L and PNPi-R were amplified from genomic DNA of Z. mobilis ZW1. In pPNP-I, the PNPi-L and PNPi-R sequences direct integration of the DNA sequence between them into the Z. mobilis genome between nt-2,119 and nt-2,129 of the pnp coding region through double cross over homologous recombination. The integration interrupts the endogenous pnp gene and is similar to the genotype of the I strain described in Example 3, with the integrated transgene as Cm-R rather than Rpi::Spec-R. It results in a truncated 723-aa pnp fusion protein product as described in Example 3, which is 25 amino acid shorter than the wild-type pnp protein product (a 748 amino acid polynucleotide phosphorylase; SEQ ID NO:2). The truncated protein shares the first 709 amino acid residues with the wild-type, but has a new 14-aa sequence attached at the C-terminus (SEQ ID NO:9).

pPNP-IN (FIG. 11B; SEQ ID NO:58) is also a pUC18 based DCO vector with a size of 6,471 bp. It was directly derived from pPNP-I by replacing PNPi-L with PNP-U and PNPi-R with PNP-D. PNP-U (SEQ ID NO:59) is a 1,369-bp genomic DNA fragment of Z. mobilis which consists of the first 96 bp of the pnp coding region and a 1,273-bp sequence upstream of the pnp coding region. PNP-D (SEQ ID NO:60) is a 1,251-bp genomic DNA fragment of Z. mobilis which includes a part of the pnp coding sequence, from nt-97 to nt-1,347. In vector pPNP-IN, PNP-U and PNP-D are homologous recombination fragments that direct integration of the sequence between two 9 bp DR elements into the Z. mobilis genome between nt-96 and nt-97 of the pnp coding region. The integration interrupts the endogenous pnp gene and results in a truncated pnp protein product with only 49 aa residues (SEQ ID NO:12), which is 699 aa shorter than the wild-type pnp protein product. This short protein shares the first 32 aa residues with the wild-type, then has 17 new amino acid residues attached at the C-terminus.

pPNP-C (SEQ ID NO:61, FIG. 11C) is a 6,342-bp pBluescript based vector. Its backbone consists of an f1(+) replication site (f1(+) Ori), an ampicillin resistance marker (Amp-R), and a pUC replication site (pUC Ori) for propagation and selection in E. coli. In the vector, a 911-bp chloramphenicol resistance gene (Cm-R) is flanked by a 1,318-bp PNP-L fragment and a 1,225-bp PNP-R fragment. The PNP-L and PNP-R fragments were amplified from Z. mobilis ZW1 genomic DNA and are identical to those in pZX6 described in Example 4. The PNP-L fragment is a segment of the pnp coding sequence, from nt-767 to nt-2,084, while the PNP-R fragment includes the last 56 bp (from nt-2189 to nt-2,244) of the pnp coding sequence, its stop codon, and the 1,166-bp downstream sequence. Therefore, pPNP-C directs integration of the Cm-R marker into the pnp coding region between nt-2,085 and nt-2,188. This integration site is near the 3' end of the pnp coding sequence and 34 bp upstream of the target integration site of pPNP-I. The truncated pnp coding region produces a 697-aa protein (SEQ ID NO:10), which is 51 amino acid residues shorter than the wild-type and shares 695 amino acid residues with the wild-type, with 2 new amino acids at the C-terminus.

Figure 11D:
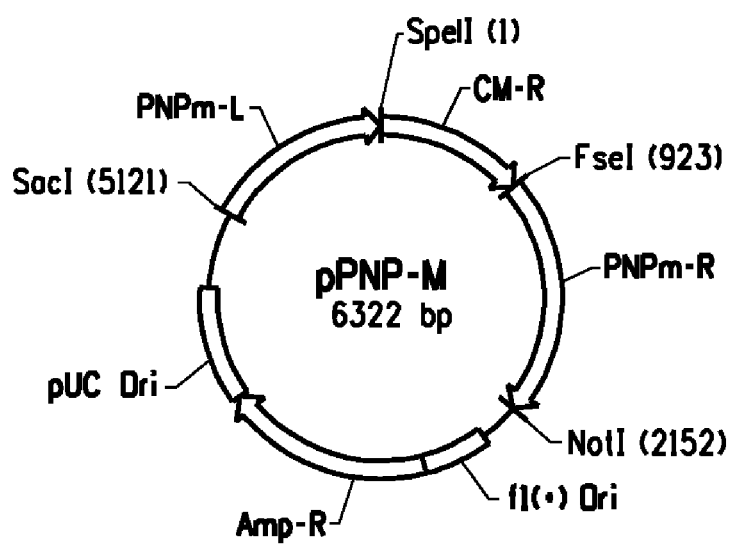
Figure 12A:
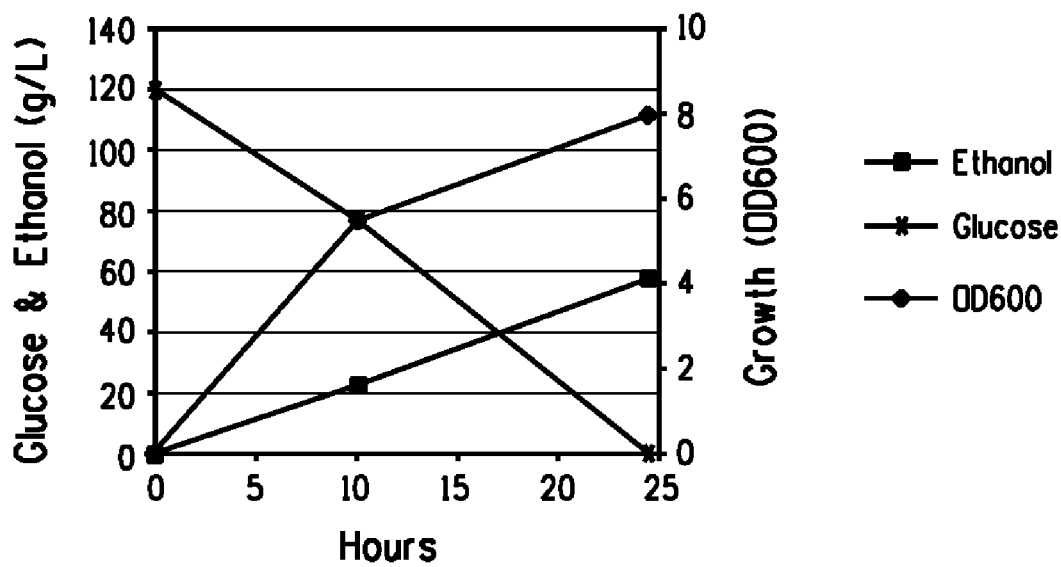
FIG. 12 shows graphs of growth, glucose used, and ethanol produced for cultures grown in mRM3-G10 of ZW1-X109-PNPi (A), ZW1-X109-PNPc (B), ZW1-X109-PNPm (C), ZW1-X109-PNPin (D), and control ZW1-X109 (E).
Figure 12B:
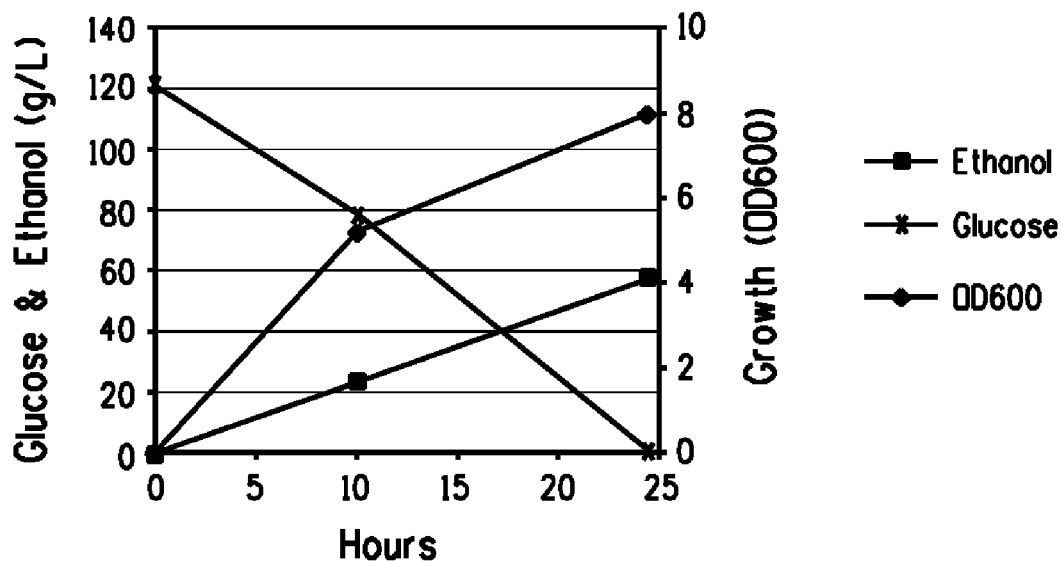
Figure 12C:
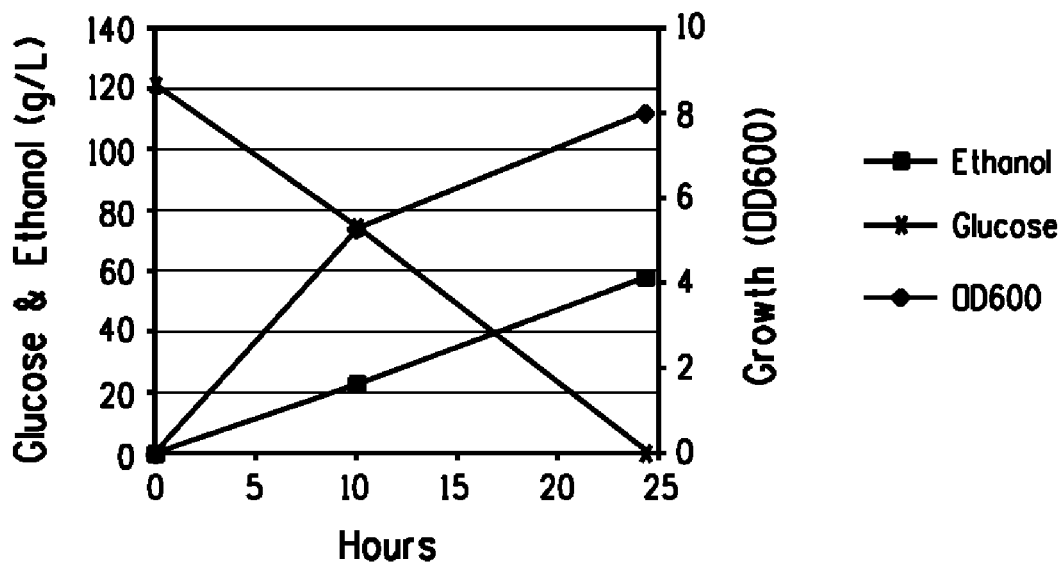
Figure 12D:
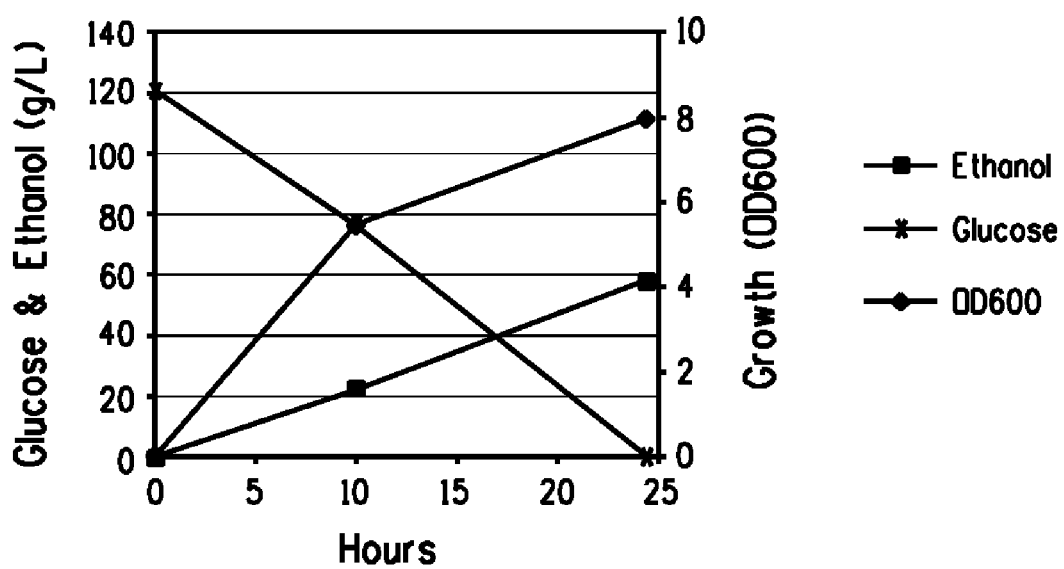
Figure 12E:
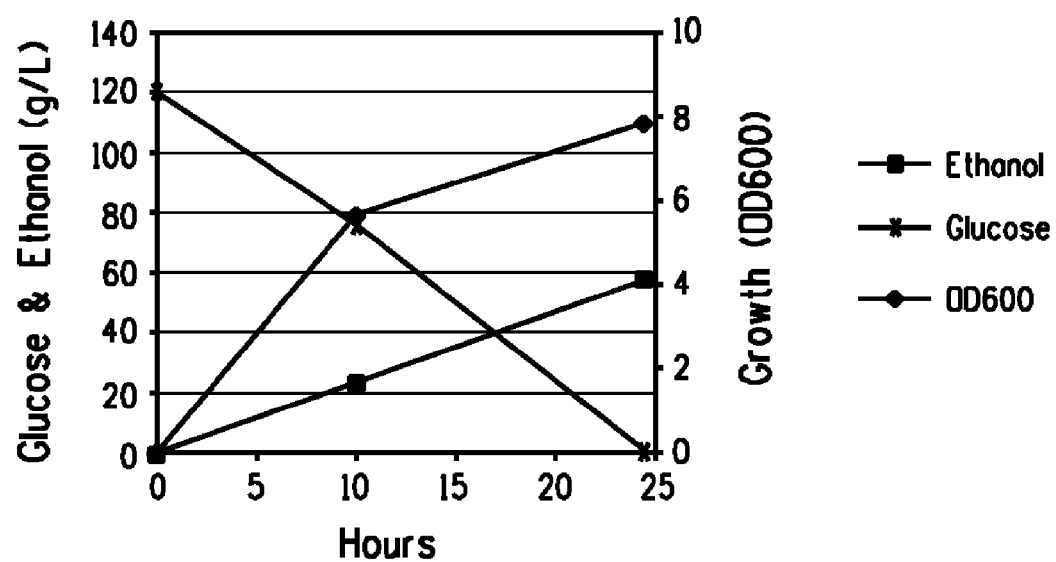
Figure 13A:
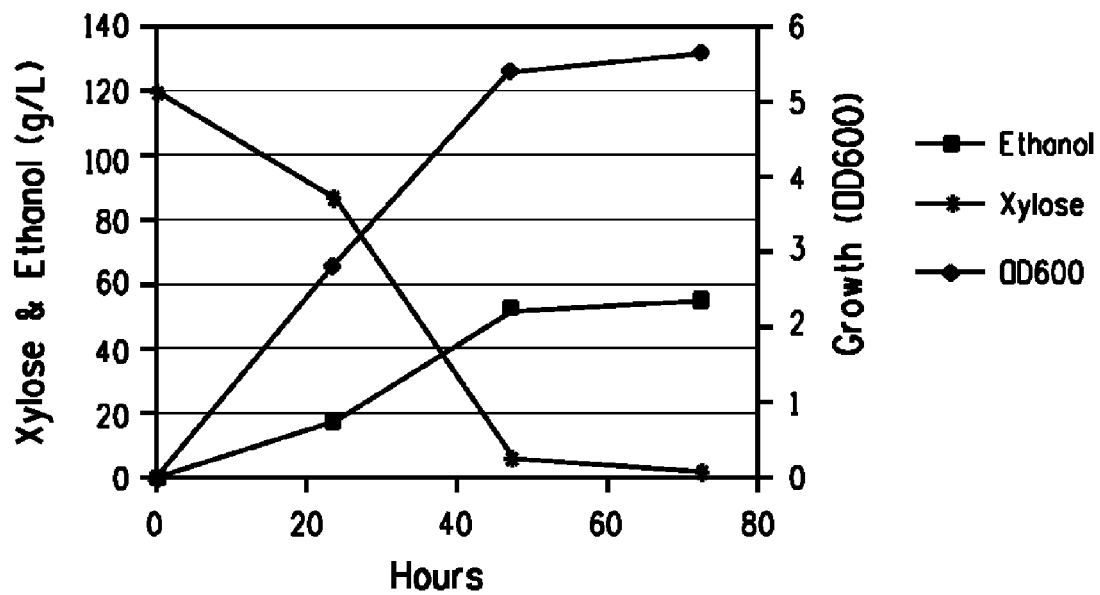
FIG. 13 shows graphs of growth, glucose used, and ethanol produced for cultures grown in mRM3-X10 of ZW1-X109-PNPi (A), ZW1-X109-PNPc (B), ZW1-X109-PNPm (C), ZW1-X109-PNPin (D), and control ZW1-X109 (E).
Figure 13B:
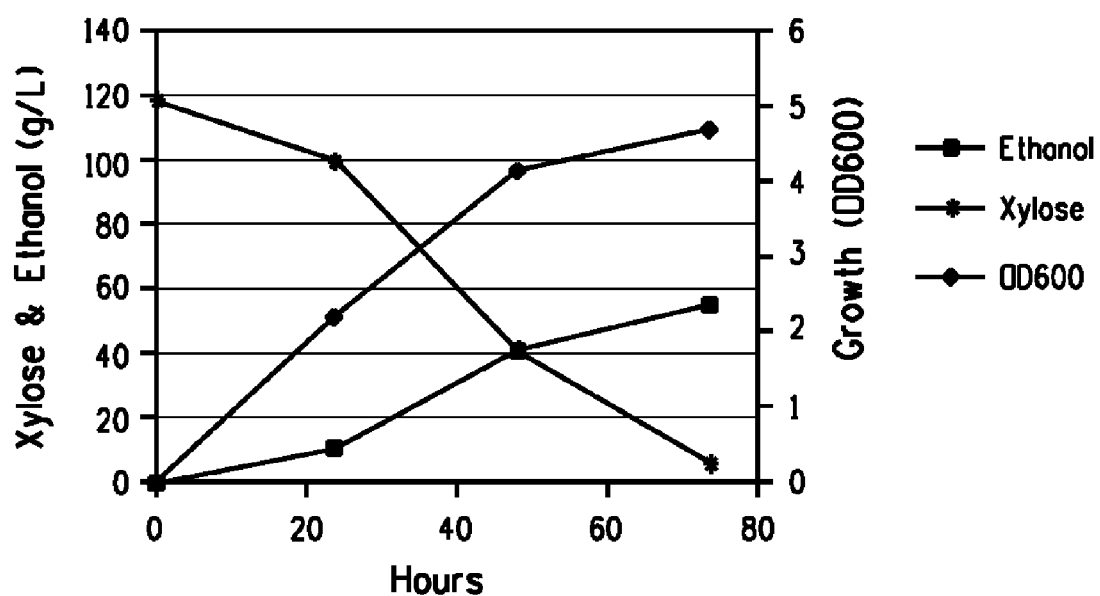
Figure 13C:
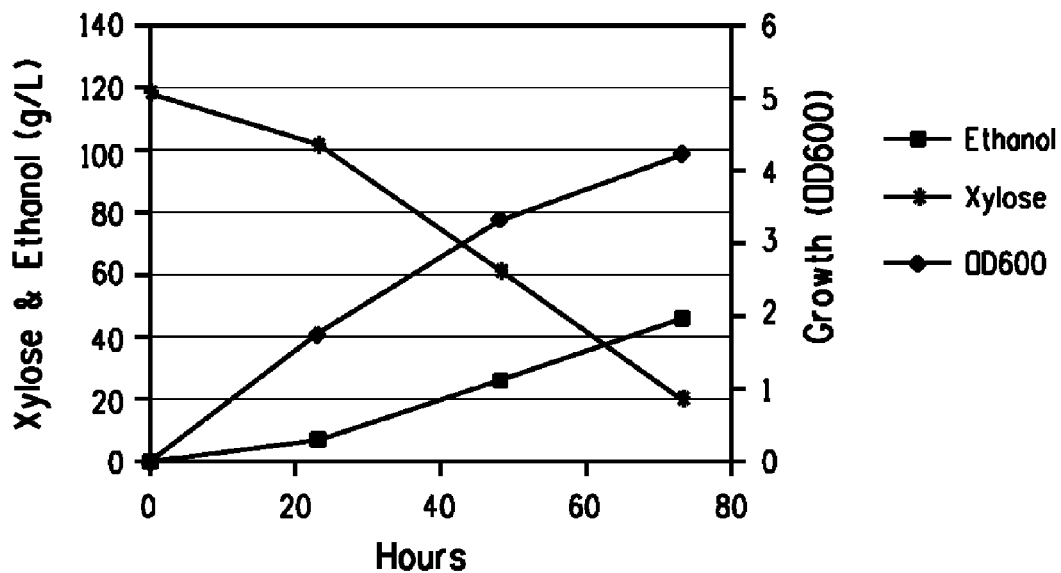
Figure 13D:
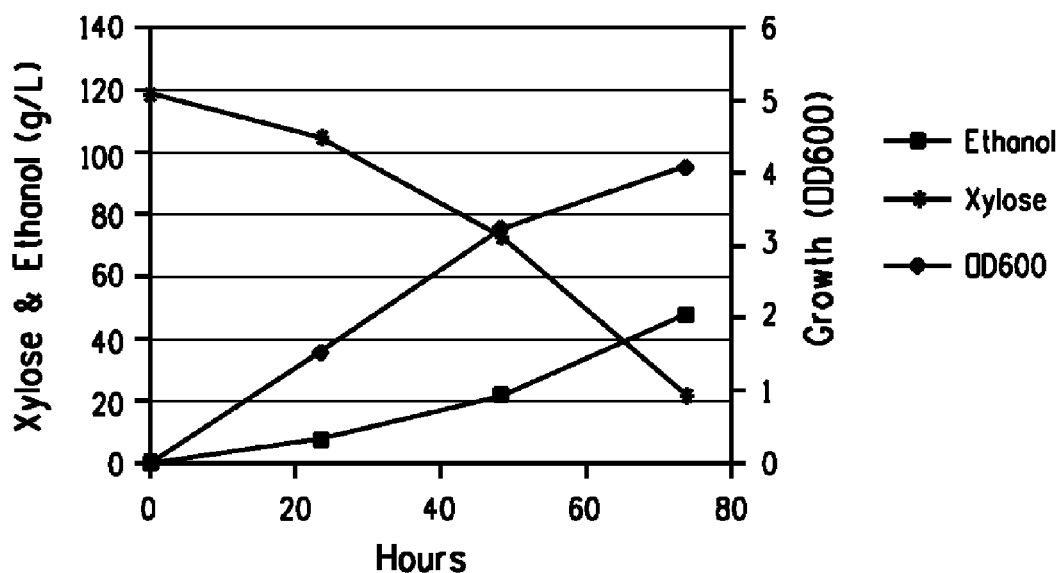
Figure 13E:
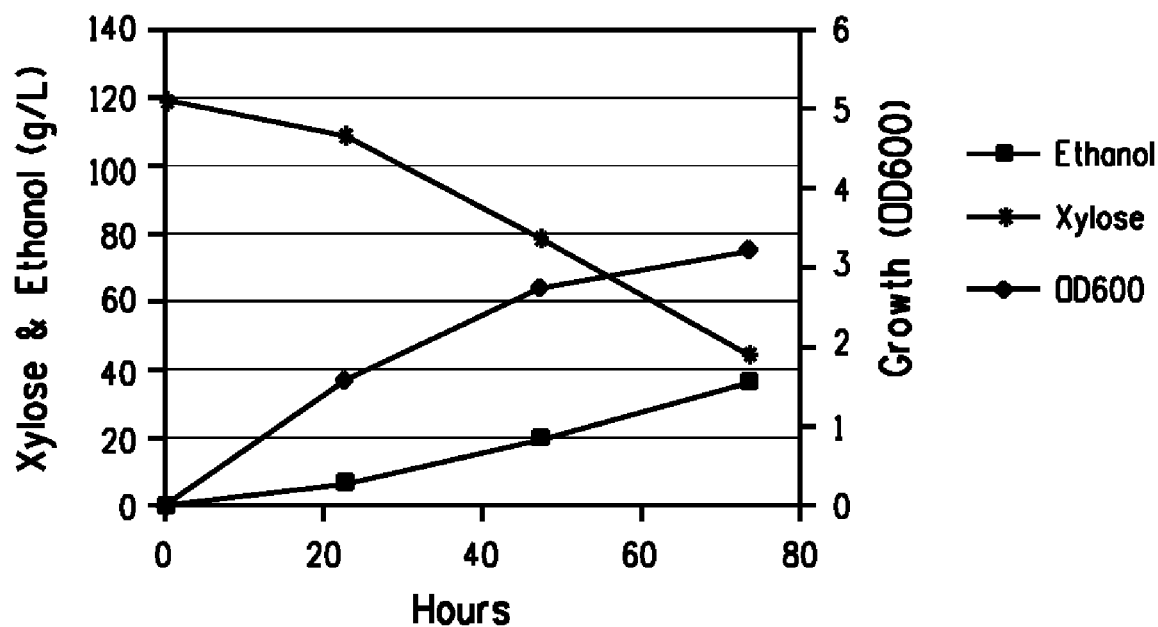

Similar to pPNP-C, pPNP-M (SEQ ID NO:62; FIG. 11D) is a 6,322-bp pBluescript based vector, which also has a backbone sequence consisting of a f1(+) Ori, an Amp-R, and a pUC Ori. However, in pPNP-M, the 911 bp chloramphenicol-resistance transgene (Cm-R) is flanked by a 1,200 bp PNPm-L fragment and a 1,324 bp PNPm-R fragment. Both flanking fragments were amplified from Z. mobilis ZW1 genomic DNA. PNPm-L (SEQ ID NO:63) includes a 96 bp genomic sequence upstream of the pnp coding sequence and the first 1,104 bp of the pnp coding sequence (from nt-1 to nt-1104), while PNPm-R (SEQ ID NO:64) includes the last 1140 bp (from nt-1,105 to nt-2,244) of the pnp coding sequence, its stop codon, and the 181 bp downstream sequence. Therefore, pPNP-M is able to direct integration of the Cm-R marker into the endogenous pnp gene between nt-1,104 to nt-1,105 in Z. mobilis genome. The integration site is near the middle of the pnp coding sequence and 1,015 bp upstream of the integration site for pPNP-I. It results in a truncated 378-aa pnp protein product (SEQ ID NO:11), 370 aa shorter than the wild-type pnp protein product. The truncated protein shares the first 368 aa residues with the wild-type, but has a new 10 aa sequence attached at the C-terminus.

Example 8

Interruption of the Endogenous pnp Gene in Strain ZW1-X109

To determine whether interruption of the endogenous pnp gene benefits xylose utilization in Z. mobilis, ZW1-X109 was transformed separately with pPNP-I, pPNP-C, pPNP-M, and pPNP-IN as described in Example 5. Since all four vectors are suicide vectors, transformants were directly selected on a MMG5-CM120 plate (MMG5 with 120 mg/L chloramphenicol and 15 g/L agar). The resulting strains were named ZW1-X109-PNPi, ZW1-X109-PNPc, ZW1-X109-PNPm, and ZW1-X109-PNPin. A few colonies of each strain were streaked and grown on fresh MMG5-CM120 plates. Transgene integration was confirmed by PCR inspection.

Five primers were employed in the PCR inspection. Forward primer ara448 (SEQ ID NO:52) is a sequence located at the beginning of the Cm-R marker in all pPNP plasmids. Reverse primer ara339 (SEQ ID NO:51) complements a Z. mobilis genomic sequence segment downstream of the pnp gene. They were used to inspect double crossover recombination mediated by the following recombination fragments: PNPi-R in pPNP-I, PNP-R in pPNP-C, PNPm-R in pPNP-M, and PNP-D in pPNP-IN. If the integration was successful, these two primers would amplify a PCR product of 2,393 bp from ZW1-X109-PNPi strain, 2,256 bp from ZW1-X109-PNPc strain, 3,361 from ZW1-X109-PNPm strain, and 4,565 bp from ZW1-X109-PNPin strain. Forward primer ara340 or 4R0 (SEQ ID NOs:50 and 53, respectively) and reverse primer ara449 (SEQ ID NO:54) were used to inspect double crossover recombination mediated by the following recombination fragments: PNPi-L in pPNP-I, PNP-L in pPNP-C, PNPm-L in pPNP-M, and PNP-U in pPNP-IN. The ara340 primer matches a segment (from nt-702 to nt-724) of the pnp coding sequence located upstream of the PNPi-L and PNP-L sequences in Z. mobilis genomic DNA. The 4R0 primer is a segment of Z. mobilis genomic sequence outside of the pnp gene and upstream of PNPm-L and PNP-U sequences. The ara449 primer complements a sequence at the end of the Cm-R marker in pPNP plasmids. Therefore, when integration was successful, ara340 and ara449 could amplify a 2,551-bp PCR product from ZW1-X109-PNPi strain and a 2,306-bp PCR product from ZW1-X109-PNPc strain, while 4R0 and ara449 could amplify a 3,424-bp PCR product from ZW1-X109-PNPm strain, and a 2,430-bp PCR product from ZW1-X109-PNPin strain. Standard PCR reactions using Invitrogene's PCR Supermix were performed directly on freshly grown strains. Results demonstrated accurate integration.

Example 9

Characterization of the pnp-Integration Strains

ZW1-X109-PNPi, ZW1-X109-PNPc, ZW1-X109-PNPm, and ZW1-X109-PNPin strains were further characterized in shake flask fermentations to determine their growth and metabolic profiles. The parental ZW1-X109 strain, which contains an uninterrupted endogenous pnp gene, was used as a control. The fermentation followed a standard protocol as described in Example 6, except that the volume of cell culture was reduced from 20 mL to 10 mL, therefore capped 14 mL Falcon round-bottom tubes with a punched hole in the top was used instead of the 45 mL VWR centrifuge tubes. The first shake flask fermentation was carried out in mRM3-G10. At 0, 10, and 24 hour of fermentation $OD_{600}$ was measured on a Shimadzu UV-1201 Spectrophotometer, while glucose and ethanol concentrations were determined by an Agilent 1100 HPLC system using a BioRad Aminex HPX-A7H ion exclusion column. Results are graphed in FIG. 12, showing that all four pnp-interrupted strains have a basal glucose metabolism similar to the parental ZW1-X109 strain. For example, after 10 hours of fermentation, ZW1-X109-PNPi (A) utilized approximately 37.7% of glucose (a reduction from 120.8 g/L to 75.3 g/L) to support an ethanol titer of 22.9 g/L and a biomass growth to $OD_{600}$ value of 5.36; ZW1-X109-PNPc (B) utilized approximately 37.7% of glucose (a reduction from 120.8 g/L to 75.3 g/L) to support an ethanol titer of 23.0 g/L and a biomass growth to $OD_{600}$ value of 4.98; ZW1-X109-PNPm (C) utilized approximately 39.1% of glucose (a reduction from 120.8 g/L to 73.6 g/L) to support an ethanol titer of 23.5 g/L and a biomass growth to $OD_{600}$ value of 5.14; ZW1-X109-PNPin (D) utilized approximately 36.8% of glucose (a reduction from 120.8 g/L to 76.4 g/L) to support an ethanol titer of 22.6 g/L and a biomass growth to $OD_{600}$ value of 5.32. The parental ZW1-X109 strain (E) utilized approximately 39.5% of glucose (a reduction from 120.8 g/L to 73.4 g/L) to support an ethanol titer of 24.0 g/L and a biomass growth to $OD_{600}$ value of 5.62. After 24 hours of fermentation, all of the pnp-interrupted strains exhaust glucose to support an ethanol titer near 58.1 g/L and biomass growth to $OD_{600}$ value of around 7.90, while ZW1-X109 also exhausted glucose to support an ethanol titer of 57.3 g/L and a biomass growth to $OD_{600}$ value of 7.64.

The shake flask fermentation was then carried out in 10 mL mRM3-X10 as described above. $OD_{600}$ value and both xylose and ethanol concentrations were measured at 0, 24, 48, and 72 hours. FIG. 13 shows graphs of the results. It shows that all four pnp-interrupted strains utilized xylose better in fermentation than the parental ZW1-X109 strain. After 48 hours of fermentation, ZW1-X109-PNPi (A) had already utilized approximately 95.5% of xylose (a reduction from 117.9 g/L to 5.3 g/L) to support an ethanol titer of 54.7 g/L and a biomass growth to $OD_{600}$ value of 5.34. After another 24 hours of fermentation, it had almost used up the xylose with only 1.4 g/L left to support an ethanol titer of 56.0 g/L and a biomass growth to $OD_{600}$ value of 5.62. In the same 72 hours period, ZW1-X109-PNPc (B) utilized approximately 94.2% of xylose (a reduction from 117.9 g/L to 6.8 g/L) to support an ethanol titer of 53.6 g/L and a biomass growth to $OD_{600}$ value of 4.64; ZW1-X109-PNPm (C) utilized approximately 83.3% of xylose (a reduction from 117.9 g/L to 19.7 g/L) to support an ethanol titer of 47.5 g/L and a biomass growth to $OD_{600}$ value of 4.24; ZW1-X109-PNPin (D) utilized approximately 79.8% glucose (a reduction from 117.9 g/L to 23.8 g/L) to support an ethanol titer of 45.5 g/L and a biomass growth to $OD_{600}$ value of 4.04. The parental ZW1-X109 strain (E) utilized approximately 61.7% of xylose (a reduction from 117.9 g/L to 45.1 g/L) to support an ethanol titer of 34.8 g/L and a biomass growth to $OD_{600}$ value of 3.26. The results also indicate that the strains with less truncation of the pnp encoded protein, such as ZW1-X109-PNPi and ZW1-X109-PNPc, use xylose more efficiently than the strains with larger truncations, such as ZW1-X109-PNPm and ZW1-X109-PNPin. Ranking of these strains in order of their ability to utilize xylose, with best first, was: ZW1-X109-PNPi, ZW1-X109-PNPc, ZW1-X109-PNPm, ZW1-X109-PNPin, and finally ZW1-X109.

In summary, this example demonstrates that integration in the endogenous pnp gene of Z. mobilis does not impact glucose metabolism but improves xylose utilization in fermentation.

Example 10

Comparative

Figure 14A:
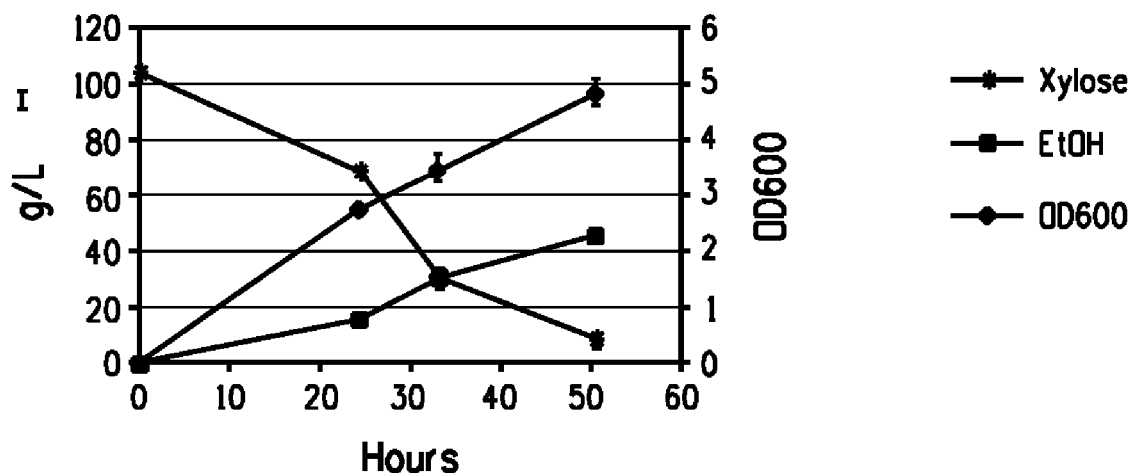
FIG. 14 shows graphs of growth, xylose used, and ethanol produced for cultures grown in mRM3-X10 of ZW801-PNPi (A), ZW801-PNPc (B), and control ZW801 (C).
Figure 14B:
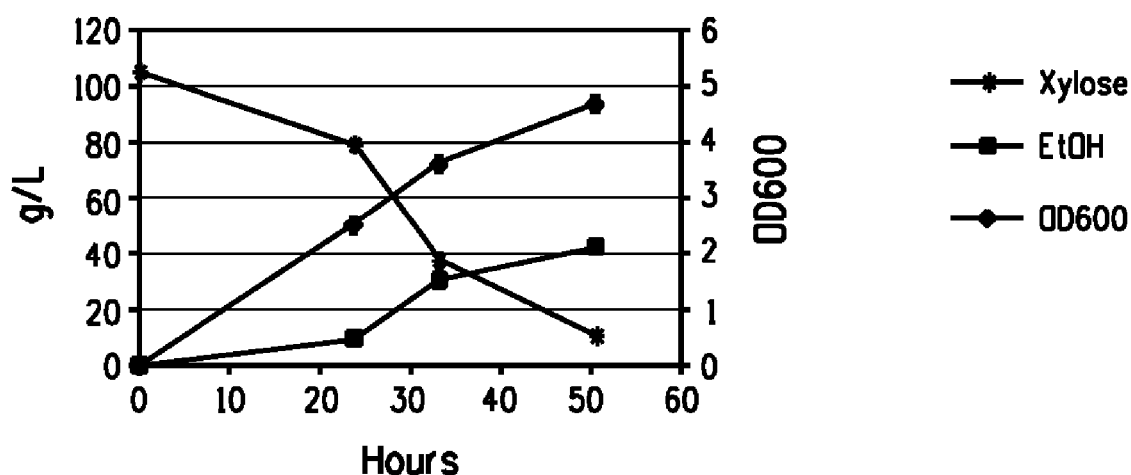
Figure 14C:
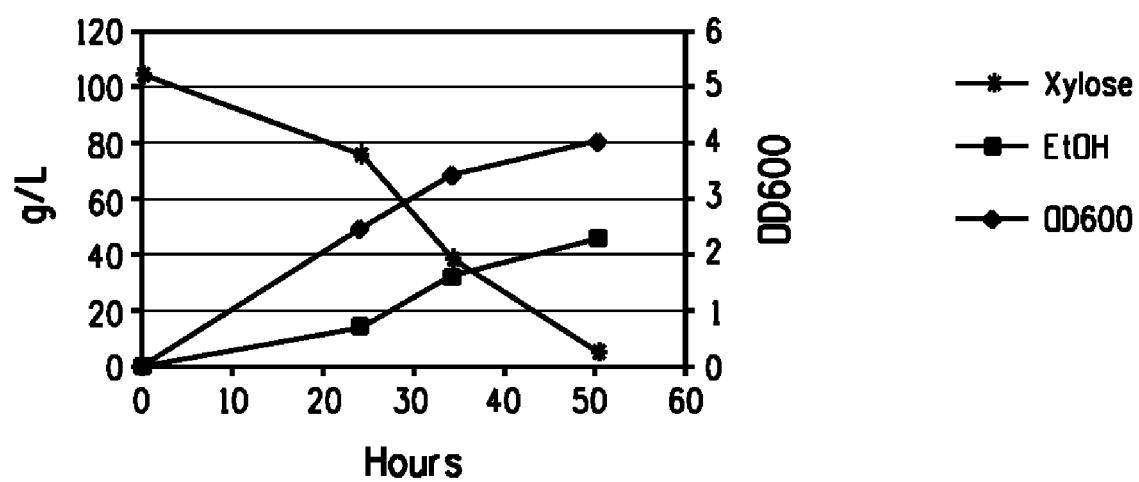

Interruption of Endogenous pnp Gene in ZW801-4 in the Absence of RPI Overexpression The effects of endogenous pnp gene modifications were assayed in ZW801-4 (see General Methods) using the two suicide constructs that had the greatest impact on xylose growth and metabolism in ZW1-X109 (e.g. pPNP-I and pPNP-C, described in Example 7). ZW801-4 was transformed with each of these suicide vectors separately, as described in Example 8. Two transformants for each construct were evaluated in shake flask experiments with xylose, and ZW801-4 was included as a control (also done in duplicate). The growth medium was mRM3-X10 and the temperature was 33° C. Samples of each culture were assayed for OD600, xylose, and ethanol as described previously. The results of this experiment are shown in FIG. 14. Only the transformant prepared with the pPNP-I construct showed slight improvement as compared to the control. Note that double-crossover homologous recombination of the pPNP-I suicide construct with the ZW801-4 chromosome results in the exact same pnp gene modification that is present in the I strain.

Example 11

Assay of Xylose Isomerase Activity

The activity of xylose isomerase in ZW658 (see General Methods) was measured in a reaction containing 20 μL of cell free extract (see General Methods), 0.256 mM NADH, 50 mM xylose, 10 mM MgSO$_4$, 10 mM triethanolamine, and 1 U/ml SDH (sorbitol dehydrogenase) at 30° C. The A$_{340}$ was read on a plate reader for 3-5 min. XI activity was calculated as follows:

1 unit of XI corresponds to the formation of 1 μmole of D-xylulose per minute at 30° C.

U (μmole/min)=slope (dA$_{340}$/min)*volume of reaction (μL)/ 6220/0.55 cm (moles of NADHP→NAD is 6220 A$_{340}$ per mole per L in a 1 cm cuvette) (pathlength of 200 μL per well in microplate=0.55 cm)

Specific Activity (μmole/min-mg)=μmole/min/protein concentration (mg)

The activity measured for ZW658 was 0.25+/−0.033 μmoles product/mg protein/minute.

What is claimed is:

1. A recombinant bacterial host cell comprising:
 a) a xylose metabolic pathway comprising at least one polypeptide having xylose isomerase activity;
 b) at least one genetic modification which increases ribose-5-phosphate isomerase activity in the host cell as compared with ribose-5-phosphate isomerase activity in the host cell lacking said genetic modification; and
 c) at least one genetic modification in the sequence of an endogenous gene encoding polynucleotide phosphorylase that shortens the coding region resulting in expression of a C-terminal truncated protein;
 wherein the bacterial host cell utilizes xylose to produce ethanol, and the xylose isomerase activity is not rate limiting in the bacterial host cell.

2. The recombinant host cell of claim 1 wherein the C-terminal truncated protein of (c) comprises at least 350 amino acids of the N-terminal amino acid sequence encoded by the endogenous gene encoding polynucleotide phosphorylase.

3. The recombinant host cell of claim 1 wherein the C-terminal truncated protein of (c) is part of a fusion protein comprising at least one non-native amino acid at the C-terminus.

4. The recombinant host cell of claim 1 wherein the at least one genetic modification which increases ribose-5-phosphate isomerase activity is over-expression of an endogenous gene encoding a polypeptide having ribose-5-phosphate isomerase activity.

5. The recombinant host cell of claim 1 wherein the at least one genetic modification which increases ribose-5-phosphate isomerase activity is expression of at least one non-endogenous gene encoding a polypeptide having ribose-5-phosphate isomerase activity.

6. The recombinant host cell of claim 1 wherein the polypeptide having ribose-5-phosphate isomerase activity has the EC classification EC 5.3.1.6.

7. The recombinant host cell of claim 6 wherein the polypeptide having ribose-5-phosphate isomerase activity is selected from the group consisting of ribose-5-phosphate isomerase A and ribose-5-phosphate isomerase B.

8. The recombinant host cell of claim 1 wherein the polypeptide having xylose isomerase activity provides xylose isomerase activity at greater than 0.25 micromoles product/mg protein/minute.

9. The recombinant host cell of claim 1 wherein the polypeptide having xylose isomerase activity has the EC classification EC 5.3.1.5.

10. The recombinant host cell of claim 1 wherein xylose isomerase activity is expressed using a method selected from the group consisting of from multiple genes, from a mutant highly active promoter, from a Group I xylose isomerase, and a combination thereof.

11. The recombinant host cell of claim 1 wherein at least one genetic modification is made which increases expression of ribulose-phosphate 3-epimerase as compared with ribulose-phosphate 3-epimerase activity in the host cell lacking said genetic modification.

12. The recombinant host cell of claim 11 wherein the polypeptide having ribulose-phosphate 3-epimerase activity has the EC classification EC 5.1.3.1.

13. The bacterial host cell of claim 1 wherein the cell is selected from the group consisting of *Zymomonas* and *Zymobacter*.

14. A process for producing ethanol comprising:
 a) providing the recombinant bacterial host cell of claim 1 or 2; and
 b) culturing the host cell of (a) in a medium comprising xylose whereby xylose is converted to ethanol.

15. The process of claim 14 wherein the polypeptide having ribose-5-phosphate isomerase activity of claim 1 (b) has the EC classification EC 5.3.1.6.

16. The process of claim 14 wherein the medium comprises either a mixture of sugars including xylose or xylose as a sole sugar.

* * * * *

SEQUENCE LISTING

<160> NUMBER OF SEQ ID NOS: 65

<210> SEQ ID NO 1
<211> LENGTH: 2247
<212> TYPE: DNA
<213> ORGANISM: Zymomonas mobilis

<400> SEQUENCE: 1

```
atgttcgata ttaaacgcca ggaaatcgat tggggcggaa aaaaactgac actggaaacc      60
ggacaggttg cccgtcaggc agatggcgcc gtcattgcga ccttaggtga aacggtcgta     120
ttatgcgcgg taacggcagc aaaaacggta aagaaggtc aggatttctt tcctttgacc      180
gtccattatc aggaaaaata ttcagcagca ggccgtattc ccggtggctt tttcaagcgt     240
gaacgtggcg caaccgaacg ggaaacgctg atttcacggt taatcgaccg tccaatccgt     300
cctctgtttc cggaaggttt ctataacgaa accttggtca ttgcgcaggt catgtcctat     360
gacggcgaga tgaaccggaa tatcttggcg atgatcgctg cttctgcggc tcttgctctt     420
tccggtgtgc ctttcttggg ccccatcggt gctgcccgtg tgggttatca agatggcgag     480
ttcattctta acccgacctt ggaacagctt gaaaaaagtg atcttgatct ggttgtcggg     540
gctacccgtg atgccgtgat gatggttgaa tcggaagcga atgagcttcc cgaagaagtc     600
atgctcaatg ccgtttcttt tgcgcatgaa tctttacagc cggttatcaa agctatcatc     660
aatctggcag aacaggccgc taaagagcct tgggaactgg tcagctatga tgacagcgca     720
ttggctgcca aagtcgaaga actctgctac gacaatttcg ataaggccta tcgtctgact     780
cgcaaggcta acgtgttga cgccttgagc aaggccaaag cggttcttga cgaagccttc     840
ccagaagctg atccgacaga aaagctgcgc atccagaagc ttgcgaagaa gctgaagca      900 aaaatcgtcc gcaccgccat tctgaaagaa ggccggagaa ttgacggacg cgatctgaaa     960
acagttcgcc cgatccgctc tcaggttgga ttcttgcccc gcacgcatgg ttctgccctg    1020
tttacgcgtg gtgaaacaca ggctttggtt tcaaccaccc ttggaacggc ggatgctgaa    1080
cagatgatcg acggtttaac cggccttcat tatgaacgct tcatgctgca ttacaacttc    1140
cccccatatt cggtcggtga agttggtcgt tttggtgctc cgggtcgtcg tgaaatcggc    1200
catggtaaac tggcatggcg tgcgcttcat ccggttttgc cgagcaaggc tgatttcccg    1260
tataccatcc gtgttttgtc ggatatcacc gaatctaatg ttcctcttc catggcaacc    1320 gtttgcggtg gctgccttgc attgatggat gccggtgttc ccttaacgcg tccggtttcc    1380
ggtatcgcca tgggtcttat tctggaaaaa gacggcttcg ctatttgtc cgatatcatg    1440 ggtgatgaag atcacttggg tgatatggac tttaaggtcg ccggtaccga aaaaggtatc    1500
accagcctcc agatggacat caaggttgct ggcattaccg aagaaatcat gcagaaagct    1560
ttggaacagg ctaaaggtgg ccgtgctcat atctctggtg aaatgtccaa agcgctgggt    1620
```

-continued

```
gaagtccgct ccgaaatttc taatttggca ccgcgcattg aaacaatgag cgtaccaaaa    1680
gacaaaatcc gtgatgttat cggaacgggc ggaaaagtta ccgtgaaat cgtggcgacc    1740 acaggtgcca aggtcgatat cgaagatgac ggcacggttc gtctgtcttc ttctgatccg    1800
gccaatattg aagcagcccg tgaatggatc aatggtattg ttgaagaacc ggaagtaggc    1860
aaaatctata cggtaaagt cgtcaatatc gttgatttcg gtgccttcgt aaacttcatg    1920
ggtggccgtg acggcttggt acatgtttcg gaaatcaaga cgaacgtgt caacaaggtc    1980 agcgatgtcc tgtccgaagg tcaggaagtc aaagtcaagg ttcttgaaat tgacaaccgt    2040
ggcaaggttc gcctgtctat gcgtgttgtc gatcaggaaa ccggcgcaga gctggatgat    2100
aaccgtccgc cacgtgagaa cgcagaacgt cgcggtggtg agcgtcctcg tcgtgatcgg    2160
ggccctcgtc gggaatctgg cgatcgtccg gcaagacgtg atatggaacc ggaatttgct    2220
ccggcattcc tgcgcaaaga tagctaa                                       2247
```

<210> SEQ ID NO 2
<211> LENGTH: 748
<212> TYPE: PRT
<213> ORGANISM: Zymomonas mobilis

<400> SEQUENCE: 2

```
Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255
```

```
Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
    290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly
        355                 360                 365

Leu His Tyr Glu Arg Phe Met Leu His Tyr Asn Phe Pro Pro Tyr Ser
    370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
        435                 440                 445

Met Asp Ala Gly Val Pro Leu Thr Arg Pro Val Ser Gly Ile Ala Met
450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
        515                 520                 525

Ala His Ile Leu Gly Glu Met Ser Lys Ala Leu Gly Glu Val Arg Ser
    530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Asn Ile Glu Ala Ala Arg Glu
        595                 600                 605

Trp Ile Asn Gly Ile Val Glu Glu Pro Glu Val Gly Lys Ile Tyr Asn
    610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
```

```
            675                 680                 685
    Val Val Asp Gln Glu Thr Gly Ala Glu Leu Asp Asp Asn Arg Pro Pro
        690                 695                 700
    Arg Glu Asn Ala Glu Arg Arg Gly Gly Glu Arg Pro Arg Arg Asp Arg
    705                 710                 715                 720
    Gly Pro Arg Arg Glu Ser Gly Asp Arg Pro Ala Arg Arg Asp Met Glu
                    725                 730                 735
    Pro Glu Phe Ala Pro Ala Phe Leu Arg Lys Asp Ser
                740                 745

<210> SEQ ID NO 3
<211> LENGTH: 2247
<212> TYPE: DNA
<213> ORGANISM: Zymomonas mobilis

<400> SEQUENCE: 3
```

| | | | | | |
|---|---|---|---|---|---|
| atgttcgata | ttaaacgcca | ggaaatcgat | tggggcggaa | aaaaactgac | actggaaacc | 60 |
| ggacaggttg | cccgtcaggc | agatggcgcc | gtcattgcga | ccttaggtga | aacggtcgta | 120 |
| ttatgcgcgg | taacggcagc | aaaaacggta | aagaaggtc | aggatttctt | tcctttgacc | 180 |
| gtccattatc | aggaaaaata | ttcagcagca | ggccgtattc | ccgtggcctt | tttcaagcgt | 240 |
| gaacgtggcg | caaccgaacg | ggaaacgctg | atttcacggt | taatcgaccg | tccaatccgt | 300 |
| cctctgtttc | cggaaggttt | ctataacgaa | accttggtca | ttgcgcaggt | catgtcctat | 360 |
| gacggcgaga | atgaaccgga | tatcttggcg | atgatcgccg | cttctgcggc | ccttgctctt | 420 |
| tccggtgtgc | ctttccttgg | tcctatcggt | gctgcccgtg | tgggttatca | agatggcgag | 480 |
| ttcattctta | acccgacctt | ggaacagctt | gaaaaaagtg | atcttgatct | ggttgtcggg | 540 |
| gctacccgtg | atgccgtgat | gatggttgaa | tcggaagcga | atgagcttcc | cgaagaagtc | 600 |
| atgctcaatg | ctgtttcttt | tgcgcatgaa | tctttacagc | cggttatcaa | agctatcatc | 660 |
| aatctggcag | aacaggccgc | taaagagcct | tgggaactgg | tcagctatga | tgacagcgca | 720 |
| ttggctgcca | agtcgaaga | actctgctac | gacaatttcg | ataaggccta | tcgtctgact | 780 |
| cgcaaggctg | aacgtgttga | cgccttgagc | aaggccaaag | cggttcttga | cgaagccttc | 840 |
| ccagaagctg | atccgacaga | aaagctgcgc | atccagaagc | ttgcgaagaa | gctggaagca | 900 |
| aaaattgtcc | gcaccgccat | tctgaaagaa | ggccggagaa | ttgacggacg | cgatctgaaa | 960 |
| acagttcgcc | cgatccgctc | tcaggttgga | ttcttgcccc | gcacgcatgg | ttctgccctg | 1020 |
| tttacgcgtg | gtgaaacaca | ggctttggtt | caaccacccc | ttggaacggc | ggatgctgaa | 1080 |
| cagatgatcg | acggtttaac | cggccttcat | tatgaacgct | tcatgctgca | ttataacttc | 1140 |
| cctccttatt | cggtcggtga | agttggtcgt | tttggtgctc | cgggtcgtcg | tgaaatcggc | 1200 |
| catggtaaac | tggcatggcg | tgcgcttcat | ccggttttgc | cgagcaaggc | tgatttcccg | 1260 |
| tataccatcc | gcgttttgtc | ggatatcacc | gaatctaatg | ttcctcttc | tatggcaacc | 1320 |
| gtttgcggtg | gctgccttgc | attgatggat | gccggtgttc | ccttaacgcg | tccggtttcc | 1380 |
| ggtatcgcca | tgggtcttat | tctagaaaaa | gacggcttcg | ctattttgtc | cgatatcatg | 1440 |
| ggtgatgaag | atcacttggg | tgatatggac | tttaaggtcg | ccggtaccga | aaaaggtatc | 1500 |
| accagcctcc | agatggacat | caaggttgct | ggcattaccg | aagaaatcat | gcagaaagct | 1560 |
| ttggaacagg | ctaaaggtgg | ccgtgctcat | atcttgggtg | aaatgtccaa | agcgctgggt | 1620 |
| gaagtccgct | ccgaaatttc | taatttggca | ccgcgcattg | aaacgatgag | cgtaccaaaa | 1680 |
| gacaaaatcc | gtgatgttat | cggaacgggc | ggaaaagtta | tccgtgaaat | cgtggcaacc | 1740 |

-continued

```
acaggtgcca aggtcgatat cgaagatgac ggaacggttc gtctgtcttc ttccgatcct    1800
gccaatattg aagcagcccg tgaatggatc aatggtattg ttgaagaacc ggaagtaggc    1860
aaaatctata acggtaaagt cgtcaatatc gttgatttcg gtgccttcgt aaacttcatg    1920
ggcggccgtg acggcttggt acatgtttcg gaaatcaaga cgaacgtgt caacaaggtc     1980 agcgatgtcc tgtctgaagg tcaggaagtc aaagtcaagg ttcttgaaat tgacaaccgt    2040
ggcaaggttc gcctgtctat gcgtgttgtc gatcaggaaa ccggcgcaga gctggatgat    2100
aaccgtccgc cacgtgagaa cgcagaacgt cgcggtggtg agcgtcctcg tcgtgatcgg    2160
ggccctcgtc gggaatctgg cgatcgtccg gcaagacgtg acatggaacc ggaatttgct    2220
ccggcattcc tgcgcaaaga tagctaa                                        2247
```

<210> SEQ ID NO 4
<211> LENGTH: 748
<212> TYPE: PRT
<213> ORGANISM: Zymomonas mobilis

<400> SEQUENCE: 4

```
Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
```

-continued

```
                275                 280                 285
Leu Arg Ile Gln Lys Leu Ala Lys Lys Leu Glu Ala Lys Ile Val Arg
290                 295                 300
Thr Ala Ile Leu Lys Glu Gly Arg Arg Ile Asp Gly Arg Asp Leu Lys
305                 310                 315                 320
Thr Val Arg Pro Ile Arg Ser Gln Val Gly Phe Leu Pro Arg Thr His
                325                 330                 335
Gly Ser Ala Leu Phe Thr Arg Gly Glu Thr Gln Ala Leu Val Ser Thr
            340                 345                 350
Thr Leu Gly Thr Ala Asp Ala Glu Gln Met Ile Asp Gly Leu Thr Gly
        355                 360                 365
Leu His Tyr Glu Arg Phe Met Leu His Tyr Asn Phe Pro Pro Tyr Ser
370                 375                 380
Val Gly Glu Val Gly Arg Phe Gly Ala Pro Gly Arg Arg Glu Ile Gly
385                 390                 395                 400
His Gly Lys Leu Ala Trp Arg Ala Leu His Pro Val Leu Pro Ser Lys
                405                 410                 415
Ala Asp Phe Pro Tyr Thr Ile Arg Val Leu Ser Asp Ile Thr Glu Ser
            420                 425                 430
Asn Gly Ser Ser Ser Met Ala Thr Val Cys Gly Gly Cys Leu Ala Leu
        435                 440                 445
Met Asp Ala Gly Val Pro Leu Thr Arg Pro Val Ser Gly Ile Ala Met
450                 455                 460
Gly Leu Ile Leu Glu Lys Asp Gly Phe Ala Ile Leu Ser Asp Ile Met
465                 470                 475                 480
Gly Asp Glu Asp His Leu Gly Asp Met Asp Phe Lys Val Ala Gly Thr
                485                 490                 495
Glu Lys Gly Ile Thr Ser Leu Gln Met Asp Ile Lys Val Ala Gly Ile
            500                 505                 510
Thr Glu Glu Ile Met Gln Lys Ala Leu Glu Gln Ala Lys Gly Gly Arg
        515                 520                 525
Ala His Ile Leu Gly Glu Met Ser Lys Ala Leu Gly Glu Val Arg Ser
530                 535                 540
Glu Ile Ser Asn Leu Ala Pro Arg Ile Glu Thr Met Ser Val Pro Lys
545                 550                 555                 560
Asp Lys Ile Arg Asp Val Ile Gly Thr Gly Gly Lys Val Ile Arg Glu
                565                 570                 575
Ile Val Ala Thr Thr Gly Ala Lys Val Asp Ile Glu Asp Asp Gly Thr
            580                 585                 590
Val Arg Leu Ser Ser Ser Asp Pro Ala Asn Ile Glu Ala Ala Arg Glu
        595                 600                 605
Trp Ile Asn Gly Ile Val Glu Pro Glu Val Gly Lys Ile Tyr Asn
610                 615                 620
Gly Lys Val Val Asn Ile Val Asp Phe Gly Ala Phe Val Asn Phe Met
625                 630                 635                 640
Gly Gly Arg Asp Gly Leu Val His Val Ser Glu Ile Lys Asn Glu Arg
                645                 650                 655
Val Asn Lys Val Ser Asp Val Leu Ser Glu Gly Gln Glu Val Lys Val
            660                 665                 670
Lys Val Leu Glu Ile Asp Asn Arg Gly Lys Val Arg Leu Ser Met Arg
        675                 680                 685
Val Val Asp Gln Glu Thr Gly Ala Glu Leu Asp Asp Asn Arg Pro Pro
690                 695                 700
```

-continued

Arg Glu Asn Ala Glu Arg Arg Gly Gly Glu Arg Pro Arg Arg Asp Arg
705                 710                 715                 720

Gly Pro Arg Arg Glu Ser Gly Asp Arg Pro Ala Arg Arg Asp Met Glu
                725                 730                 735

Pro Glu Phe Ala Pro Ala Phe Leu Arg Lys Asp Ser
            740                 745

<210> SEQ ID NO 5
<211> LENGTH: 2247
<212> TYPE: DNA
<213> ORGANISM: Zymomonas mobilis

<400> SEQUENCE: 5

| | |
|---|---|
| atgttcgata ttaaacgcca ggaaatcgat tggggcggga aaaaactgac actggaaacc | 60 |
| ggacaggttg cccgtcaggc agatggcgcc gtcattgcga ccttaggtga aacggtcgta | 120 |
| ttatgcgcgg taacggcagc aaaaacggta aagaaggtc aggatttctt tcctttgacc | 180 |
| gtccattatc aggaaaaata ttcagcagca ggccgtattc ccgtggcttt ttcaagcgt | 240 |
| gaacgtggcg caaccgaacg ggaaacgctg atttcacggt taatcgaccg tccaatccgt | 300 |
| cctctgtttc cggaaggttt ctataacgaa accttggtca ttgcgcaggt catgtcctat | 360 |
| gacggcgaga tgaaccgga tatcttggcg atgatcgccg cttctgcggc ccttgctctt | 420 |
| tccggtgtgc ctttccttgg tcccatcggt gctgcccgtg tgggttatca agatggcgag | 480 |
| ttcattctta acccgacctt ggaacagctt gaaaaaagtg atcttgatct ggttgtcggg | 540 |
| gctacccgtg atgccgtgat gatggttgaa tcggaagcga atgagcttcc cgaagaagtc | 600 |
| atgctcaatg ccgtttcttt tgcgcatgaa tctttacagc cggttatcaa agctatcatc | 660 |
| aatctggcag acaggccgc taaagagcct tgggaactgg tcagctatga tgacagcgca | 720 |
| ttggctgcca agtcgaaga actctgctac gacaatttcg ataaggccta tcgtctgact | 780 |
| cgtaaggctc agcgtgttga agccttgagc aaggccaaag cggttcttga cgaagccttc | 840 |
| ccagaagctg atccgacaga aaagctgcgt atccagaagc tcgcgaagaa gctggaagca | 900 |
| aaaatcgtcc gcaccgccat tctgaaagaa ggccggagaa ttgacggacg cgatctgaaa | 960 |
| acagttcgcc cgatccgctc tcaggttgga ttcttgcccc gcacgcatgg ttctgctctg | 1020 |
| tttacgcgcg gtgaaacaca ggctttggtt caaccaccc ttggaacggc ggatgctgaa | 1080 |
| cagatgatcg acggtttaac cggccttcat tatgaacgct tcatgctgca ttataacttc | 1140 |
| cctccttatt cggtcggtga agttggtcgt tttggggctc cgggtcgtcg tgaaatcggc | 1200 |
| catggtaaac tggcatggcg tgcgcttcat ccggttttgc cgagcaaggc tgatttcccg | 1260 |
| tataccatcc gcgttttgtc ggatatcacc gaatctaatg ttcctcttc catggcaacc | 1320 |
| gtttgcggtg gctgccttgc cttgatggat gccggtgttc ccttaacgcg tccggtttcc | 1380 |
| ggatcgccaa tgggtcttat tctggaaaaa gacggcttcg ctattttgtc ggatatcatg | 1440 |
| ggtgatgaag atcacttggg tgatatggac tttaaggtcg ccggtaccga aaaaggtatc | 1500 |
| accagcctcc agatggacat caaggttgct ggcattaccg aagaaatcat gcagaaagct | 1560 |
| ttggaacagg ctaaaggtgg ccgtgctcat atcttgggtg aaatgtccaa agcgctgggt | 1620 |
| gaagtccgct ccgaaatttc taatttggca ccgcgcattg aaacaatgag cgtaccaaaa | 1680 |
| gacaaaatcc gtgatgttat cggaacgggc ggaaaagtta ccgtgaaat cgtggcgacc | 1740 |
| acaggtgcca aggtcgatat cgaagatgac ggcacggttc gtctgtcttc ttccgatccg | 1800 |
| gccaatattg aagcagcccg tgaatggatc aatggtattg ttgaagaacc ggaagtaggc | 1860 |

```
aaaatctata acggtaaagt cgtcaatatc gttgatttcg gtgccttcgt aaacttcatg    1920
ggtggccgtg acggcttggt acatgtttcg gaaatcaaga acgaacgtgt caacaaggtc    1980
agcgatgtcc tgtctgaagg tcaggaagtc aaagtcaagg ttcttgaaat tgacaaccgt    2040
ggcaaggttc gcctgtctat gcgtgttgtc gatcaggaaa ccggcgcaga gctggatgat    2100
aaccgtccgc cacgtgagaa cgcagaacgt cgcggtggtg agcgtcctcg tcgtgatcgg    2160
ggccctcgtc gggaatctgg cgatcgtccg gcaagacgtg acatggaacc ggaatttgct    2220
ccggcattcc tgcgcaaaga tagctaa                                         2247
```

<210> SEQ ID NO 6
<211> LENGTH: 748
<212> TYPE: PRT
<213> ORGANISM: Zymomonas mobilis

<400> SEQUENCE: 6

```
Met Phe Asp Ile Lys Arg Gln Glu Ile Asp Trp Gly Gly Lys Lys Leu
  1               5                  10                  15

Thr Leu Glu Thr Gly Gln Val Ala Arg Gln Ala Asp Gly Ala Val Ile
             20                  25                  30

Ala Thr Leu Gly Glu Thr Val Leu Cys Ala Val Thr Ala Ala Lys
         35                  40                  45

Thr Val Lys Glu Gly Gln Asp Phe Phe Pro Leu Thr Val His Tyr Gln
 50                  55                  60

Glu Lys Tyr Ser Ala Ala Gly Arg Ile Pro Gly Gly Phe Phe Lys Arg
 65                  70                  75                  80

Glu Arg Gly Ala Thr Glu Arg Glu Thr Leu Ile Ser Arg Leu Ile Asp
             85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Glu Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
    290                 295                 300
```

```
Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
            325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly
            355                 360                 365

Leu His Tyr Glu Arg Phe Met Leu His Tyr Asn Phe Pro Pro Tyr Ser
        370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
            405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
        435                 440                 445

Met Asp Ala Gly Val Pro Leu Thr Arg Pro Val Ser Gly Ile Ala Met
450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
            485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
        515                 520                 525

Ala His Ile Leu Gly Glu Met Ser Lys Ala Leu Gly Glu Val Arg Ser
        530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
            565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Asn Ile Glu Ala Ala Arg Glu
        595                 600                 605

Trp Ile Asn Gly Ile Val Glu Glu Pro Glu Val Gly Lys Ile Tyr Asn
        610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
            645                 650                 655

Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Ala Glu Leu Asp Asp Asn Arg Pro Pro
        690                 695                 700

Arg Glu Asn Ala Glu Arg Arg Gly Gly Glu Arg Pro Arg Arg Asp Arg
705                 710                 715                 720
```

Gly Pro Arg Arg Glu Ser Gly Asp Arg Pro Ala Arg Arg Asp Met Glu
            725                 730                 735

Pro Glu Phe Ala Pro Ala Phe Leu Arg Lys Asp Ser
            740                 745

<210> SEQ ID NO 7
<211> LENGTH: 2265
<212> TYPE: DNA
<213> ORGANISM: Zymomonas mobilis

<400> SEQUENCE: 7

| | | | | | |
|---|---|---|---|---|---|
| atgttcgata | ttaaacgcca | ggaaatcgat | tggggcggaa | agaagctgac | gctggaaacc | 60 |
| ggacaggttg | cccgtcaggc | agatggcgcc | gtcatcgcga | ccttaggtga | aacggtcgtg | 120 |
| ctttgcgcgg | taacagcggc | caaaacggtt | aaagagggac | aggatttttt | ccctttaacg | 180 |
| gttcattatc | aagaaaaata | ttcagcagcc | ggtcgtatcc | ccgtggcctt | tttcaagcgt | 240 |
| gaacgtggtg | ctagcgaacg | cgaaactttg | gtttcacgct | tgattgatcg | tccaattcgc | 300 |
| cccctttttcc | cggacggttt | ttataacgaa | accttactta | tcgctcaggt | catgtcttat | 360 |
| gacggcgaaa | atgaacctga | catcttagcc | atgattgcgg | cctcggctgc | tcttgcgctt | 420 |
| tccggtgtgc | ctttcttggg | cccaattggt | gctgcgcgtg | ttggctatca | agatggcgaa | 480 |
| tatatttttaa | atccgacctt | ggctcagctc | gaaaacagcg | atcttgatct | ggtagtcggt | 540 |
| gcaacgcgcg | atgccgtgat | gatggttgaa | tcggaagcaa | aagagctatc | cgaagaaatc | 600 |
| atgcttgatg | cggtttcctt | tgcgcataaa | tctttacagc | ctgttatcaa | ggcgatcatc | 660 |
| aatcttgccg | agcaagccgc | gaaagaaccg | tgggagctct | caagctatga | tgacacagct | 720 |
| ttggctgcaa | aagttgaaga | actttgcaaa | gatagccttg | ataaggccta | tcgtctgacc | 780 |
| aaaaaaagtg | aacgtgtaga | ggctatttct | aaggccaaag | ccgttttgga | tgaagctttc | 840 |
| cccgatgctg | atgcctcgga | aaaactacgc | attcagaaat | ggcgaaaaa | acttgaagcc | 900 |
| aaaattgttc | gcactgcgat | cttaaaagaa | ggtcgtcgga | ttgatggtcg | tgatctaaaa | 960 |
| acggttcgtc | ctatccgttc | acaggttggt | ttcttacctc | ggacccatgg | gtctgcgctc | 1020 |
| tttacgcggg | gtgaaaccca | agccttggtt | tccacaaccc | ttggaaccgc | agatgctgag | 1080 |
| caaatgattg | atggcctgaa | tggccttcat | tacgaacgct | ttatgctgca | ttataacttc | 1140 |
| ccaccttatt | ccgttggtga | agtgggtcgt | tttggcgctc | ctggccgtcg | tgaaatcggt | 1200 |
| catggtaaac | tggcatggcg | tgctttacat | cctgtgcttc | ctagcaaggc | tgacttccct | 1260 |
| tatacgatcc | gcgttctatc | cgatattacg | gaatcaaacg | gttcttcctc | gatggcaacg | 1320 |
| gtctgcggtg | gctgtcttgc | tttgatggat | gcgggcgttc | ccttgaagcg | tccggtctcc | 1380 |
| ggcattgcga | tgggccttat | tcttgaaaaa | gatggttttg | ccattctttc | cgatattatg | 1440 |
| ggtgatgaag | atcacttagg | ggatatggac | tttaaggtag | ccggtacaga | agaaggcatt | 1500 |
| accagccttc | agatggacat | taaggttgct | ggtatcactg | aagaaatcat | gggtaaggct | 1560 |
| ttggaacagg | caaaagccgg | ccgtgcccat | atttttgggtg | aaatgtccaa | agctttgggt | 1620 |
| gaagttcgtt | cggaactttc | gaatttagcg | cctcgtattg | aaacaatgag | cgttcctaaa | 1680 |
| gacaaaattc | gtgatgttat | tggaactggc | ggtaaagtca | ttcgtgagat | tgttgcgaca | 1740 |
| accggcgcga | agttgacat | tgaagatgac | ggcaccgtac | gcttgtcttc | ttctgatccg | 1800 |
| gctcagatcg | aagctgcccg | taattggatt | accggtatca | tcgaagaacc | ggaagtcggc | 1860 |
| aaaatttata | acggtaaggt | tgtcaacatt | gttgatttcg | gtgccttttgt | gaatttcatg | 1920 |
| ggtggccgtg | atggtctggt | tcacgtctct | gaaattaaaa | acgagcgcgt | gaacaaggtc | 1980 |

```
agtgacgttc tggccgaagg ccaggaagtt aaggttaagg tgcttgaaat tgacaatcgc    2040
ggtaaagtcc gcttgtcaat gcgtgttgtc gatcaggaaa ctggcgcgga actggaagac    2100
aatcgtccgc ctagggaagc tcgtgaagtc agtgatcgcg gtccacgggg tgatcggcct    2160
cgtcgcgatc gtggcccacg tcgcgaaccg cagaatggtt caaaccattc aggccgtgat    2220
atggaacccg aatttgctcc ggcttttta cgaaaagatg attaa                     2265
```

<210> SEQ ID NO 8
<211> LENGTH: 754
<212> TYPE: PRT
<213> ORGANISM: Zymomonas mobilis

<400> SEQUENCE: 8

```
Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Ser Glu Arg Glu Thr Leu Val Ser Arg Leu Ile Asp
                85                  90                  95

Arg Pro Ile Arg Pro Leu Phe Pro Asp Gly Phe Tyr Asn Glu Thr Leu
            100                 105                 110

Leu Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Tyr Ile Leu Asn Pro Thr Leu Ala Gln Leu Glu Asn Ser Asp Leu Asp
                165                 170                 175

Leu Val Val Gly Ala Thr Arg Asp Ala Val Met Met Val Glu Ser Glu
            180                 185                 190

Ala Lys Glu Leu Ser Glu Glu Ile Met Leu Asp Ala Val Ser Phe Ala
        195                 200                 205

His Lys Ser Leu Gln Pro Val Ile Lys Ala Ile Asn Leu Ala Glu
    210                 215                 220

Gln Ala Ala Lys Glu Pro Trp Glu Leu Ser Ser Tyr Asp Asp Thr Ala
225                 230                 235                 240

Leu Ala Ala Lys Val Glu Glu Leu Cys Lys Asp Ser Leu Asp Lys Ala
                245                 250                 255

Tyr Arg Leu Thr Lys Lys Ser Glu Arg Val Glu Ala Ile Ser Lys Ala
            260                 265                 270

Lys Ala Val Leu Asp Glu Ala Phe Pro Asp Ala Asp Ala Ser Glu Lys
        275                 280                 285

Leu Arg Ile Gln Lys Leu Ala Lys Lys Leu Glu Ala Lys Ile Val Arg
    290                 295                 300

Thr Ala Ile Leu Lys Glu Gly Arg Arg Ile Asp Gly Arg Asp Leu Lys
305                 310                 315                 320
```

```
Thr Val Arg Pro Ile Arg Ser Gln Val Gly Phe Leu Pro Arg Thr His
            325                 330                 335

Gly Ser Ala Leu Phe Thr Arg Gly Glu Thr Gln Ala Leu Val Ser Thr
        340                 345                 350

Thr Leu Gly Thr Ala Asp Ala Glu Gln Met Ile Asp Gly Leu Asn Gly
        355                 360                 365

Leu His Tyr Glu Arg Phe Met Leu His Tyr Asn Phe Pro Pro Tyr Ser
        370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
            435                 440                 445

Met Asp Ala Gly Val Pro Leu Lys Arg Pro Val Ser Gly Ile Ala Met
    450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Glu Gly Ile Thr Ser Leu Gln Met Asp Ile Lys Val Ala Gly Ile
            500                 505                 510

Thr Glu Glu Ile Met Gly Lys Ala Leu Glu Gln Ala Lys Ala Gly Arg
        515                 520                 525

Ala His Ile Leu Gly Glu Met Ser Lys Ala Leu Gly Glu Val Arg Ser
    530                 535                 540

Glu Leu Ser Asn Leu Ala Pro Arg Ile Glu Thr Met Ser Val Pro Lys
545                 550                 555                 560

Asp Lys Ile Arg Asp Val Ile Gly Thr Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Gln Ile Glu Ala Ala Arg Asn
        595                 600                 605

Trp Ile Thr Gly Ile Ile Glu Glu Pro Glu Val Gly Lys Ile Tyr Asn
    610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ala Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Ala Glu Leu Glu Asp Asn Arg Pro Pro
    690                 695                 700

Arg Glu Ala Arg Glu Val Ser Asp Arg Gly Pro Arg Gly Asp Arg Pro
705                 710                 715                 720

Arg Arg Asp Arg Gly Pro Arg Arg Glu Pro Gln Asn Gly Ser Asn His
                725                 730                 735

Ser Gly Arg Asp Met Glu Pro Glu Phe Ala Pro Ala Phe Leu Arg Lys
```

-continued

```
                  740             745             750

Asp Asp

<210> SEQ ID NO 9
<211> LENGTH: 723
<212> TYPE: PRT
<213> ORGANISM: artificial sequence
<220> FEATURE:
<223> OTHER INFORMATION: engineered fusion protein

<400> SEQUENCE: 9

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Gly Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
    290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350
```

```
Thr Leu Gly Thr Ala Asp Ala Glu Gln Met Ile Asp Gly Leu Thr Gly
            355                 360                 365

Leu His Tyr Glu Arg Phe Met Leu His Tyr Asn Phe Pro Pro Tyr Ser
    370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Met Ala Thr Val Cys Gly Cys Leu Ala Leu
        435                 440                 445

Met Asp Ala Gly Val Pro Leu Thr Arg Pro Val Ser Gly Ile Ala Met
    450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
    515                 520                 525

Ala His Ile Leu Gly Glu Met Ser Lys Ala Leu Gly Glu Val Arg Ser
    530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Asn Ile Glu Ala Ala Arg Glu
    595                 600                 605

Trp Ile Asn Gly Ile Val Glu Glu Pro Glu Val Gly Lys Ile Tyr Asn
    610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
    675                 680                 685

Val Val Asp Gln Glu Thr Gly Ala Glu Leu Asp Asp Asn Arg Pro Pro
    690                 695                 700

Arg Glu Asn Ala Glu Pro Val Ser Tyr Thr His Leu Asn Pro Glu Ala
705                 710                 715                 720

Leu Val Gly
```

<210> SEQ ID NO 10
<211> LENGTH: 697
<212> TYPE: PRT
<213> ORGANISM: artificial sequence
<220> FEATURE:
<223> OTHER INFORMATION: engineered fusion protien

<400> SEQUENCE: 10

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Ile Asn Leu Ala Glu
210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
        290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly
        355                 360                 365

Leu His Tyr Glu Arg Phe Met Leu His Tyr Asn Phe Pro Pro Tyr Ser
        370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys

```
            405                 410                 415
Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
            435                 440                 445

Met Asp Ala Gly Val Pro Leu Thr Arg Pro Val Ser Gly Ile Ala Met
450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
        515                 520                 525

Ala His Ile Leu Gly Glu Met Ser Lys Ala Leu Gly Glu Val Arg Ser
    530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Asn Ile Glu Ala Ala Arg Glu
        595                 600                 605

Trp Ile Asn Gly Ile Val Glu Glu Pro Glu Val Gly Lys Ile Tyr Asn
    610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Leu Val
    690                 695

<210> SEQ ID NO 11
<211> LENGTH: 378
<212> TYPE: PRT
<213> ORGANISM: artificial sequence
<220> FEATURE:
<223> OTHER INFORMATION: engineered fusion protein

<400> SEQUENCE: 11

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
```

-continued

```
                65                  70                  75                  80
            Glu Arg Gly Ala Thr Glu Arg Glu Thr Leu Ile Ser Arg Leu Ile Asp
                            85                  90                  95

Arg Pro Ile Arg Pro Leu Phe Pro Glu Gly Phe Tyr Asn Glu Thr Leu
                        100                 105                 110

Val Ile Ala Gln Val Met Ser Tyr Asp Gly Glu Asn Glu Pro Asp Ile
                        115                 120                 125

Leu Ala Met Ile Ala Ala Ser Ala Ala Leu Ala Leu Ser Gly Val Pro
                        130                 135                 140

Phe Leu Gly Pro Ile Gly Ala Ala Arg Val Gly Tyr Gln Asp Gly Glu
            145                 150                 155                 160

Phe Ile Leu Asn Pro Thr Leu Glu Gln Leu Glu Lys Ser Asp Leu Asp
                        165                 170                 175

Leu Val Val Gly Ala Thr Arg Asp Ala Val Met Met Val Glu Ser Glu
                        180                 185                 190

Ala Asn Glu Leu Pro Glu Glu Val Met Leu Asn Ala Val Ser Phe Ala
                        195                 200                 205

His Glu Ser Leu Gln Pro Val Ile Lys Ala Ile Ile Asn Leu Ala Glu
                        210                 215                 220

Gln Ala Ala Lys Glu Pro Trp Glu Leu Val Ser Tyr Asp Asp Ser Ala
            225                 230                 235                 240

Leu Ala Ala Lys Val Glu Glu Leu Cys Tyr Asp Asn Phe Asp Lys Ala
                        245                 250                 255

Tyr Arg Leu Thr Arg Lys Ala Glu Arg Val Asp Ala Leu Ser Lys Ala
                        260                 265                 270

Lys Ala Val Leu Asp Glu Ala Phe Pro Glu Ala Asp Pro Thr Glu Lys
                        275                 280                 285

Leu Arg Ile Gln Lys Leu Ala Lys Lys Leu Glu Ala Lys Ile Val Arg
                        290                 295                 300

Thr Ala Ile Leu Lys Glu Gly Arg Arg Ile Asp Gly Arg Asp Leu Lys
            305                 310                 315                 320

Thr Val Arg Pro Ile Arg Ser Gln Val Gly Phe Leu Pro Arg Thr His
                        325                 330                 335

Gly Ser Ala Leu Phe Thr Arg Gly Glu Thr Gln Ala Leu Val Ser Thr
                        340                 345                 350

Thr Leu Gly Thr Ala Asp Ala Glu Gln Met Ile Asp Gly Leu Thr Gly
                        355                 360                 365

Thr Ser Val Thr Glu Asp His Phe Ala Glu
                        370                 375

<210> SEQ ID NO 12
<211> LENGTH: 49
<212> TYPE: PRT
<213> ORGANISM: artificial sequence
<220> FEATURE:
<223> OTHER INFORMATION: engineered fusion protein

<400> SEQUENCE: 12

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
                20                  25                  30

Asn Ala Glu Pro Val Ser Tyr Thr His Leu Asn Pro Glu Ala Leu Val
            35                  40                  45

Gly
```

<210> SEQ ID NO 13
<211> LENGTH: 474
<212> TYPE: DNA
<213> ORGANISM: Zymomonas mobilis

<400> SEQUENCE: 13

| | | | | |
|---|---|---|---|---|
| gtgacctctg ctgtgccatc aaatacgaaa aaaaagctgg tgattgcttc cgatcacgca | 60 |
| gcatttgagt tgaaatcaac cttgattact tggctgaaag agcttggtca tgaggtcgaa | 120 |
| gaccttggcc ctcatgaaaa ccattcagtc gattatcccg attacggtta taagctggct | 180 |
| gtcgctatcg cagaaaaaac cgctgatttc ggtattgctt tatgtggctc gggaatcggt | 240 |
| atctcgatcg ctgtcaatcg ccatccggct gcccgttgcg ctttgattac ggataacctt | 300 |
| accgcccgtt tggcaagaga acataacaat gccaatgtta tcgctatggg tgcgagattg | 360 |
| atcggcattg aaaccgctaa ggattgtatt tcagctttcc ttgcaacgcc gtttggaggt | 420 |
| gaacgtcatg ttcgccgtat cgataaactt tcgaatcctc agttcaatat ctag | 474 |

<210> SEQ ID NO 14
<211> LENGTH: 157
<212> TYPE: PRT
<213> ORGANISM: Zymomonas mobilis

<400> SEQUENCE: 14

Met Thr Ser Ala Val Pro Ser Asn Thr Lys Lys Leu Val Ile Ala
1               5                   10                  15

Ser Asp His Ala Ala Phe Glu Leu Lys Ser Thr Leu Ile Thr Trp Leu
            20                  25                  30

Lys Glu Leu Gly His Glu Val Glu Asp Leu Gly Pro His Glu Asn His
        35                  40                  45

Ser Val Asp Tyr Pro Asp Tyr Gly Tyr Lys Leu Ala Val Ala Ile Ala
    50                  55                  60

Glu Lys Thr Ala Asp Phe Gly Ile Ala Leu Cys Gly Ser Gly Ile Gly
65                  70                  75                  80

Ile Ser Ile Ala Val Asn Arg His Pro Ala Ala Arg Cys Ala Leu Ile
                85                  90                  95

Thr Asp Asn Leu Thr Ala Arg Leu Ala Arg Glu His Asn Asn Ala Asn
            100                 105                 110

Val Ile Ala Met Gly Ala Arg Leu Ile Gly Ile Glu Thr Ala Lys Asp
        115                 120                 125

Cys Ile Ser Ala Phe Leu Ala Thr Pro Phe Gly Gly Glu Arg His Val
    130                 135                 140

Arg Arg Ile Asp Lys Leu Ser Asn Pro Gln Phe Asn Ile
145                 150                 155

<210> SEQ ID NO 15
<211> LENGTH: 660
<212> TYPE: DNA
<213> ORGANISM: Escherichia coli

<400> SEQUENCE: 15

| | | | | |
|---|---|---|---|---|
| atgacgcagg atgaattgaa aaaagcagta ggatgggcgg cacttcagta tgttcagccc | 60 |
| ggcaccattg ttggtgtagg tacaggttcc accgccgcac actttattga cgcgctcggt | 120 |
| acaatgaaag ccagattga aggggccgtt tccagttcag atgcttccac tgaaaaactg | 180 |
| aaaagcctcg gcattcacgt ttttgatctc aacgaagtcg acagccttgg catctacgtt | 240 |

```
gatggcgcag atgaaatcaa cggccacatg caaatgatca aaggcggcgg cgcggcgctg      300
acccgtgaaa aaatcattgc ttcggttgca gaaaaattta tctgtattgc agacgcttcc      360
aagcaggttg atattctggg taaattcccg ctgccagtag aagttatccc gatggcacgt      420
agtgcagtgg cgcgtcagct ggtgaaactg ggcggtcgtc cggaataccg tcagggcgtg      480
gtgaccgata atggcaacgt gatcctcgac gtccacggca tggaaatcct tgacccgata      540
gcgatggaaa acgccataaa tgcgattcct ggcgtggtga ctgttggctt gtttgctaac      600
cgtggcgcgg acgttgcgct gattggcaca cctgacggtg tcaaaaccat tgtgaaatga      660
```

<210> SEQ ID NO 16
<211> LENGTH: 219
<212> TYPE: PRT
<213> ORGANISM: Escherichia coli

<400> SEQUENCE: 16

```
Met Thr Gln Asp Glu Leu Lys Lys Ala Val Gly Trp Ala Ala Leu Gln
  1               5                  10                  15

Tyr Val Gln Pro Gly Thr Ile Val Gly Val Gly Thr Gly Ser Thr Ala
             20                  25                  30

Ala His Phe Ile Asp Ala Leu Gly Thr Met Lys Gly Gln Ile Glu Gly
         35                  40                  45

Ala Val Ser Ser Ser Asp Ala Ser Thr Glu Lys Leu Lys Ser Leu Gly
     50                  55                  60

Ile His Val Phe Asp Leu Asn Glu Val Asp Ser Leu Gly Ile Tyr Val
 65                  70                  75                  80

Asp Gly Ala Asp Glu Ile Asn Gly His Met Gln Met Ile Lys Gly Gly
                 85                  90                  95

Gly Ala Ala Leu Thr Arg Glu Lys Ile Ile Ala Ser Val Ala Glu Lys
            100                 105                 110

Phe Ile Cys Ile Ala Asp Ala Ser Lys Gln Val Asp Ile Leu Gly Lys
        115                 120                 125

Phe Pro Leu Pro Val Glu Val Ile Pro Met Ala Arg Ser Ala Val Ala
    130                 135                 140

Arg Gln Leu Val Lys Leu Gly Gly Arg Pro Glu Tyr Arg Gln Gly Val
145                 150                 155                 160

Val Thr Asp Asn Gly Asn Val Ile Leu Asp Val His Gly Met Glu Ile
                165                 170                 175

Leu Asp Pro Ile Ala Met Glu Asn Ala Ile Asn Ala Ile Pro Gly Val
            180                 185                 190

Val Thr Val Gly Leu Phe Ala Asn Arg Gly Ala Asp Val Ala Leu Ile
        195                 200                 205

Gly Thr Pro Asp Gly Val Lys Thr Ile Val Lys
    210                 215
```

<210> SEQ ID NO 17
<211> LENGTH: 1185
<212> TYPE: DNA
<213> ORGANISM: Actinoplanes missouriensis

<400> SEQUENCE: 17

```
atgagtgtcc aagctacacg cgaagataaa tttagctttg cttgtggac agttgggtgg      60 caggcccgtg acgcctttgg tgatgccacg cgtaccgccc ttgatccggt cgaagcagtt      120
cataaacttg ccgaaatcgg agcctatggc attacatttc atgatgatga cttggtcccc      180
ttcggttcgg atgctcagac acgggatggt atcattgctg gtttcaaaaa agcccttgat      240
```

```
gaaaccggtt tgatcgttcc tatggttacc acaaatttgt ttacgcatcc ggttttaaa      300 gacggcgggt ttacctctaa cgatcgttct gtgcgccggt atgctatccg gaaagttttg    360
agacagatgg atcttggtgc ggaactgggg gccaaaacgc ttgtcttatg gggcggcaga    420
gaaggtgcga aatatgattc agcaaaagat gttagtgccg ccttggatcg ttatcgcgaa    480
gcactgaatc ttctggcaca atatagcgaa gacagaggct atggacttcg ttttgcaatt    540
gaaccgaaac ctaatgaacc acgtggcgat attctgctgc ctaccgcagg ccatgctatt    600
gcctttgtgc aagaattaga acggcccgaa cttttggca tcaatccaga aaccgggcat      660
gaacagatgt caaacttgaa ttttacccag gggattgctc aggctttgtg cataaaaaa     720 cttttttcata ttgatttgaa tggacaacat ggtcccaagt ttgatcagga ccttgtcttt    780
ggtcatggtg accttttaaa tgcctttagc ctggtcgatt tgttagaaaa tggtccagat    840
ggtgccccgg cttatgatgg cccgcgccat tttgattata aaccatctcg tactgaagat    900
tatgatggcg tttgggaatc agcgaaagcc aatatccgta tgtatctttt attaaaagaa   960
cgtgccaaag cgtttagagc tgatccggaa gttcaggaag cactggcagc aagcaaagtt   1020
gccgaattga aaaccccaac gttgaatcct ggtgaaggct atgcagaact gttagcagat   1080
cgcagtgctt ttgaagatta tgatgccgat gctgttggtg cgaaaggttt tggtttcgtg    1140
aaattgaacc aattggccat tgaacattta ttaggtgccc gctag                    1185
```

<210> SEQ ID NO 18
<211> LENGTH: 394
<212> TYPE: PRT
<213> ORGANISM: Actinoplanes missouriensis

<400> SEQUENCE: 18

```
Met Ser Val Gln Ala Thr Arg Glu Asp Lys Phe Ser Phe Gly Leu Trp
1               5                   10                  15

Thr Val Gly Trp Gln Ala Arg Asp Ala Phe Gly Asp Ala Thr Arg Thr
            20                  25                  30

Ala Leu Asp Pro Val Glu Ala Val His Lys Leu Ala Glu Ile Gly Ala
        35                  40                  45

Tyr Gly Ile Thr Phe His Asp Asp Leu Val Pro Phe Gly Ser Asp
    50                  55                  60

Ala Gln Thr Arg Asp Gly Ile Ile Ala Gly Phe Lys Lys Ala Leu Asp
65                  70                  75                  80

Glu Thr Gly Leu Ile Val Pro Met Val Thr Thr Asn Leu Phe Thr His
                85                  90                  95

Pro Val Phe Lys Asp Gly Gly Phe Thr Ser Asn Asp Arg Ser Val Arg
            100                 105                 110

Arg Tyr Ala Ile Arg Lys Val Leu Arg Gln Met Asp Leu Gly Ala Glu
        115                 120                 125

Leu Gly Ala Lys Thr Leu Val Leu Trp Gly Gly Arg Glu Gly Ala Glu
    130                 135                 140

Tyr Asp Ser Ala Lys Asp Val Ser Ala Ala Leu Asp Arg Tyr Arg Glu
145                 150                 155                 160

Ala Leu Asn Leu Leu Ala Gln Tyr Ser Glu Asp Arg Gly Tyr Gly Leu
                165                 170                 175

Arg Phe Ala Ile Glu Pro Lys Pro Asn Glu Pro Arg Gly Asp Ile Leu
            180                 185                 190

Leu Pro Thr Ala Gly His Ala Ile Ala Phe Val Gln Glu Leu Glu Arg
        195                 200                 205
```

Pro Glu Leu Phe Gly Ile Asn Pro Glu Thr Gly His Glu Gln Met Ser
    210                 215                 220

Asn Leu Asn Phe Thr Gln Gly Ile Ala Gln Ala Leu Trp His Lys Lys
225                 230                 235                 240

Leu Phe His Ile Asp Leu Asn Gly Gln His Gly Pro Lys Phe Asp Gln
                245                 250                 255

Asp Leu Val Phe Gly His Gly Asp Leu Leu Asn Ala Phe Ser Leu Val
                260                 265                 270

Asp Leu Leu Glu Asn Gly Pro Asp Gly Ala Pro Ala Tyr Asp Gly Pro
            275                 280                 285

Arg His Phe Asp Tyr Lys Pro Ser Arg Thr Glu Asp Tyr Asp Gly Val
        290                 295                 300

Trp Glu Ser Ala Lys Ala Asn Ile Arg Met Tyr Leu Leu Lys Glu
305                 310                 315                 320

Arg Ala Lys Ala Phe Arg Ala Asp Pro Glu Val Gln Glu Ala Leu Ala
                325                 330                 335

Ala Ser Lys Val Ala Glu Leu Lys Thr Pro Thr Leu Asn Pro Gly Glu
                340                 345                 350

Gly Tyr Ala Glu Leu Leu Ala Asp Arg Ser Ala Phe Glu Asp Tyr Asp
            355                 360                 365

Ala Asp Ala Val Gly Ala Lys Gly Phe Gly Phe Val Lys Leu Asn Gln
        370                 375                 380

Leu Ala Ile Glu His Leu Leu Gly Ala Arg
385                 390

<210> SEQ ID NO 19
<211> LENGTH: 663
<212> TYPE: DNA
<213> ORGANISM: Zymomonas mobilis

<400> SEQUENCE: 19
atgagtaaat taccccctgat tgctccctct atcctttcgg cggatttgc ccatttggga      60 gatgaggtcg cggcgataga tcaggccggt gccgattgga tccatattga tgtgatggat     120
ggccatttcg tgccgaatat caccataggc cccatggttg tgaaggcttt gcgtccctat     180
agccaaaagc cttttgatgt ccatttgatg attgcgcctg tcgatcaata tcgaggct      240 ttttctgaag cgggtgctga tattatcagt ttccatcccg aagcgggcgc gcatccccat     300
cgcactattc agcatatcaa atcattgggc aaaaagcgg gattagtttt taatccggcg     360
acccctttaa gctggcttga ttatctaatg atgatcttg atctgattat ggtgatgagc     420
gttaaccccg ttttggcgg ccaaaaattt atcaaaaccc aattagaaaa gattaaagat     480
atccgtcaaa gaattaccgc ctctgggcgg gatatccgct tggaagtgga tgcggaatt     540 gatgccacga ctgcaccgct tgccgtcgaa gccggtgccg atgttttggt cgcgggaacg     600
gccagcttta aggcggcgc aacatgttac accgataata tcaggatatt gcgtaaatca     660
tga                                                                  663

<210> SEQ ID NO 20
<211> LENGTH: 220
<212> TYPE: PRT
<213> ORGANISM: Zymomonas mobilis

<400> SEQUENCE: 20

Met Ser Lys Leu Pro Leu Ile Ala Pro Ser Ile Leu Ser Ala Asp Phe
1               5                   10                  15

```
Ala His Leu Gly Asp Glu Val Ala Ile Asp Gln Ala Gly Ala Asp
            20                  25                  30

Trp Ile His Ile Asp Val Met Asp Gly His Phe Val Pro Asn Ile Thr
            35                  40                  45

Ile Gly Pro Met Val Val Lys Ala Leu Arg Pro Tyr Ser Gln Lys Pro
50                  55                  60

Phe Asp Val His Leu Met Ile Ala Pro Val Asp Gln Tyr Ile Glu Ala
65                  70                  75                  80

Phe Ser Glu Ala Gly Ala Asp Ile Ile Ser Phe His Pro Glu Ala Gly
                85                  90                  95

Ala His Pro His Arg Thr Ile Gln His Ile Lys Ser Leu Gly Lys Lys
                100                 105                 110

Ala Gly Leu Val Phe Asn Pro Ala Thr Pro Leu Ser Trp Leu Asp Tyr
            115                 120                 125

Leu Met Asp Asp Leu Asp Leu Ile Met Val Met Ser Val Asn Pro Gly
130                 135                 140

Phe Gly Gly Gln Lys Phe Ile Lys Thr Gln Leu Glu Lys Ile Lys Asp
145                 150                 155                 160

Ile Arg Gln Arg Ile Thr Ala Ser Gly Arg Asp Ile Arg Leu Glu Val
                165                 170                 175

Asp Gly Gly Ile Asp Ala Thr Thr Ala Pro Leu Ala Val Glu Ala Gly
                180                 185                 190

Ala Asp Val Leu Val Ala Gly Thr Ala Ser Phe Lys Gly Gly Ala Thr
            195                 200                 205

Cys Tyr Thr Asp Asn Ile Arg Ile Leu Arg Lys Ser
        210                 215                 220

<210> SEQ ID NO 21
<211> LENGTH: 304
<212> TYPE: DNA
<213> ORGANISM: artificial sequence
<220> FEATURE:
<223> OTHER INFORMATION: mutant promoter of the Z. mobilis
      glyceraldehyde-3-phosphate dehydrogenase gene

<400> SEQUENCE: 21
gttcgatcaa caacccgaat cctatcgtaa tgatgttttg cccgatcagc ctcaatcgac      60
aattttacgc gtttcgatcg aagcagggac gacaattggc tgggaacggt atacttgaat    120
aaatggtctt cgttatggta ttgatgtttt tggtgcatcg gccccggcga atgatctata    180
tgctcatttc ggcttgaccg cagtcggcat cacgaacaag gtgttggccg cgatcgccgg    240
taagtcggca cgttaaaaaa tagctatgga atataatagc tactaataag ttaggagaat    300
aaac                                                                 304

<210> SEQ ID NO 22
<211> LENGTH: 903
<212> TYPE: DNA
<213> ORGANISM: artificial sequence
<220> FEATURE:
<223> OTHER INFORMATION: RPI expression cassette constructed

<400> SEQUENCE: 22
ccatggcgag ctcgttcgat caacaacccg aatcctatcg taatgatgtt ttgcccgatc      60
agcctcaatc gacaatttta cgcgtttcga tcgaagcagg gacgacaatt ggctgggaac    120
ggtatactgg aataaatggt cttcgttatg gtattgatgt ttttggtgca tcggccccgg    180
```

```
cgaatgatct atatgctcat ttcggcttga ccgcagtcgg catcacgaac aaggtgttgg      240
ccgcgatcgc cggtaagtcg gcacgttaaa aaatagctat ggaatataat agctacttaa      300
taagttagga gaataaacgt gacctctgct gtgccatcaa atacgaaaaa aaagctggtg      360
attgcttccg atcacgcagc atttgagttg aaatcaacct tgattacttg gctgaaagag      420
cttggtcatg aggtcgaaga ccttggccct catgaaaacc attcagtcga ttatcccgat      480
tacggttata agctggctgt cgctatcgca gaaaaaaccg ctgatttcgg tattgcttta      540
tgtggctcgg aatcggtat ctcgatcgct gtcaatcgcc atccggctgc ccgttgcgct       600
ttgattacgg ataaccttac cgcccgtttg gcaagagaac ataacaatgc caatgttatc      660
gctatgggtg cgagattgat cggcattgaa accgctaagg attgtatttc agctttcctt      720
gcaacgccgt ttggaggtga acgtcatgtt cgccgtatcg ataaactttc gaatcctcag      780
ttcaatatct agctcgaggc ggcctgaacg tactgcaagt cctgacgtca ctgtgcagtc      840
cgttggcccg gttatcggta gcgataccgg gcattttttt aaggaacgat cgatagcggc      900
cgc                                                                   903

<210> SEQ ID NO 23
<211> LENGTH: 38
<212> TYPE: DNA
<213> ORGANISM: artificial sequence
<220> FEATURE:
<223> OTHER INFORMATION: primer

<400> SEQUENCE: 23
tcactcatgg ccggcctgcg tataatattt gcccatgg                              38

<210> SEQ ID NO 24
<211> LENGTH: 37
<212> TYPE: DNA
<213> ORGANISM: artificial sequence
<220> FEATURE:
<223> OTHER INFORMATION: primer

<400> SEQUENCE: 24
ctactcatcc tgcaggctga tgaatgctca tccggaa                               37

<210> SEQ ID NO 25
<211> LENGTH: 10250
<212> TYPE: DNA
<213> ORGANISM: artificial sequence
<220> FEATURE:
<223> OTHER INFORMATION: constructed plasmid

<400> SEQUENCE: 25
ctagtgttcg atcaacaacc cgaatcctat cgtaatgatg ttttgcccga tcagcctcaa       60
tcgacaattt tacgcgtttc gatcgaagca gggacgacaa ttggctggga acggtatact      120
tgaataaatg gtcttcgtta tggtattgat gtttttggtg catcggcccc ggcgaatgat      180
ctatatgctc atttcggctt gaccgcagtc ggcatcacga acaaggtgtt ggccgcgatc      240
gccggtaagt cggcacgtta aaaatagct atggaatata atagctacta ataagttagg       300
agaataaaca tgagtgtcca agctacacgc gaagataaat ttagctttgg cttgtggaca      360
gttgggtggc aggcccgtga cgcctttggt gatgccacgc gtaccgccct tgatccggtc      420
gaagcagttc ataaacttgc cgaaatcgga gcctatggca ttacatttca tgatgatgac      480 ttggtccccct tcggttcgga tgctcagaca cgggatggta tcattgctgg tttcaaaaaa     540
gcccttgatg aaaccggttt gatcgttcct atggttacca caaatttgtt tacgcatccg      600
```

```
gtttttaaag acggcgggtt tacctctaac gatcgttctg tgcgccggta tgctatccgg      660
aaagttttga gacagatgga tcttggtgcg gaactggggg ccaaaacgct tgtcttatgg      720
ggcggcagag aaggtgcgga atatgattca gcaaaagatg ttagtgccgc cttggatcgt      780
tatcgcgaag cactgaatct tctggcacaa tatagcgaag acagaggcta tggacttcgt      840
tttgcaattg aaccgaaacc taatgaacca cgtggcgata ttctgctgcc taccgcaggc      900
catgctattg cctttgtgca agaattagaa cggcccgaac tttttggcat caatccagaa      960
accgggcatg aacagatgtc aaacttgaat tttacccagg ggattgctca ggctttgtgg     1020
cataaaaaac ttttttcatat tgatttgaat ggacaacatg gtcccaagtt tgatcaggac    1080
cttgtctttg gtcatggtga ccttttaaat gcctttagcc tggtcgattt gttagaaaat     1140
ggtccagatg gtgccccggc ttatgatggc ccgcgccatt ttgattataa accatctcgt     1200
actgaagatt atgatggcgt ttgggaatca gcgaaagcca atatccgtat gtatcttta      1260 ttaaaagaac gtgccaaagc gtttagagct gatccggaag ttcaggaagc actggcagca     1320
agcaaagttg ccgaattgaa accccaacg ttgaatcctg gtgaaggcta tgcagaactg      1380
ttagcagatc gcagtgcttt tgaagattat gatgccgatg ctgttggtgc gaaaggtttt     1440
ggtttcgtga aattgaacca attggccatt gaacatttat aggtgcccg ctagtctaga      1500 tgactgtata aaaccacagc caatcaaacg aaaccaggct atactcaagc ctggtttttt     1560
gatggatttt cagcgtggcg caggcaggtt ttatcttaac ccgacactgg cgggacaccc     1620
cgcaagggac agaagtctcc ttctggctgg cgacggacaa cgggccaagc ttccagttac     1680
tcaatacgta acaataatca gtttatccta actatagaat cgcatgagaa gcgataacgt     1740
ttcaccataa gcaatatatt cattgcaaca gtggaattgc cttatgcgtc aaggaaggat     1800
agatcattga cggactgagt tcaaaaagag actggtctaa aagattttaa gaaaggtttc     1860
gatatgtata tcgggataga tcttggcacc tcgggcgtaa aagttatttt gctcaacgag     1920
cagggtgagg tggttgctgc gcaaacggaa aagctgaccg tttcgcgccc gcatccactc     1980
tggtcggaac aagacccgga acagtggtgg caggcaactg atcgcgcaat gaaagctctg     2040
ggcgatcagc attctctgca ggacgttaaa gcattgggta ttgccggcca gatgcacgga     2100
gcaaccttgc tggatgctca gcaacgggtg ttacgccctg ccatttttgtg gaacgacggg    2160 cgctgtgcgc aagagtgcac tttgctggaa gcgcgagttc cgcaatcgcg ggtgattacc     2220
ggcaacctga tgatgcccgg atttactgcg cctaaattgc tatgggttca gcggcatgag     2280
ccggagatat tccgtcaaat cgacaaagta ttattaccga aagattactt gcgtctgcgt     2340
atgacggggg agtttgccag cgatatgtct gacgcagctg gcaccatgtg gctggatgtc     2400
gcaaagcgtg actggagtga cgtcatgctg caggcttgcg acttatctcg tgaccagatg     2460
cccgcattat acgaaggcag cgaaattact ggtgctttgt tacctgaagt tgcgaaagcg     2520
tggggtatgg cgacggtgcc agttgtcgca ggcggtggcg acaatgcagc tggtgcagtt     2580
ggtgtgggaa tggttgatgc taatcaggca atgttatcgc tggggacgtc gggggtctat    2640
tttgctgtca gcgaagggtt cttaagcaag ccagaaagcg ccgtacatag ctttttgccat   2700 gcgctaccgc aacgttggca tttaatgtct gtgatgctga gtgcagcgtc gtgtctggat    2760
tgggccgcga aattaaccgg cctgagcaat gtcccagctt taatcgctgc agctcaacag   2820
gctgatgaaa gtgccgagcc agtttggttt ctgccttatc tttccggcga gcgtacgcca   2880
cacaataatc cccaggcgaa gggggttttc tttggtttga ctcatcaaca tggccccaat  2940
```

```
gaactggcgc gagcagtgct ggaaggcgtg ggttatgcgc tggcagatgg catggatgtc    3000
gtgcatgcct gcggtattaa accgcaaagt gttacgttga ttggggcgg ggcgcgtagt    3060 gagtactggc gtcagatgct ggcggatatc agcggtcagc agctcgatta ccgtacgggg    3120
ggggatgtgg ggccagcact gggcgcagca aggctggcgc agatcgcggc gaatccagag    3180
aaatcgctca ttgaattgtt gccgcaacta ccgttagaac agtcgcatct accagatgcg    3240
cagcgttatg ccgcttatca gccacgacga gaaacgttcc gtcgcctcta tcagcaactt    3300
ctgccattaa tggcgtaaac gttatcccct gcctgaccgg gtgggggata attcacatct    3360
atatatctca gtaattaatt aatatttagt acgaatttat tctgaaaatc atttgttaat    3420 ggcattttc agttttgtct ttcgttggtt actcgtaatg tatcgctggt agatatggag    3480
atcgttatga aaacctcaaa gactgtggca aaactattat ttgttgtcgg ggcgctggtt    3540
tatctggttg ggctatggat ctcatgccca ttgttaagtg gaaaaggcta ttttcttggc    3600
gtgttaatga cagcaacttt tggcaactat gcgaattcgc gatcgcataa cttcgtataa    3660
tgtatgctat acgaagttat gcggccgcag cacaggatga cgcctaacaa ttcattcaag    3720
ccgacaccgc ttcgcggcgc ggcttaattc aggagttaaa catcatgagg gaagcggtga    3780
tcgccgaagt atcgactcaa ctatcagagg tagttggcgt catcgagcgc catctcgaac    3840
cgacgttgct ggccgtacat ttgtacggct ccgcagtgga tggcggcctg aagccacaca    3900
gtgatattga tttgctggtt acggtgactg taaggcttga tgaaacaacg cggcgagctt    3960
tgatcaacga ccttttggaa acttcggctt ccccctggaga gagcgagatt ctccgcgctg    4020
tagaagtcac cattgttgtg cacgacgaca tcattccgtg gcgttatcca gctaagcgcg    4080
aactgcaatt tggagaatgg cagcgcaatg acattcttgc aggtatcttc gagccagcca    4140
cgatcgacat tgatctggct atcttgctga caaaagcaag agaacatagc gttgccttgg    4200
taggtccagc ggcggaggaa ctctttgatc cggttcctga acaggatcta tttgaggcgc    4260
taaatgaaac cttaacgcta tggaactcgc cgcccgactg gctggcgat gagcgaaatg    4320 tagtgcttac gttgtcccgc atttggtaca gcgcagtaac cggcaaaatc gcgccgaagg    4380
atgtcgctgc cgactgggca atggagcgcc tgccggccca gtatcagccc gtcatacttg    4440
aagctaggca ggcttatctt ggacaagaag atcgcttggc ctcgcgcgca gatcagttgg    4500
aagaatttgt tcactacgtg aaaggcgaga tcaccaaggt agtcggcaaa taatgtctaa    4560
caattcgttc aagccgacgc cgcttcgcgg cgcggcttaa ctcaagcgtt agagagctgg    4620
ggaagactat gcgcgatctg ttgaaggtgg ttctaagcct cgtacttgcg atggcatcgg    4680
ggcaggcact tgctgacctg ccttaattaa ataacttcgt ataatgtatg ctatacgaag    4740
ttatggccgg cccgttactt gctgggtgaa gaaccgatcg aagtccgtgc ttacacctac    4800
agcgatccga atgatgaacg tttcgttgaa gtcgaagatc gtattatttg gcagatgcgc    4860
ttcagaagcg gtgctctgtc tcatggtgca tcttcttatt cgaccacgac gacttcacgt    4920
ttctcggtgc agggcgacaa agctgttctg ttgatggatc cggctaccgg atattatcag    4980
aatttgattt ctgtccagac cccaggccat gctaaccagt cgatgatgcc acagttcatc    5040
atgccagcga caaccagtt ctctgcacag ttggatcatc tggctgaagc cgtcatcaat    5100
aacaaaccag ttcgtagccc gggtgaagaa ggtatgcagg atgtgcgcct gattcaggcc    5160
atttatgaag cagctcgtac cggtcgcccc gtcaacacgg attggggtta tgtccgtcag    5220
ggtggttatt gattctgact taacctattt gggttaaaca gacttatttt tcctgttta    5280 ggaaaatagt taaaaaggcg tcattggttc ttccaatgac gccttttttt ataaacaaaa    5340
```

```
aaatccttt  gtcggtttta  taaaaatact  tcatattttg  ataagccgtc  ttaaaaatat   5400
aataaatttt  tataatattt  atccgatcaa  aggacccctt  tatgctagaa  gtcattatat   5460
cggcattact  accgattata  attactttaa  tgataggttt  tttcgctggc  tggcgtggtg   5520
aatttacggc  aaatcaagcc  tcgaccttga  ataaaatggt  cttacgctat  gccttaccta   5580
tgactttatt  ctctgggatt  ttatcacttc  ccaaaacaca  gattttatcg  tcgggttctg   5640
ccgcaattat  tttacttta   gccatggctg  gcggctatct  aattcacttg  gggatagga   5700 attttgtctg  ccagcgccca  gtgaatgaat  ctgctctttt  agctctttct  gttagcgcac   5760
ctgcagttcc  ttttgttggc  ataacagttc  tagggcattt  atttggcact  gccagcacga   5820
tattggtttc  aatatgtagc  ctgatgatga  acctcgtcca  ggttcccgtt  acctttttct   5880
tttgtcagcg  tattctccaa  aaagaatac   tgacaaaata  gccacggata  gttcttttt    5940 ttctcatatc  agacatgctt  ttaccgaacc  tattgttatt  gcccctattc  tggctcttat   6000
ctgtgtcagt  ctctctattc  ctttccctga  aaccttaaaa  tcttctttaa  tgctactagg   6060
aaaagcgacc  ggaggcgttg  cgcttttctc  ttctggtata  attttatttt  ctcgaaaagt   6120
tattttaagt  aaaacagtag  catctttagt  tttatcaaaa  aatattatta  ttccaacagc   6180
ggtattggtt  cttgcgtcgg  tacccaattc  gccctatagt  gagtcgtatt  acgcgcgctc   6240
actggccgtc  gttttacaac  gtcgtgactg  ggaaaaccct  ggcgttaccc  aacttaatcg   6300
ccttgcagca  catccccctt  tcgccagctg  gcgtaatagc  gaagaggccc  gcaccgatcg   6360
cccttcccaa  cagttgcgca  gcctgaatgg  cgaatgggac  gcgccctgta  gcggcgcatt   6420
aagcgcggcg  ggtgtggtgg  ttacgcgcag  cgtgaccgct  acacttgcca  gcgccctagc   6480
gcccgctcct  ttcgctttct  tcccttcctt  tctcgccacg  ttcgccggct  ttccccgtca   6540
agctctaaat  cgggggctcc  ctttagggtt  ccgatttagt  gctttacggc  acctcgaccc   6600
caaaaaactt  gattagggtg  atggttcacg  tagtgggcca  tcgccctgat  agacggtttt   6660
tcgccctttg  acgttggagt  ccacgttctt  taatagtgga  ctcttgttcc  aaactggaac   6720
aacactcaac  cctatctcgg  tctattcttt  tgatttataa  gggattttgc  cgatttcggc   6780
ctattggtta  aaaaatgagc  tgatttaaca  aaaatttaac  gcgaatttta  acaaaatatt   6840
aacgcttaca  atttaggtgg  cacttttcgg  ggaaatgtgc  gcggaacccc  tatttgttta   6900
tttttctaaa  tacattcaaa  tatgtatccg  ctcatgagac  aataaccctg  ataaatgctt   6960
caataatatt  gaaaaaggaa  gagtatgagt  attcaacatt  tccgtgtcgc  ccttattccc   7020
ttttttgcgg  cattttgcct  tcctgttttt  gctcacccag  aaacgctggt  gaaagtaaaa   7080
gatgctgaag  atcagttggg  tgcacgagtg  ggttacatcg  aactggatct  caacagcggt   7140
aagatccttg  agagttttcg  ccccgaagaa  cgttttccaa  tgatgagcac  ttttaaagtt   7200
ctgctatgtg  gcgcggtatt  atcccgtatt  gacgccgggc  aagagcaact  cggtcgccgc   7260
atacactatt  ctcagaatga  cttggttgag  tactcaccag  tcacagaaaa  gcatcttacg   7320
gatggcatga  cagtaagaga  attatgcagt  gctgccataa  ccatgagtga  taacactgcg   7380
gccaacttac  ttctgacaac  gatcggagga  ccgaaggagc  taaccgcttt  tttgcacaac   7440
atgggggatc  atgtaactcg  ccttgatcgt  tgggaaccgg  agctgaatga  agccatacca   7500
aacgacgagc  gtgacaccac  gatgcctgta  gcaatggcaa  caacgttgcg  caaactatta   7560
actggcgaac  tacttactct  agcttcccgg  caacaattaa  tagactggat  ggaggcggat   7620
aaagttgcag  gaccacttct  gcgctcggcc  cttccggctg  gctggtttat  tgctgataaa   7680
```

```
tctggagccg gtgagcgtgg gtctcgcggt atcattgcag cactgggcc  agatggtaag   7740 ccctcccgta tcgtagttat ctacacgacg gggagtcagg caactatgga tgaacgaaat   7800
agacagatcg ctgagatagg tgcctcactg attaagcatt ggtaactgtc agaccaagtt   7860
tactcatata tactttagat tgatttaaaa cttcatttt  aatttaaaag gatctaggtg   7920
aagatccttt ttgataatct catgaccaaa atcccttaac gtgagttttc gttccactga   7980
gcgtcagacc ccgtagaaaa gatcaaagga tcttcttgag atcctttttt tctgcgcgta   8040
atctgctgct tgcaaacaaa aaaccaccg  ctaccagcgg tggtttgttt gccggatcaa   8100
gagctaccaa ctctttttcc gaaggtaact ggcttcagca gagcgcagat accaaatact   8160
gtccttctag tgtagccgta gttaggccac cacttcaaga actctgtagc accgcctaca   8220
tacctcgctc tgctaatcct gttaccagtg gctgctgcca gtggcgataa gtcgtgtctt   8280
accgggttgg actcaagacg atagttaccg gataaggcgc agcggtcggg ctgaacgggg   8340
ggttcgtgca cacagcccag cttggagcga acgacctaca ccgaactgag atacctacag   8400
cgtgagctat gagaaagcgc cacgcttccc gaagggagaa aggcggacag gtatccggta   8460
agcggcaggg tcggaacagg agagcgcacg agggagcttc caggggggaaa cgcctggtat   8520 ctttatagtc ctgtcgggtt tcgccacctc tgacttgagc gtcgattttt gtgatgctcg   8580 tcagggggc  ggagcctatg gaaaaacgcc agcaacgcgg cctttttacg gttcctggcc   8640
ttttgctggc cttttgctca catgttcttt cctgcgttat cccctgattc tgtggataac   8700
cgtattaccg cctttgagtg agctgatacc gctcgccgca gccgaacgac cgagcgcagc   8760
gagtcagtga gcgaggaagc ggaagagcgc ccaatacgca aaccgcctct ccccgcgcgt   8820
tggccgattc attaatgcag ctggcacgac aggtttcccg actggaaagc gggcagtgag   8880
cgcaacgcaa ttaatgtgag ttagctcact cattaggcac cccaggcttt acactttatg   8940
cttccggctc gtatgttgtg tggaattgtg agcggataac aatttcacac aggaaacagc   9000
tatgaccatg attacgccaa gcgcgcaatt aaccctcact aaagggaaca aaagctggag   9060
ctcgtccaga aaagacagca ttccttctca ataaagaaat attatttttt gttttgaaa    9120 aattttccca aaatctagaa tgctacatta aatatacaaa aatattatta tacaaataag   9180
gcttttaaat acccatattt tttagaattt ctttacaaag aaacatgtta aatatagatt   9240
tagagattaa tatcagccat ttttatcaaa aattctttt  ttgttttata atattatgct   9300
gcaaaactaa taaaaacgcc ctttcgaaat taacgatcac ccacaagaaa taattatctg   9360
acagcgctta ccaatcaatt attgccgaac gcagagtccc gtattaggac ggtcaacaat   9420
ctaaaccgtt tttcagaaaa tattgcttta taagcctcaa aacttaaaag ctgcggtatt   9480
ttaatatacc aaaattttct ggaaaagccg gcgaatcaga taacagttcc gcacaggtga   9540
gaaccacgac ggatcttctc tgaattgttg gttagttaag aaagaaacaa ggattatgac   9600
gaacaaaatc tcgtcttcag ataatctttc caatgctgtt tcagcaacgg atgcaacgc    9660 ttcccgtacg ccaaatctga cccgtcgcgc tctcgttggt ggtggtgttg gactggccgc   9720
agctggcgcc ttagccagtg gtcttcaggc agcgacgctt cctgctggtg ccagccaggt   9780
tccgaccacg cctgcaggtc gcccgatgcc ttacgcgatc cgcccgatgc cggaagatcg   9840
tcgtttcggt tatgctatcg tcggtctggg taaatatgcc cttaaccaga ttttaccggg   9900
ttttgccgga tgccagcatt cccgcatcga agctttggtc agcggtaacg ctgaaaaagc   9960
taaaatcgtt gccgctgaat atggcgtcga tccccgtaaa atttatgatt acagcaactt  10020
cgacaagatc gctaaagatc caaaaatcga cgctgtttac atcattttgc caaactcttt  10080
```

```
gcatgctgaa tttgctatcc gtgctttcaa agccggcaag catgttatgt gtgaaaagcc    10140
gatggcaacc tctgttgctg attgtcagcg gatgatcgat gcagccaagg ctgctaataa    10200
aaagctgatg atcggttacc gttgccacta tgatccaatg aaccgtgcaa                10250

<210> SEQ ID NO 26
<211> LENGTH: 1186
<212> TYPE: DNA
<213> ORGANISM: artificial sequence
<220> FEATURE:
<223> OTHER INFORMATION: sonstructed fragment

<400> SEQUENCE: 26
gtccagaaaa gacagcattc cttctcaata agaaatatt attttttgtt tttgaaaaat       60
ttttccaaaa tctagaatgc tacattaaat atacaaaaat attattatac aaataaggct      120
tttaaatacc catattttt agaatttctt tacaaagaaa catgttaaat atagatttag       180
agattaatat cagccatttt tatcaaaaat tcttttttg ttttataata ttatgctgca       240
aaactaataa aaacgccctt tcgaaattaa cgatcaccca caagaaataa ttatctgaca      300
gcgcttacca atcaattatt gccgaacgca gagtcccgta ttaggacggt caacaatcta     360
aaccgttttt cagaaaatat tgctttataa gcctcaaaac ttaaaagctg cggtatttta    420
atataccaaa attttctgga aaagccggcg aatcagataa cagttccgca caggtgagaa    480
ccacgacgga tcttctctga attgttggtt agttaagaaa gaaacaagga ttatgacgaa    540
caaaatctcg tcttcagata atcttttccaa tgctgtttca gcaacggatg acaacgcttc    600
ccgtacgcca aatctgaccc gtcgcgctct cgttggtggt ggtgttggac tggccgcagc    660
tggcgcctta gccagtggtc ttcaggcagc gacgcttcct gctggtgcca gccaggttcc    720
gaccacgcct gcaggtcgcc cgatgcctta cgcgatccgc ccgatgccgg aagatcgtcg    780
tttcggttat gctatcgtcg gtctgggtaa atatgccctt aaccagattt taccgggttt    840
tgccggatgc cagcattccc gcatcgaagc tttggtcagc ggtaacgctg aaaaagctaa    900
aatcgttgcc gctgaaatatg gcgtcgatcc ccgtaaaatt tatgattaca gcaacttcga    960
caagatcgct aaagatccaa aaatcgacgc tgtttacatc attttgccaa actctttgca   1020
tgctgaattt gctatccgtg cttttcaaagc cggcaagcat gttatgtgtg aaaagccgat  1080
ggcaacctct gttgctgatt gtcagcggat gatcgatgca gccaaggctg ctaataaaaa   1140
gctgatgatc ggttaccgtt gccactatga tccaatgaac cgtgca                     1186

<210> SEQ ID NO 27
<211> LENGTH: 1302
<212> TYPE: DNA
<213> ORGANISM: Zymomonas mobilis

<400> SEQUENCE: 27
atgacgaaca aaatctcgtc ttcagataat cttttccaatg ctgtttcagc aacggatgac     60
aacgcttccc gtacgccaaa tctgacccgt cgcgctctcg ttggtggtgg tgttggactg    120
gccgcagctg gcgccttagc cagtggtctt caggcagcga cgcttcctgc tggtgccagc    180
caggttccga ccacgcctgc aggtcgcccg atgccttacg cgatccgccc gatgccggaa    240
gatcgtcgtt tcggttatgc tatcgtcggt ctgggtaaat atgcccttaa ccagattta    300 ccggggtttg ccggatgcca gcattcccgc atcgaagctt tggtcagcgg taacgctgaa    360
aaagctaaaa tcgttgccgc tgaatatggc gtcgatcccc gtaaaattta tgattacagc    420
```

| | |
|---|---|
| aacttcgaca agatcgctaa agatccaaaa atcgacgctg tttacatcat tttgccaaac | 480 |
| tctttgcatg ctgaatttgc tatccgtgct ttcaaagccg gcaagcatgt tatgtgtgaa | 540 |
| aagccgatgg caacctctgt tgctgattgt cagcggatga tcgatgcagc caaggctgct | 600 |
| aataaaaagc tgatgatcgg ttaccgttgc cactatgatc caatgaaccg tgcagcggta | 660 |
| aaattgatcc gtgaaaacca gttgggtaaa ctgggcatgg ttaccaccga caactcagac | 720 |
| gttatggatc agaacgatcc tgcacagcag tggcgtctgc gtcgtgaact cgccggtggc | 780 |
| ggttctttga tggatatcgg tatttatggc ttgaacggta cccgttactt gctgggtgaa | 840 |
| gaaccgatcg aagtccgtgc ttacacctac agcgatccga atgatgaacg tttcgttgaa | 900 |
| gtcgaagatc gtattatttg gcagatgcgc ttcagaagcg gtgctctgtc tcatggtgca | 960 |
| tcttcttatt cgaccacgac gacttcacgt ttctcggtgc agggcgacaa agctgttctg | 1020 |
| ttgatggatc cggctaccgg atattatcag aatttgattt ctgtccagac cccaggccat | 1080 |
| gctaaccagt cgatgatgcc acagttcatc atgccagcga caaccagtt ctctgcacag | 1140 |
| ttggatcatc tggctgaagc cgtcatcaat aacaaaccag ttcgtagccc gggtgaagaa | 1200 |
| ggtatgcagg atgtgcgcct gattcaggcc atttatgaag cagctcgtac cggtcgcccc | 1260 |
| gtcaacacgg attggggtta tgtccgtcag ggtggttatt ga | 1302 |

<210> SEQ ID NO 28
<211> LENGTH: 1446
<212> TYPE: DNA
<213> ORGANISM: artificial sequence
<220> FEATURE:
<223> OTHER INFORMATION: constructed fragment

<400> SEQUENCE: 28

| | |
|---|---|
| cgttacttgc tgggtgaaga accgatcgaa gtccgtgctt acacctacag cgatccgaat | 60 |
| gatgaacgtt tcgttgaagt cgaagatcgt attatttggc agatgcgctt cagaagcggt | 120 |
| gctctgtctc atggtgcatc ttcttattcg accacgacga cttcacgttt ctcggtgcag | 180 |
| ggcgacaaag ctgttctgtt gatggatccg gctaccggat attatcagaa tttgatttct | 240 |
| gtccagaccc caggccatgc taaccagtcg atgatgccac agttcatcat gccagcgaac | 300 |
| aaccagttct ctgcacagtt ggatcatctg gctgaagccg tcatcaataa caaaccagtt | 360 |
| cgtagcccgg gtgaagaagg tatgcaggat gtgcgcctga ttcaggccat ttatgaagca | 420 |
| gctcgtaccg gtcgccccgt caacacggat tggggttatg tccgtcaggg tggttattga | 480 |
| ttctgactta acctatttgg gttaaacaga cttattttc ctgttttagg aaaatagtta | 540 |
| aaaaggcgtc attggttctt ccaatgacgc cttttttat aaacaaaaaa atcctttgt | 600 |
| cggtttata aaaatacttc atattttgat aagccgtctt aaaaatataa taatttta | 660 |
| taatatttat ccgatcaaag gaccccttta tgctagaagt cattatatcg gcattactac | 720 |
| cgattataat tacttaatg ataggttttt tcgctggctg gcgtggtgaa tttacggcaa | 780 |
| atcaagcctc gaccttgaat aaaatggtct tacgctatgc cttacctatg actttattct | 840 |
| ctgggatttt atcacttccc aaaacacaga ttttatcgtc gggttctgcc gcaattattt | 900 |
| tactttagc catggctggc ggctatctaa ttacacttgg gataggatat tttgtctgcc | 960 |
| agcgcccagt gaatgaatct gctctttag ctctttctgt tagcgcacct gcagttcctt | 1020 |
| ttgttggcat aacagttcta gggcatttat ttggcactgc cagcacgata ttggtttcaa | 1080 |
| tatgtagcct gatgatgaac ctcgtccagg ttcccgttac cttttttctt tgtcagcgta | 1140 |
| ttctccaaaa aagaatactg acaaaatagc cacggatagt tctttttttt ctcatatcag | 1200 |

```
acatgctttt accgaaccta ttgttattgc ccctattctg gctcttatct gtgtcagtct    1260
ctctattcct ttccctgaaa ccttaaaatc ttctttaatg ctactaggaa aagcgaccgg    1320
aggcgttgcg cttttctctt ctggtataat tttattttct cgaaaagtta ttttaagtaa    1380
aacagtagca tctttagttt tatcaaaaaa tattattatt ccaacagcgg tattggttct    1440
tgcgtc                                                               1446

<210> SEQ ID NO 29
<211> LENGTH: 1661
<212> TYPE: DNA
<213> ORGANISM: artificial sequence
<220> FEATURE:
<223> OTHER INFORMATION: constructed fragment

<400> SEQUENCE: 29
gttcgatcaa caacccgaat cctatcgtaa tgatgttttg cccgatcagc ctcaatcgac      60
aattttacgc gtttcgatcg aagcagggac gacaattggc tgggaacggt atacttgaat    120
aaatggtctt cgttatggta ttgatgtttt tggtgcatcg gccccggcga atgatctata    180
tgctcatttc ggcttgaccg cagtcggcat cacgaacaag gtgttggccg cgatcgccgg    240
taagtcggca cgttaaaaaa tagctatgga atataatagc tactaataag ttaggagaat    300
aaacatgagt gtccaagcta cacgcgaaga taaatttagc tttggcttgt ggacagttgg    360
gtggcaggcc cgtgacgcct tggtgatgc cacgcgtacc gcccttgatc cggtcgaagc    420
agttcataaa cttgccgaaa tcggagccta tggcattaca tttcatgatg atgacttggt    480
ccccttcggt tcggatgctc agacacggga tggtatcatt gctggtttca aaaaagccct    540
tgatgaaacc ggtttgatcg ttcctatggt taccacaaat ttgtttacgc atccggtttt    600
taaagacggc gggtttacct ctaacgatcg ttctgtgcgc cggtatgcta tccggaaagt    660
tttgagacag atggatcttg gtgcggaact gggggccaaa acgcttgtct tatggggcgg    720
cagagaaggt gcggaatatg attcagcaaa agatgttagt gccgccttgg atcgttatcg    780
cgaagcactg aatcttctgg cacaatatag cgaagacaga ggctatggac ttcgttttgc    840
aattgaaccg aaacctaatg aaccacgtgg cgatattctg ctgcctaccg caggccatgc    900
tattgccttt gtgcaagaat tagaacggcc cgaacttttt ggcatcaatc cagaaaccgg    960
gcatgaacag atgtcaaact tgaattttac ccagggggatt gctcaggctt tgtggcataa   1020 aaaactttt catattgatt tgaatggaca acatggtccc aagtttgatc aggaccttgt   1080
ctttggtcat ggtgaccttt taaatgcctt tagcctggtc gatttgttag aaaatggtcc   1140
agatggtgcc ccggcttatg atggcccgcg ccattttgat tataaaccat ctcgtactga   1200
agattatgat ggcgtttggg aatcagcgaa agccaatatc cgtatgtatc tttattaaa   1260 agaacgtgcc aaagcgttta gagctgatcc ggaagttcag gaagcactgg cagcaagcaa   1320
agttgccgaa ttgaaaaccc caacgttgaa tcctggtgaa ggctatgcag aactgttagc   1380
agatcgcagt gcttttgaag attatgatgc cgatgctgtt ggtgcgaaag ttttggtttt   1440
cgtgaaattg aaccaattgg ccattgaaca tttattaggt gcccgctagt ctagatgact   1500
gtataaaacc acagccaatc aaacgaaacc aggctatact caagcctggt tttttgatgg   1560 atttcagcg tggcgcaggc aggtttatc ttaacccgac actggcggga cacccgcaa    1620 gggacagaag tctccttctg gctggcgacg gacaacgggc c                      1661

<210> SEQ ID NO 30
```

<211> LENGTH: 1960
<212> TYPE: DNA
<213> ORGANISM: artificial sequence
<220> FEATURE:
<223> OTHER INFORMATION: constructed fragment containing a 191 bp Peno,
a 1,455-bp E. coli xylB coding sequence (ECxylB) and a 314-bp
E.coli xylB 3'UTR

<400> SEQUENCE: 30

```
ccagttactc aatacgtaac aataatcagt ttatcctaac tatagaatcg catgagaagc      60
gataacgttt caccataagc aatatattca ttgcaacagt ggaattgcct tatgcgtcaa     120
ggaaggatag atcattgacg gactgagttc aaaaagagac tggtctaaaa gattttaaga     180
aaggtttcga tatgtatatc gggatagatc ttggcacctc gggcgtaaaa gttattttgc     240
tcaacgagca gggtgaggtg gttgctgcgc aaacggaaaa gctgaccgtt tcgcgcccgc     300
atccactctg gtcggaacaa gacccggaac agtggtggca ggcaactgat cgcgcaatga     360
aagctctggg cgatcagcat tctctgcagg acgttaaagc attgggtatt gccggccaga     420
tgcacggagc aaccttgctg gatgctcagc aacgggtgtt acgccctgcc attttgtgga     480
acgacgggcg ctgtgcgcaa gagtgcactt tgctggaagc gcgagttccg caatcgcggg     540
tgattaccgg caacctgatg atgcccggat ttactgcgcc taaattgcta tgggttcagc     600
ggcatgagcc ggagatattc cgtcaaatcg acaaagtatt attaccgaaa gattacttgc     660
gtctgcgtat gacgggggag tttgccagcg atatgtctga cgcagctggc accatgtggc     720
tggatgtcgc aaagcgtgac tggagtgacg tcatgctgca ggcttgcgac ttatctcgtg     780
accagatgcc cgcattatac gaaggcagcg aaattactgg tgctttgtta cctgaagttg     840
cgaaagcgtg gggtatggcg acggtgccag ttgtcgcagg cggtggcgac aatgcagctg     900
gtgcagttgg tgtgggaatg gttgatgcta atcaggcaat gttatcgctg gggacgtcgg     960
gggtctattt tgctgtcagc gaagggttct taagcaagcc agaaagcgcc gtacatagct    1020
tttgccatgc gctaccgcaa cgttggcatt taatgtctgt gatgctgagt gcagcgtcgt    1080
gtctggattg ggccgcgaaa ttaaccggcc tgagcaatgt cccagcttta atcgctgcag    1140
ctcaacaggc tgatgaaagt gccgagccag tttggttttct gccttatctt tccggcgagc    1200
gtacgccaca caataatccc caggcgaagg gggttttctt tggtttgact catcaacatg    1260
gccccaatga actggcgcga gcagtgctgg aaggcgtggg ttatgcgctg gcagatggca    1320
tggatgtcgt gcatgcctgc ggtattaaac cgcaaagtgt tacgttgatt ggggcgggg    1380
cgcgtagtga gtactggcgt cagatgctgg cggatatcag cggtcagcag ctcgattacc    1440
gtacgggggg ggatgtgggg ccagcactgg gcgcagcaag gctggcgcag atcgcggcga    1500
atccagagaa atcgctcatt gaattgttgc cgcaactacc gttagaacag tcgcatctac    1560
cagatgcgca gcgttatgcc gcttatcagc cacgacgaga aacgttccgt cgcctctatc    1620
agcaacttct gccattaatg gcgtaaacgt tatcccctgc ctgaccgggt ggggataat    1680
tcacatctat atatctcagt aattaattaa tatttagtac gaatttattc tgaaaatcat    1740
ttgttaatgg cattttttcag ttttgtcttt cgttggttac tcgtaatgta tcgctggtag    1800
atatggagat cgttatgaaa acctcaaaga ctgtggcaaa actattattt gttgtcgggg    1860
cgctggttta tctggttggg ctatggatct catgcccatt gttaagtgga aaaggctatt    1920
ttcttggcgt gttaatgaca gcaacttttg gcaactatgc                          1960
```

<210> SEQ ID NO 31
<211> LENGTH: 1014

```
<212> TYPE: DNA
<213> ORGANISM: artificial sequence
<220> FEATURE:
<223> OTHER INFORMATION: constructed fragment with spec resistance gene
      bounded by lox recombination sites

<400> SEQUENCE: 31
agcacaggat gacgcctaac aattcattca agccgacacc gcttcgcggc gcggcttaat      60
tcaggagtta aacatcatga gggaagcggt gatcgccgaa gtatcgactc aactatcaga    120
ggtagttggc gtcatcgagc gccatctcga accgacgttg ctggccgtac atttgtacgg    180
ctccgcagtg gatggcggcc tgaagccaca cagtgatatt gatttgctgg ttacggtgac    240
tgtaaggctt gatgaaacaa cgcggcgagc tttgatcaac gaccttttgg aaacttcggc    300
ttccccctgga gagagcgaga ttctccgcgc tgtagaagtc accattgttg tgcacgacga    360
catcattccg tggcgttatc cagctaagcg cgaactgcaa tttggagaat ggcagcgcaa    420
tgacattctt gcaggtatct tcagccagc cacgatcgac attgatctgg ctatcttgct    480
gacaaaagca agagaacata cgttgcctt ggtaggtcca cgcggcggag aactctttga    540
tccggttcct gaacaggatc tatttgaggc gctaaatgaa accttaacgc tatggaactc    600
gccgcccgac tgggctggcg atgagcgaaa tgtagtgctt acgttgtccc gcatttggta    660
cagcgcagta accggcaaaa tcgcgccgaa ggatgtcgct gccgactggg caatggagcg    720
cctgccggcc cagtatcagc ccgtcatact tgaagctagg caggcttatc ttggacaaga    780
agatcgcttg gcctcgcgcg cagatcagtt ggaagaattt gttcactacg tgaaaggcga    840
gatcaccaag gtagtcggca aataatgtct aacaattcgt tcaagccgac gccgcttcgc    900
ggcgcggctt aactcaagcg ttagagagct ggggaagact atgcgcgatc tgttgaaggt    960
ggttctaagc ctcgtacttg cgatggcatc ggggcaggca cttgctgacc tgcc         1014

<210> SEQ ID NO 32
<211> LENGTH: 12198
<212> TYPE: DNA
<213> ORGANISM: artificial sequence
<220> FEATURE:
<223> OTHER INFORMATION: constructed plasmid

<400> SEQUENCE: 32
ctagtgttcg atcaacaacc cgaatcctat cgtaatgatg ttttgcccga tcagcctcaa      60
tcgacaattt tacgcgtttc gatcgaaaca gggacgacaa ttggctggga acggtatact    120
ggaataaatg gtcttcgtta tggtattgat gtttttggtg catcggcccc ggcgaatgat    180
ctatatgctc atttcggctt gaccgcagtc ggcatcacga acaaggtgtt ggccgcgatc    240
gccggtaagt cggcacgtta aaaaatagct atggaatata atagctacta ataagttagg    300
agaataaaca tgacggacaa attgacctcc cttcgtcagt acaccaccgt agtggccgac    360
actggggaca tcgcggcaat gaagctgtat caaccgcagg atgccacaac caacccttct    420
ctcattctta acgcagcgca gattccggaa taccgtaagt tgattgatga tgctgtcgcc    480
tgggcgaaac agcagagcaa cgatcgcgcg cagcagatcg tggacgcgac cgacaaactg    540
gcagtaaata ttggtctgga aatcctgaaa ctggttccgg gccgtatctc aactgaagtt    600
gatgcgcgcc tttcctatga caccgaagcg tcaattgcga aagcaaaacg cctgatcaaa    660
ctctacaacg atgctggtat tagcaacgat cgtattctga tcaaactggc ttctacctgg    720
cagggtatcc gtgctgcaga acagctggaa aagaaggca tcaactgtaa cctgaccctg    780
ctgttctcct tcgctcaggc tcgtgcttgt gcggaagcgg gcgtgttcct gatctcgccg    840
```

-continued

```
tttgttggcc gtattcttga ctggtacaaa gcgaataccg ataagaaaga gtacgctccg    900
gcagaagatc cgggcgtggt ttctgtatct gaaatctacc agtactacaa agagcacggt    960
tatgaaaccg tggttatggg cgcaagcttc cgtaacatcg gcgaaattct ggaactggca   1020
ggctgcgacc gtctgaccat cgcaccggca ctgctgaaag agctggcgga gagcgaaggg   1080
gctatcgaac gtaaactgtc ttacaccggc gaagtgaaag cgcgtccggc gcgtatcact   1140
gagtccgagt tcctgtggca gcacaaccag ggtccaatgg cagtagataa actggcggaa   1200
ggtatccgta agtttgctat tgaccaggaa aaactggaaa aaatgatcgg cgatctgctg   1260
taatctagac gatctggagt caaaatgtcc tcacgtaaag agcttgccaa tgctattcgt   1320
gcgctgagca tggacgcagt acagaaagcc aaatccggtc acccgggtgc ccctatgggt   1380
atggctgaca ttgccgaagt cctgtggcgt gatttcctga acacaaccc gcagaatccg   1440
tcctgggctg accgtgaccg cttcgtgctg tccaacggcc acggctccat gctgatctac   1500
agcctgctgc acctcaccgg ttacgatctg ccgatggaag aactgaaaaa cttccgtcag   1560
ctgcactcta aaactccggg tcacccggaa gtgggttaca ccgctggtgt ggaaaccacc   1620
accggtccgc tgggtcaggg tattgccaac gcagtcggta tggcgattgc agaaaaaacg   1680
ctggcggcgc agtttaaccg tccgggccac gacattgtcg accactacac ctacgccttc   1740
atgggcgacg gctgcatgat ggaaggcatc tcccacgaag tttgctctct ggcgggtacg   1800
ctgaagctgg gtaaactgat tgcattctac gatgacaacg gtatttctat cgatggtcac   1860
gttgaaggct ggttcaccga cgacaccgca atgcgtttcg aagcttacgg ctggcacgtt   1920
attcgcgaca tcgacggtca tgacgcggca tctatcaaac gcgcagtaga agaagcgcgc   1980
gcagtgactg acaaaccttc cctgctgatg tgcaaaacca tcatcggttt cggttccccg   2040
aacaaagccg gtacccacga ctcccacggt gcgccgctgg gcgacgctga aattgccctg   2100
acccgcgaac aactgggctg gaaatatgcg ccgttcgaaa tcccgtctga atctatgct   2160
cagtgggatg cgaaagaagc aggccaggcg aaagaatccg catggaacga gaaattcgct   2220
gcttacgcga aagcttatcc gcaggaagcc gctgaattta cccgccgtat gaaaggcgaa   2280
atgccgtctg acttcgacgc taaagcgaaa gagttcatcg ctaaactgca ggctaatccg   2340
gcgaaaatcg ccagccgtaa agcgtctcag aatgctatcg aagcgttcgg tccgctgttg   2400
ccggaattcc tcgcggttc tgctgacctg gcgccgtcta acctgaccct gtggtctggt   2460
tctaaagcaa tcaacgaaga tgctgcgggt aactacatcc actacggtgt tcgcgagttc   2520
ggtatgaccg cgattgctaa cggtatctcc ctgcacggtg gcttcctgcc gtacacctcc   2580
accttcctga tgttcgtgga atacgcacgt aacgccgtac gtatggctgc gctgatgaaa   2640
cagcgtcagg tgatggttta cacccacgac tccatcggtc tgggcgaaga cggcccgact   2700
caccagccgg ttgagcaggt cgcttctctg cgcgtaaccc cgaacatgtc tacatggcgt   2760
ccgtgtgacc aggttgaatc cgcggtcgcg tggaaatacg tgttgagcg tcaggacggc   2820
ccgaccgcac tgatcctctc ccgtcagaac ctggcgcagc aggaacgaac tgaagagcaa   2880
ctggcaaaca tcgcgcgcgg tggttatgtg ctgaaagact cgccggtca gccgaactg   2940
attttcatcg ctaccggttc agaagttgaa ctggctgttg ctgcctacga aaactgact   3000
gccgaaggcg tgaaagcgcg cgtggtgtcc atgccgtcta ccgacgcatt tgacaagcag   3060
gatgctgctt accgtgaatc cgtactgccg aaagcggtta ctgcacgcgt tgctgtagaa   3120
gcgggtattg ctgactactg gtacaagtat gttggcctga cggtgctat cgtcggtatg   3180
```

```
accaccttcg gtgaatctgc tccggcagag ctgctgtttg aagagttcgg cttcactgtt    3240
gataacgttg ttgcgaaagc aaaagaactg ctgtaattag catttcgggt aaaaaaggtc    3300
gcttcggcga ccttttttat taccttgata atgtccgttt gcgcggcgcg ccccagttac    3360
tcaatacgta acaataatca gtttatccta actatagaat cgcatgagaa gcgataacgt    3420
ttcaccataa gcaatatatt cattgcaaca gtggaattgc cttatgcgtc aaggaaggat    3480
agatcattga cggactgagt tcaaaaagag actggtctaa aagattttaa gaaaggtttc    3540
gatatgacct ctgctgtgcc atcaaatacg aaaaaaaagc tggtgattgc ttccgatcac    3600
gcagcatttg agttgaaatc aaccttgatt acttggctga aagagcttgg tcatgaggtc    3660
gaagaccttg gccctcatga aaaccattca gtcgattatc ccgattacgg ttataagctg    3720
gctgtcgcta tcgcagaaaa aaccgctgat ttcggtattg cttttatgtgg ctcgggaatc    3780 ggtatctcga tcgctgtcaa tcgccatccg gctgcccgtt gcgctttgat tacggataac    3840
cttaccgccc gtttggcaag agaacataac aatgccaatg ttatcgctat gggtgcgaga    3900
ttgatcggca ttgaaaccgc taaggattgt atttcagctt tccttgcaac gccgtttgga    3960
ggtgaacgtc atgttcgccg tatcgataaa cttttcgaatc ctcagttcaa tatctagata    4020
agttaggaga ataaacatga gtaaattacc cctgattgct ccctctatcc tttcggcgga    4080
ttttgcccat ttgggagatg aggtcgcggc gatagatcag gccggtgccg attggatcca    4140
tattgatgtg atggatggcc atttcgtgcc gaatatcacc ataggcccca tggttgtgaa    4200
ggctttgcgt ccctatagcc aaaagccttt tgatgtccat ttgatgattg cgcctgtcga    4260
tcaatatatc gaggcttttt ctgaagcggg tgctgatatt atcagtttcc atcccgaagc    4320
gggcgcgcat ccccatcgca ctattcagca tatcaaatca ttgggcaaaa agcgggatt    4380 agttttaat ccggcgaccc ctttaagctg gcttgattat ctaatggatg atcttgatct    4440
gattatggtg atgagcgtta accccggttt tggcggccaa aaatttatca aaacccaatt    4500
agaaaagatt aaagatatcc gtcaaagaat taccgcctct gggcgggata tccgcttgga    4560
agtggatggc ggaattgatg ccacgactgc accgcttgcc gtcgaagccg gtgccgatgt    4620
tttggtcgcg ggaacggcca gctttaaagg cggcgcaaca tgttacaccg ataatatcag    4680
gatattgcgt aaatcatgat taattaactc gaggcggcct gaacgtactg caagtcctga    4740
cgtcactgtg cagtccgttg gcccggttat cggtagcgat accgggcatt ttttaagga    4800 acgatcgata gaattcgcgg gccggccaag cttgaattca tggttttggt gccaatgtta    4860
tcgcctataa accgcatcca gaccccgaat tggcgaaaaa ggtcggtttc cgcttccacct    4920 ctctcgatga agtgatcgag accagcgaca tcatttcgct tcactgtccg ctcacgccag    4980
aaaatcatca catgattaat gaagaaacac tggcaagggc aaaaaaaggc ttttaccctcg    5040 tcaataccag tcgcggcggc ttggttgata ccaaggcggt gattaaatcg ctgaaagcca    5100
aacatctcgg cggttatgcg gcggatgttt acgaagagga ggggccttta ttcttcgaaa    5160
atcacgctga cgatattatc gaagatgata ttctcgaaag gttgatcgct ttcccgaatg    5220
tggttttcac gggacatcag gccttttttga cgaaagaggc cttatcaaac attgctcaca    5280
gtattctaca agatatcagc gatgccgaag ctggaaaaga aatgccggat gcgcttgttt    5340
agtagacaag cgacaattaa ccttttgaag atcataatga tcaaattttt gggttaattc    5400
ggtagttatg gcataggcta ttacgcgcta attgatatca aaaaaagca tagccggaca    5460 tcataccggc tatgtttttt attaggaaaa aatttccttt cacccttgctt agccatcgcc    5520 gcattattta atcaatatgc cgagttttc ttgaaatccc tatcttacac caaggccaac    5580
```

```
aagggaatca tccatactcg gtgtcctatc ctatgacttt ttaaattttc tccaaattta    5640
ctaaaatcac gccatctcag cggctgctat tttcaaaaag cgcctctcaa aaccgctttt    5700
tcctgctcaa atatcggatc ccaaaattcc ctcaaaaaag gcagggtatt ttttacaaaa    5760
tcgcccctaa tatctctcaa tccgctgcct tgttcatatg ttttttgcaaa tgattttttat   5820 taaactttt taggcgtatt tttatcaaga aaatttaaat aatcacattt ttattatttt      5880
agatttaagt attgatacaa gtgatatcta taaatgtttt tataactttc tggatcgtaa    5940
tcggctggca atcgttttcc ctatattcgc aagatgtatg tcagccgcgc ggccgcctaa    6000
ttccggatga gcattcatca ggcgggcaag aatgtgaata aaggccggat aaaacttgtg    6060 cttattttc tttacggtct ttaaaaaggc cgtaatatcc agctgaacgg tctggttata     6120
ggtacattga gcaactgact gaaatgcctc aaaatgttct ttacgatgcc attgggatat    6180
atcaacggtg gtatatccag tgatttttt ctccatttta gcttccttag ctcctgaaaa     6240
tctcgataac tcaaaaaata cgcccggtag tgatcttatt tcattatggt gaaagttgga   6300
acctcttacg tgccgatcaa cgtctcattt tcgccaaaag ttgggccagg gcttcccggt    6360
atcaacaggg acaccaggat ttatttattc tgcgaagtga tcttccgtca caggtattta    6420
ttcggcgcaa agtgcgtcgg gtgatgctgc caacttactg atttagtgta tgatggtgtt    6480
tttgaggtgc tccagtggct tctgtttcta tcagctgtcc ctcctgttca gctactgacg    6540
gggtggtgcg taacggcaaa agcaccgccg gacatcagcg ctagcggagt gtatactggc    6600
ttactatgtt ggcactgatg agggtgtcag tgaagtgctt catgtggcag gagaaaaaag    6660
gctgcaccgg tgcgtcagca gaatatgtga tacaggatat attccgcttc ctcgctcact    6720
gactcgctac gctcggtcgt tcgactgcgg cgagcgaaa tggcttacga acggggcgga    6780
gatttcctgg aagatgccag gaagatactt aacagggaag tgagagggcc gcggcaaagc   6840 cgttttttcca taggctccgc cccctgaca agcatcacga atctgacgc tcaaatcagt     6900 ggtggcgaaa cccgacagga ctataaagat accaggcgtt tccccctggc ggctccctcg    6960
tgcgctctcc tgttcctgcc tttcggttta ccggtgtcat tccgctgtta tggccgcgtt    7020
tgtctcattc cacgcctgac actcagttcc gggtaggcag ttcgctccaa gctggactgt    7080
atgcacgaac cccccgttca gtccgaccgc tgcgccttat ccggtaacta tcgtcttgag    7140
tccaacccgg aaagacatgc aaaagcacca ctggcagcag ccactggtaa ttgatttaga    7200
ggagttagtc ttgaagtcat gcgccggtta aggctaaact gaaaggacaa gttttggtga    7260
ctgcgctcct ccaagccagt tacctcggtt caaagagttg gtagctcaga gaaccttcga    7320
aaaaccgccc tgcaaggcgg ttttttcgtt ttcagagcaa gagattacgc gcagaccaaa    7380
acgatctcaa gaagatcatc ttattaatca gataaaatat ttctagattt cagtgcaatt    7440
tatctcttca aatgtagcac ctgaagtcag ccccatacga tataagttgt aattctcatg    7500
tttgacagct tatcatcgat gtgacggaag atcacttcgc agaataaata aatcctggtg    7560
tccctgttga taccgggaag ccctgggcca acttttggcg aaaatgagac gttgatcggc    7620
acgtaagagg ttccaacttt caccataatg aaataagatc actaccgggc gtatttttg     7680 agttatcgag attttcagga gctaaggaag ctaaaatgga gaaaaaatc actggatata   7740 ccaccgttga tatatcccaa tggcatcgta aagaacattt tgaggcattt cagtcagttg    7800
ctcaatgtac ctataaccag accgttcagc tggatattac ggccttttta aagaccgtaa    7860
agaaaaataa gcacaagttt tatccggcct ttattcacat tcttgcccgc ctgatgaatg    7920
```

```
ctcatccgga attccgtatg gcaatgaaag acggtgagct ggtgatatgg gatagtgttc    7980
acccttgtta caccgttttc catgagcaaa ctgaaacgtt ttcatcgctc tggagtgaat    8040
accacgacga tttccggcag tttctacaca tatattcgca agatgtggcg tgttacggtg    8100
aaaacctggc ctatttccct aaagggttta ttgagaatat gttttttcgtc tcagccaatc   8160
cctgggtgag tttcaccagt tttgatttaa acgtggccaa tatggacaac ttcttcgccc    8220
ccgttttcac catgggcaaa tattatacgc aaggcgacaa ggtgctgatg ccgctggcga    8280
ttcaggttca tcatgccgtt tgtgatggct tccatgtcgg cagaatgctt aatgaattac    8340
aacagtactg cgatgagtgg cagggcgggg cgtaattttt ttaaggcagt tattggtgcc    8400
cttaaacgcc tggttgctac gcctgaataa gtcgaccttt gtagtcttgg cctgttgtgt    8460
gcatgagcaa atcaatggca ccacccccctc ctttttgagc tgaatggtca taaaatttat    8520
aattatctat cgtaattcgg aatctatgtt cagggtctcg ccattgcttt ttgtctgctg    8580
ggtcaagttc catgcctaag gttttttaaga catcagaaag aggtattgca cgcatgctat    8640
cagcttttct tctagctaat gacagggctt cctctgctct atctgctcgt ttttttttctt    8700
ccacatatct cgccgctttg tcagccagcg gctgtattac ggaaagtgcc gattttttggg   8760
cttttaggcg ttctttttct gcccattctt ccttatttgt aaaaattgag ggtgggatgg    8820
gtgcctgaat cttgggatct agctgtaaag ttttgttgat atttccgtaa tgtctttgga    8880
ctctttgatg cgttgctttt gaaccttta cgcctctggc cagccctaga ggctccatag     8940
aagccgcata atccgtctgg agggcagaaa gggcttttcg accatcaaac catctcgatg    9000
cgtttaaacg gcctgtatcg gggtctctag gcaccataaa gccggttaag tggggtgttg    9060
tttcatcagc atgtagctga agagatacaa ggttgttttc tccaaaggtt tgttccgccc    9120
attgctgggt gattgttttc cagtgttcga gttttttcagg agtggcctgt tttgaccatt    9180
ctggagacat accaaagaac agttctatgg cctgcacacc gttttttcta agaggctttc    9240
ccgtttcttt ctgaattttta ttcagcatag atttaacatc tgctgatggg tcagtagagc    9300
ctttgagtat ttcgtttagt tcttttctat ctgggtcagc gttttgtgtt tcgcggcctc    9360
gcgtcatatg caggctcgcg gctttaatcg tgccaactgt tttatgtttt tcaaacctaa    9420
agattgcata gttcggcatg ttttaactgc tttaatttga gaaaagacca gaggaaataa    9480
tccagcctat atttctttcc ctagtagcga actggaattg ttttttccgaa ggaaaaaagc    9540
aattccgtag tgagtactga atttattctg attcgtcttg cttttggagc gtcttttttgc    9600
gttctataac tgttgtgaaa gctacgcggt cgccattgaa aacgaaatta ggattaataa    9660
aataccatcc ttggcgaaca tgctttgcaa tgattttagc ttttttctaat tcggctagac    9720
ctcttgcaaa ggtagcttga gatagtgcca gttttttttc ttgtgcgtta agaaagtcct    9780
ctaaaacgaa tttgtctaaa gggacgaggt cttttgctgat gcctttgtct tgaagtatcc    9840
aaaccagaac gctgaaagct tttattccag cggctcctag ttcaaaagtt agcgcgatat    9900
tggtgctaaa taatttttaca aattcttcac tatcaacacg tctgtaagtc gtcacatgag    9960
tgccttgcat ctcaccagtg gcttgattga ccagaatgtt atcatctcgt cctaatcgag   10020
ataactgaac cctctgactt ttaactgcca caaccatacc ttcgatgaaa ggattctcgt   10080
catatctgat tggctgcttt ctcaatttttg tcgccatatt tgataaacct ttaatcaaaa    10140
aaaccacatt ttttgattat acctattcat cgaatgaggc aaggtctatc aattttaccc   10200
cttttttttga tagacggttt aatcaatatt gatagacccc ttcacagatt ctgaaaatcg   10260
acttccctat tttagggata ttttcacgat tcccttttctt agttcttcct agtggggaaa   10320
```

```
ttcgttgaat cctgcctcgg aaaaaccatg agaaagctgt tggttatata cacgggcaaa    10380
gccaccctat ttttagctac tggggaaaga gataaggcag ggtatttgta aaattaaaac    10440
cggattttc  gctttacggt ttgtttaggc gcaactgtct ttttaagacc gcgtttaacc    10500
atcaaaagat cgttccaatc ttttccgtgt atcatctgtt ctttaggtgg gagccagttt    10560
tcaactttt  ttgttggaaa cgcggcttta atcgctccga ctaatagcga tgctgctctt    10620
tgtcctacag catcccaatc ataggcaata tggacagaag atgccttttc aacgattttt    10680
cggagagttt tagtaagaga cgttcttacg ccgctggtgc ttaataattt tacgccagct    10740
ttaattttt  ctgggcttaa aaagccgact actgaaatcg cgtctatcgc actttcagcg    10800
atataaagat catacttttc gtcatttttt acattgatgc tgccagtaaa atgggcttcg    10860
cgactgcttc ccaaggctaa ccctttaaaa ccactgcttg ttccgcgtaa ttctgcgccc    10920
tgaagtgtat ctttatcgtc atacatcaag aaggctacat taccgcgatc atctgttcgg    10980
atagagtcag gaatattgtt aaatgatatt cctcgggcag cgttgggtcc tggccacggg    11040
tgcgcatgat cgtgctcctg tcgttgagga cccggctagg ctggcggggt tgccttactg    11100
gttagcagaa tgaatcaccg atacgcgagc gaacgtgaag cgactgctgc tgcaaaacgt    11160
ctgcgacctg agcaacaaca tgaatggtct tcggtttccg tgtttcgtaa agtctggaaa    11220
cgcggaagtc ccctacgtgc tgctgaagtt gcccgcaaca gagagtggaa ccaaccggtg    11280
ataccacgat actatgactg agagtcaacg ccatgggagc tcgttttct  atccccatca    11340
cctcggtttt gttgacaaaa aaaggtggcc actaaattgg cttccgcac  cgatgggatg    11400
attttattc  tttgctattc ttcgctcttt gcccaattca ttaaaagcgg aaatcatcac    11460
caaagataga agacgcagcc ttcaccattt cagattgccc ttctcgggca ttttctgctg    11520
ctagaatcct cttaaaaata ttaaattcca ctctattggt aatatgtttc cctctttagg    11580
gaacaaataa agcccttctt tgttctataa agttagctt  accgatttta caaaaaataa    11640
taccgcttca ttcaatcggt aatacatatc ttttttcttc aaaaaacttt tcaagagggt    11700
gtctatgcgc gtcgcaatat tcagttccaa aaactatgac catcattcta ttgaaaaaga    11760
aaatgaacat tatggccatg accttgtttt tctgaatgag cggcttacca aagagacagc    11820
agaaaaagcc aaagacgcag aagctgtttg tatctttgtg aatgacgaag ccaatgccga    11880
agtgctggaa attttggcag gcttaggcat caagttggtt gctcttcgtt gcgccggtta    11940
taacaatgtc gatctcgatg cggccaaaaa gctgaatatc aaggttgtgc gcgtgcctgc    12000
ctattcgccc tattcggttg ccgaatatgc agtagggatg ttgctcaccc tgaatcggca    12060
aatttcacgc ggtttgaagc gggttcggga aaataacttc tccttggaag gtttgattgg    12120
ccttgatgtg catgacaaaa cagtcggcat tatcggtgtt ggtcatatcg ggagcgtctt    12180
tgcccatatt atgaccca                                                 12198
```

<210> SEQ ID NO 33
<211> LENGTH: 875
<212> TYPE: DNA
<213> ORGANISM: artificial sequence
<220> FEATURE:
<223> OTHER INFORMATION: constructed fragment for targeting integration
      into the ldh locus of Z. mobilis

<400> SEQUENCE: 33

```
gttttctat  cccatcacc tcggttttgt tgacaaaaaa aggtggccac taaattggct     60
ttccgcaccg atgggatgat ttttattctt tgctattctt cgctctttgc ccaattcatt    120
```

```
aaaagcggaa atcatcacca aagatagaag acgcagcctt caccatttca gattgccctt      180
ctcgggcatt ttctgctgct agaatcctct taaaaatatt aaattccact ctattggtaa      240 tatgttccc tctttaggga acaaataaag cccttctttg ttctataaaa gttagcttac       300
cgattttaca aaaaataata ccgcttcatt caatcggtaa tacatatctt ttttcttcaa      360 aaaactttc aagagggtgt ctatgcgcgt cgcaatattc agttccaaaa actatgacca       420
tcattctatt gaaaagaaa atgaacatta tggccatgac cttgttttc tgaatgagcg        480 gcttaccaaa gagacagcag aaaaagccaa agacgcagaa gctgtttgta tctttgtgaa      540
tgacgaagcc aatgccgaag tgctggaaat tttggcaggc ttaggcatca agttggttgc      600
tcttcgttgc gccggttata acaatgtcga tctcgatgcg ccaaaaagc tgaatatcaa       660 ggttgtgcgc gtgcctgcct attcgcccta ttcggttgcc gaatatgcag tagggatgtt     720
gctcaccctg aatcggcaaa tttcacgcgg tttgaagcgg gttcgggaaa taacttctc      780 cttggaaggt ttgattggcc ttgatgtgca tgacaaaaca gtcggcatta tcggtgttgg     840
tcatatcggg agcgtctttg cccatattat gaccc                                 875

<210> SEQ ID NO 34
<211> LENGTH: 1149
<212> TYPE: DNA
<213> ORGANISM: artificial sequence
<220> FEATURE:
<223> OTHER INFORMATION: constructed fragment for integration into the
      Z. mobilis ldh locus

<400> SEQUENCE: 34
atggttttgg tgccaatgtt atcgcctata aaccgcatcc agaccccgaa ttggcgaaaa       60
aggtcggttt ccgcttcacc tctctcgatg aagtgatcga gaccagcgac atcatttcgc      120
ttcactgtcc gctcacgcca gaaaatcatc acatgattaa tgaagaaaca ctggcaaggg      180
caaaaaaagg cttttaccte gtcaatacca gtcgcggcgg cttggttgat accaaggcgg      240
tgattaaatc gctgaaagcc aaacatctcg gcggttatgc ggcggatgtt tacgaagagg      300
aggggccttt attcttcgaa aatcacgctg acgatattat cgaagatgat attctcgaaa     360
ggttgatcgc tttcccgaat gtggttttca cgggacatca ggccttttg acgaaagagg      420 ccttatcaaa cattgctcac agtattctac aagatatcag cgatgccgaa gctgaaaag      480 aaatgccgga tgcgcttgtt tagtagacaa gcgacaatta accttttgaa gatcataatg     540 atcaaattt tgggttaatt cggtagttat ggcataggct attacgcgct aattgatatc      600
aaaaaaaagc atagccggac atcataccgg ctatgttttt tattaggaaa aaatttcctt     660
tcaccttgct tagccatcgc cgcattattt aatcaatatg ccgagttttt cttgaaatcc    720
ctatcttaca ccaaggccaa caagggaatc atccatactc ggtgtcctat cctatgactt    780
tttaaatttt ctccaaattt actaaaatca cgccatctca gcggctgcta ttttcaaaaa    840
gcgcctctca aaaccgcttt ttcctgctca aatatcggat cccaaaattc cctcaaaaaa    900
ggcagggtat ttttacaaa atcgcccta atatctctca atccgctgcc ttgttcatat     960 gttttgcaa atgatttta ttaaactttt ttaggcgtat tttatcaag aaatttaaa       1020 taatcacatt tttattattt tagatttaag tattgataca agtgatatct ataaatgttt     1080
ttataacttt ctggatcgta atcggctggc aatcgttttc cctatattcg caagatgtat    1140
gtcagccgc                                                            1149
```

<210> SEQ ID NO 35
<211> LENGTH: 996
<212> TYPE: DNA
<213> ORGANISM: Zymomonas mobilis

<400> SEQUENCE: 35

| | | | | | |
|---|---|---|---|---|---|
| atgcgcgtcg | caatattcag | ttccaaaaac | tatgaccatc | attctattga | aaagaaaat | 60 |
| gaacattatg | ccatgaccct | tgtttttctg | aatgagcggc | ttaccaaaga | gacagcagaa | 120 |
| aaagccaaag | acgcagaagc | tgtttgtatc | tttgtgaatg | acgaagccaa | tgccgaagtg | 180 |
| ctggaaattt | tggcaggctt | aggcatcaag | ttggttgctc | ttcgttgcgc | cggttataac | 240 |
| aatgtcgatc | tcgatgcggc | caaaaagctg | aatatcaagg | ttgtgcgcgt | gcctgcctat | 300 |
| tcgccctatt | cggttgccga | atatgcagta | gggatgttgc | tcaccctgaa | tcggcaaatt | 360 |
| tcacgcggtt | tgaagcgggt | tcgggaaaat | aacttctcct | tggaaggttt | gattggcctt | 420 |
| gatgtgcatg | acaaaacagt | cggcattatc | ggtgttggtc | atatcgggag | cgtcttttgcc | 480 |
| catattatga | cccatggttt | tggtgccaat | gttatcgcct | ataaaccgca | tccagacccc | 540 |
| gaattggcga | aaaaggtcgg | tttccgcttc | acctctctcg | atgaagtgat | cgagaccagc | 600 |
| gacatcattt | cgcttcactg | tccgctcacg | ccagaaaatc | atcacatgat | taatgaagaa | 660 |
| acactggcaa | gggcaaaaaa | aggcttttac | ctcgtcaata | ccagtcgcgg | cggcttggtt | 720 |
| gataccaagg | cggtgattaa | atcgctgaaa | gccaaacatc | tcggcggtta | tgcggcggat | 780 |
| gtttacgaag | aggaggggcc | tttattcttc | gaaaatcacg | ctgacgatat | tatcgaagat | 840 |
| gatattctcg | aaaggttgat | cgcttttccg | aatgtggttt | tcacgggaca | tcaggccttt | 900 |
| ttgacgaaag | aggccttatc | aaacattgct | cacagtattc | tacaagatat | cagcgatgcc | 960 |
| gaagctggaa | agaaatgcc | ggatgcgctt | gtttag | | | 996 |

<210> SEQ ID NO 36
<211> LENGTH: 3339
<212> TYPE: DNA
<213> ORGANISM: artificial sequence
<220> FEATURE:
<223> OTHER INFORMATION: constructed fragment containing a 304-bp
    T-mutant of the Z. mobilis GAP promoter (PgapT), a 954-bp E. coli
    Tal coding region (ECTal), a 1,992-bp E. coli Tkt coding region,
    and a 68-bp E. coli Tkt 3'UTR (ECTkt 3'UTR)

<400> SEQUENCE: 36

| | | | | | |
|---|---|---|---|---|---|
| gttcgatcaa | caacccgaat | cctatcgtaa | tgatgttttg | cccgatcagc | ctcaatcgac | 60 |
| aattttacgc | gtttcgatcg | aaacagggac | gacaattggc | tgggaacggt | atactggaat | 120 |
| aaatggtctt | cgttatggta | ttgatgtttt | tggtgcatcg | gccccggcga | atgatctata | 180 |
| tgctcatttc | ggcttgaccg | cagtcggcat | cacgaacaag | gtgttggccg | cgatcgccgg | 240 |
| taagtcggca | cgttaaaaaa | tagctatgga | atataatagc | tactaataag | ttaggagaat | 300 |
| aaacatgacg | gacaaattga | cctcccttcg | tcagtacacc | accgtagtgg | ccgacactgg | 360 |
| ggacatcgcg | gcaatgaagc | tgtatcaacc | gcaggatgcc | acaaccaacc | cttctctcat | 420 |
| tcttaacgca | gcgcagattc | cggaataccg | taagttgatt | gatgatgctg | tcgcctgggc | 480 |
| gaaacagcag | agcaacgatc | gcgcgcagca | gatcgtggac | gcgaccgaca | aactggcagt | 540 |
| aaatattggt | ctggaaatcc | tgaaactggt | tccgggccgt | atctcaactg | aagttgatgc | 600 |
| gcgcctttcc | tatgacaccg | aagcgtcaat | tgcgaaagca | aaacgcctga | tcaaactcta | 660 |
| caacgatgct | ggtattagca | acgatcgtat | tctgatcaaa | ctggcttcta | cctggcaggg | 720 |
| tatccgtgct | gcagaacagc | tggaaaaaga | aggcatcaac | tgtaacctga | ccctgctgtt | 780 |

```
ctccttcgct caggctcgtg cttgtgcgga agcgggcgtg ttcctgatct cgccgtttgt    840
tggccgtatt cttgactggt acaaagcgaa taccgataag aaagagtacg ctccggcaga    900
agatccgggc gtggtttctg tatctgaaat ctaccagtac tacaaagagc acggttatga    960
aaccgtggtt atgggcgcaa gcttccgtaa catcggcgaa attctggaac tggcaggctg   1020
cgaccgtctg accatcgcac cggcactgct gaaagagctg gcggagagcg aaggggctat   1080
cgaacgtaaa ctgtcttaca ccggcgaagt gaaagcgcgt ccggcgcgta tcactgagtc   1140
cgagttcctg tggcagcaca accagggtcc aatggcagta gataaactgg cggaaggtat   1200
ccgtaagttt gctattgacc aggaaaaact ggaaaaaatg atcggcgatc tgctgtaatc   1260
tagacgatct ggagtcaaaa tgtcctcacg taaagagctt gccaatgcta ttcgtgcgct   1320
gagcatggac gcagtacaga aagccaaatc cggtcacccg ggtgccccta tgggtatggc   1380
tgacattgcc gaagtcctgt ggcgtgattt cctgaaacac aacccgcaga atccgtcctg   1440
ggctgaccgt gaccgcttcg tgctgtccaa cggccacggc tccatgctga tctacagcct   1500
gctgcacctc accggttacg atctgccgat ggaagaactg aaaaacttcc gtcagctgca   1560
ctctaaaact ccgggtcacc cggaagtggg ttacaccgct ggtgtggaaa ccaccaccgg   1620
tccgctgggt cagggtattg ccaacgcagt cggtatggcg attgcagaaa aaacgctggc   1680
ggcgcagttt aaccgtccgg ccacgacatt gtcgaccac tacacctacg ccttcatggg   1740
cgacggctgc atgatggaag gcatctccca cgaagtttgc tctctggcgg gtacgctgaa   1800
gctgggtaaa ctgattgcat ctacgatga caacggtatt tctatcgatg gtcacgttga   1860
aggctggttc accgacgaca ccgcaatgcg tttcgaagct tacggctggc acgttattcg   1920
cgacatcgac ggtcatgacg cggcatctat caaacgcgca gtagaagaag cgcgcgcagt   1980
gactgacaaa ccttccctgc tgatgtgcaa accatcatc ggtttcggtt ccccgaacaa   2040
agccggtacc cacgactccc acggtgcgcc gctgggcgac gctgaaattg ccctgacccg   2100
cgaacaactg ggctggaaat atgcgccgtt cgaaatcccg tctgaaatct atgctcagtg   2160
ggatgcgaaa gaagcaggcc aggcgaaaga atccgcatgg aacgagaaat tcgctgctta   2220
cgcgaaagct tatccgcagg aagccgctga atttacccgc cgtatgaaag cgaaatgcc   2280
gtctgacttc gacgctaaag cgaaagagtt catcgctaaa ctgcaggcta atccggcgaa   2340
aatcgccagc cgtaaagcgt ctcagaatgc tatcgaagcc ttcggtccgc tgttgccgga   2400
attcctcggc ggttctgctg acctggcgcc gtctaacctg accctgtggt ctggttctaa   2460
agcaatcaac gaagatgctg cgggtaacta catccactac ggtgttcgcg agttcggtat   2520
gaccgcgatt gctaacggta tctccctgca cggtggcttc ctgccgtaca cctccacctt   2580
cctgatgttc gtggaatacg cacgtaacgc cgtacgtatg gctgcgctga tgaaacagcg   2640
tcaggtgatg gtttacaccc acgactccat cggtctgggc gaagacggcc cgactcacca   2700
gccggttgag caggtcgctt ctctgcgcgt aaccccgaac atgtctacat ggcgtccgtg   2760
tgaccaggtt gaatccgcgg tcgcgtggaa atacggtgtt gagcgtcagg acggcccgac   2820
cgcactgatc ctctcccgtc agaacctggc gcagcaggaa cgaactgaag agcaactggc   2880
aaacatcgcg cgcggtggtt atgtgctgaa agactgcgcc ggtcagccgg aactgatttt   2940
catcgctacc ggttcagaag ttgaactggc tgttgctgcc tacgaaaaac tgactgccga   3000
aggcgtgaaa gcgcgcgtgg tgtccatgcc gtctaccgac gcatttgaca agcaggatgc   3060
tgcttaccgt gaatccgtac tgccgaaagc ggttactgca cgcgttgctg tagaagcggg   3120
```

| | |
|---|---|
| tattgctgac tactggtaca agtatgttgg cctgaacggt gctatcgtcg gtatgaccac | 3180 |
| cttcggtgaa tctgctccgg cagagctgct gtttgaagag ttcggcttca ctgttgataa | 3240 |
| cgttgttgcg aaagcaaaag aactgctgta attagcattt cgggtaaaaa aggtcgcttc | 3300 |
| ggcgaccttt tttattacct tgataatgtc cgtttgcgc | 3339 |

<210> SEQ ID NO 37
<211> LENGTH: 304
<212> TYPE: DNA
<213> ORGANISM: artificial sequence
<220> FEATURE:
<223> OTHER INFORMATION: mutant Pgap promoter with a "G" to an "A"
change at position 83 in SEQ ID NO:21

<400> SEQUENCE: 37

| | |
|---|---|
| gttcgatcaa caacccgaat cctatcgtaa tgatgttttg cccgatcagc ctcaatcgac | 60 |
| aattttacgc gtttcgatcg aaacagggac gacaattggc tgggaacggt atactggaat | 120 |
| aaatggtctt cgttatggta ttgatgtttt tggtgcatcg gccccggcga atgatctata | 180 |
| tgctcatttc ggcttgaccg cagtcggcat cacgaacaag gtgttggccg cgatcgccgg | 240 |
| taagtcggca cgttaaaaaa tagctatgga atataatagc tactaataag ttaggagaat | 300 |
| aaac | 304 |

<210> SEQ ID NO 38
<211> LENGTH: 1443
<212> TYPE: DNA
<213> ORGANISM: artificial sequence
<220> FEATURE:
<223> OTHER INFORMATION: constructed fragment containing a 191 bp Peno,
a 471 bp Z. mobilis Rpi coding sequence (ZMRpi), a 663 bp Z.
mobilis Rpe coding sequence (ZMRpe), and a 35 bp E.coli xylA 3'UTR
(ECxylA 3'UTR)

<400> SEQUENCE: 38

| | |
|---|---|
| ccagttactc aatacgtaac aataatcagt ttatcctaac tatagaatcg catgagaagc | 60 |
| gataacgttt caccataagc aatatattca ttgcaacagt ggaattgcct tatgcgtcaa | 120 |
| ggaaggatag atcattgacg gactgagttc aaaaagagac tggtctaaaa gattttaaga | 180 |
| aaggtttcga tatgacctct gctgtgccat caaatacgaa aaaaaagctg gtgattgctt | 240 |
| ccgatcacgc agcatttgag ttgaaatcaa ccttgattac ttggctgaaa gagcttggtc | 300 |
| atgaggtcga agaccttggc cctcatgaaa accattcagt cgattatccc gattacggtt | 360 |
| ataagctggc tgtcgctatc gcagaaaaaa ccgctgattt cggtattgct ttatgtggct | 420 |
| cgggaatcgg tatctcgatc gctgtcaatc gccatccggc tgcccgttgc gctttgatta | 480 |
| cggataaccct taccgcccgt ttggcaagag aacataacaa tgccaatgtt atcgctatgg | 540 |
| gtgcgagatt gatcggcatt gaaaccgcta aggattgtat ttcagctttc cttgcaacgc | 600 |
| cgtttggagg tgaacgtcat gttgccgta tcgataaact ttcgaatcct cagttcaata | 660 |
| tctagataag ttaggagaat aaacatgagt aaattacccc tgattgctcc ctctatcctt | 720 |
| tcggcggatt ttgccccattt gggagatgag gtcgcggcga tagatcaggc cggtgccgat | 780 |
| tggatccata ttgatgtgat ggatggccat ttcgtgccga atatcaccat aggccccatg | 840 |
| gttgtgaagg ctttgcgtcc ctatagccaa aagccttttg atgtccattt gatgattgcg | 900 |
| cctgtcgatc aatatatcga ggcttttttct gaagcgggtg ctgatattat cagtttccat | 960 |
| cccgaagcgg gcgcgcatcc ccatcgcact attcagcata tcaaatcatt gggcaaaaaa | 1020 |
| gcgggattag tttttaatcc ggcgaccccct ttaagctggc ttgattatct aatggatgat | 1080 |

```
cttgatctga ttatggtgat gagcgttaac cccggttttg gcggccaaaa atttatcaaa    1140
acccaattag aaaagattaa agatatccgt caaagaatta ccgcctctgg gcgggatatc    1200
cgcttggaag tggatggcgg aattgatgcc acgactgcac cgcttgccgt cgaagccggt    1260
gccgatgttt tggtcgcggg aacggccagc tttaaaggcg gcgcaacatg ttacaccgat    1320
aatatcagga tattgcgtaa atcatgatta attaactcga ggcggcctga acgtactgca    1380
agtcctgacg tcactgtgca gtccgttggc ccggttatcg gtagcgatac cgggcatttt    1440
ttt                                                                  1443
```

<210> SEQ ID NO 39
<211> LENGTH: 12704
<212> TYPE: DNA
<213> ORGANISM: artificial sequence
<220> FEATURE:
<223> OTHER INFORMATION: constructed plasmid

<400> SEQUENCE: 39

```
ctagtgttcg atcaacaacc cgaatcctat cgtaatgatg ttttgcccga tcagcctcaa      60
tcgacaattt tacgcgtttc gatcgaagca gggacgacaa ttggctggga acggtatact     120
ggaataaatg gtcttcgtta tggtattgat gttttttggtg catcggcccc ggcgaatgat     180
ctatatgctc atttcggctt gaccgcagtc ggcatcacga acaaggtgtt ggccgcgatc     240
gccggtaagt cggcacgtta aaaaatagct atggaatata atagctacta ataagttagg     300
agaataaaca tgacggacaa attgacctcc cttcgtcagt acaccaccgt agtggccgac     360
actggggaca tcgcggcaat gaagctgtat caaccgcagg atgccacaac caacccttct     420
ctcattctta acgcagcgca gattccggaa taccgtaagt tgattgatga tgctgtcgcc     480
tgggcgaaac agcagagcaa cgatcgcgcg cagcagatcg tggacgcgac cgacaaactg     540
gcagtaaata ttggtctgga atcctgaaa ctggttccgg gccgtatctc aactgaagtt     600
gatgcgcgtc tttcctatga caccgaagcg tcaattgcga aagcaaaacg cctgatcaaa     660
ctctacaacg atgctggtat tagcaacgat cgtattctga tcaaactggc ttctacctgg     720
cagggtatcc gtgctgcaga acagctggaa aaagaaggca tcaactgtaa cctgaccctg     780
ctgttctcct tcgctcaggc tgtgcttgt gcggaagcgg gcgtgttcct gatctcgccg     840
tttgttggcc gtattcttga ctggtacaaa gcgaataccg ataagaaaga gtacgctccg     900
gcagaagatc cgggcgtggt ttctgtatct gaaatctacc agtactacaa agagcacggt     960
tatgaaaccg tggttatggg cgcaagcttc cgtaacatcg gcgaaattct ggaactggca    1020
ggctgcgacc gtctgaccat cgcaccggca ctgctgaaag agctggcgga gagcgaaggg    1080
gctatcgaac gtaaactgtc ttacaccggc gaagtgaaag cgcgtccggc gcgtatcact    1140
gagtccgagt cctgtggca gcacaaccag gatccaatgg cagtagataa actggcggaa    1200
ggtatccgta gtttgctat tgaccaggaa aaactgaaaa aatgatcgg cgatctgctg    1260 taatctagac gatctggagt caaaatgtcc tcacgtaaag agcttgccaa tgctattcgt    1320
gcgctgagca tggacgcagt acagaaagcc aaatccggtc acccgggggc ccctatgggt    1380
atggctgaca ttgccgaagt cctgtggcgt gatttcctga acacaacccc gcagaatccg    1440
tcctgggctg accgtgaccg cttcgtgctg tccaacggcc acggctccat gctgatctac    1500
agcctgctgc acctcaccgg ttacgatctg ccgatggaag aactgaaaaa cttccgtcag    1560
ctgcactcta aaactccggg tcacccggaa gtgggttaca ccgctggtgt ggaaaccacc    1620
```

```
accggtccgc tgggtcaggg tattgccaac gcagtcggta tggcgattgc agaaaaaacg    1680
ctggcggcgc agtttaaccg tccgggccac gacattgtcg accactacac ctacgccttc    1740
atgggcgacg gctgcatgat ggaaggcatc tcccacgaag tttgctctct ggcgggtacg    1800
ctgaagctgg gtaaactgat tgcattctac gatgacaacg gtatttctat cgatggtcac    1860
gttgaaggct ggttcaccga cgacaccgca atgcgtttcg aagcttacgg ctggcacgtt    1920
attcgcgaca tcgacggtca tgacgcggca tctatcaaac gcgcagtaga agaagcgcgc    1980
gcagtgactg acaaaccttc cctgctgatg tgcaaaacca tcatcggttt cggttccccg    2040
aacaaagccg gtacccacga ctcccacggt gcgccgctgg gcgacgctga aattgccctg    2100
acccgcgaac aactgggctg gaaatatgcg ccgttcgaaa tcccgtctga aatctatgct    2160
cagtgggatg cgaaagaagc aggccaggcg aaagaatccg catggaacga gaaattcgct    2220
gcttacgcga aagcttatcc gcaggaagcc gctgaattta cccgccgtat gaaaggcgaa    2280
atgccgtctg acttcgacgc taaagcgaaa gagttcatcg ctaaactgca ggctaatccg    2340
gcgaaaatcg ccagccgtaa agcgtctcag aatgctatcg aagcgttcgg tccgctgttg    2400
ccggaattcc tcggcggttc tgctgacctg cgcgccgtcta acctgaccct gtggtctggt    2460
tctaaagcaa tcaacgaaga tgctgcgggt aactacatcc actacggtgt cgcgagttc    2520 ggtatgaccg cgattgctaa cggtatctcc ctgcacggtg gcttcctgcc gtacacctcc    2580
accttcctga tgttcgtgga atacgcacgt aacgccgtac gtatggctgc gctgatgaaa    2640
cagcgtcagg tgatggttta cacccacgac tccatcggtc tgggcgaaga cgggccgact    2700
caccagccgg ttgagcaggt cgcttctctg cgcgtaaccc cgaacatgtc tacatggcgt    2760
ccgtgtgacc aggttgaatc cgcggtcgcg tggaaatacg gtgttgagcg tcaggacggc    2820
ccgaccgcac tgatcctctc ccgtcagaac ctggcgcagc aggaacgaac tgaagagcaa    2880
ctggcaaaca tcgcgcgcgg tggttatgtg ctgaaagact cgccggtca gccggaactg    2940 attttcatcg ctaccggttc agaagttgaa ctggctgttg ctgcctacga aaaactgact    3000
gccgaaggcg tgaaagcgcg cgtggtgtcc atgtcgtcta ccgacgcatt tgacaagcag    3060
gatgctgctt accgtgaatc cgtactgccg aaagcggtta ctgcacgcgt tgctgtagaa    3120
gcgggtattg ctgactactg gtacaagtat gttggcctga cggtgctat cgtcggtatg    3180 accaccttcg gtgaatctgc tccggcagag ctgctgtttg aagagttcgg cttcactgtt    3240
gataacgttg ttgcgaaagc aaaagaactg ctgtaattag catttcgggt aaaaaaggtc    3300
gcttcggcga cctttttttat taccttgata atgtccgttt gcgcggcgcg ccccagttac    3360
tcaatacgta acaataatca gtttatccta actatagaat cgcatgagaa gcgataacgt    3420
ttcaccataa gcaatatatt cattgcaaca gtggaattgc cttatgcgtc aaggaaggat    3480
agatcattga cggactgagt tcaaaaagag actcgtctaa aagatttaa gaaaggtttc    3540 gatatgacct ctgctgtgcc atcaaatacg aaaaaaaagc tggtgattgc ttccgatcac    3600
gcagcatttg agttgaaatc aaccttgatt acttggctga aagagcttgg tcatgaggtc    3660
gaagaccttg ccctcatga aaaccattca gtcgattatc ccgattacgg ttataagctg    3720
gctgtcgcta tcgcagaaaa aaccgctgat ttcggtattg cttatgtgg ctcgggaatc    3780 ggtatctcga tcgctgtcaa tcgccatccg gctgcccgtt gcgctttgat tacggataac    3840
cttaccgccc gtttggcaag agaacataac aatgccaatg ttatcgctat gggtgcgaga    3900
ttgatcggca ttgaaaccgc taaggattgt atttcagctt tccttgcaac gccgtttgga    3960
ggtgaacgtc atgttcgccg tatcgataaa cttttcgaatc ctcagttcaa tatctagata    4020
```

```
agttaggaga ataaacatga gtaaattacc cctgattgct ccctctatcc tttcggcgga    4080
ttttgcccat ttgggagatg aggtcgcggc gatagatcag gccggtgccg attggatcca    4140
tattgatgtg atggatggcc atttcgtgcc gaatatcacc ataggcccca tggttgtgaa    4200
ggctttgcgt ccctatagcc aaaagccttt tgatgtccat ttgatgattg cgcctgtcga    4260
tcaatatatc gaggcttttt ctgaagcggg tgctgatatt atcagtttcc atcccgaagc    4320
gggcgcgcat ccccatcgca ctattcagca tatcaaatca ttgggcaaaa aagcgggatt    4380 agttttaat ccggcgaccc ctttaagctg gcttgattat ctaatggatg atcttgatct    4440
gattatggtg atgagcgtta acccggtttt tggcggccaa aaatttatca aacccaatt    4500 agaaaagatt aaagatatcc gtcaaagaat taccgcctct gggcgggata tccgcttgga    4560
agtggatggc ggaattgatg ccacgactgc accgcttgcc gtcgaagccg gtgccgatgt    4620
tttggtcgcg ggaacggcca gctttaaagg cggcgcaaca tgttacaccg ataatatcag    4680
gatattgcgt aaatcatgat taattaactc gaggcggcct gaacgtactg caagtcctga    4740
cgtcactgtg cagtccgttg gcccggttat cggtagcgat accgggcatt ttttaagga    4800 acgatcgata gaattcgcgg ccggcccggc aagacgtgat atggaaccgg aatttgctcc    4860
ggcattcctg cgcaaagata gctaatatct ttcatatttt gtatcgaaaa aggagggtct    4920
ttaaagatcc tcctttttt tgcataaaaa gaaggccata gaacaaacag tgataaagac    4980
agtctcaaac tgtcttttta tagaaaatac cagaatattg tatctggggg aggatgcatg    5040
gtcttaatcc ggaataccc ggtcatgcac aggatgttag agcttttgcc tttatgcaa    5100 aataaaccat ggctcgggaa tatctgcgct ttgattttg taggatgtgc cttccttgtc    5160
cgtagtatta ttgggcattt tttaccggca ggttatcctt tcgtgacctt tatgccgaca    5220
atgcttgtgg ttactttcct ctttgggaca agaccgggta ttatcgcggc tattcttagc    5280
ttgatggttg cgccttattt tatcgaagaa ggaagccgat ttaacggtgt attggtctgg    5340
tttctttgcc tgctagaaac agtcactgat atgggattgg tgattgcgct acagcaaggt    5400
aattaccgcc tccagaaaaa gcgtgcctat aatcagatgc tggctgaacg caatgagttg    5460
ctgtttcatg aattacagca tcgcatttca ataacttac aggttattgc gtcattattg    5520
cggatgcaaa gccgcagcat caccgatgaa aaagccaagg aagctattga tgcctctgtt    5580
cgtcggattc atatgatcgg tgaattacag cgggcgcttt atattaaaaa cgggaatcag    5640
cttggggcaa aattgatcct tgatcgcttg atcaaagagg tcattgcgtc cagtaatctc    5700
ccgaacatcc gctataaaat agaagctgaa gacctgatct taccgtcaga tatggcaatc    5760
cctttagcgc ttgtatctgc tgaatccgtt tcaaacgcgt tagagcatgg ctttaaaggc    5820
gatcataaag acgcgtttat tgaaattaag cttcaaaaaa ttagcgggca aatcgaactt    5880
accatttcca ataatggcaa acctcttccc caaggctttt cccttgaaaa ggtcgatagc    5940
ttaggcctga aaattgcggc tatgtttgcc cgacaattca aaggaaaatt caccttaagt    6000
aatcagccta accgttatgt ggtttctagc cttatttgc cttgcggtta ggcggccgcc    6060
taattccgga tgagcattca tcaggcgggc aagaatgtga ataaaggccg ataaaacttt    6120
gtgcttattt ttctttacgg tctttaaaaa ggccgtaata tccagctgaa cggtctggtt    6180
ataggtacat tgagcaactg actgaaatgc ctcaaaatgt tctttacgat gccattggga    6240
tatatcaacg gtggtatatc cagtgatttt ttctccatt ttagcttcct tagctcctga    6300
aaatctcgat aactcaaaaa atacgcccgg tagtgatctt atttcattat ggtgaaagtt    6360
```

```
ggaacctctt acgtgccgat caacgtctca ttttcgccaa aagttggccc agggcttccc   6420
ggtatcaaca gggacaccag gatttattta ttctgcgaag tgatcttccg tcacaggtat   6480
ttattcggcg caaagtgcgt cgggtgatgc tgccaactta ctgatttagt gtatgatggt   6540
gttttttgagg tgctccagtg gcttctgttt ctatcagctg tccctcctgt tcagctactg   6600
acggggtggt gcgtaacggc aaaagcaccg ccggacatca gcgctagcgg agtgtatact   6660
ggcttactat gttggcactg atgagggtgt cagtgaagtg cttcatgtgg caggagaaaa   6720
aaggctgcac cggtgcgtca gcagaatatg tgatacagga tatattccgc ttcctcgctc   6780
actgactcgc tacgctcggt cgttcgactc cggcgagcgg aaatggctta cgaacggggc   6840
ggagatttcc tggaagatgc caggaagata cttaacaggg aagtgagagg gccgcggcaa   6900
agccgttttt ccataggctc cgcccccctg acaagcatca cgaaatctga cgctcaaatc   6960
agtggtggcg aaacccgaca ggactataaa gataccaggc gtttccccct ggcggctccc   7020
tcgtgcgctc tcctgttcct gcctttcggt ttaccggtgt cattccgctg ttatggccgc   7080
gtttgtctca ttccacgcct gacactcagt tccgggtagg cagttcgctc caagctggac   7140
tgtatgcacg aaccccccgt tcagtccgac cgctgcgcct tatccggtaa ctatcgtctt   7200
gagtccaacc cggaaagaca tgcaaaagca ccactggcag cagccactgg taattgattt   7260
agaggagtta gtcttgaagt catgcgccgg ttaaggctaa actgaaagga caagttttgg   7320
tgactgcgct cctccaagcc agttacctcg gttcaaagag ttggtagctc agagaacctt   7380
cgaaaaaccg ccctgcaagg cggttttttc gttttcagag caagagatta cgcgcagacc   7440
aaaacgatct caagaagatc atcttattaa tcagataaaa tatttctaga tttcagtgca   7500
atttatctct tcaaatgtag cacctgaagt cagccccata cgatataagt tgtaattctc   7560
atgtttgaca gcttatcatc gatgtgacgg aagatcactt cgcagaataa ataaatcctg   7620
gtgtccctgt tgataccggg aagccctggg ccaacttttg gcgaaaatga cgttgatc     7680
ggcacgtaag aggttccaac tttcaccata atgaaataag atcactaccg ggcgtatttt   7740
ttgagttatc gagattttca ggagctaagg aagctaaaat ggagaaaaaa atcactggat   7800
ataccaccgt tgatatatcc caatggcatc gtaaagaaca ttttgaggca tttcagtcag   7860
ttgctcaatg tacctataac cagaccgttc agctggatat tacggccttt ttaaagaccg   7920
taaagaaaaa taagcacaag ttttatccgg cctttattca cattcttgcc cgcctgatga   7980
atgctcatcc ggaattccgt atggcaatga aagacggtga gctggtgata tgggatagtg   8040
ttcacccttg ttacaccgtt ttccatgagc aaactgaaac gttttcatcg ctctggagtg   8100
aataccacga cgatttccgg cagtttctac acatatattc gcaagatgtg gcgtgttacg   8160
gtgaaaacct ggcctatttc cctaaagggt ttattgagaa tatgtttttc gtctcagcca   8220
atccctgggt gagtttcacc agttttgatt taaacgtggc caatatggac aacttcttcg   8280
cccccgtttt caccatgggc aaatattata cgcaaggcga caaggtgctg atgccgctgg   8340
cgattcaggt tcatcatgcc gtttgtgatg gcttccatgt cggcagaatg cttaatgaat   8400
tacaacagta ctgcgatgag tggcagggcg gggcgtaatt tttttaaggc agttattggt   8460
gcccttaaac gcctggttgc tacgcctgaa taagtcgacc tttgtagtct tggcctgttg   8520
tgtgcatgag caaatcaatg gcaccacccc ctccttttg agctgaatgg tcataaaatt   8580
tataattatc tatcgtaatt cggaatctat gttcagggtc tcgccattgc ttttttgtctg   8640
ctgggtcaag ttccatgcct aaggttttta agacatcaga aagaggtatt gcacgcatgc   8700
tatcagcttt tcttctagct aatgacaggg cttcctctgc tctatctgct cgttttttttt   8760
```

```
cttccacata tctcgccgct tgtcagcca gcggctgtat tacggaaagt gccgattttt    8820
gggcttttag gcgttctttt tctgcccatt cttccttatt tgtaaaaatt gagggtggga    8880
tgggtgcctg aatcttggga tctagctgta aagttttgtt gatatttccg taatgtcttt    8940
ggactctttg atgcgttgct tttgaacctt ttacgcctct ggccagccct agaggctcca    9000
tagaagccgc ataatccgtc tggagggcag aaagggcttt tcgaccatca aaccatctcg    9060
atgcgtttaa acggcctgta tcggggtctc taggcaccat aaagccggtt aagtggggtg    9120
ttgtttcatc agcatgtagc tgaagagata caaggttgtt ttctccaaag gtttgttccg    9180
cccattgctg ggtgattgtt ttccagtgtt cgagttttc aggagtggcc tgttttgacc     9240
attctggaga cataccaaag aacagttcta tggcctgcac accgtttttt ctaagaggct    9300
ttcccgtttc tttctgaatt ttattcagca tagatttaac atctgctgat gggtcagtag    9360
agcctttgag tatttcgttt agttcttttc tatctgggtc agcgttttgt gtttcgcggc    9420
ctcgcgtcat atgcaggctc gcggcttttaa tcgtgccaac tgttttatgt ttttcaaacc    9480
taaagattgc atagttcggc atgttttaac tgctttaatt tgagaaaaga ccagaggaaa    9540
taatccagcc tatatttctt tccctagtag cgaactggaa ttgttttttcc gaaggaaaaa    9600 agcaattccg tagtgagtac tgaatttatt ctgattcgtc ttgcttttgg agcgtctttt    9660
tgcgttctat aactgttgtg aaagctacgc ggtcgccatt gaaaacgaaa ttaggattaa    9720
taaaatacca tccttggcga acatgctttg caatgatttt agcttttct aattcggcta     9780 gacctcttgc aaaggtagct tgagatagtc ccagtttttt ttcttgtgcg ttaagaaagt    9840
cctctaaaac gaatttgtct aaagggacga ggtctttgct gatgcctttg tcttgaagta    9900
tccaaaccag aacgctgaaa gcttttattc cagcggctcc tagttcaaaa gttagcgcga    9960
tattggtgct aaataatttt acaaattctt cactatcaac acgtctgtaa gtcgtcacat   10020
gagtgccttg catctcacca gtggcttgat tgaccagaat gttatcatct cgtcctaatc   10080
gagataactg aaccctctga cttttaactg gcacaaccat accttcgatg aaaggattct   10140
cgtcatatct gattggctgc tttctcaatt ttgtcgccat atttgataaa cctttaatca   10200
aaaaaaccac attttttgat tatacctatt catcgaatga ggcaaggtct atcaatttta   10260
cccctttttt tgatagacgg tttaatcaat attgatagac cccttcacag attctgaaaa   10320
tcgacttccc tattttaggg atattttcac gattcccttt cttagttctt cctagtgggg   10380
aaattcgttg aatcctgcct cggaaaaacc atgagaaagc tgttggttat atacacgggc   10440
aaagccaccc tattttagc tactggggaa agagataagg cagggtattt gtaaaattaa    10500
aaccggattt ttcgctttac ggtttgttta ggcgcaactg tctttttaag accgcgttta   10560
accatcaaaa gatcgttcca atcttttccg tgtatcatct gttctttagg tgggagccag   10620
ttttcaactt tttttgttgg aaacgcggct ttaatcgctc cgactaatag cgatgctgct   10680
ctttgtccta cagcatccca atcataggca atatggacag aagatgcctt ttcaacgatt   10740
tttcggagag tttttagtaag agacgttctt acgccgctgg tgcttaataa ttttacgcca   10800 gctttaatttt tttctgggct taaaaagccg actactgaaa tcgcgtctat cgcactttca   10860
gcgatataaa gatcatactt ttcgtcattt tttacattga tgctgccagt aaaatgggct   10920
tcgcgactgc ttcccaaggc taaccctta aaaccactgc ttgttccgcg taattctgcg    10980
ccctgaagtg tatctttatc gtcatacatc aagaaggcta cattaccgcg atcatctgtt   11040
cggatagagt caggaatatt gttaaatgat attcctcggg cagcgttggg tcctggccac   11100
```

```
gggtgcgcat gatcgtgctc ctgtcgttga ggacccggct aggctggcgg ggttgcctta   11160
ctggttagca gaatgaatca ccgatacgcg agcgaacgtg aagcgactgc tgctgcaaaa   11220
cgtctgcgac ctgagcaaca acatgaatgg tcttcggttt ccgtgtttcg taaagtctgg   11280
aaacgcggaa gtccctacg tgctgctgaa gttgcccgca acagagagtg gaaccaaccg    11340
```

```
gtgataccac gatactatga ctgagagtca acgccatggg agctccctat cgtctgactc   11400
gcaaggctga acgtgttgac gccttgagca aggccaaagc ggttcttgac gaagccttcc   11460
cagaagctga tccgacagaa aagctgcgca tccagaagct tgcgaagaag ctggaagcaa   11520
aaatcgtccg caccgccatt ctgaaagaag gccggagaat tgacggacgc gatctgaaaa   11580
cagttcgccc gatccgctct caggttggat tcttgccccg cacgcatggt tctgccctgt   11640
ttacgcgtgg tgaaacacag gctttggttt caaccaccct tggaacgcgc gatgctgaac   11700
agatgatcga cggtttaacc ggccttcatt atgaacgctt catgctgcat tacaacttcc   11760
ccccatattc ggtcggtgaa gttggtcgtt ttggtgctcc gggtcgtcgt gaaatcggcc   11820 atggtaaaact ggcatggcgt gcgcttcatc cggttttgcc gagcaaggct gatttcccgt   11880
ataccatccg tgttttgtcg gatatcaccg aatctaatgg ttcctcttcc atggcaaccg   11940
tttgcggtgg ctgccttgca ttgatggatg ccggtgttcc cttaacgcgt ccggtttccg   12000
gtatcgccat gggtcttatt ctggaaaaag acggcttcgc tattttgtcc gatatcatgg   12060
gtgatgaaga tcacttgggt gatatggact ttaaggtcgc cggtaccgaa aaaggtatca   12120
ccagcctcca gatggacatc aaggttgctg gcattaccga agaaatcatg cagaaagctt   12180
tggaacaggc taaaggtggc cgtgctcata tcttgggtga aatgtccaaa gcgctgggtg   12240
aagtccgctc cgaaatttct aatttggcac cgcgcattga acaatgagc gtaccaaaag   12300 acaaaatccg tgatgttatc ggaacgggcg gaaaagttat ccgtgaaatc gtggcgacca   12360
caggtgccaa ggtcgatatc gaagatgacg gcacggttcg tctgtcttct tctgatccgg   12420
ccaatattga agcagcccgt gaatggatca atggtattgt tgaagaaccg gaagtaggca   12480
aaatctataa cggtaaagtc gtcaatatcg ttgatttcgg tgccttcgta aacttcatgg   12540
gtggccgtga cggcttggta catgtttcgg aaatcaagaa cgaacgtgtc aacaaggtca   12600
gcgatgtcct gtccgaaggt caggaagtca aagtcaaggt tcttgaaatt gacaaccgtg   12660
gcaaggttcg cctgtctatg cgtgttgtcg atcaggaaac cgga                   12704
```

<210> SEQ ID NO 40
<211> LENGTH: 1318
<212> TYPE: DNA
<213> ORGANISM: artificial sequence
<220> FEATURE:
<223> OTHER INFORMATION: constructed fragment for integration into Z.
      m pnp gene

<400> SEQUENCE: 40

```
cctatcgtct gactcgcaag gctgaacgtg ttgacgcctt gagcaaggcc aaagcggttc     60
ttgacgaagc cttcccagaa gctgatccga cagaaaagct gcgcatccag aagcttgcga    120
agaagctgga agcaaaaatc gtccgcaccg ccattctgaa agaaggccgg agaattgacg    180
gacgcgatct gaaaacagtt cgcccgatcc gctctcaggt tggattcttg ccccgcacgc    240
atggttctgc cctgtttacg cgtggtgaaa cacaggcttt ggtttcaacc accttggaa    300 cggcggatgc tgaacagatg atcgacggtt taaccggcct tcattatgaa cgcttcatgc    360
tgcattacaa cttccccca tattcggtcg gtgaagttgg tcgttttggt gctccgggtc     420
```

-continued

```
gtcgtgaaat cggccatggt aaactggcat ggcgtgcgct tcatccggtt ttgccgagca      480
aggctgattt cccgtatacc atccgtgttt tgtcggatat caccgaatct aatggttcct      540
cttccatggc aaccgtttgc ggtggctgcc ttgcattgat ggatgccggt gttcccttaa      600
cgcgtccggt ttccggtatc gccatgggtc ttattctgga aaaagacggc ttcgctattt      660
tgtccgatat catgggtgat gaagatcact ggggtgatat ggactttaag gtcgccggta      720
ccgaaaaagg tatcaccagc ctccagatgg acatcaaggt tgctggcatt accgaagaaa      780
tcatgcagaa agctttggaa caggctaaag gtggccgtgc tcatatcttg ggtgaaatgt      840
ccaaagcgct gggtgaagtc cgctccgaaa tttctaattt ggcaccgcgc attgaaacaa      900
tgagcgtacc aaaagacaaa atccgtgatg ttatcggaac gggcggaaaa gttatccgtg      960
aaatcgtggc gaccacaggt gccaaggtcg atatcgaaga tgacggcacg ttcgtctgt      1020 cttcttctga tccggccaat attgaagcag cccgtgaatg gatcaatggt attgttgaag      1080
aaccggaagt aggcaaaatc tataacggta aagtcgtcaa tatcgttgat tcggtgcct      1140 tcgtaaactt catgggtggc cgtgacgct tggtacatgt ttcggaaatc aagaacgaac      1200
gtgtcaacaa ggtcagcgat gtcctgtccg aaggtcagga agtcaaagtc aaggttcttg      1260
aaattgacaa ccgtggcaag gttcgcctgt ctatgcgtgt tgtcgatcag gaaaccgg       1318
```

<210> SEQ ID NO 41
<211> LENGTH: 1225
<212> TYPE: DNA
<213> ORGANISM: artificial sequence
<220> FEATURE:
<223> OTHER INFORMATION: constructed fragment for integration into the
      Z. m pnp gene

<400> SEQUENCE: 41

```
cggcaagacg tgatatggaa ccggaatttg ctccggcatt cctgcgcaaa gatagctaat       60
atctttcata ttttgtatcg aaaaaggagg gtctttaaag atcctccttt tttttgcata      120 aaagaaggc catagaacaa acagtgataa agacagtctc aaactgtctt tttatagaaa       180
ataccagaat attgtatctg ggggaggatg catggtctta atccggaata ccccggtcat      240
gcacaggatg ttagagcttt tgcctttatg gcaaaataaa ccatggctcg ggaatatctg      300
cgctttgatt tttgtaggat gtgccttcct tgtccgtagt attattgggc atttttacc       360 ggcaggttat cctttcgtga cctttatgcc gacaatgctt gtggttactt tcctctttgg      420
gacaagaccg ggtattatcg cggctattct tagcttgatg gttgcgcctt attttatcga      480
agaaggaagc cgatttaacg gtgtattggt ctggtttctt tgcctgctag aaacagtcac      540
tgatatggga ttggtgattg cgctacagca aggtaattac cgcctccaga aaaagcgtgc      600
ctataatcag atgctggctg aacgcaatga gttgctgttt catgaattac agcatcgcat      660
ttcaaataac ttacaggtta ttgcgtcatt attgcggatg caaagccgca gcatcaccga      720
tgaaaaagcc aaggaagcta ttgatgcctc tgttcgtcgg attcatatga tcggtgaatt      780
acagcgggcg ctttatatta aaaacgggaa tcagcttggg gcaaaattga tccttgatcg      840
cttgatcaaa gaggtcattg cgtccagtaa tctcccgaac atccgctata aaatagaagc      900
tgaagacctg atcttaccgt cagatatggc aatccctta gcgcttgtat ctgctgaatc      960
cgtttcaaac gcgttagagc atggcttaa aggcgatcat aaagacgcgt ttattgaaat      1020
taagcttcaa aaaattagcg ggcaaatcga acttaccatt tccaataatg gcaaacctct      1080
tccccaaggc ttttcccttg aaaaggtcga tagcttaggc ctgaaaattg cggctatgtt      1140
```

-continued

```
tgcccgacaa ttcaaaggaa aattcacctt aagtaatcag cctaaccgtt atgtggtttc    1200
tagccttatt ttgccttgcg gttag                                          1225

<210> SEQ ID NO 42
<211> LENGTH: 25
<212> TYPE: DNA
<213> ORGANISM: artificial sequence
<220> FEATURE:
<223> OTHER INFORMATION: primer

<400> SEQUENCE: 42
cggcttcaat cggattgtta gcagg                                          25

<210> SEQ ID NO 43
<211> LENGTH: 38
<212> TYPE: DNA
<213> ORGANISM: artificial sequence
<220> FEATURE:
<223> OTHER INFORMATION: primer

<400> SEQUENCE: 43
cgtgtagctt ggacactcat gtttattctc ctaactta                            38

<210> SEQ ID NO 44
<211> LENGTH: 20
<212> TYPE: DNA
<213> ORGANISM: artificial sequence
<220> FEATURE:
<223> OTHER INFORMATION: synthetic primer

<400> SEQUENCE: 44
ccagtatcag cccgtcatac                                                20

<210> SEQ ID NO 45
<211> LENGTH: 20
<212> TYPE: DNA
<213> ORGANISM: artificial sequence
<220> FEATURE:
<223> OTHER INFORMATION: synthetic primer

<400> SEQUENCE: 45
ccagcatggt tgtgatggct                                                20

<210> SEQ ID NO 46
<211> LENGTH: 20
<212> TYPE: DNA
<213> ORGANISM: artificial sequence
<220> FEATURE:
<223> OTHER INFORMATION: synthetic primer

<400> SEQUENCE: 46
gccttgggct tttaaagcct                                                20

<210> SEQ ID NO 47
<211> LENGTH: 22
<212> TYPE: DNA
<213> ORGANISM: artificial sequence
<220> FEATURE:
<223> OTHER INFORMATION: synthetic primer

<400> SEQUENCE: 47
gagaagggtt ggttgtggca tc                                             22

<210> SEQ ID NO 48
<211> LENGTH: 22
```

<212> TYPE: DNA
<213> ORGANISM: artificial sequence
<220> FEATURE:
<223> OTHER INFORMATION: synthetic primer

<400> SEQUENCE: 48
gtggatggcg gaattgatgc ca                                           22

<210> SEQ ID NO 49
<211> LENGTH: 26
<212> TYPE: DNA
<213> ORGANISM: artificial sequence
<220> FEATURE:
<223> OTHER INFORMATION: synthetic primer

<400> SEQUENCE: 49
tctcggagag atagaggtca gtcgac                                       26

<210> SEQ ID NO 50
<211> LENGTH: 23
<212> TYPE: DNA
<213> ORGANISM: artificial sequence
<220> FEATURE:
<223> OTHER INFORMATION: synthetic primer

<400> SEQUENCE: 50
cagctatgat gacagcgcat tgg                                          23

<210> SEQ ID NO 51
<211> LENGTH: 23
<212> TYPE: DNA
<213> ORGANISM: artificial sequence
<220> FEATURE:
<223> OTHER INFORMATION: synthetic primer

<400> SEQUENCE: 51
gggcggttcg atccatagaa agg                                          23

<210> SEQ ID NO 52
<211> LENGTH: 34
<212> TYPE: DNA
<213> ORGANISM: artificial sequence
<220> FEATURE:
<223> OTHER INFORMATION: synthetic primer

<400> SEQUENCE: 52
gggagctcac tagtgtgacg gaagatcact tcgc                              34

<210> SEQ ID NO 53
<211> LENGTH: 20
<212> TYPE: DNA
<213> ORGANISM: artificial sequence
<220> FEATURE:
<223> OTHER INFORMATION: synthetic primer

<400> SEQUENCE: 53
tcgtcatgga caacaaacgg                                              20

<210> SEQ ID NO 54
<211> LENGTH: 33
<212> TYPE: DNA
<213> ORGANISM: artificial sequence
<220> FEATURE:
<223> OTHER INFORMATION: wynthetic primer

<400> SEQUENCE: 54

<210> SEQ ID NO 55
<211> LENGTH: 5548
<212> TYPE: DNA
<213> ORGANISM: artificial sequence
<220> FEATURE:
<223> OTHER INFORMATION: constructed plasmid

<400> SEQUENCE: 55

```
gcaattggcc ggccttattc aggcgtagca acc                                    33 cgaattcgta atcatggtca tagctgtttc ctgtgtgaaa ttgttatccg ctcacaattc        60
cacacaacat acgagccgga agcataaagt gtaaagcctg gggtgcctaa tgagtgagct      120
aactcacatt aattgcgttg cgctcactgc ccgctttcca gtcgggaaac ctgtcgtgcc      180
agctgcatta atgaatcggc caacgcgcgg ggagaggcgg tttgcgtatt gggcgctctt      240
ccgcttcctc gctcactgac tcgctgcgct cggtcgttcg gctgcggcga gcggtatcag      300
ctcactcaaa ggcggtaata cggttatcca gaatcagg ggataacgca ggaaagaaca        360
tgtgagcaaa aggccagcaa aaggccagga accgtaaaaa ggccgcgttg ctggcgtttt      420
tccataggct ccgcccccct gacgagcatc acaaaaatcg acgctcaagt cagaggtggc      480
gaaacccgac aggactataa agataccagg cgtttccccc tggaagctcc ctcgtgcgct      540
ctcctgttcc gaccctgccg cttaccggat acctgtccgc ctttctccct cgggaagcg      600
tggcgctttc tcatagctca cgctgtaggt atctcagttc ggtgtaggtc gttcgctcca      660
agctgggctg tgtgcacgaa ccccccgttc agcccgaccg ctgcgcctta tccggtaact      720
atcgtcttga gtccaacccg gtaagacacg acttatcgcc actggcagca gccactggta      780
acaggattag cagagcgagg tatgtaggcg gtgctacaga gttcttgaag tggtggccta      840
actacggcta cactagaagg acagtatttg gtatctgcgc tctgctgaag ccagttacct      900
tcggaaaaag agttggtagc tcttgatccg gcaaacaaac caccgctggt agcggtggtt      960
tttttgtttg caagcagcag attacgcgca gaaaaaaagg atctcaagaa gatcctttga     1020
tcttttctac ggggtctgac gctcagtgga acgaaaactc acgttaaggg attttggtca     1080
tgagattatc aaaaaggatc ttcacctaga tccttttaaa ttaaaaatga agttttaaat     1140
caatctaaag tatatatgag taaacttggt ctgacagtta ccaatgctta atcagtgagg     1200
cacctatctc agcgatctgt ctatttcgtt catccatagt tgcctgactc cccgtcgtgt     1260
agataactac gatacgggag ggcttaccat ctggccccag tgctgcaatg ataccgcgag     1320
acccacgctc accggctcca gatttatcag caataaacca gccagccgga agggccgagc     1380
gcagaagtgg tcctgcaact ttatccgcct ccatccagtc tattaattgt tgccgggaag     1440
ctagagtaag tagttcgcca gttaatagtt tgcgcaacgt tgttgccatt gctacaggca     1500
tcgtggtgtc acgctcgtcg tttggtatgg cttcattcag ctccggttcc caacgatcaa     1560
ggcgagttac atgatccccc atgttgtgca aaaaagcggt tagctccttc ggtcctccga     1620
tcgttgtcag aagtaagttg gccgcagtgt tatcactcat ggttatggca gcactgcata     1680
attctcttac tgtcatgcca tccgtaagat gcttttctgt gactggtgag tactcaacca     1740
agtcattctg agaatagtgt atgcggcgac cgagttgctc ttgcccggcg tcaatacggg     1800
ataataccgc gccacatagc agaactttaa aagtgctcat cattggaaaa cgttcttcgg     1860
ggcgaaaact ctcaaggatc ttaccgctgt tgagatccag ttcgatgtaa cccactcgtg     1920
cacccaactg atcttcagca tcttttactt tcaccagcgt ttctgggtga gcaaaaacag     1980
gaaggcaaaa tgccgcaaaa aagggaataa gggcgacacg gaaatgttga atactcatac     2040
```

```
tcttccttttt tcaatattat tgaagcattt atcagggtta ttgtctcatg agcggataca    2100
tatttgaatg tatttagaaa aataaacaaa taggggttcc gcgcacattt ccccgaaaag    2160
tgccacctga cgtctaagaa accattatta tcatgacatt aacctataaa aataggcgta    2220
tcacgaggcc ctttcgtctc gcgcgtttcg gtgatgacgg tgaaacctc  tgacacatgc    2280
agctcccgga cacggtcaca gcttgtctgt aagcggatgc cgggagcaga caagcccgtc    2340
agggcgcgtc agcgggtgtt ggcgggtgtc gggctggct  taactatgcg gcatcagagc    2400
agattgtact gagagtgcac catatgcggt gtgaaatacc gcacagatgc gtaaggagaa    2460
aataccgcat caggcgccat cgccattca  ggctgcgcaa ctgttgggaa gggcgatcgg    2520
tgcgggcctc ttcgctatta cgccagctgg cgaaagggg  atgtgctgca aggcgattaa    2580
gttgggtaac gccagggttt tcccagtcac gacgttgtaa aacgacggcc agtgccaagc    2640
ttgcatgcct gcaggtcgac gacctctttg atcaagcgat caaggatcaa ttttgcccca    2700
agctgattcc cgttttttaat ataaagcgcc cgctgtaatt caccgatcat atgaatccga    2760
cgaacagagg catcaatagc ttccttggct ttttcatcgg tgatgctgcg gctttgcatc    2820
cgcaataatg acgcaataac ctgtaagtta tttgaaatgc gatgctgtaa ttcatgaaac    2880
agcaactcat tgcgttcagc cagcatctga ttataggcac gcttttctg  gaggcggtaa    2940
ttaccttgct gtagcgcaat caccaatccc atatcagtga ctgtttctag caggcaaaga    3000
aaccagacca atacaccgtt aaatcggctt ccttcttcga taaaataagg cgcaaccatc    3060
aagctaagaa tagccgcgat aatacccggt cttgtcccaa agaggaaagt aaccacaagc    3120
attgtcggca taaaggtcac gaaaggataa cctgccggta aaaaatgccc aataatacta    3180
cggacaagga aggcacatcc tacaaaaatc aaagcgcaga tattcccgag ccatggttta    3240
ttttgccata aaggcaaaag ctctaacatc ctgtgcatga ccggggtatt ccggattaag    3300
accatgcatc ctcccccaga tacaatattc tggtattttc tataaaaga  cagtttgaga    3360
ctgtctttat cactgtttgt tctatggcct tcttttatg  caaaaaaag  gaggatcttt    3420
aaagaccctc cttttcgat  acaaaatatg aaagatatta gctatctttg cgcaggaatg    3480
ccggagcaaa ttccggttcc atatcacgtc ttgccggacg atcgccagat tcccgacgag    3540
ggccccgatc acgacgagga cgctcaccac cgcgacgttc tgcgtctgtc tcttatacac    3600
atctcaacca tcatcgatga attttctcgg gtgttctcgc atattggctc gaattctacc    3660
tgcaggctga tgaatgctca tccggaatta gcggccgctt aattaactta ttcaggcgta    3720
gcaaccaggc gtttaagggc accaataact gccttaaaaa aattacgccc cgccctgcca    3780
ctcatcgcag tactgttgta attcattaag cattctgccg acatggaagc catcacaaac    3840
ggcatgatga acctgaatcg ccagcggcat cagcaccttg tcgccttgcg tataatattt    3900
gcccatggtg aaaacggggg cgaagaagtt gtccatattg gccacgttta aatcaaaact    3960
ggtgaaactc acccagggat tggctgagac gaaaaacata ttctcaataa acccttaggg    4020
gaaataggcc aggttttcac cgtaacacgc cacatcttgc gaatatatgt gtagaaactg    4080
ccggaaatcg tcgtggtatt cactccagag cgatgaaaac gtttcagttt gctcatggaa    4140
aacggtgtaa caagggtgaa cactatccca tatcaccagc tcaccgtctt tcattgccat    4200
acggaattcc ggatgagcat tcatcaggcg ggcaagaatg tgaataaagg ccggataaaa    4260
cttgtgctta ttttctttta cggtctttaa aaaggccgta atatccagct gaacggtctg    4320
gttataggta cattgagcaa ctgactgaaa tgcctcaaaa tgttctttac gatgccattg    4380
```

-continued

| | |
|---|---|
| ggatatatca acggtggtat atccagtgat ttttttctcc attttagctt ccttagctcc | 4440 |
| tgaaaatctc gataactcaa aaatacgcc cggtagtgat cttatttcat tatggtgaaa | 4500 |
| gttggaacct cttacgtgcc gatcaacgtc tcattttcgc caaaagttgg cccagggctt | 4560 |
| cccggtatca acagggacac caggatttat ttattctgcg aagtgatctt ccgtcacgcg | 4620 |
| gccgcataac ttcgtatagc atacattata cgaagttatg cgatcgcaag cttgccaacg | 4680 |
| actacgcact agccaacaag agcttcaggg ttgagatgtg tataagagac aggttctgcg | 4740 |
| ttctcacgtg gcggacggtt atcatccagc tctgcgccgg tttcctgatc gacaacacgc | 4800 |
| atagacaggc gaaccttgcc acggttgtca atttcaagaa ccttgacttt gacttcctga | 4860 |
| ccttcggaca ggacatcgct gaccttgttg acacgttcgt tcttgatttc cgaaacatgt | 4920 |
| accaagccgt cacggccacc catgaagttt acgaaggcac cgaaatcaac gatattgacg | 4980 |
| actttaccgt tatagatttt gcctacttcc ggttcttcaa caataccatt gatccattca | 5040 |
| cgggctgctt caatattggc cggatcagaa aagacagac gaaccgtgcc gtcatcttcg | 5100 |
| atatcgacct tggcacctgt ggtcgccacg atttcacgga taacttttcc gcccgttccg | 5160 |
| ataacatcac ggattttgtc ttttggtacg ctcattgttt caatgcgcgg tgccaaatta | 5220 |
| gaaatttcgg agcggacttc acccagcgct ttggacattt cacccaagat atgagcacgg | 5280 |
| ccacctttag cctgttccaa agctttctgc atgatttctt cggtaatgcc agcaaccttg | 5340 |
| atgtccatct ggaggctggt gatacctttt tcggtaccgg cgaccttaaa gtccatatca | 5400 |
| cccaagtgat cttcatcacc catgatatcg gacaaaatag cgaagccgtc ttttccaga | 5460 |
| ataagaccca tggcgatacc ggaaaccgga cgcgttaagg gaacaccggc atccatgtcg | 5520 |
| actctagagg atccccgggt accgagct | 5548 |

<210> SEQ ID NO 56
<211> LENGTH: 891
<212> TYPE: DNA
<213> ORGANISM: artificial sequence
<220> FEATURE:
<223> OTHER INFORMATION: constructed fragment for integration into Z. mobilis pnp locus

<400> SEQUENCE: 56

| | |
|---|---|
| ataacttcgt atagcataca ttatacgaag ttatgcgatc gcaagcttgc caacgactac | 60 |
| gcactagcca acaagagctt cagggttgag atgtgtataa gagacaggtt ctgcgttctc | 120 |
| acgtggcgga cggttatcat ccagctctgc gccggtttcc tgatcgacaa cacgcataga | 180 |
| caggcgaacc ttgccacggt tgtcaatttc aagaaccttg actttgactt cctgaccttc | 240 |
| ggacaggaca tcgctgacct tgttgacacg ttcgttcttg atttccgaaa catgtaccaa | 300 |
| gccgtcacgg ccacccatga agtttacgaa ggcaccgaaa tcaacgatat tgacgacttt | 360 |
| accgttatag attttgccta cttccggttc ttcaacaata ccattgatcc attcacgggc | 420 |
| tgcttcaata ttggccggat cagaagaaga cagacgaacc gtgccgtcat cttcgatatc | 480 |
| gaccttggca cctgtggtcg ccacgatttc acggataact tttccgcccg ttccgataac | 540 |
| atcacggatt ttgtcttttg gtacgctcat tgtttcaatg cgcggtgcca aattagaaat | 600 |
| ttcggagcgg acttcaccca gcgctttgga catttcaccc aagatatgag cacggccacc | 660 |
| tttagcctgt tccaaagctt tctgcatgat ttcttcggta atgccagcaa ccttgatgtc | 720 |
| catctggagg ctggtgatac cttttcggt accggcgacc ttaaagtcca tatcacccaa | 780 |
| gtgatcttca tcacccatga tatcggacaa aatagcgaag ccgtcttttt ccagaataag | 840 |

```
acccatggcg ataccggaaa ccggacgcgt taagggaaca ccggcatcca t        891
```

<210> SEQ ID NO 57
<211> LENGTH: 1030
<212> TYPE: DNA
<213> ORGANISM: artificial sequence
<220> FEATURE:
<223> OTHER INFORMATION: constructed fragment for integration into Z.
      mobilis pnp locus

<400> SEQUENCE: 57

```
gacctctttg atcaagcgat caaggatcaa ttttgcccca agctgattcc cgttttaat    60
ataaagcgcc cgctgtaatt caccgatcat atgaatccga cgaacagagg catcaatagc  120
ttccttggct ttttcatcgg tgatgctgcg gctttgcatc cgcaataatg acgcaataac  180
ctgtaagtta tttgaaatgc gatgctgtaa ttcatgaaac agcaactcat tgcgttcagc  240
cagcatctga ttataggcac gctttttctg gaggcggtaa ttaccttgct gtagcgcaat  300
caccaatccc atatcagtga ctgtttctag caggcaaaga aaccagacca atacaccgtt  360
aaatcggctt ccttcttcga taaaataagg cgcaaccatc aagctaagaa tagccgcgat  420
aatacccggt cttgtcccaa agaggaaagt aaccacaagc attgtcggca taaaggtcac  480
gaaaggataa cctgccggta aaaatgcccc aataatacta cggacaagga aggcacatcc  540
tacaaaaatc aaagcgcaga tattcccgag ccatggttta ttttgccata aaggcaaaag  600
ctctaacatc ctgtgcatga ccggggtatt ccggattaag accatgcatc ctcccccaga  660
tacaatattc tggtattttc tataaaaaga cagtttgaga ctgtctttat cactgtttgt  720
tctatggcct tctttttatg caaaaaaaag gaggatcttt aaagaccctc cttttttcgat  780
acaaaatatg aaagatatta gctatctttg cgcaggaatg ccggagcaaa ttccggttcc  840
atatcacgtc ttgccggacg atcgccagat tcccgacgag ggccccgatc acgacgagga  900
cgctcaccac cgcgacgttc tgcgtctgtc tcttatacac atctcaacca tcatcgatga  960
attttctcgg gtgttctcgc atattggctc gaattctacc tgcaggctga tgaatgctca 1020
tccggaatta                                                        1030
```

<210> SEQ ID NO 58
<211> LENGTH: 6471
<212> TYPE: DNA
<213> ORGANISM: artificial sequence
<220> FEATURE:
<223> OTHER INFORMATION: constructed plasmid

<400> SEQUENCE: 58

```
cgaattcgta atcatggtca tagctgtttc ctgtgtgaaa ttgttatccg ctcacaattc    60
cacacaacat acgagccgga agcataaagt gtaaagcctg gggtgcctaa tgagtgagct  120
aactcacatt aattgcgttg cgctcactgc ccgctttcca gtcgggaaac ctgtcgtgcc  180
agctgcatta atgaatcggc caacgcgcgg ggagaggcgg tttgcgtatt gggcgctctt  240
ccgcttcctc gctcactgac tcgctgcgct cggtcgttcg gctgcggcga gcggtatcag  300
ctcactcaaa ggcggtaata cggttatcca cagaatcagg ggataacgca ggaaagaaca  360
tgtgagcaaa aggccagcaa aaggccagga accgtaaaaa ggccgcgttg ctggcgtttt  420
tccataggct ccgccccccct gacgagcatc acaaaaatcg acgctcaagt cagaggtggc  480
gaaacccgac aggactataa agataccagg cgtttccccc tggaagctcc ctcgtgcgct  540
ctcctgttcc gaccctgccg cttaccggat acctgtccgc ctttctccct tcgggaagcg  600
```

```
tggcgctttc tcatagctca cgctgtaggt atctcagttc ggtgtaggtc gttcgctcca    660
agctgggctg tgtgcacgaa ccccccgttc agcccgaccg ctgcgcctta tccggtaact    720
atcgtcttga gtccaacccg gtaagacacg acttatcgcc actggcagca gccactggta    780
acaggattag cagagcgagg tatgtaggcg gtgctacaga gttcttgaag tggtggccta    840
actacggcta cactagaagg acagtatttg gtatctgcgc tctgctgaag ccagttacct    900
tcggaaaaag agttggtagc tcttgatccg gcaaacaaac caccgctggt agcggtggtt    960
ttttttgtttg caagcagcag attacgcgca gaaaaaagg atctcaagaa gatcctttga   1020
tcttttctac ggggtctgac gctcagtgga acgaaaactc acgttaaggg attttggtca   1080
tgagattatc aaaaaggatc ttcacctaga tccttttaaa ttaaaaatga agttttaaat   1140
caatctaaag tatatatgag taaacttggt ctgacagtta ccaatgctta atcagtgagg   1200
cacctatctc agcgatctgt ctatttcgtt catccatagt tgcctgactc cccgtcgtgt   1260
agataactac gatacgggag ggcttaccat ctggccccag tgctgcaatg ataccgcgag   1320
acccacgctc accggctcca gatttatcag caataaacca gccagccgga agggccgagc   1380
gcagaagtgg tcctgcaact ttatccgcct ccatccagtc tattaattgt tgccgggaag   1440
ctagagtaag tagttcgcca gttaatagtt tgcgcaacgt tgttgccatt gctacaggca   1500
tcgtggtgtc acgctcgtcg tttggtatgg cttcattcag ctccggttcc caacgatcaa   1560
ggcgagttac atgatccccc atgttgtgca aaaaagcggt tagctccttc ggtcctccga   1620
tcgttgtcag aagtaagttg gccgcagtgt tatcactcat ggttatggca gcactgcata   1680
attctcttac tgtcatgcca tccgtaagat gcttttctgt gactggtgag tactcaacca   1740
agtcattctg agaatagtgt atgcggcgac cgagttgctc ttgcccggcg tcaatacggg   1800
ataataccgc gccacatagc agaactttaa aagtgctcat cattggaaaa cgttcttcgg   1860
ggcgaaaact ctcaaggatc ttaccgctgt tgagatccag ttcgatgtaa cccactcgtg   1920
cacccaactg atcttcagca tcttttactt tcaccagcgt ttctgggtga gcaaaaacag   1980
gaaggcaaaa tgccgcaaaa aagggaataa gggcgacacg gaaatgttga atactcatac   2040
tcttcctttt tcaatattat tgaagcattt atcagggtta ttgtctcatg agcggataca   2100
tatttgaatg tatttagaaa aataaacaaa taggggttcc gcgcacattt ccccgaaaag   2160
tgccacctga cgtctaagaa accattatta tcatgacatt aacctataaa aataggcgta   2220
tcacgaggcc ctttcgtctc gcgcgtttcg gtgatgacgg tgaaaacctc tgacacatgc   2280
agctcccgga cggtcaca gcttgtctgt aagcggatgc cgggagcaga caagcccgtc   2340
agggcgcgtc agcgggtgtt ggcgggtgtc ggggctggct taactatgcg gcatcagagc   2400
agattgtact gagagtgcac catatgcggt gtgaaatacc gcacagatgc gtaaggagaa   2460
aataccgcat caggcgccat tcgccattca ggctgcgcaa ctgttgggaa gggcgatcgg   2520
tgcgggcctc ttcgctatta cgccagctgg cgaaaggggg atgtgctgca aggcgattaa   2580
gttgggtaac gccagggttt tcccagtcac gacgttgtaa aacgacggcc agtgccaagc   2640
ttgcatgcct gcaggtcgac catcaatgca aggcagccac cgcaaacggt tgccatggaa   2700
gaggaaccat tagattcggt gatatccgac aaaacacgga tggtatacgg gaaatcagcc   2760
ttgctcggca aaaccggatg aagcgcacgc catgccagtt accatggcc gatttcacga   2820
cgacccggag caccaaaacg accaacttca ccgaccgaat atgggggaa gttgtaatgc   2880
agcatgaagc gttcataatg aaggccggtt aaaccgtcga tcatctgttc agcatccgcc   2940
gttccaaggg tggttgaaac caaagcctgt gtttcaccac gcgtaaacag gcagaaccca   3000
```

```
tgcgtgcggg gcaagaatcc aacctgagag cggatcgggc gaactgtttt cagatcgcgt    3060
ccgtcaattc tccggccttc tttcagaatg gcggtgcgga cgattttgc ttccagcttc      3120 ttcgcaagct tctggatgcg cagcttttct gtcggatcag cttctgggaa ggcttcgtca    3180
agaaccgctt tggccttgct caaggcgtca cacgttcag ccttgcgagt cagacgatag      3240
gccttatcga aattgtcgta gcagagttct tcgactttgg cagccaatgc gctgtcatca    3300
tagctgacca gttcccaagg ctctttagcg gcctgttctg ccagattgat gatagctttg    3360
ataaccggct gtaaagattc atgcgcaaaa gaaacggcat tgagcatgac ttcttcggga    3420
agctcattcg cttccgattc aaccatcatc acggcatcac gggtagcccc gacaaccaga    3480
tcaagatcac ttttttcaag ctgttccaag gtcgggttaa gaatgaactc gccatcttga    3540
taacccacac gggcagcacc gatggggccc aagaaaggca caccggaaag agcaagagcc    3600
gcagaagcag cgatcatcgc caagatatcc ggttcattct cgccgtcata ggacatgacc    3660
tgcgcaatga ccaaggtttc gttatagaaa ccttccggaa acagaggacg gattggacgg    3720
tcgattaacc gtgaaatcag cgtttcccgt tcggttgcgc cacgttcacg cttgaaaaag    3780
ccaccgggaa tacggcctgc tgctgaatat ttttcctgat aatggacggt caaaggaaag    3840
aaatcctgac cttcttttac cgttttttgct gccgttaccg cgcataatac gaccgtttca    3900
cctaaggtcg cgttctgcgt ctgtctctta tacacatctc aaccatcatc gatgaatttt    3960
ctcgggtgtt ctcgcatatt ggctcgaatt ctacctgcag gctgatgaat gctcatccgg    4020
aattagcggc cgcttaatta acttattcag gcgtagcaac caggcgttta agggcaccaa    4080
taactgcctt aaaaaaatta cgccccgccc tgccactcat cgcagtactg ttgtaattca    4140
ttaagcattc tgccgacatg gaagccatca caaacggcat gatgaacctg aatcgccagc    4200
ggcatcagca ccttgtcgcc ttgcgtataa tatttgccca tggtgaaaac gggggcgaag    4260
aagttgtcca tattggccac gtttaaatca aaactggtga aactcaccca gggattggct    4320
gagacgaaaa acatattctc aataaaccct ttagggaaat aggccaggtt ttcaccgtaa    4380
cacgccacat cttgcgaata tatgtgtaga actgccgga atcgtcgtg gtattcactc       4440 cagagcgatg aaaacgtttc agtttgctca tggaaaacgg tgtaacaagg gtgaacacta    4500
tcccatatca ccagctcacc gtctttcatt gccatacgga attccggatg agcattcatc    4560
aggcgggcaa gaatgtgaat aaaggccgga taaaacttgt gcttattttt ctttacggtc    4620
tttaaaaagg ccgtaatatc cagctgaacg gtctggttat aggtacattg agcaactgac    4680
tgaaatgcct caaaatgttc tttacgatgc cattgggata tatcaacggt ggtatatcca    4740
gtgatttttt tctccatttt agcttcctta gctcctgaaa atctcgataa ctcaaaaaat    4800
acgcccggta gtgatcttat ttcattatgg tgaaagttgg aacctcttac gtgccgatca    4860
acgtctcatt ttcgccaaaa gttggcccag gcttcccgg tatcaacagg gacaccagga      4920
tttatttatt ctgcgaagtg atcttccgtc acgcggccgc ataacttcgt atagcataca    4980
ttatacgaag ttatgcgatc gcaagcttgc caacgactac gcactagcca acaagagctt    5040
cagggttgag atgtgtataa gagacaggtt ctgcgttaat gacggcgcca tctgcctgac    5100
gggcaacctg tccggtttcc agtgtcagtt ttttccgcc ccaatcgatt tcctggcgtt      5160
taatatcgaa cattcaattt ccttctggct ccgacctat gtcaggagct gccttttcc       5220 ggattcgccg gattgcgaga taaccggatg cgaaacggcc tcccgataag gaggccgcat    5280 cgtctttac ttacgaagac ccagtcttgc gataaggctg ctgtagcggt ctttgtcgtt      5340
```

-continued

```
attcttgacg taatcaagca ggctacgacg cttgttaacc aaacggagca aaccacgacg      5400
ggaatggtta tccttagcgt gggttttgaa atgttcggtc aggttaacaa tccgttcggt      5460
cagaatagca acctggactt ccggagaacc cgtatcgcct tcgacgcgtg catattcttt      5520
gattaacgct tctttgcgtt ctgctgtgat cgacatcagt cgtcctttct attttaaaaa      5580
ttgaaaccgc gcaaaacccg agcttcttgc ccagtgactt caataagagc aaccggaatt      5640
tgtgattcca ttgccatatt caagccggat tctgcgttaa ttccgatcaa tttctgcccc      5700
tgacggagtg cttttgcctg atcggaggaa actgctaaag ccgggatgtc gtccagccct      5760
gctgttaaag gcaaaagcat ttgatacagc tttccagctt gcgccatttc cattaatttg      5820
tccagtgaaa ttgcctgttc actcgtaaat ggccccgatt caatcgacg caaatagctg      5880 acatgaccat aacaattcag tttatgggca atgtcgcggg caaggcttct aatataggtg      5940
cctttagaaa ccttagcgat aaaagtagcc tgatcggggc taaaatcgtc taaggtcaat      6000
tcatggatag taatatcgcg tcctttgacg gtcaccgttt ctccggcgcg gacgcggtcg      6060
caggcgcgtt tcccattgat tttcaaggca gaataaacgg gggggatttg gtgtatttca      6120
cctcggaagc aagatagaac agattccact tcttcccttg gggacgtttt atctgattga      6180
gcggtgatgc tcccctctct atccaagcta tccgtttccg ctccaaaagc gagggtaaag      6240
gcatagactt tgtcggaatt aagcgcatag cccgccaatt tcgtcgcctc gcctaaggca      6300
acaggtaaaa cgccagaggc aagggggatct aacgtcccgc catgaccgac ttttactttc      6360
ggtaatccgg cgatacggat agcgcgtttg acagcagaga cggcttgggt tgagcctaag      6420
ccttcttgct tgtcgagaat gatccagcgg cgcgcccccg ggtaccgagc t               6471
```

<210> SEQ ID NO 59
<211> LENGTH: 1369
<212> TYPE: DNA
<213> ORGANISM: artificial sequence
<220> FEATURE:
<223> OTHER INFORMATION: constructed fragment for integration into Z.
      mobilis pnp locus

<400> SEQUENCE: 59

```
aatgacggcg ccatctgcct gacgggcaac ctgtccggtt tccagtgtca gtttttttcc        60
gccccaatcg atttcctggc gtttaatatc gaacattcaa tttccttctg gctccgaccc       120
tatgtcagga gctgcctttt tccggattcg ccggattgcg agataaccgg atgcgaaacg       180
gcctcccgat aaggaggccg catcgtcttt tacttacgaa gacccagtct tgcgataagg       240
ctgctgtagc ggtctttgtc gttattcttg acgtaatcaa gcaggctacg acgcttgtta       300
accaaacgga gcaaaccacg acgggaatgg ttatccttag cgtgggtttt gaaatgttcg       360
gtcaggttaa caatccgttc ggtcagaata gcaacctgga cttccggaga acccgtatcg       420
ccttcgacgc gtgcatattc tttgattaac gcttctttgc gttctgctgt gatcgacatc       480
agtcgtcctt tctattttaa aaattgaaac gcgcaaaac ccgagcttct tgcccagtga       540
cttcaataag agcaaccgga atttgtgatt ccattgccat attcaagccg gattctgcgt       600
taattccgat caatttctgc ccctgacgga gtgcttttgc ctgatcggag gaaactgcta       660
aagccgggat gtcgtccagc cctgctgtta aaggcaaaag catttgatac agcttttcag       720
cttgcgccat ttccattaat ttgtccagtg aaattgcctg ttcactcgta aatggccccg       780
atttcaatcg acgcaaatag ctgacatgac cataacaatt cagtttatgg caatgtcgc       840 gggcaaggct tctaatatag gtgcctttag aaaccttagc gataaaagta gcctgatcgg       900
```

```
ggctaaaatc gtctaaggtc aattcatgga tagtaatatc gcgtcctttg acggtcaccg      960
tttctccggc gcggacgcgg tcgcaggcgc gtttcccatt gattttcaag gcagaataaa     1020
cgggggggat tggtgtatt tcacctcgga agcaagatag aacagattcc acttcttccc     1080
ttgtgggacg tttatctgat tgagcggtga tgctcccctc tctatccaag ctatccgttt     1140
ccgctccaaa agcgagggta aaggcataga ctttgtcgga attaagcgca tagcccgcca     1200
atttcgtcgc ctcgcctaag gcaacaggta aaacgccaga ggcaagggga tctaacgtcc     1260
cgccatgacc gactttttact ttcggtaatc cggcgatacg gatagcgcgt ttgacagcag     1320
agacggcttg ggttgagcct aagccttctt gcttgtcgag aatgatcca                 1369
```

<210> SEQ ID NO 60
<211> LENGTH: 1251
<212> TYPE: DNA
<213> ORGANISM: artificial sequence
<220> FEATURE:
<223> OTHER INFORMATION: constructed fragment for integration into Z. mobilis pnp locus

<400> SEQUENCE: 60

```
catcaatgca aggcagccac cgcaaacggt tgccatggaa gaggaaccat tagattcggt       60
gatatccgac aaaacacgga tggtatacgg gaaatcagcc ttgctcggca aaaccggatg      120
aagcgcacgc catgccagtt taccatggcc gatttcacga cgaccccggag caccaaaacg     180 accaacttca ccgaccgaat atgggggggaa gttgtaatgc agcatgaagc gttcataatg     240
aaggccggtt aaaccgtcga tcatctgttc agcatccgcc gttccaaggg tggttgaaac     300
caaagcctgt gtttcaccac gcgtaaacag ggcagaacca tgcgtgcggg gcaagaatcc     360
aacctgagag cggatcgggc gaactgtttt cagatcgcgt ccgtcaattc tccggccttc     420
tttcagaatg gcggtgcgga cgattttgc ttccagcttc ttcgcaagct tctggatgcg     480 cagctttttct gtcggatcag cttctgggaa ggcttcgtca agaaccgctt tggccttgct     540
caaggcgtca acacgttcag ccttgcgagt cagacgatag gccttatcga aattgtcgta     600
gcagagttct tcgactttgg cagccaatgc gctgtcatca tagctgacca gttcccaagg     660
ctctttagcg gcctgttctg ccagattgat gatagctttg ataaccggct gtaaagattc     720
atgcgcaaaa gaaacggcat tgagcatgac ttcttcggga agctcattcg cttccgattc     780
aaccatcatc acggcatcac gggtagcccc gacaaccaga tcaagatcac ttttttcaag     840
ctgttccaag gtcgggttaa gaatgaactc gccatcttga taccccacac gggcagcacc     900 gatgggccc aagaaaggca caccggaaag agcaagagcc gcagaagcag cgatcatcgc     960
caagatatcc ggttcattct cgccgtcata ggacatgacc tgcgcaatga ccaaggtttc    1020
gttatagaaa ccttccggaa acagaggacg gattggacgg tcgattaacc gtgaaatcag    1080
cgtttcccgt tcggttgcgc cacgttcacg cttgaaaaag ccaccgggaa tacggcctgc    1140
tgctgaatat ttttcctgat aatggacggt caaggaaag aaatcctgac cttcttttac    1200
cgtttttgct gccgttaccg cgcataatac gaccgtttca cctaaggtcg c             1251
```

<210> SEQ ID NO 61
<211> LENGTH: 6342
<212> TYPE: DNA
<213> ORGANISM: artificial sequence
<220> FEATURE:
<223> OTHER INFORMATION: constructed plasmid

<400> SEQUENCE: 61

-continued

```
ctagtgtgac ggaagatcac ttcgcagaat aaataaatcc tggtgtccct gttgataccg      60
ggaagccctg ggccaacttt tggcgaaaat gagacgttga tcggcacgta agaggttcca     120
actttcacca taatgaaata agatcactac cgggcgtatt ttttgagtta tcgagatttt     180
caggagctaa ggaagctaaa atggagaaaa aaatcactgg atataccacc gttgatatat     240
cccaatggca tcgtaaagaa cattttgagg catttcagtc agttgctcaa tgtacctata     300
accagaccgt tcagctggat attacggcct ttttaaagac cgtaaagaaa ataagcaca      360 agttttatcc ggcctttatt cacattcttg cccgcctgat gaatgctcat ccggaattcc     420
gtatggcaat gaaagacggt gagctggtga tatgggatag tgttcaccct tgttacaccg     480
ttttccatga gcaaactgaa acgttttcat cgctctggag tgaataccac gacgatttcc     540
ggcagtttct acacatatat tcgcaagatg tggcgtgtta cggtgaaaac ctggcctatt     600
tccctaaagg gtttattgag aatatgtttt tcgtctcagc caatccctgg gtgagtttca     660
ccagttttga tttaaacgtg gccaatatgg acaacttctt cgcccccgtt ttcaccatgg     720
gcaaatatta tacgcaaggc gacaaggtgc tgatgccgct ggcgattcag gttcatcatg     780
ccgtttgtga tggcttccat gtcggcagaa tgcttaatga attacaacag tactgcgatg     840
agtggcaggg cggggcgtaa tttttttaag gcagttattg gtgcccttaa acgcctggtt     900
gctacgcctg aataagggcc ggccggcaa gacgtgatat ggaaccggaa tttgctccgg     960
cattcctgcg caaagatagc taatatcttt catattttgt atcgaaaaag agggtcttt    1020 aaagatcctc cttttttttg cataaaaaga aggccataga acaaacagtg ataaagacag    1080
tctcaaactg tctttttata gaaaatacca gaatattgta tctgggggag gatgcatggt    1140
cttaatccgg aataccccgg tcatgcacag gatgttagag cttttgcctt tatggcaaaa    1200
taaaccatgc tcgggaata tctgcgcttt gattttgta ggatgtgcct tccttgtccg     1260
tagtattatt gggcattttt taccggcagg ttatcctttc gtgacctta tgccgacaat     1320 gcttgtggtt actttcctct ttgggacaag accgggtatt atcgcggcta ttcttagctt    1380
gatggttgcg ccttatttta tcgaagaagg aagccgattt aacggtgtat tggtctggtt    1440
tctttgcctt ctagaaacag tcactgtatat gggattggtg attgcgctac agcaaggtaa    1500
ttaccgcctc cagaaaaagc gtgcctataa tcagatgctg gctgaacgca atgagttgct    1560
gtttcatgaa ttacagcatc gcatttcaaa taacttacag gttattgcgt cattattgcg    1620
gatgcaaagc cgcagcatca ccgatgaaaa agccaaggaa gctattgatg cctctgttcg    1680
tcggattcat atgatcggtg aattacagcg ggcgctttat attaaaaacg gaatcagct    1740 tggggcaaaa ttgatccttg atcgcttgat caaagaggtc attgcgtcca gtaatctccc    1800
gaacatccgc tataaaatag aagctgaaga cctgatctta ccgtcagata tggcaatccc    1860
tttagcgctt gtatctgctg aatccgtttc aaacgcgtta gagcatggct ttaaaggcga    1920
tcataaagac gcgtttattg aaattaagct tcaaaaaatt agcgggcaaa tcgaacttac    1980
catttccaat aatggcaaac ctcttcccca aggcttttcc cttgaaaagg tcgatagctt    2040
aggcctgaaa attgcggcta tgtttgcccg acaattcaaa ggaaaattca ccttaagtaa    2100
tcagcctaac cgttatgtgg tttctagcct tattttgcct tgcggttagg cggccgctgg    2160
tacccaattc gccctatagt gagtcgtatt acgcgcgctc actggccgtc gttttacaac    2220
gtcgtgactg ggaaaaccct ggcgttaccc aacttaatcg ccttgcagca catccccctt    2280
tcgccagctg gcgtaatagc gaagaggccc gcaccgatcg cccttcccaa cagttgcgca    2340
gcctgaatgg cgaatgggac gcgccctgta gcggcgcatt aagcgcggcg ggtgtggtgg    2400
```

```
ttacgcgcag cgtgaccgct acacttgcca gcgccctagc gcccgctcct ttcgctttct   2460
tcccttcctt tctcgccacg ttcgccggct ttccccgtca agctctaaat cgggggctcc   2520
ctttagggtt ccgatttagt gctttacggc acctcgaccc caaaaaactt gattagggtg   2580
atggttcacg tagtgggcca tcgccctgat agacggtttt tcgccctttg acgttggagt   2640
ccacgttctt taatagtgga ctcttgttcc aaactggaac aacactcaac cctatctcgg   2700
tctattcttt tgatttataa gggattttgc cgatttcggc ctattggtta aaaaatgagc   2760
tgatttaaca aaaatttaac gcgaatttta acaaaatatt aacgcttaca atttaggtgg   2820
cacttttcgg ggaaatgtgc gcggaacccc tatttgttta ttttttctaaa tacattcaaa   2880
tatgtatccg ctcatgagac aataaccctg ataaatgctt caataatatt gaaaaaggaa   2940
gagtatgagt attcaacatt tccgtgtcgc ccttattccc ttttttgcgg cattttgcct   3000
tcctgttttt gctcacccag aaacgctggt gaaagtaaaa gatgctgaag atcagttggg   3060
tgcacgagtg ggttacatcg aactggatct caacagcggt aagatccttg agagttttcg   3120
ccccgaagaa cgttttccaa tgatgagcac ttttaaagtt ctgctatgtg gcgcggtatt   3180
atcccgtatt gacgccgggc aagagcaact cggtcgccgc atacactatt ctcagaatga   3240
cttggttgag tactcaccag tcacagaaaa gcatcttacg gatggcatga cagtaagaga   3300
attatgcagt gctgccataa ccatgagtga taacactgcg gccaacttac ttctgacaac   3360
gatcggagga ccgaaggagc taaccgcttt tttgcacaac atgggggatc atgtaactcg   3420
ccttgatcgt tgggaaccgg agctgaatga agccatacca aacgacgagc gtgacaccac   3480
gatgcctgta gcaatggcaa caacgttgcg caaactatta actggcgaac tacttactct   3540
agcttcccgg caacaattaa tagactggat ggaggcggat aaagttgcag gaccacttct   3600
gcgctcggcc cttccggctg gctggtttat tgctgataaa tctggagccg gtgagcgtgg   3660
gtctcgcggt atcattgcag cactggggcc agatggtaag ccctcccgta tcgtagttat   3720
ctacacgacg gggagtcagg caactatgga tgaacgaaat agacagatcg ctgagatagg   3780
tgcctcactg attaagcatt ggtaactgtc agaccaagtt tactcatata ctttttagat   3840
tgatttaaaa cttcattttt aatttaaaag gatctaggtg aagatccttt ttgataatct   3900
catgaccaaa atcccttaac gtgagttttc gttccactga gcgtcagacc ccgtagaaaa   3960
gatcaaagga tcttcttgag atcctttttt tctgcgcgta atctgctgct tgcaaacaaa   4020
aaaaccaccg ctaccagcgg tggtttgttt gccggatcaa gagctaccaa ctctttttcc   4080
gaaggtaact ggcttcagca gagcgcagat accaaatact gtccttctag tgtagccgta   4140
gttaggccac cacttcaaga actctgtagc accgcctaca tacctcgctc tgctaatcct   4200
gttaccagtg gctgctgcca gtggcgataa gtcgtgtctt accgggttgg actcaagacg   4260
atagttaccg gataaggcgc agcggtcggg ctgaacgggg ggttcgtgca cacagcccag   4320
cttggagcga acgacctaca ccgaactgag atacctacag cgtgagctat gagaaagcgc   4380
cacgcttccc gaagggagaa aggcggacag gtatccggta agcggcaggg tcggaacagg   4440
agagcgcacg agggagcttc cagggggaaa cgcctggtat ctttatagtc ctgtcgggtt   4500
tcgccacctc tgacttgagc gtcgattttt gtgatgctcg tcaggggggc ggagcctatg   4560
gaaaaacgcc agcaacgcgg ccttttacg gttcctggcc ttttgctggc cttttgctca   4620
catgttcttt cctgcgttat cccctgattc tgtggataac cgtattaccg cctttgagtg   4680
agctgatacc gctcgccgca gccgaacgac cgagcgcagc gagtcagtga gcgaggaagc   4740
```

| | |
|---|---:|
| ggaagagcgc ccaatacgca aaccgcctct ccccgcgcgt tggccgattc attaatgcag | 4800 |
| ctggcacgac aggtttcccg actggaaagc gggcagtgag cgcaacgcaa ttaatgtgag | 4860 |
| ttagctcact cattaggcac cccaggcttt acactttatg cttccggctc gtatgttgtg | 4920 |
| tggaattgtg agcggataac aatttcacac aggaaacagc tatgaccatg attacgccaa | 4980 |
| gcgcgcaatt aaccctcact aaagggaaca aaagctggag ctccctatcg tctgactcgc | 5040 |
| aaggctgaac gtgttgacgc cttgagcaag gccaaagcgg ttcttgacga agccttccca | 5100 |
| gaagctgatc cgacagaaaa gctgcgcatc cagaagcttg cgaagaagct ggaagcaaaa | 5160 |
| atcgtccgca ccgccattct gaaagaaggc cggagaattg acggacgcga tctgaaaaca | 5220 |
| gttcgcccga tccgctctca ggttggattc ttgccccgca cgcatggttc tgccctgttt | 5280 |
| acgcgtggtg aaacacaggc tttggtttca accaccttg gaacggcgga tgctgaacag | 5340 |
| atgatcgacg gtttaaccgg ccttcattat gaacgcttca tgctgcatta caacttcccc | 5400 |
| ccatattcgg tcggtgaagt tggtcgtttt ggtgctccgg tcgtcgtga atcggccat | 5460 |
| ggtaaactgg catggcgtgc gcttcatccg gttttgccga gcaaggctga tttcccgtat | 5520 |
| accatccgtg ttttgtcgga tatcaccgaa tctaatggtt cctcttccat ggcaaccgtt | 5580 |
| tgcggtggct gccttgcatt gatggatgcc ggtgttccct taacgcgtcc ggtttccggt | 5640 |
| atcgccatgg gtcttattct ggaaaaagac ggcttcgcta ttttgtccga tatcatgggt | 5700 |
| gatgaagatc acttgggtga tatggacttt aaggtcgccg gtaccgaaaa aggtatcacc | 5760 |
| agcctccaga tggacatcaa ggttgctggc attaccgaag aaatcatgca gaaagctttg | 5820 |
| gaacaggcta aggtggccg tgctcatatc ttgggtgaaa tgtccaaagc gctgggtgaa | 5880 |
| gtccgctccg aaatttctaa tttggcaccg cgcattgaaa caatgagcgt accaaaagac | 5940 |
| aaaatccgtg atgttatcgg aacgggcgga aaagttatcc gtgaaatcgt ggcgaccaca | 6000 |
| ggtgccaagg tcgatatcga agatgacggc acggttcgtc tgtcttcttc tgatccggcc | 6060 |
| aatattgaag cagcccgtga atggatcaat ggtattgttg aagaaccgga agtaggcaaa | 6120 |
| atctataacg gtaaagtcgt caatatcgtt gatttcggtg ccttcgtaaa cttcatgggt | 6180 |
| ggccgtgacg gcttggtaca tgtttcggaa atcaagaacg aacgtgtcaa caaggtcagc | 6240 |
| gatgtcctgt ccgaaggtca ggaagtcaaa gtcaaggttc ttgaaattga caaccgtggc | 6300 |
| aaggttcgcc tgtctatgcg tgttgtcgat caggaaaccg ga | 6342 |

<210> SEQ ID NO 62
<211> LENGTH: 6322
<212> TYPE: DNA
<213> ORGANISM: artificial sequence
<220> FEATURE:
<223> OTHER INFORMATION: constructed plasmid

<400> SEQUENCE: 62

| | |
|---|---:|
| ctagtgtgac ggaagatcac ttcgcagaat aaataaatcc tggtgtccct gttgataccg | 60 |
| ggaagccctg ggccaacttt tggcgaaaat gagacgttga tcggcacgta agaggttcca | 120 |
| actttcacca taatgaaata agatcactac cgggcgtatt ttttgagtta tcgagatttt | 180 |
| caggagctaa ggaagctaaa atggagaaaa aaatcactgg atataccacc gttgatatat | 240 |
| cccaatggca tcgtaaagaa cattttgagg catttcagtc agttgctcaa tgtacctata | 300 |
| accagaccgt tcagctggat attacggcct ttttaaagac cgtaaagaaa aataagcaca | 360 |
| agttttatcc ggcctttatt cacattcttg cccgcctgat gaatgctcat ccggaattcc | 420 |
| gtatggcaat gaaagacggt gagctggtga tatgggatag tgttcaccct tgttacaccg | 480 |

```
ttttccatga gcaaactgaa acgttttcat cgctctggag tgaataccac gacgatttcc    540
ggcagtttct acacatatat tcgcaagatg tggcgtgtta cggtgaaaac ctggcctatt    600
tccctaaagg gtttattgag aatatgtttt tcgtctcagc caatccctgg gtgagtttca    660
ccagttttga tttaaacgtg gccaatatgg acaacttctt cgcccccgtt ttcaccatgg    720
gcaaatatta tacgcaaggc gacaaggtgc tgatgccgct ggcgattcag gttcatcatg    780
ccgtttgtga tggcttccat gtcggcagaa tgcttaatga attacaacag tactgcgatg    840
agtggcaggg cggggcgtaa ttttttttaag gcagttattg gtgcccttaa acgcctggtt    900
gctacgcctg aataagggcc ggccttcatt atgaacgctt catgctgcat tacaacttcc    960
ccccatattc ggtcggtgaa gttggtcgtt ttggtgctcc gggtcgtcgt gaaatcggcc   1020
atggtaaact ggcatggcgt gcgcttcatc cggttttgcc gagcaaggct gatttcccgt   1080
ataccatccg tgttttgtcg gatatcaccg aatctaatgg ttcctcttcc atggcaaccg   1140
tttgcggtgg ctgccttgca ttgatggatg ccggtgttcc cttaacgcgt ccggtttccg   1200
gtatcgccat gggtcttatt ctggaaaaag acggcttcgc tattttgtcc gatatcatgg   1260
gtgatgaaga tcacttgggt gatatggact ttaaggtcgc cggtaccgaa aaaggtatca   1320
ccagcctcca gatggacatc aaggttgctg gcattaccga agaaatcatg cagaaagctt   1380
tggaacaggc taaaggtggc cgtgctcata tcttgggtga aatgtccaaa gcgctgggtg   1440
aagtccgctc cgaaatttct aatttggcac cgcgcattga acaatgagc gtaccaaaag   1500
acaaaatccg tgatgttatc ggaacgggcg gaaaagttat ccgtgaaatc gtggcgacca   1560
caggtgccaa ggtcgatatc gaagatgacg gcacggttcg tctgtcttct tctgatccgg   1620
ccaatattga agcagcccgt gaatggatca atggtattgt tgaagaaccg gaagtaggca   1680
aaatctataa cggtaaagtc gtcaatatcg ttgatttcgg tgccttcgta aacttcatgg   1740
gtggccgtga cggcttggta catgtttcgg aaatcaagaa cgaacgtgtc aacaaggtca   1800
gcgatgtcct gtccgaaggt caggaagtca agtcaaggt tcttgaaatt gacaaccgtg   1860
gcaaggttcg cctgtctatg cgtgttgtcg atcaggaaac cggcgcagag ctggatgata   1920
accgtccgcc acgtgagaac gcagaacgtc gcggtggtga gcgtcctcgt cgtgatcggg   1980
gccctcgtcg ggaatctggc gatcgtccgg caagacgtga tatggaaccg gaatttgctc   2040
cggcattcct gcgcaaagat agctaatatc tttcatattt tgtatcgaaa aaggagggtc   2100
tttaaagatc ctcctttttt ttgcataaaa agaaggccat agaacaaaca gtgataaaga   2160
cagtctcaaa ctgtcttttt atagaaaata ccagaatatt gtatctgggg gaggatgcat   2220
ggtcttaatc cggaataccc cggtcatgcg gccgctggta cccaattcgc cctatagtga   2280
gtcgtattac gcgcgctcac tggccgtcgt tttacaacgt cgtgactggg aaaaccctgg   2340
cgttacccaa cttaatcgcc ttgcagcaca tccccctttc gccagctggc gtaatagcga   2400
agaggcccgc accgatcgcc cttcccaaca gttgcgcagc ctgaatggcg aatgggacgc   2460
gccctgtagc ggcgcattaa gcgcggcggg tgtggtggtt acgcgcagcg tgaccgctac   2520
acttgccagc gccctagcgc ccgctccttt cgctttcttc ccttcctttc tcgccacgtt   2580
cgccggcttt ccccgtcaag ctctaaatcg ggggctccct ttagggttcc gatttagtgc   2640
tttacggcac ctcgacccca aaaaacttga ttagggtgat ggttcacgta gtgggccatc   2700
gccctgatag acgttttttc gcccttgac gttggagtcc acgttcttta atagtggact   2760
cttgttccaa actggaacaa cactcaaccc tatctcggtc tattcttttg atttataagg   2820
```

-continued

```
gattttgccg atttcggcct attggttaaa aaatgagctg atttaacaaa aatttaacgc   2880
gaattttaac aaaatattaa cgcttacaat ttaggtggca cttttcgggg aaatgtgcgc   2940 ggaacccta tttgtttatt tttctaaata cattcaaata tgtatccgct catgagacaa    3000
taaccctgat aaatgcttca ataatattga aaaggaaga gtatgagtat tcaacatttc   3060
cgtgtcgccc ttattccctt ttttgcggca ttttgccttc ctgttttgc tcacccagaa    3120 acgctggtga agtaaaaga tgctgaagat cagttgggtg cacgagtggg ttacatcgaa   3180
ctggatctca acagcggtaa gatccttgag agttttcgcc ccgaagaacg ttttccaatg   3240
atgagcactt ttaaagttct gctatgtggc gcggtattat cccgtattga cgccgggcaa   3300
gagcaactcg gtcgccgcat acactattct cagaatgact tggttgagta ctcaccagtc   3360
acagaaaagc atcttacgga tggcatgaca gtaagagaat tatgcagtgc tgccataacc   3420
atgagtgata acactgcggc caacttactt ctgacaacga tcggaggacc gaaggagcta   3480
accgcttttt tgcacaacat gggggatcat gtaactcgcc ttgatcgttg ggaaccggag   3540
ctgaatgaag ccataccaaa cgacgagcgt gacaccacga tgcctgtagc aatggcaaca   3600
acgttgcgca aactattaac tggcgaacta cttactctag cttcccggca acaattaata   3660
gactggatgg aggcggataa agttgcagga ccacttctgc gctcggccct tccggctggc   3720
tggtttattg ctgataaatc tggagccggt gagcgtgggt ctcgcggtat cattgcagca   3780
ctggggccag atggtaagcc ctcccgtatc gtagttatct acacgacggg gagtcaggca   3840
actatggatg aacgaaatag acagatcgct gagataggtg cctcactgat taagcattgg   3900
taactgtcag accaagttta ctcatatata ctttagattg atttaaaact tcatttttaa   3960
tttaaaagga tctaggtgaa gatcctttt gataatctca tgaccaaaat cccttaacgt   4020
gagttttcgt tccactgagc gtcagacccc gtagaaaaga tcaaaggatc ttcttgagat   4080 ccttttttc tgcgcgtaat ctgctgcttg caaacaaaaa aaccaccgct accagcggtg   4140
gtttgtttgc cggatcaaga gctaccaact cttttttccga aggtaactgg cttcagcaga   4200
gcgcagatac caaatactgt ccttctagtg tagccgtagt taggccacca cttcaagaac   4260
tctgtagcac cgcctacata cctcgctctg ctaatcctgt taccagtggc tgctgccagt   4320
ggcgataagt cgtgtcttac cgggttggac tcaagacgat agttaccgga taaggcgcag   4380
cggtcgggct gaacggggg ttcgtgcaca cagcccagct tggagcgaac gacctacacc   4440
gaactgagat acctacagcg tgagctatga aaagcgcca cgcttcccga agggagaaag   4500
gcggacaggt atccggtaag cggcagggtc ggaacaggag agcgcacgag ggagcttcca   4560
gggggaaacg cctggtatct ttatagtcct gtcgggtttc gccacctctg acttgagcgt   4620 cgattttgt gatgctcgtc agggggggcgg agcctatgga aaaacgccag caacgcggcc   4680 ttttttacggt tcctggcctt ttgctggcct tttgctcaca tgttctttcc tgcgttatcc   4740
cctgattctg tggataaccg tattaccgcc tttgagtgag ctgataccgc tcgccgcagc   4800
cgaacgaccg agcgcagcga gtcagtgagc gaggaagcgg aagagcgccc aatacgcaaa   4860
ccgcctctcc ccgcgcgttg gccgattcat taatgcagct ggcacgacag gtttcccgac   4920
tggaaagcgg gcagtgagcg caacgcaatt aatgtgagtt agctcactca ttaggcaccc   4980
caggctttac actttatgct tccggctcgt atgttgtgtg gaattgtgag cggataacaa   5040
tttcacacag gaaacagcta tgaccatgat tacgccaagc gcgcaattaa ccctcactaa   5100
agggaacaaa agctggagct cttatcggga ggccgtttcg catccggtta tctcgcaatc   5160
cggcgaatcc ggaaaaaggc agctcctgac ataggtgtcgg agccagaagg aaattgaatg   5220
```

```
ttcgatatta aacgccagga aatcgattgg ggcggaaaaa aactgacact ggaaaccgga    5280
caggttgccc gtcaggcaga tggcgccgtc attgcgacct aggtgaaac  ggtcgtatta    5340 tgcgcggtaa cggcagcaaa aacggtaaaa gaaggtcagg atttctttcc tttgaccgtc    5400
cattatcagg aaaaatattc agcagcaggc cgtattcccg gtggctttt  caagcgtgaa    5460 cgtggcgcaa ccgaacggga aacgctgatt tcacggttaa tcgaccgtcc aatccgtcct    5520
ctgtttccgg aaggtttcta taacgaaacc ttggtcattg cgcaggtcat gtcctatgac    5580
ggcgagaatg aaccggatat cttggcgatg atcgctgctt ctgcggctct tgctctttcc    5640
ggtgtgcctt tcttgggccc catcggtgct gcccgtgtgg ttatcaaga  tggcgagttc    5700 attcttaacc cgaccttgga acagcttgaa aaaagtgatc ttgatctggt tgtcggggct    5760
acccgtgatg ccgtgatgat ggttgaatcg gaagcgaatg agcttcccga agaagtcatg    5820
ctcaatgccg tttctttgc  gcatgaatct ttacagccgg ttatcaaagc tatcatcaat    5880
ctggcagaac aggccgctaa agagccttgg gaactggtca gctatgatga cagcgcattg    5940
gctgccaaag tcgaagaact ctgctacgac aatttcgata aggcctatcg tctgactcgc    6000
aaggctgaac gtgttgacgc cttgagcaag gccaaagcgg ttcttgacga agccttccca    6060
gaagctgatc cgacagaaaa gctgcgcatc cagaagcttg cgaagaagct ggaagcaaaa    6120
atcgtccgca ccgccattct gaaagaaggc cggagaattg acggacgcga tctgaaaaca    6180
gttcgcccga tccgctctca ggttggattc ttgccccgca cgcatggttc tgccctgttt    6240
acgcgtggtg aaacacaggc tttggtttca accaccccttg gaacggcgga tgctgaacag    6300
atgatcgacg gtttaaccgg ca                                              6322

<210> SEQ ID NO 63
<211> LENGTH: 1200
<212> TYPE: DNA
<213> ORGANISM: artificial sequence
<220> FEATURE:
<223> OTHER INFORMATION: constructed fragment for integration into Z.
      mobilis pnp locus

<400> SEQUENCE: 63
ttatcgggag gccgtttcgc atccggttat ctcgcaatcc ggcgaatccg gaaaaaggca      60
gctcctgaca tagggtcgga gccagaagga aattgaatgt tcgatattaa acgccaggaa     120
atcgattggg gcggaaaaaa actgacactg gaaaccggac aggttgcccg tcaggcagat     180
ggcgccgtca ttgcgacctt aggtgaaacg gtcgtattat gcgcggtaac ggcagcaaaa     240
acggtaaaag aaggtcagga tttctttcct ttgaccgtcc attatcagga aaaatattca     300
gcagcaggcc gtattcccgg tggcttttc  aagcgtgaac gtggcgcaac cgaacgggaa     360
acgctgattt cacggttaat cgaccgtcca atccgtcctc tgtttccgga aggtttctat     420
aacgaaacct tggtcattgc gcaggtcatg tcctatgacg gcgagaatga accggatatc     480
ttggcgatga tcgctgcttc tgcggctctt gctctttccg gtgtgccttt cttgggcccc     540
atcggtgctg cccgtgtggg ttatcaagat ggcgagttca ttcttaaccc gaccttggaa     600
cagcttgaaa aaagtgatct tgatctggtt gtcggggcta cccgtgatgc cgtgatgatg     660
gttgaatcgg aagcgaatga gcttcccgaa gaagtcatgc tcaatgccgt ttcttttgcg     720
catgaatctt tacagccggt tatcaaagct atcatcaatc tggcagaaca ggccgctaaa     780
gagccttggg aactggtcag ctatgatgac agcgcattgg ctgccaaagt cgaagaactc     840
tgctacgaca atttcgataa ggcctatcgt ctgactcgca aggctgaacg tgttgacgcc     900
```

```
ttgagcaagg ccaaagcggt tcttgacgaa gccttcccag aagctgatcc gacagaaaag    960
ctgcgcatcc agaagcttgc gaagaagctg aagcaaaaa tcgtccgcac cgccattctg   1020
aaagaaggcc ggagaattga cggacgcgat ctgaaaacag ttcgcccgat ccgctctcag   1080
gttggattct tgccccgcac gcatggttct gccctgttta cgcgtggtga acacaggct   1140
ttggtttcaa ccacccttgg aacggcggat gctgaacaga tgatcgacgg tttaaccggc   1200
```

<210> SEQ ID NO 64
<211> LENGTH: 1323
<212> TYPE: DNA
<213> ORGANISM: artificial sequence
<220> FEATURE:
<223> OTHER INFORMATION: constructed fragment for integration into Z. mobilis pnp locus

<400> SEQUENCE: 64

```
ttcattatga acgcttcatg ctgcattaca acttccccccc atattcggtc ggtgaagttg     60
gtcgttttgg tgctccgggt cgtcgtgaaa tcggccatgg taaactggca tggcgtgcgc    120
ttcatccggt tttgccgagc aaggctgatt tcccgtatac catccgtgtt ttgtcggata    180
tcaccgaatc taatggttcc tcttccatgg caaccgtttg cggtggctgc cttgcattga    240
tggatgccgg tgttccctta acgcgtccgg tttccggtat cgccatgggt cttattctgg    300
aaaaagacgg cttcgctatt ttgtccgata tcatgggtga tgaagatcac ttgggtgata    360
tggactttaa ggtcgccggt accgaaaaag gtatcaccag cctccagatg gacatcaagg    420
ttgctggcat taccgaagaa atcatgcaga agctttgga acaggctaaa ggtggccgtg    480
ctcatatctt gggtgaaatg tccaaagcgc tgggtgaagt ccgctccgaa atttctaatt    540
tggcaccgcg cattgaaaca atgagcgtac caaaagacaa aatccgtgat gttatcggaa    600
cgggcggaaa agttatccgt gaaatcgtgg cgaccacagg tgccaaggtc gatatcgaag    660
atgacggcac ggttcgtctg tcttcttctg atccggccaa tattgaagca gcccgtgaat    720
ggatcaatgg tattgttgaa gaaccggaag taggcaaaat ctataacggt aaagtcgtca    780
atatcgttga tttcggtgcc ttcgtaaact tcatgggtgg ccgtgacggc ttggtacatg    840
tttcggaaat caagaacgaa cgtgtcaaca aggtcagcga tgtcctgtcc gaaggtcagg    900
aagtcaaagt caaggttctt gaaattgaca ccgtggcaa ggttcgcctg tctatgcgtg    960
ttgtcgatca ggaaaccggc gcagagctgg atgataaccg tccgccacgt gagaacgcag   1020
aacgtcgcgg tggtgagcgt cctcgtcgtg atcggggccc tcgtcgggaa tctgcgatc   1080
gtccggcaag acgtgatatg gaaccggaat ttgctccggc attcctgcgc aaagatagct   1140
aatatctttc atattttgta tcgaaaaagg agggtctta aagatcctcc ttttttttgc   1200
ataaaagaa ggccatagaa caaacagtga taaagacagt ctcaaactgt ctttttatag   1260
aaaataccag aatattgtat ctggggggagg atgcatggtc ttaatccgga atacccggt   1320
cat                                                                1323
```

<210> SEQ ID NO 65
<211> LENGTH: 474
<212> TYPE: DNA
<213> ORGANISM: artificial sequence
<220> FEATURE:
<223> OTHER INFORMATION: start codon changed to ATG

<400> SEQUENCE: 65

```
atgacctctg ctgtgccatc aaatacgaaa aaaaagctgg tgattgcttc cgatcacgca     60
```

```
gcatttgagt tgaaatcaac cttgattact tggctgaaag agcttggtca tgaggtcgaa      120
gaccttggcc ctcatgaaaa ccattcagtc gattatcccg attacggtta taagctggct      180
gtcgctatcg cagaaaaaac cgctgatttc ggtattgctt tatgtggctc gggaatcggt      240
atctcgatcg ctgtcaatcg ccatccggct gcccgttgcg ctttgattac ggataaccct      300
accgcccgtt tggcaagaga acataacaat gccaatgtta tcgctatggg tgcgagattg      360
atcggcattg aaaccgctaa ggattgtatt tcagctttcc ttgcaacgcc gtttggaggt      420
gaacgtcatg ttcgccgtat cgataaactt tcgaatcctc agttcaatat ctag            474
```